(12) United States Patent
Mevellec et al.

(10) Patent No.: US 10,087,187 B2
(45) Date of Patent: Oct. 2, 2018

(54) IMIDAZOPYRIDAZINE DERIVATIVES AS PI3KB INHIBITORS

(71) Applicant: Janssen Pharmaceutica NV, Beerse (BE)

(72) Inventors: Laurence Anne Mevellec, Louviers (FR); Lieven Meerpoel, Beerse (BE); Sophie Coupa, Belbeuf (FR); Virginie Sophie Poncelet, Le Manoir sur Seine (FR); Isabelle Noelle Constance Pilatte, Louviers (FR); Elisabeth Therese Jeanne Pasquier, Val de Reuil (FR); Didier Jean-Claude Berthelot, La Neuville Chant d'Oisel (FR); Olivier Alexis Georges Querolle, Saint Vigor (FR); Christophe Meyer, Les Authieux sur le Port St Ouen (FR); Patrick Rene Angibaud, Saint Pierre d'Autils (FR); Christophe Gabriel Marcel Demestre, Saint Jean du Thenney (FR); Guillaume Jean Maurice Mercey, Montaure (FR)

(73) Assignee: Janssen Pharmaceutica NV, Beerse (BE)

(*) Notice: Subject to any disclaimer, the term of this patent is extended or adjusted under 35 U.S.C. 154(b) by 0 days.

(21) Appl. No.: 15/537,551

(22) PCT Filed: Dec. 18, 2015

(86) PCT No.: PCT/EP2015/080604
§ 371 (c)(1),
(2) Date: Jun. 19, 2017

(87) PCT Pub. No.: WO2016/097347
PCT Pub. Date: Jun. 23, 2016

(65) Prior Publication Data
US 2018/0002336 A1    Jan. 4, 2018

(30) Foreign Application Priority Data
Dec. 19, 2014 (EP) .................... 14199322

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ............................ C07D 487/04; C07D 519/00
See application file for complete search history.

(56) References Cited
U.S. PATENT DOCUMENTS
2013/0157977 A1   6/2013   Rivero et al.

FOREIGN PATENT DOCUMENTS

| WO | WO 2007038314 A3 | 4/2007 | |
|---|---|---|---|
| WO | WO 2008008539 A3 | 1/2008 | |
| WO | WO 2008014219 A3 | 1/2008 | |
| WO | WO 2008030579 A3 | 3/2008 | |
| WO | WO 2008138834 A1 | 11/2008 | |
| WO | WO 2009060197 A1 | 5/2009 | |
| WO | WO 2009091374 A3 | 7/2009 | |
| WO | WO 2010/007099 | * 1/2010 | ........... C07D 487/04 |
| WO | WO 2010007099 A1 | 1/2010 | |
| WO | WO 2011022439 A1 | 2/2011 | |
| WO | WO 2011047770 A2 | 4/2011 | |
| WO | WO 2011058109 A1 | 5/2011 | |
| WO | WO 2011123751 A3 | 10/2011 | |
| WO | WO 2012047538 A1 | 4/2012 | |
| WO | WO 2012116237 A3 | 8/2012 | |
| WO | WO 2013028263 A1 | 2/2013 | |
| WO | WO 2013095761 A1 | 6/2013 | |
| WO | WO 2014078211 A1 | 5/2014 | |

OTHER PUBLICATIONS

Calnan, D.R. and Brunet, A., The FoxO code, Oncogene 27; 2008, 2276-2288.
Courtney, K.D., et al., Journal of Clinical Oncology, 28,6; 1075-1083.
Jackson, S.P., et al., Nature Medicine, PI 2-kinase p110B: a new target for antithrombotic therapy, 11,5; 2005, 507-514.
Jia, S., et al., Essential roles of PI(3)k-p110B in cell growth, metabolism and tumorigenesis, Nature; 454; 2008, 776-779.
Marques, R.B., et al., High Efficacy of Combination Therapy Using PI3K/AKT Inhibitors with Androgen Deprivation in Prostate Cancer Preclinical Models. Eur Assoc of Urol, 67; 2015, 1177-1185.
Myers, M.P., et al., The lipid phosphatase activity of PTEN is critical for its tumor suppressor function, Proc. Natl. Acad. Sci. USA 95; 1998, 13513-13518.
Stokoe, David., et al., Dual Role of Phosphatidylinositol-3,5-trisphosphate in the Activation of Protein Kinase B, Science 277; 567-570.

(Continued)

*Primary Examiner* — Erich A Leeser

(57) ABSTRACT

The present invention relates to substituted imidazopyridazine derivatives of Formula (I)

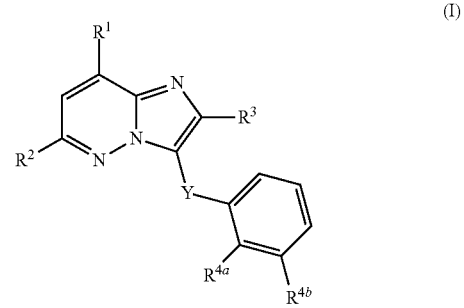

wherein the variables have the meaning defined in the claims. The compounds according to the present invention are useful as pI3Kβ inhibitors. The invention further relates to processes for preparing such novel compounds, pharmaceutical compositions comprising said compounds as an active ingredient as well as the use of said compounds as a medicament.

14 Claims, No Drawings

(56) References Cited

OTHER PUBLICATIONS

Vanhaesebroeck, B., et al., Signaling by Distinct Classes of Phosphoinositide 3-Kinases, Experimental Cell Research, 253; 239-254.
Wee, Susan, et al., PTEN-deficient cancers depend on PIK3CB, PNAS, 105; 13057-13062.
Zhao. L. and Vogt, P.K., Class I PI3K in oncogenic cellular transformation, Oncogene 27; 2008, 5486-5496.
International Search Report and Written Opinion relating to International Patent Application PCT/EP2015/080604, dated Feb. 5, 2016. dated Oct. 12, 2016.
International Search Report and Written Opinion relating to International Patent Application PCT/EP2015/080623, dated Feb. 15, 2016. dated Oct. 12, 2016.

\* cited by examiner

IMIDAZOPYRIDAZINE DERIVATIVES AS PI3KB INHIBITORS

CROSS REFERENCE TO RELATED APPLICATIONS

This application is a national stage application of International Patent Application No. PCT/EP2015/080604, filed 18 Dec. 2015, which claims priority from EP Application 14199322.0 filed 19 Dec. 2014. The complete disclosures of the aforementioned related patent applications are hereby incorporated herein by reference for all purposes.

FIELD OF THE INVENTION

The present invention relates to substituted imidazopyridazine derivatives useful as PI3Kβ inhibitors. The invention further relates to processes for preparing such compounds, pharmaceutical compositions comprising said compounds as an active ingredient as well as the use of said compounds as a medicament.

BACKGROUND OF THE INVENTION

There are three classes of phosphoinositide-3-kinases (PI3Ks): class I, class II and class III. Class I PI3Ks are the most associated with human cancer [K. D Courtney, R. B. Corcoran and J. A. Engelman (2010), *Journal of Clinical Oncology.*, 28; 1075]. The class I phosphoinositide-3-kinases (PI3Ks) are divided into 2 subclasses: class $I_A$, composed of a p110 catalytic subunit (p110a, p110b or p110d) and a p85 regulatory subunit (p85a, p55a and p50a, p85b or p55g) and class $1_B$ PI3K represented by the p110g catalytic subunit and the p101 and p84 regulatory subunits [B. Vanhaesebroeck and M. D. Waterfield (1999) *Experimental Cell Research.*, 253, 239-254]. The class $I_A$ PI3Ks are activated in a variety of solid and non-solid tumors via mutation or deletion of the tumor suppressor PTEN (phosphatase and tensin homolog) or in the case of p110a by activating mutations [K. D Courtney, R. B. Corcoran and J. A. Engelman (2010), *Journal of Clinical Oncology.*, 28; 1075]. PI3Ks can also be activated by receptor tyrosine kinases (RTKs); p110b can be activated by G-protein coupled receptors [K. D Courtney, R. B. Corcoran and J. A. Engelman (2010), *Journal of Clinical Oncology.*, 28; 1075]. Once activated the phosphoinositide-3-kinases catalyze the phosphorylation of phosphatidyl 4,5-diphosphate leading to the generation of phosphatidyl, 3, 4, 5-triphosphate (PIP3) [Zhao L., Vogt P. K. (2008) Oncogene 27, 5486-5496]. PTEN antagonizes the activity of the PI3Ks through the dephosphorylation PIP3 [Myers M. P., Pass I., Batty I. H., Van der Kaay J., Stolarov J. P., Hemmings B. A., Wigler M. H., Downes C. P., Tonks N. K. (1998) *Proc. Natl. Acad. Sci. U.S.A.* 95, 13513-13518]. The PIP3 generated by activation of PI3K or sustained by the inactivation of PTEN binds to a subset of lipid-binding domains in downstream targets such as the pleckstrin homology domain of the oncogene Akt thereby recruiting it to the plasma membrane [Stokoe D., Stephens L. R, Copeland T., Gaffney P. R., Reese C. B., Painter G. F., Holmes A. B., McCormick F., Hawkins P. T. (1997) *Science* 277, 567-570]. Once at the plasma membrane Akt phosphorylates several effector molecules that are involved in numerous biologically relevant processes such as metabolism, differentiation, proliferation, longevity and apoptosis [D. R. Calnan and A. Brunet (2008) *Oncogene* 27; 2276)].

Several studies suggest a key role for p110b in PTEN-deficient tumors. For example the genetic knockout of p110b, but not p110a, is able to block tumor formation and Akt activation driven by Pten loss in the anterior prostate in a mouse model [Jia S, Liu Z, Zhang S, Liu P, Zhang L, Lee S H, Zhang J, Signoretti S, Loda M, Roberts T M, Zhao J J. *Nature* 2008; 454:776-9]. Furthermore other studies have shown that a subset of PTEN-deficient human tumor cell lines is sensitive to inactivation of p110b rather than p110a [Wee S, Wiederschain D, Maira S M, Loo A, Miller C, deBeaumont R, Stegmeier F, Yao Y M, Lengauer C (2008) *Proc. Natl. Acad. Sci* (USA); 105 13057]. PTEN deficiency either by genetic inactivation or reduced expression frequently occurs in human cancers such as GBM, endometrial, lung, breast cancers and prostate cancer among others [K. D Courtney, R. B. Corcoran and J. A. Engelman (2010), *Journal of Clinical Oncology.*, 28; 1075].

These studies suggest that treatment of PTEN-deficient cancer with agents that inhibition p110b may be therapeutically beneficial. In addition to its role in cancer, p110b may be a target for antithrombotic therapy. It has been reported in mouse models that PI3Kb inhibition can prevent stable integrin $a_{IIb}b_3$ adhesion contacts that eliminates occulusive thrombus formation without prolongation of bleed time [S. P. Jackson et al. (2005) *Nature Medicine.*, 11, 507-514].

Furthermore, the phosphatidylinositol-4,5-bisphosphate 3-kinase (PI3K)/AKT pathway is frequently activated during prostate cancer (PCa) progression through loss or mutation of the phosphatase and tensin homolog (PTEN) gene. Following the androgen receptor (AR) pathway, it is the second major driver of PCa growth. Combination with hormonal therapy improved efficacy of PI3K/AKT-targeted agents in PTEN-negative PCa models. Upregulation of AR-target genes upon PI3K/AKT inhibition suggests a compensatory crosstalk between the PI3K-AR pathways which, for optimal efficacy treatment, could require cotargeting of the AR axis [Marques R B, et al., High Efficacy of Combination Therapy Using PI3K/AKT Inhibitors with Androgen Deprivation in Prostate Cancer Preclinical Models. *Eur Urol* (2014), http://dx.doi.org/10.1016/j.eururo.2014.08.053]. Therefore PI3KJ3 inhibitors can be advantageously combined with anti-androgen therapies including androgen receptor antagonists and inhibitors of androgen biosynthesis in PTEN-negative prostate cancers.

WO 2009/060197 discloses imidazopyridazines for use as protein kinase inhibitors.

WO 2012/116237 discloses heterocyclic entitites that modulate PI3 kinase activity.

WO 2011/123751 describes heterocyclic compounds as selective inhibitors of PI3K activity.

WO 2011/058109 relates to a series of fused bicyclic pyrrole and imidazole derivatives as kinase inhibitors.

WO 2011/022439 discloses heterocyclic entities that modulate PI3 kinase activity.

WO 2008/014219 describes thiozolidinedione derivatives as PI3 kinase inhibitors.

WO 2013/028263 relates to pyrazolopyrimidine derivatives as PI3 kinase inhibitors.

WO 2012/047538 relates to benzimidazole derivatives as PI3 kinase inhibitors.

WO 2013/095761 relates to imidazopyridine derivatives as PI3 kinase inhibitors.

US 2013/0157977 relates to benzimidazole boronic acid derivatives as PI3 kinase inhibitors.

WO 2007/038314 discloses heterocyclic compounds useful as kinase modulators.

WO 2008/030579 describes modulators of IRAK kinase.

WO 2009/091374 and WO 2008/008539 relate to fused heterocyclic derivatives for prophylaxis and treatment of diseases, such as HGF mediated diseases.

WO 2014/078211 discloses heteroaromatic compounds as PI3 kinase modulators.

WO 2008/138834 relates to substituted imidazopyridazines as PI3K lipid kinase inhibitors.

WO 2010/007099 describes 2-aminoimidazo[1,2-b]pyridazine derivatives as PI3K inhibitors.

WO 2011/047770 discloses pyrazolopyrimidine derivatives as PI3K inhibitors.

There is thus a strong need for novel PI3Kβ kinase inhibitors thereby opening new avenues for the treatment or prevention of cancer, in particular PTEN-deficient cancers, more in particular prostate cancer. It is accordingly an object of the present invention to provide such compounds.

SUMMARY OF THE INVENTION

It has been found that the compounds of the present invention are useful as PI3Kβ inhibitors. The compounds according to the invention and compositions thereof, may be useful for the treatment or prevention, in particular for the treatment, of diseases such as cancer, autoimmune disorders, cardiovascular diseases, inflammatory diseases, neurodegenerative diseases, allergy, pancreatitis, asthma, multiorgan failure, kidney diseases, platelet aggregation, sperm motility, transplantation rejection, graft rejection, lung injuries and the like.

This invention concerns compounds of Formula (I)

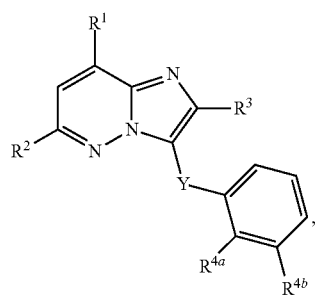
(I)

tautomers and stereoisomeric forms thereof, wherein
$R^1$ represents —C(=O)OH, —C(=O)NH$_2$, —NH$_2$,

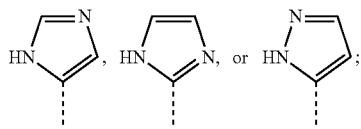

$R^2$ represents

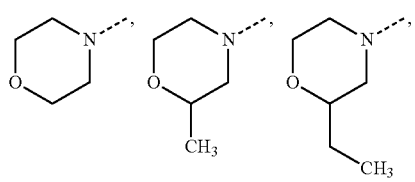

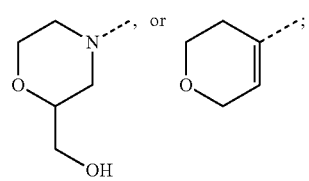

$R^3$ represents $C_{1-4}$alkyl; —CH(OH)—CH$_2$—$R^q$; or $C_{1-4}$alkyl substituted with one substituent selected from the group consisting of halo, —OH, —NH$_2$, —O—(C=O)—$C_{1-4}$alkyl, —NH—(C=O)—$C_{1-4}$alkyl, —NH—(SO$_2$)—$C_{1-4}$alkyl, —N(CH$_3$)—$C_{1-4}$alkyl-SO$_2$—CH$_3$, —NH—$C_{1-4}$alkyl-SO$_2$—CH$_3$, —N(CH$_3$)—$C_{1-4}$alkyl-OH, —(C=O)—NH—$C_{1-4}$alkyl-OH, —O—(C=O)—CH(NH$_2$)—$C_{1-4}$alkyl, —O—(C=O)—CH(NH$_2$)—$C_{1-4}$alkyl-Ar,

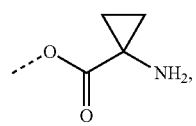

and —NH—$C_{1-4}$alkyl-OH;
$R^q$ represents halo, —OH, —NH$_2$, —O—(C=O)—$C_{1-4}$alkyl, —NH—(C=O)—$C_{1-4}$alkyl, —NH—(SO$_2$)—$C_{1-4}$alkyl, —N(CH$_3$)—$C_{1-4}$alkyl-SO$_2$—CH$_3$, —NH—$C_{1-4}$alkyl-SO$_2$—CH$_3$, —N(CH$_3$)—$C_{1-4}$alkyl-OH, —O—(C=O)—CH(NH$_2$)—$C_{1-4}$alkyl, —O—(C=O)—CH(NH$_2$)—$C_{1-4}$alkyl-Ar,

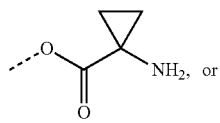

or —NH—$C_{1-4}$alkyl-OH;
Y represents —CH$_2$— or —NH—;
$R^{4a}$ represents hydrogen, $C_{1-4}$alkyl, Het$^a$, or $C_{1-4}$alkyl substituted with one or more substituents each independently selected from the group consisting of —OH, —NR$^5$R$^6$ and Het$^a$;
$R^{4b}$ represents hydrogen, halo, $C_{1-4}$alkyl, or $C_{1-4}$alkyl substituted with one or more halo substituents;
or $R^{4a}$ and $R^{4b}$ are taken together to form together with the phenyl ring to which they are attached a structure of Formula (a-1), (a-2), (a-3), (a-4) or (a-5):

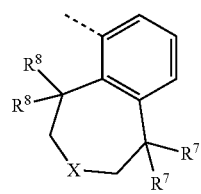
(a-1)

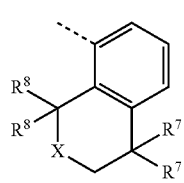

(a-2)

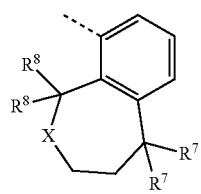

(a-3)

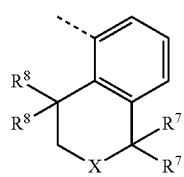

(a-4)

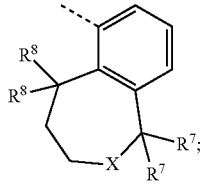

(a-5)

X represents —NH—, —O— or —N($C_{1-3}$alkyl)-;
both $R^7$ substituents are the same and are selected from the group consisting of hydrogen, fluoro and methyl; or both $R^7$ substituents are taken together to form together with the common carbon atom to which they are attached a cyclopropyl, cyclobutyl or oxetanyl;
both $R^8$ substituents are the same and are selected from the group consisting of hydrogen and methyl; or both $R^8$ substituents are taken together to form together with the common carbon atom to which they are attached a cyclopropyl, cyclobutyl or oxetanyl;
$R^5$ represents hydrogen, $C_{1-6}$alkyl, or $C_{1-6}$alkyl substituted with one —OH;
$R^6$ represents hydrogen, $C_{1-6}$alkyl, or $C_{1-6}$alkyl substituted with one —OH;
Ar represents phenyl optionally substituted with hydroxy;
each $Het^a$ independently represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of $C_{1-4}$alkyl, —S(=O)$_2$—$C_{1-6}$alkyl, hydroxy, —$C_{1-4}$alkyl-S(=O)$_2$—$C_{1-6}$alkyl, and $C_{1-4}$alkyl substituted with one hydroxy; or two substituents on the same carbon atom of said 4-, 5- or 6-membered saturated heterocyclyl are taken together to form together with the common carbon atom to which they are attached Ring B;
Ring B represents cyclobutyl, cyclopentyl, cyclohexyl or a 4-, 5- or 6-membered saturated heterocyclyl containing at least one heteroatom each independently selected from O, S, S(=O)$_p$ and N; said cyclobutyl, cyclopentyl, cyclohexyl or 4-, 5- or 6-membered saturated heterocyclyl is optionally substituted with one or two $C_{1-4}$alkyl substituents, with one $C_{1-4}$alkyl and one hydroxy substituent, or with one hydroxy substituent;
p represents 1 or 2;
and the N-oxides, the pharmaceutically acceptable addition salts, and the solvates thereof.

The present invention also concerns methods for the preparation of compounds of the present invention and pharmaceutical compositions comprising them.

The compounds of the present invention were found to inhibit PI3K, and therefore may be useful in the treatment or prevention, in particular in the treatment, of diseases such as cancer, autoimmune disorders, cardiovascular diseases, inflammatory diseases, neurodegenerative diseases, allergy, pancreatitis, asthma, multiorgan failure, kidney diseases, platelet aggregation, sperm motility, transplantation rejection, graft rejection, lung injuries and the like.

Some of the compounds of the present invention may undergo metabolism to a more active form in vivo (prodrugs).

In view of the aforementioned pharmacology of the compounds of Formula (I) and N-oxides, pharmaceutically acceptable addition salts, and solvates thereof, it follows that they may be suitable for use as a medicament.

In particular the compounds of Formula (I) and N-oxides, pharmaceutically acceptable addition salts, and solvates thereof, may be suitable in the treatment or prevention, in particular in the treatment, of cancer.

The present invention also concerns the use of compounds of Formula (I) and N-oxides, pharmaceutically acceptable addition salts, and solvates thereof, for the manufacture of a medicament for the inhibition of PI3Kβ, for the treatment or prevention of cancer.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

When any variable occurs more than one time in any constituent or in any formula (e.g. Formula (I)), its definition in each occurrence is independent of its definition at every other occurrence.

Whenever the term "substituted" is used in the present invention, it is meant, unless otherwise is indicated or is clear from the context, to indicate that one or more hydrogens, in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The skilled person will understand that the term "optionally substituted" means that the atom or radical indicated in the expression using "optionally substituted" may or may not be substituted (this means substituted or unsubstituted respectively).

When two or more substituents are present on a moiety they may, unless otherwise is indicated or is clear from the context, replace hydrogens on the same atom or they may replace hydrogen atoms on different atoms in the moiety.

It will be clear for the skilled person that, unless otherwise is indicated or is clear from the context, a substituent on a heterocyclyl group may replace any hydrogen atom on a ring carbon atom or on a ring heteroatom.

The prefix "$C_{x-y}$" (where x and y are integers) as used herein refers to the number of carbon atoms in a given group. Thus, a $C_{1-6}$alkyl group contains from 1 to 6 carbon atoms, a $C_{1-4}$alkyl group contains from 1 to 4 carbon atoms, a $C_{1-3}$alkyl group contains from 1 to 3 carbon atoms and so on.

It will be clear for the skilled person that $S(=O)_2$, $(SO_2)$ or $SO_2$ represents a sulfonyl moiety.

The term "halo" as a group or part of a group is generic for fluoro, chloro, bromo, iodo unless otherwise is indicated or is clear from the context.

The term "$C_{1-6}$alkyl" as a group or part of a group refers to a hydrocarbyl radical of Formula $C_nH_{2n+1}$ wherein n is a number ranging from 1 to 6. $C_{1-6}$alkyl groups comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl includes all linear, or branched alkyl groups with between 1 and 6 carbon atoms, and thus includes such as for example methyl, ethyl, n-propyl, i-propyl, 2-methyl-ethyl, butyl and its isomers (e.g. n-butyl, isobutyl and tert-butyl), pentyl and its isomers, hexyl and its isomers, and the like.

The term "$C_{1-4}$alkyl" as a group or part of a group refers to a hydrocarbyl radical of Formula $C_nH_{2n}+_1$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl groups may be linear or branched and may be substituted as indicated herein. When a subscript is used herein following a carbon atom, the subscript refers to the number of carbon atoms that the named group may contain. $C_{1-4}$alkyl includes all linear, or branched alkyl groups with between 1 and 4 carbon atoms, and thus includes methyl, ethyl, n-propyl, i-propyl, 2-methyl-ethyl, butyl and its isomers (e.g. n-butyl, isobutyl and tert-butyl), and the like.

The term "$C_{1-3}$alkyl" as a group or part of a group refers to a hydrocarbyl radical of Formula $C_nH_{2+1}$ wherein n is a number ranging from 1 to 3. $C_{1-3}$alkyl groups comprise from 1 to 3 carbon atoms, preferably 1 to 2 carbon atoms. $C_{1-3}$alkyl groups may be linear or branched and may be substituted as indicated herein. When a subscript is used herein following a carbon atom, the subscript refers to the number of carbon atoms that the named group may contain. $C_{1-3}$alkyl includes all linear, or branched alkyl groups with between 1 and 3 carbon atoms, and thus includes methyl, ethyl, n-propyl, i-propyl, 2-methyl-ethyl, and the like.

A 4-, 5- or 6-membered saturated heterocyclyl containing at least one heteroatom each independently selected from O, S, $S(=O)_p$ and N (as occurring for example in the definitions of $Het^a$ and Ring B); in a particular embodiment is a 4-, 5- or 6-membered saturated heterocyclyl containing 1, 2 or 3 heteroatoms selected from O, S, $S(=O)_p$ and N; in a more particular embodiment a 4-, 5- or 6-membered saturated heterocyclyl containing 1 or 2 heteroatoms selected from O, S, $S(=O)_p$ and N.

Examples of a 4-, 5- or 6-membered saturated heterocyclyl containing at least one heteroatom each independently selected from O, S, $S(=O)_p$ and N, include, but are not limited to azetidinyl, morpholinyl, piperidinyl, pyrrolidinyl, 1,1-dioxido-thietanyl, 1,1-dioxido-thiomorpholinyl, piperazinyl, dioxolanyl, oxazolidinyl, oxetanyl, tetrahydrofuranyl, and the like.

$Het^a$ may be attached to the remainder of the molecule of Formula (I) through any available ring carbon atom or ring heteroatom as appropriate, if not otherwise specified.

It will be clear that when two substituents on the same carbon atom in the $Het^a$ definition are taken together to form together with the common carbon atom to which they are attached Ring B, a spiro moiety is formed. For example, when $Het^a$ represents 1-piperidinyl wherein two substituents on the carbon atom in position β are taken together to form together with the common carbon atom to which they are attached ring B, the following spiro moiety is formed:

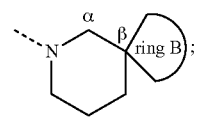

in particular if in the above example ring B represents 3-azetidinyl, the following spiro moiety is formed:

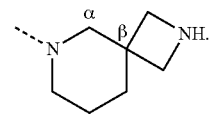

Examples of such spiro moieties, include, but are not limited to

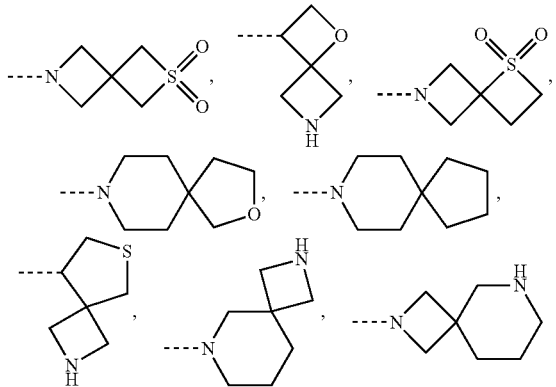

the like.

Whenever substituents are represented by chemical structure, "---" represents the bond of attachment to the remainder of the molecule of Formula (I).

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compounds of the invention" as used herein, is meant to include the compounds of Formula (I) and N-oxides, pharmaceutically acceptable addition salts, and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Whenever one of the ring systems, is substituted with one or more substituents, those substituents may replace, unless otherwise is indicated or is clear from the context, any hydrogen atom bound to a carbon or nitrogen atom of the ring system.

Hereinbefore and hereinafter, the term "compound of Formula (I)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds of Formula (I) may also exist in their tautomeric form. Such forms in so far as they may exist, are intended to be included within the scope of the present invention. It follows that a single compound may exist in both stereoisomeric and tautomeric form.

For example, it will be clear for the skilled person that when R¹ represents

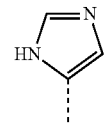

also

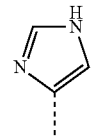

also is included.

For therapeutic use, salts of the compounds of Formula (I), N-oxides and solvates thereof, are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove or hereinafter are meant to comprise the therapeutically active non-toxic acid and base addition salt forms which the compounds of Formula (I), N-oxides and solvates thereof, are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I), N-oxides and solvates thereof containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of Formula (I) are able to form, as well as N-oxides and pharmaceutically acceptable addition salts thereof. Examples of such forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and N-oxides, pharmaceutically acceptable addition salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, an element, in particular when mentioned in relation to a compound of Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^2$H, $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^2$H, $^3$H, $^{11}$C and $^{18}$F. More preferably, the radioactive isotope is $^2$H. In particular, deuterated compounds are intended to be included within the scope of the present invention In an embodiment, the present invention concerns novel compounds of Formula (I),
tautomers and stereoisomeric forms thereof, wherein
$R^1$ represents —C(=O)OH, —C(=O)NH$_2$, —NH$_2$,

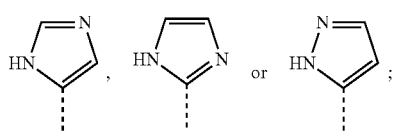

$R^2$ represents

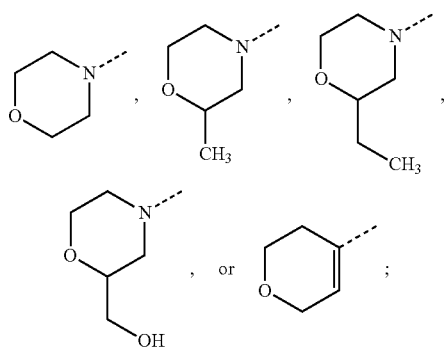

$R^3$ represents $C_{1-4}$alkyl; or $C_{1-4}$alkyl substituted with one substituent selected from the group consisting of halo, —OH, —NH$_2$, —O—(C=O)—$C_{1-4}$alkyl, —NH—(C=O)—$C_{1-4}$alkyl, —NH—(SO$_2$)—$C_{1-4}$alkyl, —N(CH$_3$)—$C_{1-4}$alkyl-SO$_2$—CH$_3$, —NH—$C_{1-4}$alkyl-SO$_2$—CH$_3$, —N(CH$_3$)—$C_{1-4}$alkyl-OH, —(C=O)—NH—$C_{1-4}$alkyl-OH, —O—(C=O)—CH(NH$_2$)—$C_{1-4}$alkyl, —O—(C=O)—CH(NH$_2$)—$C_{1-4}$alkyl-Ar,

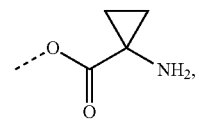

and —NH—$C_{1-4}$alkyl-OH;

Y represents —CH$_2$— or —NH—;

$R^{4a}$ represents hydrogen, $C_{1-4}$alkyl, Het$^a$, or $C_{1-4}$alkyl substituted with one or more substituents each independently selected from the group consisting of —OH, —NR$^5$R$^6$ and Het$^a$;

$R^{4b}$ represents hydrogen, halo, $C_{1-4}$alkyl, or $C_{1-4}$alkyl substituted with one or more halo substituents;

or $R^{4a}$ and $R^{4b}$ are taken together to form together with the phenyl ring to which they are attached a structure of Formula (a-1), (a-2), (a-3), (a-4) or (a-5):

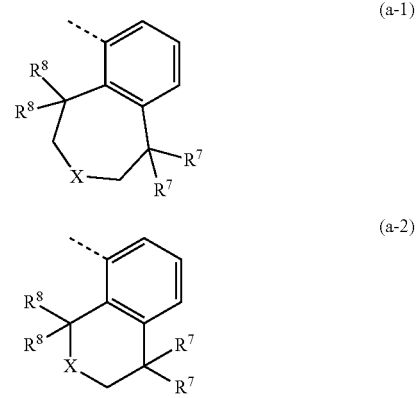

-continued

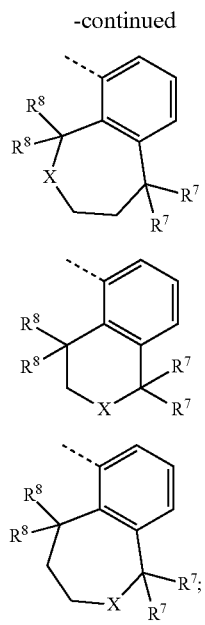

(a-3)

(a-4)

(a-5)

X represents —NH—, —O— or —N(C$_{1-3}$alkyl)-;

both R$^7$ substituents are the same and are selected from the group consisting of hydrogen, fluoro and methyl; or both R$^7$ substituents are taken together to form together with the common carbon atom to which they are attached a cyclopropyl, cyclobutyl or oxetanyl;

both R$^8$ substituents are the same and are selected from the group consisting of hydrogen and methyl; or both R$^8$ substituents are taken together to form together with the common carbon atom to which they are attached a cyclopropyl, cyclobutyl or oxetanyl;

R$^5$ represents hydrogen, C$_{1-6}$alkyl, or C$_{1-6}$alkyl substituted with one —OH;

R$^6$ represents hydrogen, C$_{1-6}$alkyl, or C$_{1-6}$alkyl substituted with one —OH;

Ar represents phenyl optionally substituted with hydroxy;

each Het$^a$ independently represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of C$_{1-4}$alkyl, —S(=O)$_2$—C$_{1-6}$alkyl, hydroxy, —C$_{1-4}$alkyl-S(=O)$_2$—C$_{1-4}$alkyl, and C$_{1-4}$alkyl substituted with one hydroxy; or two substituents on the same carbon atom of said 4-, 5- or 6-membered saturated heterocyclyl are taken together to form together with the common carbon atom to which they are attached Ring B;

Ring B represents cyclobutyl, cyclopentyl, cyclohexyl or a 4-, 5- or 6-membered saturated heterocyclyl containing at least one heteroatom each independently selected from O, S, S(=O)$_p$ and N; said cyclobutyl, cyclopentyl, cyclohexyl or 4-, 5- or 6-membered saturated heterocyclyl is optionally substituted with one or two C$_{1-4}$alkyl substituents, with one C$_{1-4}$alkyl and one hydroxy substituent, or with one hydroxy substituent;

p represents 1 or 2;

and the N-oxides, the pharmaceutically acceptable addition salts, and the solvates thereof.

In an embodiment, the present invention concerns novel compounds of Formula (I), tautomers and stereoisomeric forms thereof, wherein R$^1$ represents —C(=O)OH, —C(=O)NH$_2$, —NH$_2$,

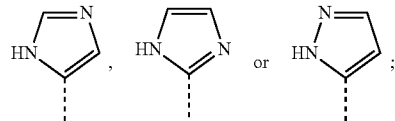

R$^2$ represents

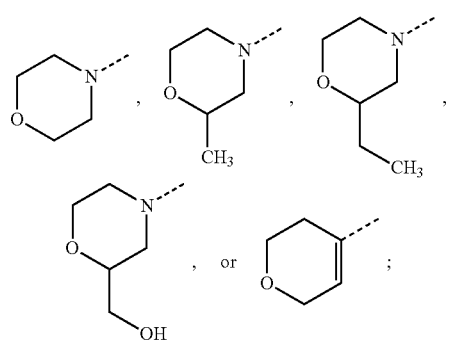

R$^3$ represents C$_{1-4}$alkyl; —CH(OH)—CH$_2$—R$^q$; or C$_{1-4}$alkyl substituted with one substituent selected from the group consisting of halo, —OH, —NH$_2$, —O—(C=O)—C$_{1-4}$alkyl, —NH—(C=O)—C$_{1-4}$alkyl, —NH—(SO$_2$)—C$_{1-4}$alkyl, —N(CH$_3$)—C$_{1-4}$alkyl-SO$_2$—CH$_3$, —NH—C$_{1-4}$alkyl-SO$_2$—CH$_3$, —N(CH$_3$)—C$_{1-4}$alkyl-OH, —(C=O)—NH—C$_{1-4}$alkyl-OH, —O—(C=O)—CH(NH$_2$)—C$_{1-4}$alkyl, —O—(C=O)—CH(NH$_2$)—C$_{1-4}$alkyl-Ar,

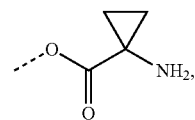

and —NH—C$_{1-4}$alkyl-OH;

R$^q$ represents halo, —OH, —NH$_2$, —O—(C=O)—C$_{1-4}$alkyl, —NH—(C=O)—C$_{1-4}$alkyl, —NH—(SO$_2$)—C$_{1-4}$alkyl, —N(CH$_3$)—C$_{1-4}$alkyl-SO$_2$—CH$_3$, —NH—C$_{1-4}$alkyl-SO$_2$—CH$_3$, —N(CH$_3$)—C$_{1-4}$alkyl-OH, —O—(C=O)—CH(NH$_2$)—C$_{1-4}$alkyl, —O—(C=O)—CH(NH$_2$)—C$_{1-4}$alkyl-Ar,

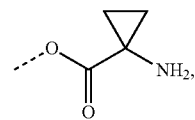

or —NH—C$_{1-4}$alkyl-OH;

Y represents —CH$_2$— or —NH—;

R$^{4a}$ represents C$_{1-4}$alkyl, Het$^a$, or C$_{1-4}$alkyl substituted with one or more substituents each independently selected from the group consisting of —OH, —NR$^5$R$^6$ and Het$^a$;

R$^{4b}$ represents hydrogen, halo, C$_{1-4}$alkyl, or C$_{1-4}$alkyl substituted with one or more halo substituents;

or R$^{4a}$ and R$^{4b}$ are taken together to form together with the phenyl ring to which they are attached a structure of Formula (a-1), (a-2), (a-3), (a-4) or (a-5);

X represents —NH— or —O—;
both R⁷ substituents are the same and are selected from the group consisting of hydrogen, fluoro and methyl;
both R⁸ substituents are the same and are selected from the group consisting of hydrogen and methyl;
$R^5$ represents hydrogen, $C_{1-6}$alkyl, or $C_{1-6}$alkyl substituted with one —OH;
$R^6$ represents hydrogen, $C_{1-6}$alkyl, or $C_{1-6}$alkyl substituted with one —OH;
Ar represents phenyl optionally substituted with hydroxy;
each Het$^a$ independently represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of $C_{1-4}$alkyl, —S(=O)$_2$—$C_{1-6}$alkyl, hydroxy, —$C_{1-4}$alkyl-S(=O)$_2$—$C_{1-6}$alkyl, and $C_{1-4}$alkyl substituted with one hydroxy; or two substituents on the same carbon atom of said 4-, 5- or 6-membered saturated heterocyclyl are taken together to form together with the common carbon atom to which they are attached Ring B;
Ring B represents cyclobutyl, cyclopentyl, cyclohexyl or a 4-, 5- or 6-membered saturated heterocyclyl containing one S(=O)$_2$;
p represents 1 or 2;
and the N-oxides, the pharmaceutically acceptable addition salts, and the solvates thereof.

In an embodiment, the present invention concerns novel compounds of Formula (I),
tautomers and stereoisomeric forms thereof, wherein
$R^1$ represents —C(=O)OH, —C(=O)NH$_2$, —NH$_2$,

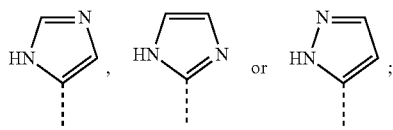

$R^2$ represents

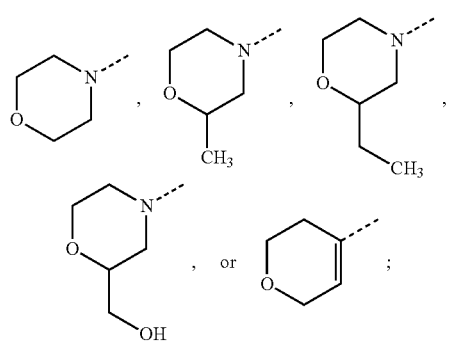

$R^3$ represents $C_{1-4}$alkyl; or $C_{1-4}$alkyl substituted with one substituent selected from the group consisting of halo, —OH, —NH$_2$, —O—(C=O)—$C_{1-4}$alkyl, —NH—(C=O)—$C_{1-4}$alkyl, —NH—(SO$_2$)—$C_{1-4}$alkyl, —N(CH$_3$)—$C_{1-4}$alkyl-SO$_2$—CH$_3$, —NH—$C_{1-4}$alkyl-SO$_2$—CH$_3$, —N(CH$_3$)—$C_{1-4}$alkyl-OH, —(C=O)—NH—$C_{1-4}$alkyl-OH, —O—(C=O)—CH(NH$_2$)—$C_{1-4}$alkyl, —O—(C=O)—CH(NH$_2$)—$C_{1-4}$alkyl-Ar,

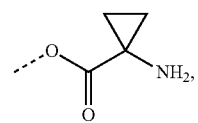

and —NH—$C_{1-4}$alkyl-OH;
Y represents —CH$_2$— or —NH—;
$R^{4a}$ represents $C_{1-4}$alkyl, Het$^a$, or $C_{1-4}$alkyl substituted with one or more substituents each independently selected from the group consisting of —OH, —NR$^5$R$^6$ and Het$^a$;
$R^{4b}$ represents hydrogen, halo, $C_{1-4}$alkyl, or $C_{1-4}$alkyl substituted with one or more halo substituents;
or $R^{4a}$ and $R^{4b}$ are taken together to form together with the phenyl ring to which they are attached a structure of Formula (a-1), (a-2), (a-3), (a-4) or (a-5);
X represents —NH— or —O—;
both R⁷ substituents are the same and are selected from the group consisting of hydrogen, fluoro and methyl;
both R⁸ substituents are the same and are selected from the group consisting of hydrogen and methyl;
$R^5$ represents hydrogen, $C_{1-6}$alkyl, or $C_{1-6}$alkyl substituted with one —OH;
$R^6$ represents hydrogen, $C_{1-6}$alkyl, or $C_{1-6}$alkyl substituted with one —OH;
Ar represents phenyl optionally substituted with hydroxy;
each Het$^a$ independently represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of $C_{1-4}$alkyl, —S(=O)$_2$—$C_{1-6}$alkyl, hydroxy, —$C_{1-4}$alkyl-S(=O)$_2$—$C_{1-4}$alkyl, and $C_{1-4}$alkyl substituted with one hydroxy; or two substituents on the same carbon atom of said 4-, 5- or 6-membered saturated heterocyclyl are taken together to form together with the common carbon atom to which they are attached Ring B;
Ring B represents cyclobutyl, cyclopentyl, cyclohexyl or a 4-, 5- or 6-membered saturated heterocyclyl containing one S(=O)$_2$;
p represents 1 or 2;
and the N-oxides, the pharmaceutically acceptable addition salts, and the solvates thereof.

In an embodiment, the present invention concerns novel compounds of Formula (I),
tautomers and stereoisomeric forms thereof, wherein
$R^1$ represents —C(=O)OH, —C(=O)NH$_2$, —NH$_2$,

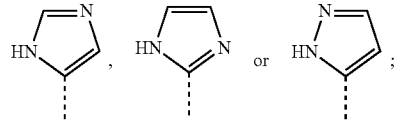

$R^2$ represents

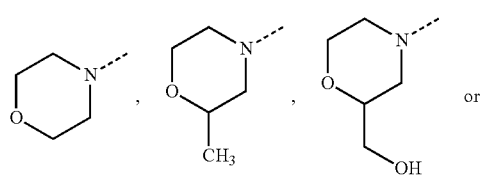

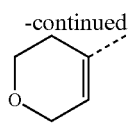

$R^3$ represents $C_{1-4}$alkyl; —CH(OH)—CH$_2$—R$^q$; or $C_{1-4}$alkyl substituted with one substituent selected from the group consisting of halo, —OH, —NH$_2$, —O—(C=O)—C$_{1-4}$alkyl, —NH—(C=O)—C$_{1-4}$alkyl, —N(CH$_3$)—C$_{1-4}$alkyl-SO$_2$—CH$_3$, —NH—C$_{1-4}$alkyl-SO$_2$—CH$_3$, —O—(C=O)—CH(NH$_2$)—C$_{1-4}$alkyl, —O—(C=O)—CH(NH$_2$)—C$_{1-4}$alkyl-Ar,

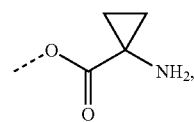

and —NH—C$_{1-4}$alkyl-OH;
R$^q$ represents —NH$_2$;
Y represents —CH$_2$— or —NH—;
R$^{4a}$ represents C$_{1-4}$alkyl, Het$^a$, or C$_{1-4}$alkyl substituted with one or more substituents each independently selected from the group consisting of —OH, —NR$^5$R$^6$ and Het$^a$;
R$^{4b}$ represents hydrogen, halo, C$_{1-4}$alkyl, or C$_{1-4}$alkyl substituted with one or more halo substituents;
or R$^{4a}$ and R$^{4b}$ are taken together to form together with the phenyl ring to which they are attached a structure of Formula (a-2) or (a-4);
X represents —NH— or —N(C$_{1-3}$alkyl)-;
both R$^7$ substituents are hydrogen;
both R$^8$ substituents are hydrogen;
R$^5$ represents hydrogen;
R$^6$ represents C$_{1-6}$alkyl substituted with one —OH;
Ar represents phenyl;
each Het$^a$ independently represents a 4-, 5- or 6-membered saturated heterocyclyl containing at least one heteroatom each independently selected from O, S(=O)$_p$ and N; said 4-, 5- or 6-membered saturated heterocyclyl is optionally substituted with one or two substituents each independently selected from the group consisting of C$_{1-4}$alkyl, —S(=O)$_2$—C$_{1-6}$alkyl, hydroxy, and C$_{1-4}$alkyl substituted with one hydroxy; or two substituents on the same carbon atom of said 4-, 5- or 6-membered saturated heterocyclyl are taken together to form together with the common carbon atom to which they are attached Ring B;
Ring B represents a 4-membered saturated heterocyclyl containing one S(=O)$_p$;
p represents 2;
and the N-oxides, the pharmaceutically acceptable addition salts, and the solvates thereof.

In an embodiment, the present invention concerns novel compounds of Formula (I),
tautomers and stereoisomeric forms thereof, wherein
R$^1$ represents —C(=O)OH, —C(=O)NH$_2$, —NH$_2$,

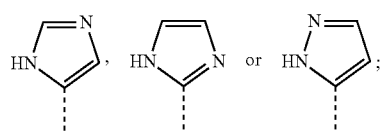

R$^2$ represents

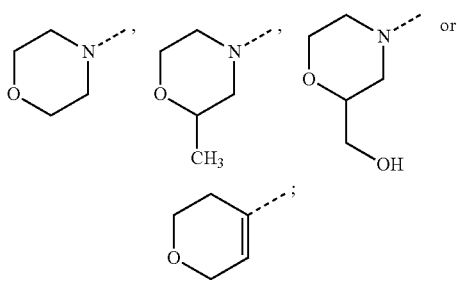

R$^3$ represents C$_{1-4}$alkyl; —CH(OH)—CH$_2$—R$^q$; or C$_{1-4}$alkyl substituted with one substituent selected from the group consisting of halo, —OH, —NH$_2$, —O—(C=O)—C$_{1-4}$alkyl, —NH—(C=O)—C$_{1-4}$alkyl, —N(CH$_3$)—C$_{1-4}$alkyl-SO$_2$—CH$_3$, —NH—C$_{1-4}$alkyl-SO$_2$—CH$_3$, —O—(C=O)—CH(NH$_2$)—C$_{1-4}$alkyl, —O—(C=O)—CH(NH$_2$)—C$_{1-4}$alkyl-Ar,

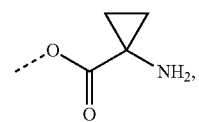

and —NH—C$_{1-4}$alkyl-OH;
R$^q$ represents —NH$_2$;
Y represents —CH$_2$— or —NH—;
R$^{4a}$ represents C$_{1-4}$alkyl, Het$^a$, or C$_{1-4}$alkyl substituted with one or more substituents each independently selected from the group consisting of —OH, —NR$^5$R$^6$ and Het$^a$;
R$^{4b}$ represents hydrogen, halo, C$_{1-4}$alkyl, or C$_{1-4}$alkyl substituted with one or more halo substituents;
or R$^{4a}$ and R$^{4b}$ are taken together to form together with the phenyl ring to which they are attached a structure of Formula (a-2) or (a-4);
X represents —NH—;
both R$^7$ substituents are hydrogen;
both R$^8$ substituents are hydrogen;
R$^5$ represents hydrogen;
R$^6$ represents C$_{1-4}$alkyl substituted with one —OH;
Ar represents phenyl;
each Het$^a$ independently represents a 4-, 5- or 6-membered saturated heterocyclyl containing at least one heteroatom each independently selected from O, S(=O)$_p$ and N; said 4-, 5- or 6-membered saturated heterocyclyl is optionally substituted with one or two substituents each independently selected from the group consisting of C$_{1-4}$alkyl, —S(=O)$_2$—C$_{1-6}$alkyl, hydroxy, and C$_{1-4}$alkyl substituted with one hydroxy; or two substituents on the same carbon atom of said 4-, 5- or 6-membered saturated heterocyclyl are taken together to form together with the common carbon atom to which they are attached Ring B;
Ring B represents a 4-membered saturated heterocyclyl containing one S(=O)$_p$;
p represents 2;
and the N-oxides, the pharmaceutically acceptable addition salts, and the solvates thereof.

In an embodiment, the present invention concerns novel compounds of Formula (I),
tautomers and stereoisomeric forms thereof, wherein
$R^1$ represents —NH$_2$;
$R^2$ represents

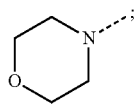

$R^3$ represents C$_{1-4}$alkyl; —CH(OH)—CH$_2$—R$^q$; or C$_{1-4}$alkyl substituted with one —OH or halo substituent; in particular R$^3$ represents C$_{1-4}$alkyl; —CH(OH)—CH$_2$—R$^q$; or C$_{1-4}$alkyl substituted with one —OH substituent;
$R^4$ represents —NH$_2$;
Y represents —CH$_2$—;
$R^{4a}$ represents C$_{1-4}$alkyl, or C$_{1-4}$alkyl substituted with one Het$^a$ substituent;
$R^{4b}$ represents halo, or C$_{1-4}$alkyl substituted with one or more halo substituents;
each Het$^a$ independently represents a 4-, 5- or 6-membered saturated heterocyclyl containing one or two heteroatoms each independently selected from O, S(=O)$_p$ and N; said 4-, 5- or 6-membered saturated heterocyclyl is optionally substituted with one or two substituents each independently selected from the group consisting of hydroxy, and C$_{1-4}$alkyl substituted with one hydroxy;
p represents 1 or 2;
and the N-oxides, the pharmaceutically acceptable addition salts, and the solvates thereof.

In an embodiment, the present invention concerns novel compounds of Formula (I),
tautomers and stereoisomeric forms thereof, wherein
$R^1$ represents —C(=O)OH, —C(=O)NH$_2$, —NH$_2$,

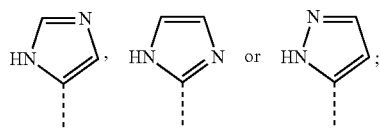

$R^2$ represents

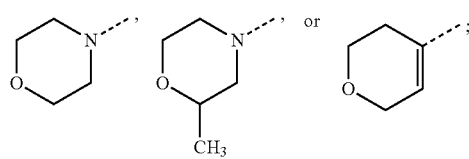

$R^3$ represents C$_{1-4}$alkyl; or C$_{1-4}$alkyl substituted with one substituent selected from the group consisting of halo, —OH, —NH—(C=O)—C$_{1-4}$alkyl, —N(CH$_3$)—C$_{1-4}$alkyl-SO$_2$—CH$_3$, —NH—C$_{1-4}$alkyl-SO$_2$—CH$_3$, and —NH—C$_{1-4}$alkyl-OH;
Y represents —CH$_2$— or —NH—;
$R^{4a}$ represents C$_{1-4}$alkyl, or C$_{1-4}$alkyl substituted with one or more Het$^a$ substituents;
$R^{4b}$ represents halo, C$_{1-4}$alkyl, or C$_{1-4}$alkyl substituted with one or more halo substituents;

or $R^{4a}$ and $R^{4b}$ are taken together to form together with the phenyl ring to which they are attached a structure of Formula (a-2);
X represents —NH—;
both $R^7$ substituents are hydrogen;
both $R^8$ substituents are hydrogen;
each Het$^a$ independently represents a 6-membered saturated heterocyclyl containing at least one heteroatom each independently selected from O, S(=O)$_p$ and N;
p represents 2;
and the N-oxides, the pharmaceutically acceptable addition salts, and the solvates thereof.

Another embodiment of the present invention relates to those compounds of Formula (I) and the N-oxides, the pharmaceutically acceptable addition salts, and the solvates thereof, or any subgroup thereof as mentioned in any of the other embodiments wherein one or more of the following restrictions apply:
(i) $R^2$ represents

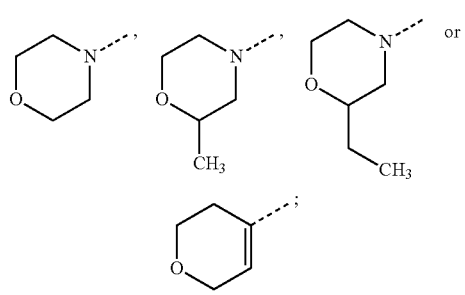

(ii) $R^3$ represents C$_{1-4}$alkyl; —CH(OH)—CH$_2$—R$^q$; or C$_{1-4}$alkyl substituted with one substituent selected from the group consisting of halo, —OH, —NH$_2$, —O—(C=O)—C$_{1-4}$alkyl, —NH—(C=O)—C$_{1-4}$alkyl, —N(CH$_3$)—C$_{1-4}$alkyl-SO$_2$—CH$_3$, —NH—C$_{1-4}$alkyl-SO$_2$—CH$_3$, —O—(C=O)—CH(NH$_2$)—C$_{1-4}$alkyl, —O—(C=O)—CH(NH$_2$)—C$_{1-4}$alkyl-Ar,

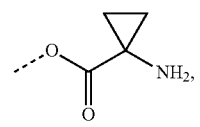

and —NH—C$_{1-4}$alkyl-OH; and R$^q$ represents —NH$_2$;
in particular R$^3$ represents C$_{1-4}$alkyl; or C$_{1-4}$alkyl substituted with one substituent selected from the group consisting of halo, —OH, —NH$_2$, —O—(C=O)—C$_{1-4}$alkyl, —NH—(C=O)—C$_{1-4}$alkyl, —N(CH$_3$)—C$_{1-4}$alkyl-SO$_2$—CH$_3$, —NH—C$_{1-4}$alkyl-SO$_2$—CH$_3$, —O—(C=O)—CH(NH$_2$)—C$_{1-4}$alkyl, —O—(C=O)—CH(NH$_2$)—C$_{1-4}$alkyl-Ar,

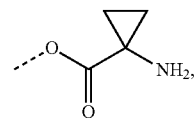

and —NH—C$_{1-4}$alkyl-OH;
(iii) $R^{4a}$ represents C$_{1-4}$alkyl, Het$^a$, or C$_{1-4}$alkyl substituted with one or more substituents each independently selected from the group consisting of —OH, —NR$^5$R$^6$ and Het$^a$;

$R^{4b}$ represents hydrogen, halo, $C_{1-4}$alkyl, or $C_{1-4}$alkyl substituted with one or more halo substituents;
or $R^{4a}$ and $R^{4b}$ are taken together to form together with the phenyl ring to which they are attached a structure of Formula (a-2) or (a-4);
(iv) X represents —NH—;
(v) both $R^7$ substituents are hydrogen;
(vi) both $R^8$ substituents are hydrogen;
(vii) $R^5$ represents hydrogen;
(viii) $R^6$ represents $C_{1-6}$alkyl substituted with one —OH;
(ix) Ar represents phenyl;
(x) each $Het^a$ independently represents a 4-, 5- or 6-membered saturated heterocyclyl containing at least one heteroatom each independently selected from O, $S(=O)_p$ and N; said 4-, 5- or 6-membered saturated heterocyclyl is optionally substituted with one or two substituents each independently selected from the group consisting of $C_{1-4}$alkyl, —$S(=O)_2$—$C_{1-6}$alkyl, hydroxy, and $C_{1-4}$alkyl substituted with one hydroxy; or two substituents on the same carbon atom of said 4-, 5- or 6-membered saturated heterocyclyl are taken together to form together with the common carbon atom to which they are attached Ring B;
(xi) Ring B represents a 4-membered saturated heterocyclyl containing one $S(=O)_p$;
(xii) p represents 2.

Another embodiment of the present invention relates to those compounds of Formula (I) and the N-oxides, the pharmaceutically acceptable addition salts, and the solvates thereof, or any subgroup thereof as mentioned in any of the other embodiments wherein one or more of the following restrictions apply:
(i) $R^2$ represents

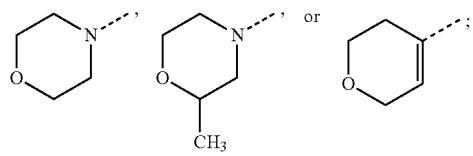

(ii) $R^3$ represents $C_{1-4}$alkyl; or $C_{1-4}$alkyl substituted with one substituent selected from the group consisting of halo, —OH, —NH—(C=O)—$C_{1-4}$alkyl, —N(CH$_3$)—$C_{1-4}$alkyl-SO$_2$—CH$_3$, —NH—$C_{1-4}$alkyl-SO$_2$—CH$_3$, and —NH—$C_{1-4}$alkyl-OH;
(iii) $R^{4a}$ represents $C_{1-4}$alkyl, or $C_{1-4}$alkyl substituted with one or more $Het^a$ substituents;
$R^{4b}$ represents halo, $C_{1-4}$alkyl, or $C_{1-4}$alkyl substituted with one or more halo substituents;
or $R^{4a}$ and $R^{4b}$ are taken together to form together with the phenyl ring to which they are attached a structure of Formula (a-2);
(iv) X represents —NH—;
(v) both $R^7$ substituents are hydrogen;
(vi) both $R^8$ substituents are hydrogen;
(vii) each $Het^a$ independently represents a 6-membered saturated heterocyclyl containing at least one heteroatom each independently selected from O, $S(=O)_p$ and N;
(viii) p represents 2.

Another embodiment of the present invention relates to those compounds of Formula (I) and the N-oxides, the pharmaceutically acceptable addition salts, and the solvates thereof, or any subgroup thereof as mentioned in any of the other embodiments wherein one or more of the following restrictions apply:

(i) $R^1$ represents —C(=O)NH$_2$, —NH$_2$,

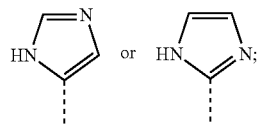

(ii) $R^2$ represents

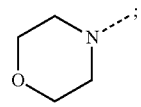

(iii) $R^3$ represents $C_{1-4}$alkyl; or $C_{1-4}$alkyl substituted with one —OH substituent; in particular $R^3$ represents CH$_3$ or —CH$_2$—OH;
(iv) $R^{4a}$ represents $C_{1-4}$alkyl; in particular $R^{4a}$ represents methyl;
$R^{4b}$ represents $C_{1-4}$alkyl substituted with one or more halo substituents; in particular $R^{4b}$ represents CF$_3$.

Another embodiment of the present invention relates to those compounds of Formula (I) and the N-oxides, the pharmaceutically acceptable addition salts, and the solvates thereof, or any subgroup thereof as mentioned in any of the other embodiments wherein one or more of the following restrictions apply:
(i) $R^1$ represents —NH$_2$;
(ii) $R^2$ represents

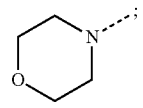

(iii) $R^3$ represents $C_{1-4}$alkyl substituted with one —OH substituent; in particular $R^3$ represents —CH$_2$—OH;
(iv) Y represents —CH$_2$—;
(v) $R^{4a}$ represents $C_{1-4}$alkyl; in particular $R^{4a}$ represents methyl;
$R^{4b}$ represents $C_{1-4}$alkyl substituted with one or more halo substituents; in particular $R^{4b}$ represents CF$_3$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^1$ represents —NH$_2$;
$R^2$ represents

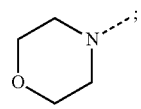

Y represents —CH$_2$—.

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^{4a}$ represents hydrogen, C$_{1-4}$alkyl, or C$_{1-4}$alkyl substituted with one or more substituents each independently selected from the group consisting of —NR$^5$R$^6$ and Het$^a$;

R$^{4b}$ represents hydrogen, halo, C$_{1-4}$alkyl, or C$_{1-4}$alkyl substituted with one or more halo substituents.

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^{4a}$ represents C$_{1-4}$alkyl; in particular R$^{4a}$ represents methyl;

R$^{4b}$ represents C$_{1-4}$alkyl substituted with one or more halo substituents; in particular R$^{4b}$ represents CF$_3$.

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^{4a}$ represents C$_{1-4}$alkyl; in particular R$^{4a}$ represents methyl.

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^{4a}$ represents hydrogen, C$_{1-4}$alkyl, Het$^a$, or C$_{1-4}$alkyl substituted with one substituent selected from the group consisting of —OH, —NR$^5$R$^6$ and Het$^a$.

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^{4b}$ represents C$_{1-4}$alkyl substituted with one or more halo substituents; in particular R$^{4b}$ represents CF$_3$.

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^{4a}$ and R$^{4b}$ are other than hydrogen.

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^{4a}$ and R$^{4b}$ are taken together to form together with the phenyl ring to which they are attached a structure of Formula (a-1), (a-2), (a-3), (a-4) or (a-5); in particular a structure of Formula (a-2) or (a-4); more in particular a structure of Formula (a-2).

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^{4a}$ represents C$_{1-4}$alkyl, Het$^a$, or C$_{1-4}$alkyl substituted with one or more substituents each independently selected from the group consisting of —OH, —NR$^5$R$^6$ and Het$^a$;

R$^{4b}$ represents hydrogen, halo, C$_{1-4}$alkyl, or C$_{1-4}$alkyl substituted with one or more halo substituents;

or R$^{4a}$ and R$^{4b}$ are taken together to form together with the phenyl ring to which they are attached a structure of Formula (a-2) or (a-4).

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^{4a}$ represents C$_{1-4}$alkyl, Het$^a$, or C$_{1-4}$alkyl substituted with one or more substituents each independently selected from the group consisting of —OH, —NR$^5$R$^6$ and Het$^a$;

R$^{4b}$ represents C$_{1-4}$alkyl, or C$_{1-4}$alkyl substituted with one or more halo substituents.

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^{4a}$ represents C$_{1-4}$alkyl, Het$^a$, or C$_{1-4}$alkyl substituted with one or more substituents each independently selected from the group consisting of —OH, —NR$^5$R$^6$ and Het$^a$;

R$^{4b}$ represents C$_{1-4}$alkyl.

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^{4a}$ represents C$_{1-4}$alkyl, Het$^a$, or C$_{1-4}$alkyl substituted with one or more substituents each independently selected from the group consisting of —OH, —NR$^5$R$^6$ and Het$^a$;

R$^{4b}$ represents C$_{1-4}$alkyl, or C$_{1-4}$alkyl substituted with one or more halo substituents;

or R$^{4a}$ and R$^{4b}$ are taken together to form together with the phenyl ring to which they are attached a structure of Formula (a-2) or (a-4).

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^3$ represents C$_{1-4}$alkyl; or C$_{1-4}$alkyl substituted with one substituent selected from the group consisting of halo, —OH, —NH$_2$, —O—(C=O)—C$_{1-4}$alkyl, —NH—(C=O)—C$_{1-4}$alkyl, —NH—(SO$_2$)—C$_{1-4}$alkyl, —N(CH$_3$)—C$_{1-4}$alkyl-SO$_2$—CH$_3$, —NH—C$_{1-4}$alkyl-SO$_2$—CH$_3$, —N(CH$_3$)—C$_{1-4}$alkyl-OH, —(C=O)—NH—C$_{1-4}$alkyl-OH, —O—(C=O)—CH(NH$_2$)—C$_{1-4}$alkyl, —O—(C=O)—CH(NH$_2$)—C$_{1-4}$alkyl-Ar,

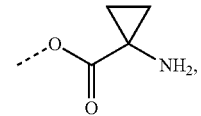

and —NH—C$_{1-4}$alkyl-OH.

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^3$ represents C$_{1-4}$alkyl; —CH(OH)—CH$_2$—R$^q$; or C$_{1-4}$alkyl substituted with one substituent selected from the group consisting of halo, —OH, —NH$_2$, —NH—(C=O)—C$_{1-4}$alkyl, —NH—(SO$_2$)—C$_{1-4}$alkyl, —N(CH$_3$)—C$_{1-4}$alkyl-SO$_2$—CH$_3$, —NH—C$_{1-4}$alkyl-SO$_2$—CH$_3$, —N(CH$_3$)—C$_{1-4}$alkyl-OH, —(C=O)—NH—C$_{1-4}$alkyl-OH, and —NH—C$_{1-4}$alkyl-OH;

R$^q$ represents —OH, or —NH$_2$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents $C_{1-4}$alkyl substituted with one substituent selected from the group consisting of halo, —OH, —NH$_2$, —O—(C=O)—$C_{1-4}$alkyl, —NH—(C=O)—$C_{1-4}$alkyl, —NH—(SO$_2$)—$C_{1-4}$alkyl, —N(CH$_3$)—$C_{1-4}$alkyl-SO$_2$—CH$_3$, —NH—$C_{1-4}$alkyl-SO$_2$—CH$_3$, —N(CH$_3$)—$C_{1-4}$alkyl-OH, —(C=O)—NH—$C_{1-4}$alkyl-OH, —O—(C=O)—CH(NH$_2$)—$C_{1-4}$alkyl, —O—(C=O)—CH(NH$_2$)—$C_{1-4}$alkyl-Ar,

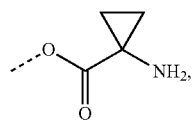

and —NH—$C_{1-4}$alkyl-OH.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents $C_{1-4}$alkyl; or $C_{1-4}$alkyl substituted with one substituent selected from the group consisting of halo, —OH, —NH$_2$, —O—(C=O)—$C_{1-4}$alkyl, —NH—(C=O)—$C_{1-4}$alkyl, —N(CH$_3$)—$C_{1-4}$alkyl-SO$_2$—CH$_3$, —NH—$C_{1-4}$alkyl-SO$_2$—CH$_3$, —O—(C=O)—CH(NH$_2$)—$C_{1-4}$alkyl, —O—(C=O)—CH(NH$_2$)—$C_{1-4}$alkyl-Ar,

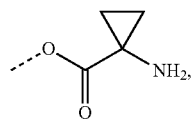

and —NH—$C_{1-4}$alkyl-OH.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents —CH(OH)—CH$_2$—$R^q$; or $C_{1-4}$alkyl substituted with one substituent selected from the group consisting of halo, —OH, —NH$_2$, —O—(C=O)—$C_{1-4}$alkyl, —NH—(C=O)—$C_{1-4}$alkyl, —NH—(SO$_2$)—$C_{1-4}$alkyl, —N(CH$_3$)—$C_{1-4}$alkyl-SO$_2$—CH$_3$, —NH—$C_{1-4}$alkyl-SO$_2$—CH$_3$, —N(CH$_3$)—$C_{1-4}$alkyl-OH, —(C=O)—NH—$C_{1-4}$alkyl-OH, —O—(C=O)—CH(NH$_2$)—$C_{1-4}$alkyl, —O—(C=O)—CH(NH$_2$)—$C_{1-4}$alkyl-Ar,

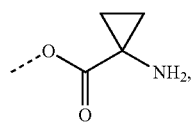

and —NH—$C_{1-4}$alkyl-OH.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^3$ represents $C_{1-4}$alkyl substituted with one substituent as defined in any of the other embodiments.

In an embodiment, the present invention relates to those compounds of Formula (I) and the N-oxides, the pharmaceutically acceptable addition salts, and the solvates thereof, or any subgroup thereof as mentioned in any of the other embodiments, wherein Y represents —CH$_2$—.

In an embodiment, the present invention relates to those compounds of Formula (I) and the N-oxides, the pharmaceutically acceptable addition salts, and the solvates thereof, or any subgroup thereof as mentioned in any of the other embodiments, wherein Y represents —NH—.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^1$ represents

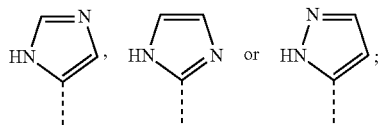

and
Y represents —NH—.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^2$ represents

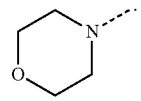

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^2$ represents

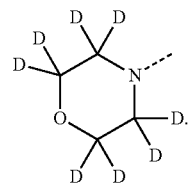

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^1$ represents $C_{1-4}$alkyl substituted with one —OH substituent; in particular $R^3$ represents —CH$_2$—OH.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^1$ represents —C(=O)NH$_2$, —NH$_2$,

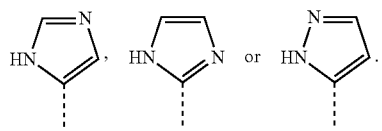

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^1$ represents —C(=O)NH$_2$, —NH$_2$,

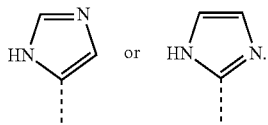

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^1$ represents

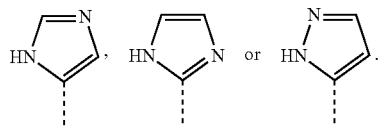

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^1$ represents —C(=O)NH$_2$ or —NH$_2$.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^1$ represents —NH$_2$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^q$ represents halo, —OH, —NH$_2$, —O—(C=O)—C$_{1-4}$alkyl, —NH—(C=O)—C$_{1-4}$alkyl, —NH—(SO$_2$)—C$_{1-4}$alkyl, —N(CH$_3$)—C$_{1-4}$alkyl-SO$_2$—CH$_3$, —NH—C$_{1-4}$alkyl-SO$_2$—CH$_3$, —N(CH$_3$)—C$_{1-4}$alkyl-OH, —O—(C=O)—CH(NH$_2$)—C$_{1-4}$alkyl, or —NH—C$_{1-4}$alkyl-OH.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^q$ represents —OH or —NH$_2$; in particular wherein $R^q$ represents —NH$_2$.

In an embodiment, the present invention relates to those compounds of Formula (I) and the N-oxides, the pharmaceutically acceptable addition salts, and the solvates thereof, or any subgroup thereof as mentioned in any of the other embodiments, wherein
$R^3$ represents C$_{1-4}$alkyl; or C$_{1-4}$alkyl substituted with one substituent selected from the group consisting of halo, —OH, —O—(C=O)—C$_{1-4}$alkyl, —NH—(SO$_2$)—C$_{1-4}$alkyl, —N(CH$_3$)—C$_{1-4}$alkyl-SO$_2$—CH$_3$, —NH—C$_{1-4}$alkyl-SO$_2$—CH$_3$, —N(CH$_3$)—C$_{1-4}$alkyl-OH, —(C=O)—NH—C$_{1-4}$alkyl-OH and —NH—C$_{1-4}$alkyl-OH;

in particular wherein $R^3$ represents C$_{1-4}$alkyl; or C$_{1-4}$alkyl substituted with one substituent selected from the group consisting of halo, —OH, —N(CH$_3$)—C$_{1-4}$alkyl-SO$_2$—CH$_3$, —NH—C$_{1-4}$alkyl-SO$_2$—CH$_3$, —N(CH$_3$)—C$_{1-4}$alkyl-OH, and —NH—C$_{1-4}$alkyl-OH; more in particular wherein $R^3$ represents C$_{1-4}$alkyl; or C$_{1-4}$alkyl substituted with one substituent selected from the group consisting of halo and —OH;

even more in particular wherein $R^3$ represents C$_{1-4}$alkyl; or C$_{1-4}$alkyl substituted with one —OH substituent;
still more in particular wherein $R^3$ represents C$_{1-4}$alkyl.

In an embodiment, the present invention relates to those compounds of Formula (I) and the N-oxides, the pharmaceutically acceptable addition salts, and the solvates thereof, or any subgroup thereof as mentioned in any of the other embodiments, wherein the following proviso is applicable: when Y represents —NH—, then $R^3$ represents C$_{1-4}$alkyl, or C$_{1-4}$alkyl substituted with one —OH substituent.

In an embodiment, the present invention relates to those compounds of Formula (I) and the N-oxides, the pharmaceutically acceptable addition salts, and the solvates thereof, or any subgroup thereof as mentioned in any of the other embodiments, wherein each Het$^a$ independently represents

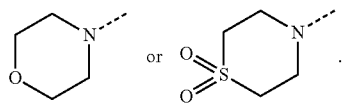

In an embodiment, the present invention relates to those compounds of Formula (I) and the N-oxides, the pharmaceutically acceptable addition salts, and the solvates thereof, or any subgroup thereof as mentioned in any of the other embodiments, wherein each Het$^a$ independently represents a 4-, 5- or 6-membered saturated heterocyclyl containing one or two heteroatoms each independently selected from O, S(=O)$_p$ and N; said 4-, 5- or 6-membered saturated heterocyclyl is optionally substituted with one or two substitutents each independently selected from the group consisting of hydroxy, and C$_{1-4}$alkyl substituted with one hydroxy;
p represents 1 or 2.

In an embodiment, the present invention relates to those compounds of Formula (I) and the N-oxides, the pharmaceutically acceptable addition salts, and the solvates thereof, or any subgroup thereof as mentioned in any of the other embodiments, wherein both $R^7$ substituents are hydrogen; and wherein both $R^8$ substituents are hydrogen.

In an embodiment, the present invention relates to those compounds of Formula (I) and the N-oxides, the pharmaceutically acceptable addition salts, and the solvates thereof, or any subgroup thereof as mentioned in any of the other embodiments, wherein both $R^7$ substituents are the same and are selected from the group consisting of hydrogen, fluoro and methyl; and wherein both R[8] substituents are the same and are selected from the group consisting of hydrogen and methyl.

In an embodiment, the present invention relates to a subgroup of Formula (I) and the N-oxides, the pharmaceutically acceptable addition salts, and the solvates thereof, as defined in the general reaction schemes.

In an embodiment, the present invention relates to those compounds of Formula (I) and the N-oxides, the pharmaceutically acceptable addition salts, and the solvates thereof, or any subgroup thereof as mentioned in any of the other embodiments, wherein Het[a] represents

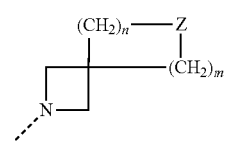

Z represents —NH—, —S—, —O— or —S(O)$_2$—; in particular Z represents —S(O)$_2$—;

n represents 0, 1 or 2;

m represents 1, 2 or 3; provided however that m does not have value 1 when n is 0.

In an embodiment, the present invention relates to those compounds of Formula (I) and the N-oxides, the pharmaceutically acceptable addition salts, and the solvates thereof, or any subgroup thereof as mentioned in any of the other embodiments, wherein Het[a] represents

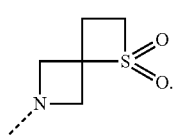

In an embodiment, the present invention relates to those compounds of Formula (I) and the N-oxides, the pharmaceutically acceptable addition salts, and the solvates thereof, or any subgroup thereof as mentioned in any of the other embodiments, wherein R[2] represents

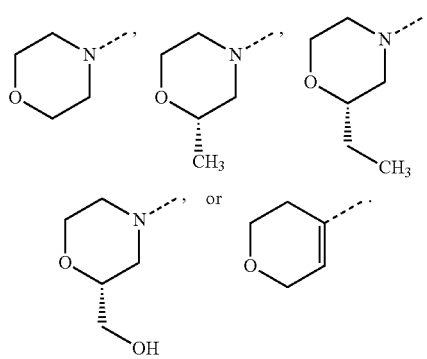

In an embodiment, the present invention relates to those compounds of Formula (I) and the N-oxides, the pharmaceutically acceptable addition salts, and the solvates thereof, or any subgroup thereof as mentioned in any of the other embodiments, wherein R[2] represents

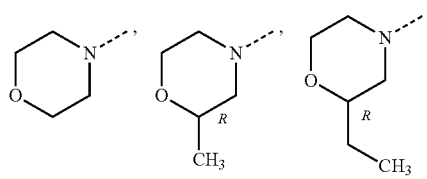

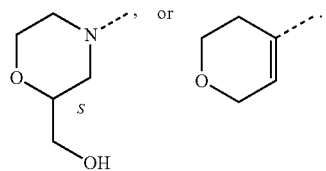

In an embodiment, the present invention relates to those compounds of Formula (I) and the N-oxides, the pharmaceutically acceptable addition salts, and the solvates thereof, or any subgroup thereof as mentioned in any of the other embodiments, wherein
R[2] representing

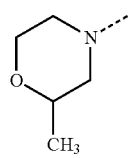

is limited to

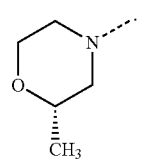

In an embodiment, the present invention relates to those compounds of Formula (I) and the N-oxides, the pharmaceutically acceptable addition salts, and the solvates thereof, or any subgroup thereof as mentioned in any of the other embodiments, wherein
R[2] representing

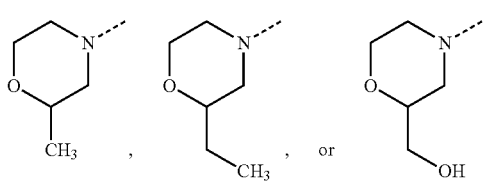

are limited respectively to

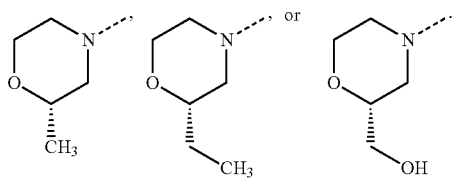

In an embodiment the compound of Formula (I) is selected from the group consisting of compounds 14, 15, 18, 19, 33, and 35, tautomers and stereoisomeric forms thereof, and the N-oxides, the pharmaceutically acceptable addition salts, and the solvates thereof.

In an embodiment the compound of Formula (I) is selected from the group consisting of compound 14, tautomers and stereoisomeric forms thereof, and the N-oxides, the pharmaceutically acceptable addition salts, and the solvates thereof.

In an embodiment the compound of Formula (I) is compound 14.

In an embodiment the compound of Formula (I) is selected from the group consisting of compound 19, tautomers and stereoisomeric forms thereof, and the N-oxides, the pharmaceutically acceptable addition salts, and the solvates thereof.

In an embodiment the compound of Formula (I) is compound 19.

In an embodiment the compound of Formula (I) is selected from the group consisting of compound 33, tautomers and stereoisomeric forms thereof, and the N-oxides, the pharmaceutically acceptable addition salts, and the solvates thereof.

In an embodiment the compound of Formula (I) is compound 33.

In an embodiment the compound of Formula (I) is selected from the group consisting of compound 15, tautomers and stereoisomeric forms thereof, and the N-oxides, the pharmaceutically acceptable addition salts, and the solvates thereof.

In an embodiment the compound of Formula (I) is compound 15.

In an embodiment the compound of Formula (I) is selected from the group consisting of compound 18, tautomers and stereoisomeric forms thereof, and the N-oxides, the pharmaceutically acceptable addition salts, and the solvates thereof.

In an embodiment the compound of Formula (I) is compound 18.

In an embodiment the compound of Formula (I) is selected from the group consisting of compound 35, tautomers and stereoisomeric forms thereof, and the N-oxides, the pharmaceutically acceptable addition salts, and the solvates thereof.

In an embodiment the compound of Formula (I) is compound 35.

All possible combinations of the above-indicated embodiments are considered to be embraced within the scope of this invention.

Methods for the Preparation of Compounds of Formula (I)

In this section, as in all other sections unless the context indicates otherwise, references to Formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry.

The skilled person will realize that in the reactions described in the Schemes, it may be necessary to protect reactive functional groups, for example hydroxy, amino, or carboxy groups, where these are desired in the final product, to avoid their unwanted participation in the reactions. Conventional protecting groups can be used in accordance with standard practice. This is illustrated in the specific examples. The protecting groups may be removed at a convenient subsequent stage using methods known from the art.

The skilled person will realize that in the reactions described in the Schemes, it may be advisable or necessary to perform the reaction under an inert atmosphere, such as for example under $N_2$-gas atmosphere.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of Formula (I).

The skilled person will realize that intermediates and final compounds shown in the schemes below may be further functionalized according to methods well-known by the person skilled in the art.

As mentioned before, the prefix "$C_{x\text{-}y}$" (where x and y are integers) as used herein refers to the number of carbon atoms in a given group. The skilled person will realize that $C_0$ corresponds to a covalent bond. Thus the term "$C_{0\text{-}3}$alkyl" as a group or part of a group refers to a covalent bond ($C_0$) and a hydrocarbyl radical of Formula $C_nH_{2n+1}$ wherein n is a number ranging from 1 to 3.

In general, compounds of Formula (I) wherein $R^1$ is —C(=O)NH$_2$, and wherein the other variables are as shown in Formula (Ia); and compounds of Formula (I) wherein $R^1$ is a —C(=O)OH, and wherein the other variables are as shown in Formula (Ib), can be prepared according to the following reaction Scheme 1, wherein halo$^1$ is defined as Cl, Br or I; W and $W_1$ represent a leaving group such as Cl, Br, F or I; and $W_2$ represents a suitable leaving group, such as for example Br, Cl or I. All other variables in Scheme 1 are defined according to the scope of the present invention.

Scheme 1
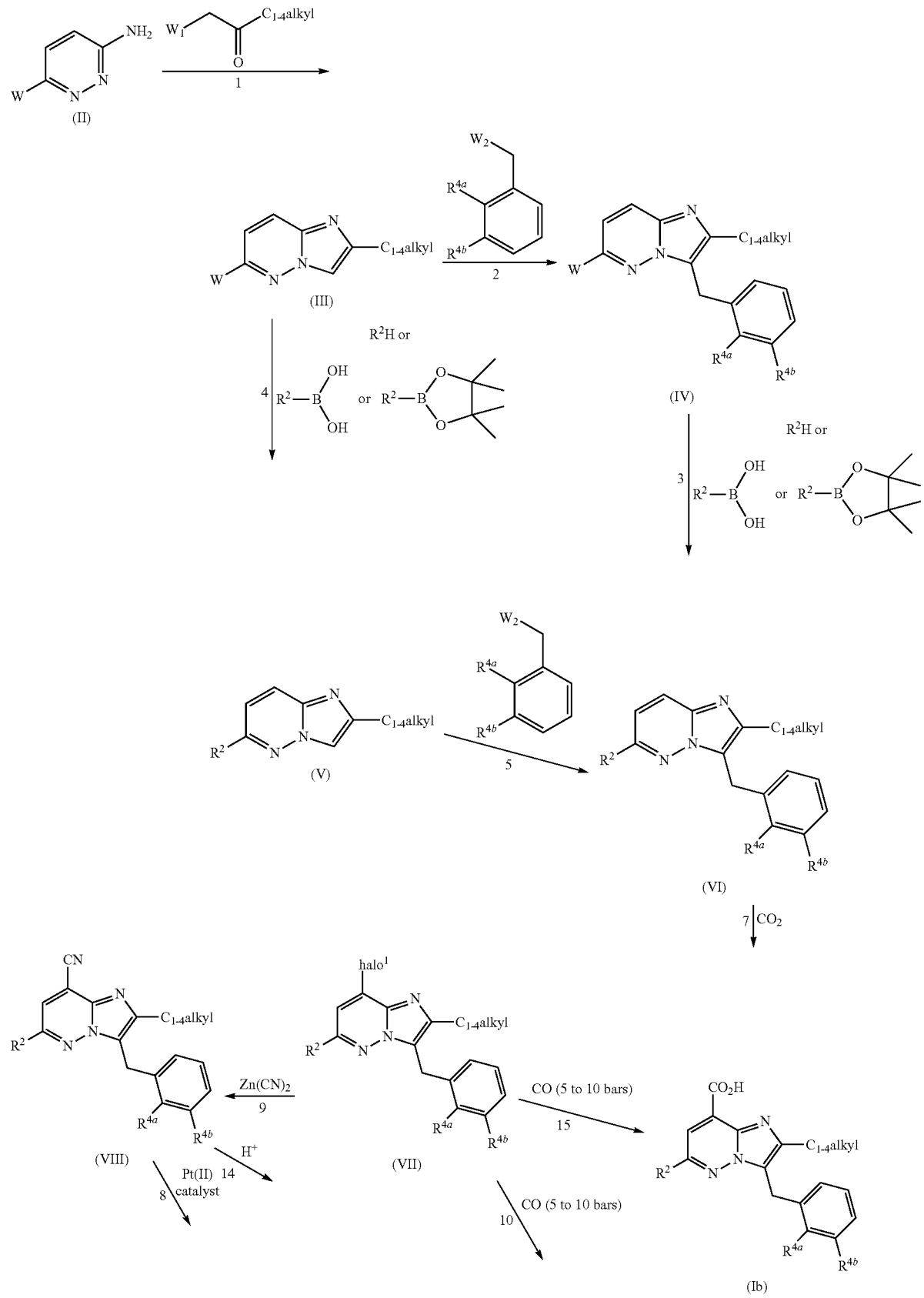

-continued

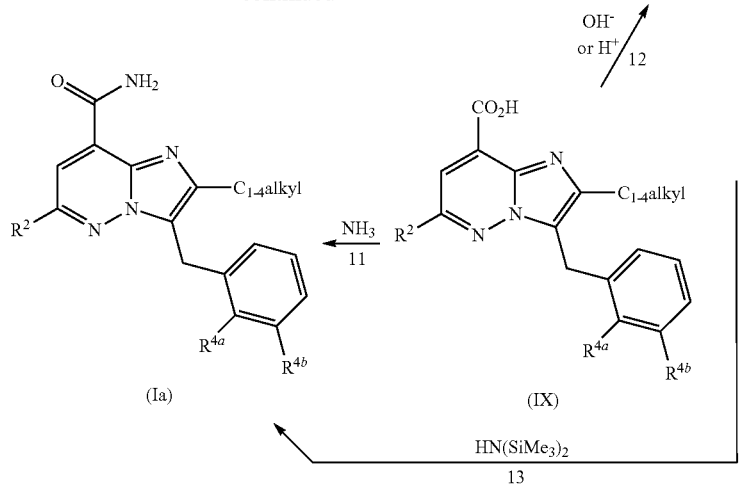

In Scheme 1, the following reaction conditions apply:
1: at a suitable temperature such as for example 90° C., optionally in the presence of a suitable solvent such as for example N,N-dimethylformamide or dimethoxyethane;
2: in the presence of a suitable catalyst such as for example palladium acetate, a suitable ligand such as triphenylphosphine, a suitable base such as for example $K_2CO_3$, a suitable solvent such as for example dioxane, and a suitable temperature such as for example 100° C., optionally in a sealed vessel;
3: in case of $R_2H$:
  Without any solvent at a suitable temperature such as 120° C.
  Alternatively in the presence of a suitable ligand such as 2-dicyclohexylphosphino-2',6'-diisopropoxybiphenyl (Ruphos), a suitable catalyst such as for example tris(dibenzylideneacetone)dipalladium ($Pd_2dba_3$), a suitable base such as for example $Cs_2CO_3$, and a suitable solvent such as for example 2-methyl-2-butanol, at a suitable temperature such as for example between 100 and 120° C.;
  in case of $R_2B(OH)_2$ or $R_2(4,4,5,5$-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium phosphate, and a suitable solvent such as for example a mixture dioxane and water, at a suitable temperature such as for example at 80° C.;
4: in case of $R_2H$:
  Without any solvent at a suitable temperature such as 120° C.
  Alternatively in the presence of a suitable ligand such as Ruphos, a suitable catalyst such as for example $Pd_2dba_3$, a suitable base such as for example $Cs_2CO_3$, and a suitable solvent such as for example 2-methyl-2-butanol, at a suitable temperature such as for example between 100 and 120° C.;
  in case of $R_2B(OH)_2$ or $R_2(4,4,5,5$-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium phosphate, and a suitable solvent such as for example dioxane, at a suitable temperature such as for example at 80° C.;
5: in the presence of a suitable catalyst such as for example palladium acetate, a suitable ligand such as for example triphenylphosphine, a suitable base such as for example $K_2CO_3$, and a suitable solvent such as for example dioxane, at a suitable temperature such as for example at 100° C., optionally in a sealed vessel;
6: in the presence of a suitable base, such as for example lithium diisopropylamide, and a suitable solvent such as for example tetrahydrofuran (THF), at a suitable temperature such as for example at −70° C.;
7: in the presence of a suitable base such as for example lithium diisopropylamide, a suitable source of carbon dioxide such as for example dry ice, and a suitable solvent such as for example THF, at a suitable temperature such as for example at −70° C.;
8: in the presence of a suitable catalyst such as for example hydrido(dimethylphosphinous acid-kP)[hydrogen bis(dimethylphosphinito-kP)]platinum(II), and a suitable solvent or a mixture of solvents such as for example a mixture of THF/water, at a suitable temperature such as for example at 95° C.;
9: in the presence of a suitable catalyst such as for example tetrakis(triphenylphosphine)palladium ($Pd(PPh_3)_4$), and a suitable solvent such as a for example N,N-dimethylformamide (DMF), at a suitable temperature such as for example at 100° C.;
10: in the presence of a suitable catalyst such as for example $Pd(PPh_3)_4$, a suitable base such as for example triethylamine ($Et_3N$), and a suitable solvent such as for example methanol or ethanol, at a suitable temperature such as for example at 100° C. or 120° C.;
11: in a suitable solvent such as for example methanol, at a suitable temperature such as for example at 65° C., in a sealed vessel;
12: in the presence of a suitable base such as lithium hydroxide monohydrate, and a suitable solvent or a mixture of solvents such as for example a mixture of THF/water or methanol/water;
  Alternatively, in the presence of a suitable acid such as for example hydrochloric acid, and a suitable solvent such as for example THF;
13: in the presence of a suitable peptidic coupling reagent such as 1-[bis(dimethylamino)methylene]-1H-[1,2,3]triazolo[4,5-b]pyridin-1-ium 3-oxide hexafluorophosphate (HATU), in the presence of a suitable base such as for example diisopropylamine, and a suitable solvent such as for example DMF;
14: in the presence of a suitable acid such as for example sulphuric acid, and a suitable solvent such as methanol (MeOH), at a suitable temperature such as for example at 100° C.;
15: in the presence of a suitable catalyst such as for example Pd(PPh$_3$)$_4$, a suitable base such as for example an aqueous solution of Na$_2$CO$_3$, and a suitable solvent such as for example DMF, at a suitable temperature such as for example at 120° C.

In general, compounds of Formula (I) wherein R$^1$ is restricted to R$^{1a}$ being

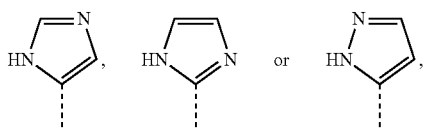

and wherein the other variables are as shown in Formula (Ic); and compounds of Formula (I) wherein R$^1$ is —NH$_2$, and wherein the other variables are as shown in Formula (Id), can be prepared according to the following reaction Scheme 2 wherein PG is a protecting group such as for example 2-tetrahydropyran, N,N-dimethylsulfonamide, and R$^{1a}$ is as defined above. All other variables in Scheme 2 are defined according to the scope of the present invention.

suitable solvent such as dimethylformamide, at a suitable temperature such as for example 185° C.;
2: in case of (PG)R$^{1a}$B(OH)$_2$ or (PG)R$^{1a}$(4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium carbonate, and a suitable solvent such as for example a mixture of dioxane and water, at a suitable temperature such as for example at 100° C.;
In case of R$^{1a}$(PG), first, in the presence of zinc chloride, a suitable deprotonating agent such as for example butyl lithium, a suitable solvent such as for example THF, at a suitable temperature such as for example –78° C., followed by addition (of/to) this solution (to) a mixture of intermediate (VII), optionally in solution in THF, and a suitable catalyst such as for example Pd(PPh$_3$)$_4$, heating at a suitable temperature ranging from 60 to 100° C.;
3: in the presence of a suitable acid such as for example p-toluenesulfonic acid hydrochloric acid or trifluoroacetic acid, in a suitable solvent such as for example dioxane or methanol, at a suitable temperature such as for example 50 or 100° C.;
4: in the presence of a suitable catalyst such as for example copper iodide, a suitable ligand such as for example L-proline, a suitable base such as for example cesium carbonate, a suitable solvent such as for example N,N-dimethylformamide, at a suitable temperature such as 110° C. in a sealed vessel.

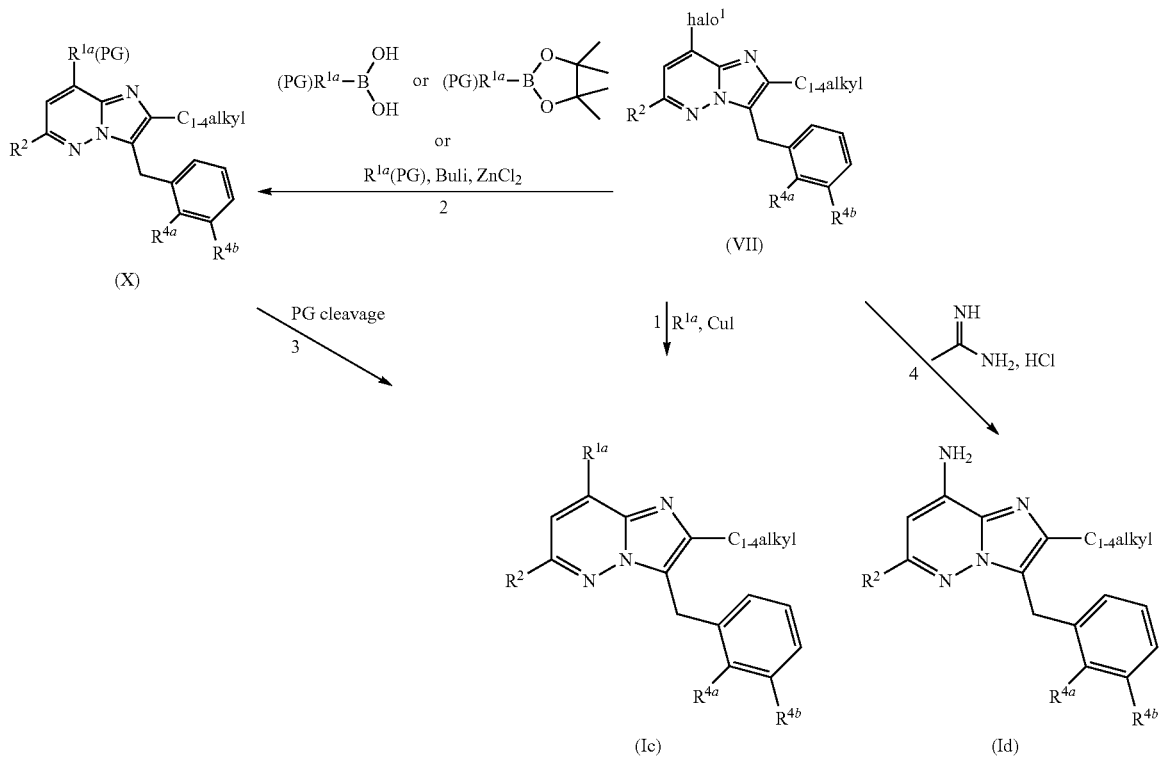

In Scheme 2, the following reaction conditions apply:
1: in the presence of copper iodide, a suitable catalyst such as for example palladium acetate, in a microwave, and a Intermediates of Formula (VIII) and (IX) used in the above Scheme 1 can alternatively be prepared according to the following reaction Scheme 3, wherein all variables are defined as above or according to the scope of the present invention.

Alternatively in the presence of a suitable ligand such as Ruphos, a suitable catalyst such as for example tris(dibenzylideneacetone)dipalladium ($Pd_2dba_3$), a suit-

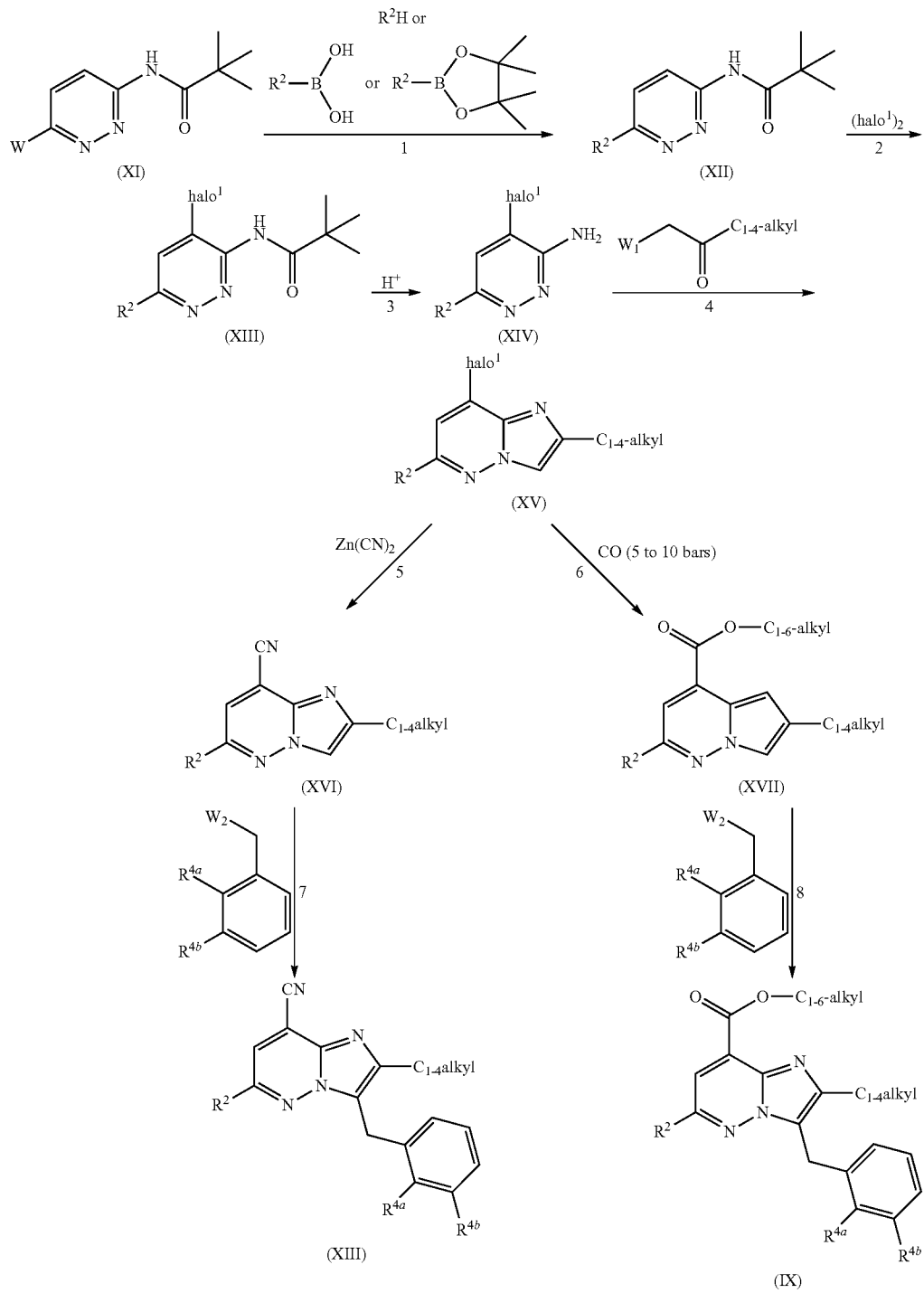

In Scheme 3, the following reaction conditions apply:
1: in case of $R_2H$:
  Without any solvent at a suitable temperature such as 120° C.

able such as for example $Cs_2CO_3$, and a suitable solvent such as for example 2-methyl-2-butanol, at a suitable temperature such as for example between 100 and 120° C.;

in case of R₂B(OH)₂ or R₂(4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium phosphate, and a suitable solvent such as for example a mixture dioxane and water, at a suitable temperature such as for example at 80° C.;
2: in the presence of an amine such as for example 2,2,6,6-tetramethylpiperidine, a deprotonating agent such as for example butyl lithium, and a suitable solvent such as for example THF at a suitable temperature ranging for 0 to −78° C.;
3: in the presence of a suitable acid such as for example hydrochloric acid, a suitable solvent such as for example dioxane, and a suitable temperature such as for example 70° C.;
4: at a suitable temperature such as for example 90° C., optionally in the presence of a suitable solvent such as for example N,N-dimethylformamide or dimethoxyethane;

solvent such as for example dioxane, and a suitable temperature such as for example 100° C., optionally in a sealed vessel;
8: in the presence of a suitable catalyst such as for example palladium acetate, a suitable ligand such as triphenylphosphine, a suitable base such as for example K₂CO₃, a suitable solvent such as for example dioxane, and a suitable temperature such as for example 100° C., optionally in a sealed vessel.

Intermediates of Formula (VIII) used in the above Scheme 1 can alternatively be prepared according to the following reaction Scheme 4, wherein W₃ represents a suitable leaving group such as for example halo, e.g. bromo, chloro or iodo.

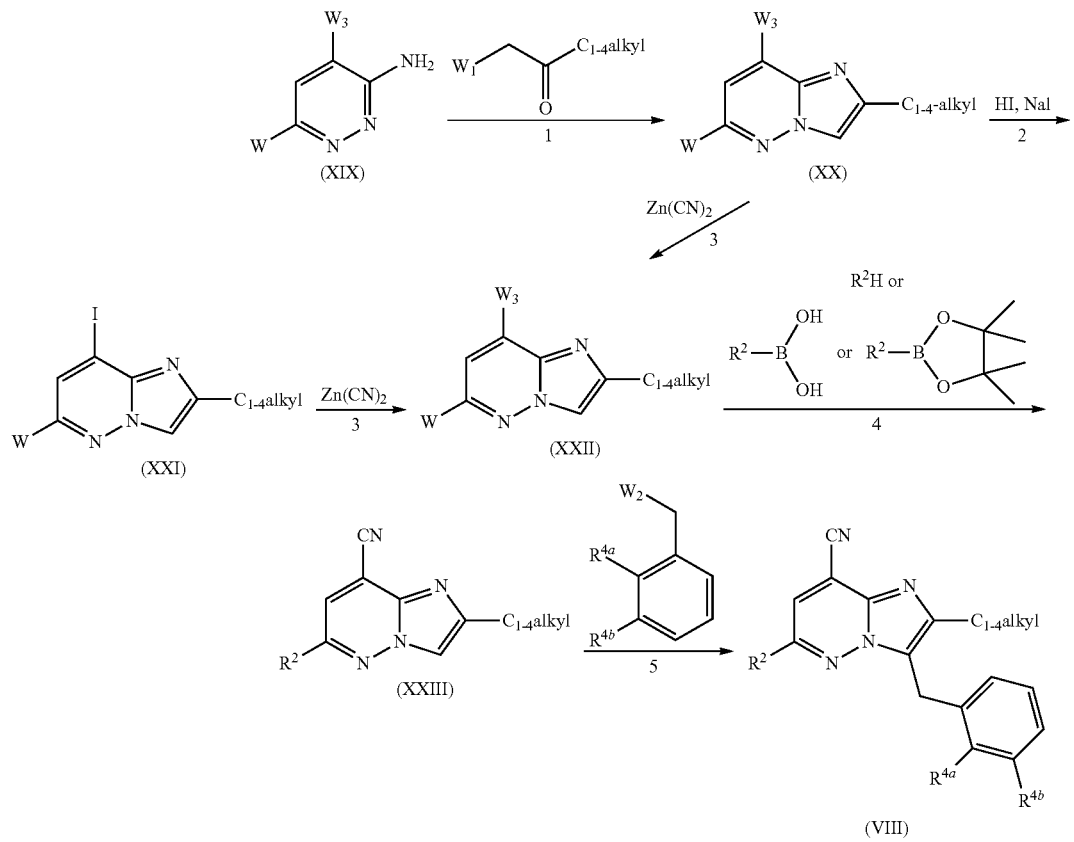

5: in the presence of a suitable catalyst such as for example Pd(PPh₃)₄, and a suitable solvent such as a for example N,N-dimethylformamide (DMF), at a suitable temperature such as for example at 100° C.;
6: in the presence of a suitable catalyst such as for example Pd(PPh₃)₄, a suitable base such as for example triethylamine (Et₃N), and a suitable solvent such as for example methanol or ethanol, at a suitable temperature such as for example at 100° C. or 120° C.;
7: in the presence of a suitable catalyst such as for example palladium acetate, a suitable ligand such as triphenylphosphine, a suitable base such as for example K₂CO₃, a suitable In Scheme 4, the following reaction conditions apply:
1: at a suitable temperature such as for example 90° C., optionally in the presence of a suitable solvent such as for example N,N-dimethylformamide or dimethoxyethane;
2: in the presence of a suitable solvent such as for example acetonitrile, and in a sealed tube under microwave conditions, at a suitable temperature such as for example 160° C.
3: (in case W₃ represents iodo) in the presence of a suitable catalyst such as for example Pd(PPh₃)₄, and a suitable solvent such as a for example N,N-dimethylformamide (DMF), at a suitable temperature such as for example at 80° C.;

4: in case of R₂H: Without any solvent at a suitable temperature such as 25° C.

in case of R₂B(OH)₂ or R₂(4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium phosphate, and a suitable solvent such as for example a mixture dioxane and water, at a suitable temperature such as for example at 80° C.;

5: in the presence of a suitable catalyst such as for example palladium acetate, a suitable ligand such as triphenylphosphine, a suitable base such as for example $K_2CO_3$, a suitable solvent such as for example dioxane, and a suitable temperature such as for example 100° C., optionally in a sealed vessel.

Intermediates of Formula (XXIX) used in the below Scheme 7 can be prepared according to the following reaction Scheme 5, wherein all variables are defined as above or according to the scope of the present invention.

Scheme 5

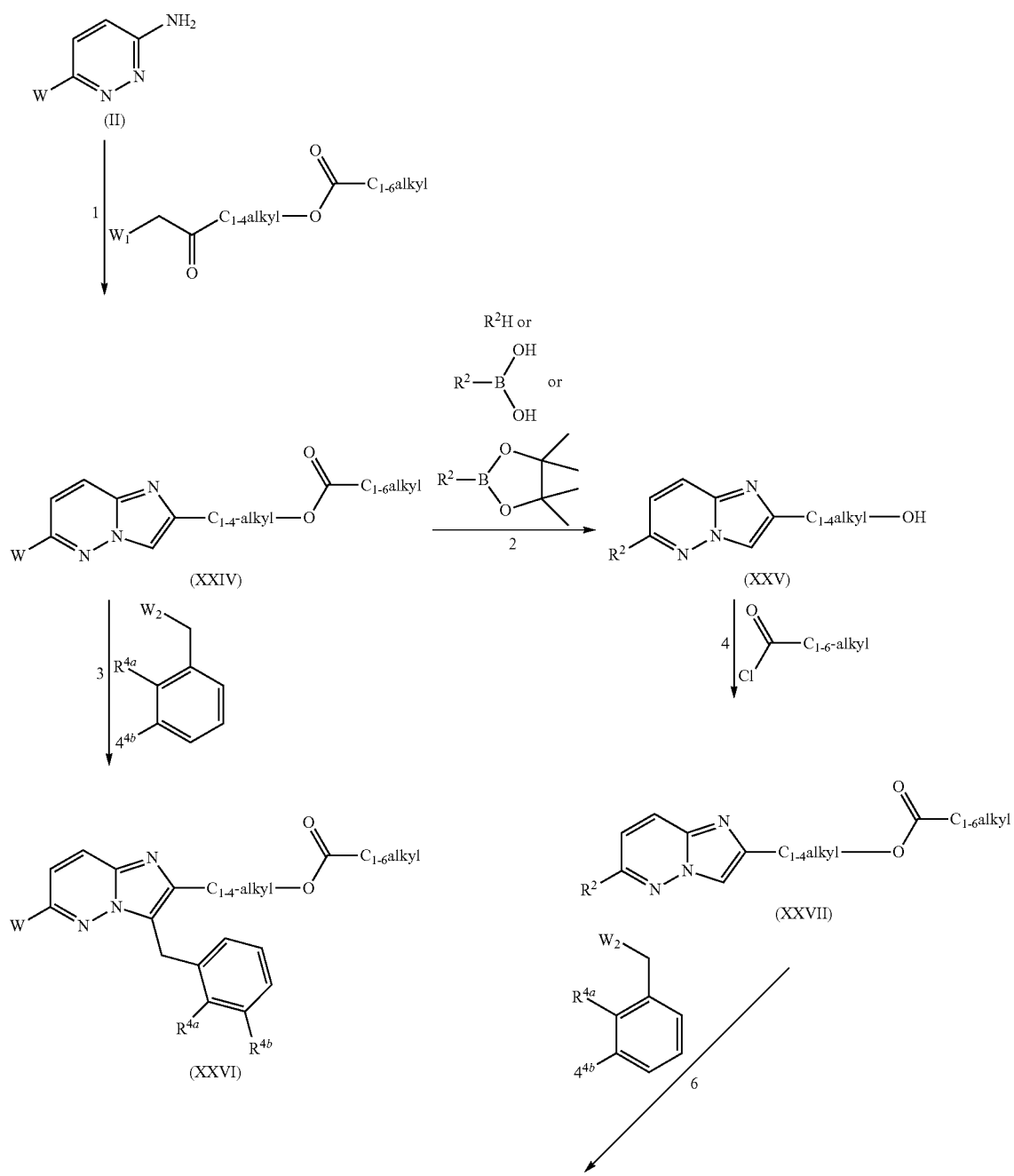

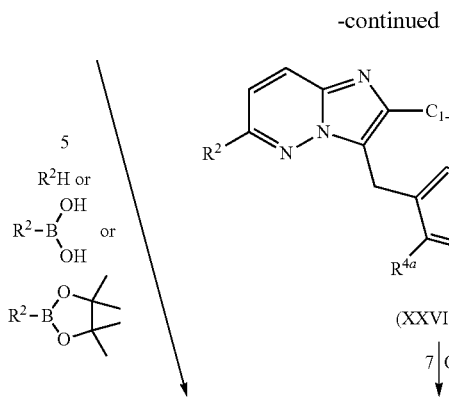

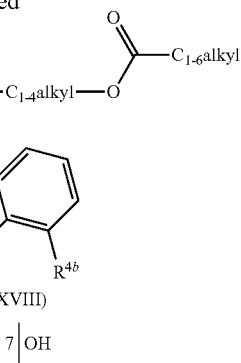

In Scheme 5, the following reaction conditions apply:
1: at a suitable temperature such as for example 90° C., in the presence of a suitable solvent such as for example N,N-dimethylformamide or dimethoxyethane;
2: in case of R$_2$H:
   Without any solvent at a suitable temperature such as 105° C.
   Alternatively in the presence of a suitable ligand such as Ruphos, a suitable catalyst such as for example tris(dibenzylideneacetone)dipalladium (Pd$_2$dba$_3$), a suitable base such as for example Cs$_2$CO$_3$, and a suitable solvent such as for example 2-methyl-2-butanol, at a suitable temperature such as for example between 100 and 120° C.;
   in case of R$_2$B(OH)$_2$ or R$_2$(4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium phosphate, and a suitable solvent such as for example a mixture dioxane and water, at a suitable temperature such as for example at 80° C.;
3: in the presence of a suitable catalyst such as for example palladium acetate, a suitable ligand such as triphenylphosphine, a suitable base such as for example K$_2$CO$_3$, a suitable solvent such as for example dioxane, and a suitable temperature such as for example 100° C., optionally in a sealed vessel;
4: in the presence of a suitable base such as for example triethylamine and a suitable solvent such as for example dichloromethane;
5: in case of R$_2$H:
   Without any solvent at a suitable temperature such as 120° C.
   Alternatively in the presence of a suitable ligand such as Ruphos, a suitable catalyst such as for example tris(dibenzylideneacetone)dipalladium (Pd$_2$dba$_3$), a suitable base such as for example Cs$_2$CO$_3$, and a suitable solvent such as for example 2-methyl-2-butanol, at a suitable temperature such as for example between 100 and 120° C.;
   in case of R$_2$B(OH)$_2$ or R$_2$(4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium phosphate, and a suitable solvent such as for example a mixture dioxane and water, at a suitable temperature such as for example at 80° C.;
6: in the presence of a suitable catalyst such as for example palladium acetate, a suitable ligand such as triphenylphosphine, a suitable base such as for example K$_2$CO$_3$, a suitable solvent such as for example dioxane, and a suitable temperature such as for example 100° C., optionally in a sealed vessel;
7: in the presence of a suitable base such as for example lithium hydroxide monohydrate, a suitable solvent such as for example a mixture of methanol and water.

Intermediates of Formula (XXV) and (XXIX) depicted in the above Scheme 5 can alternatively be prepared according to the following reaction Scheme 6, wherein all variables are defined as above or according to the scope of the present invention.

Scheme 6
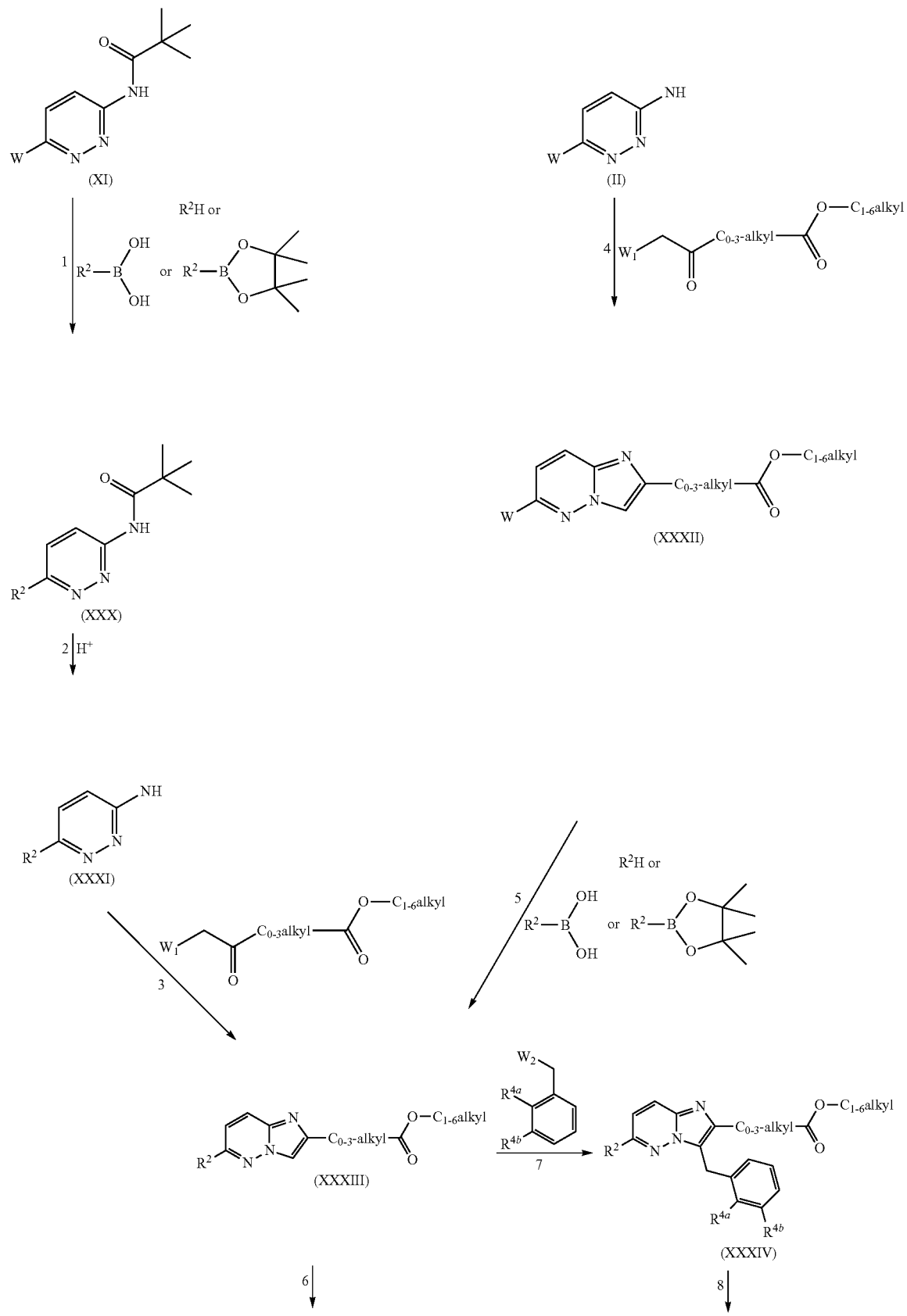

-continued

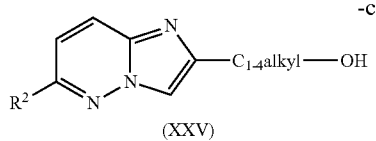

(XXV)

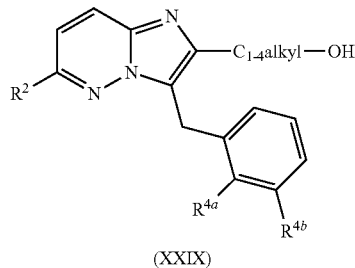

(XXIX)

In Scheme 6, the following reaction conditions apply:
1: in case of R$_2$H:
Without any solvent at a suitable temperature such as 120° C.
Alternatively in the presence of a suitable ligand such as Ruphos, a suitable catalyst such as for example tris(dibenzylideneacetone)dipalladium (Pd$_2$dba$_3$), a suitable base such as for example Cs$_2$CO$_3$, and a suitable solvent such as for example 2-methyl-2-butanol, at a suitable temperature such as for example between 100 and 120° C.;
in case of R$_2$B(OH)$_2$ or R$_2$(4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium phosphate, and a suitable solvent such as for example a mixture dioxane and water, at a suitable temperature such as for example at 80° C.;
2: in the presence of a suitable acid such as for example hydrochloric acid, a suitable solvent such as for example dioxane, and a suitable temperature such as for example 70° C.;
3: at a suitable temperature such as for example 70° C. or 90° C., in the presence of a suitable solvent such as for example ethanol, N,N-dimethylformamide or dimethoxyethane;
4: at a suitable temperature such as for example 70° C. or 90° C., in the presence of a suitable solvent such as for example ethanol, N,N-dimethylformamide or dimethoxyethane;
5: in case of R$_2$H, without any solvent at a suitable temperature such as 90° C.; in case of R$_2$B(OH)$_2$ or R$_2$(4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium phosphate, and a suitable solvent such as for example a mixture dioxane and water, at a suitable temperature such as for example at 80° C.;
6: in the presence of a suitable reducing reagent such as for example potassium borohydride or lithium aluminium hydride, optionally a suitable additive such as for example lithium chloride, a suitable solvent such as for example THF or and a suitable temperature such as 0° C. or solvent reflux based on the reducing reagent;
7: in the presence of a suitable catalyst such as for example palladium acetate, a suitable ligand such as triphenylphosphine, a suitable base such as for example K$_2$CO$_3$, a suitable solvent such as for example dioxane, and a suitable temperature such as for example 100° C., optionally in a sealed vessel;
8: in the presence of a suitable reducing reagent such as for example lithium aluminium hydride, a suitable solvent such as for example THF or and a suitable temperature such as 0° C.

In general, compounds of Formula (I) wherein R$^1$ is —C(=O)NH$_2$, and wherein the other variables are as shown in Formula (Ie); and compounds of Formula (I) wherein R$^1$ is —C(=O)OH, and wherein the other variables are as shown in Formula (If), can be prepared according to the following reaction Scheme 7. In Scheme 7, R$^x$ and R$^y$ represent C$_{1-4}$alkyl, and R$^z$ represents C$_{1-4}$alkyl or phenyl, for instance R$^x$ and R$^y$ represent CH$_3$ and R$^z$ represents C(CH$_3$)$_3$ or phenyl. All other variables are as defined as above or according to the scope of the present invention.

Scheme 7

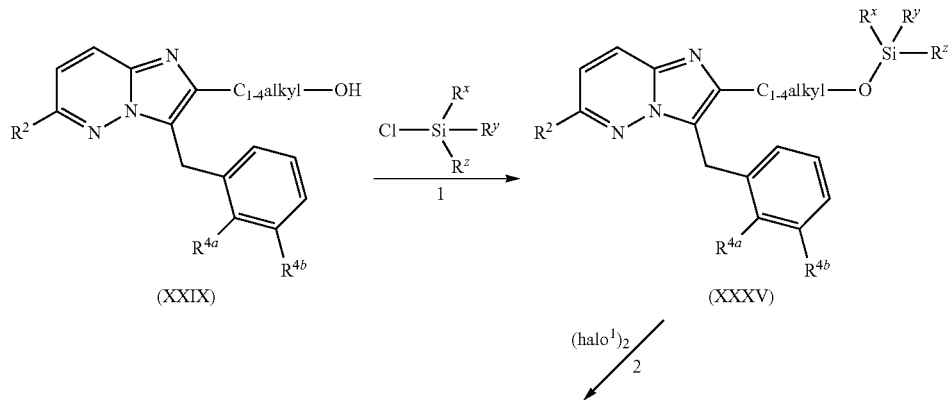

-continued

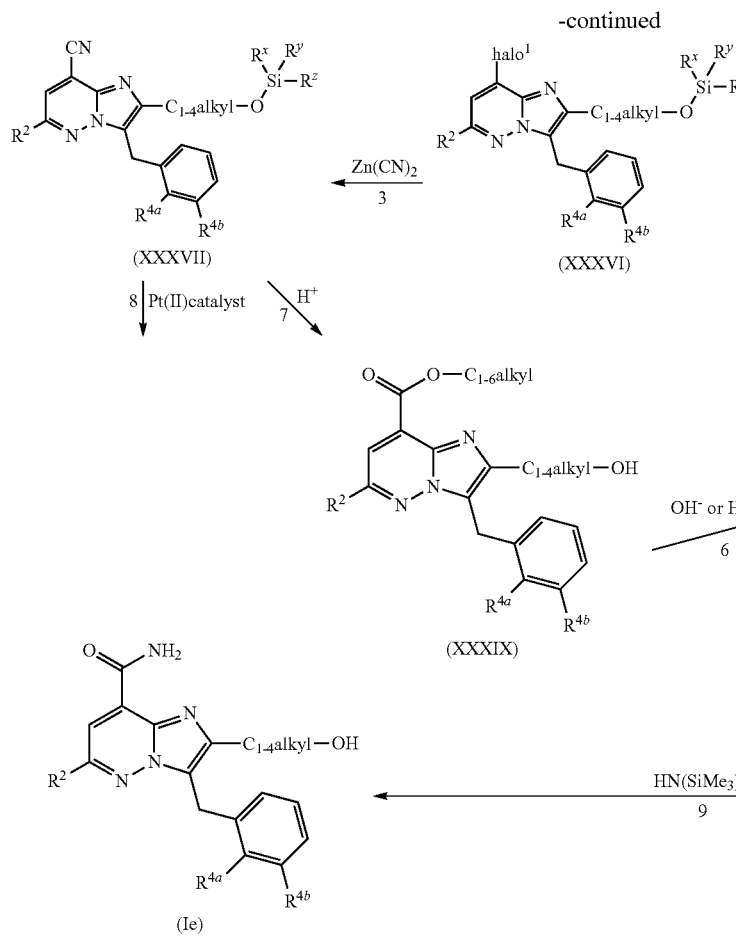

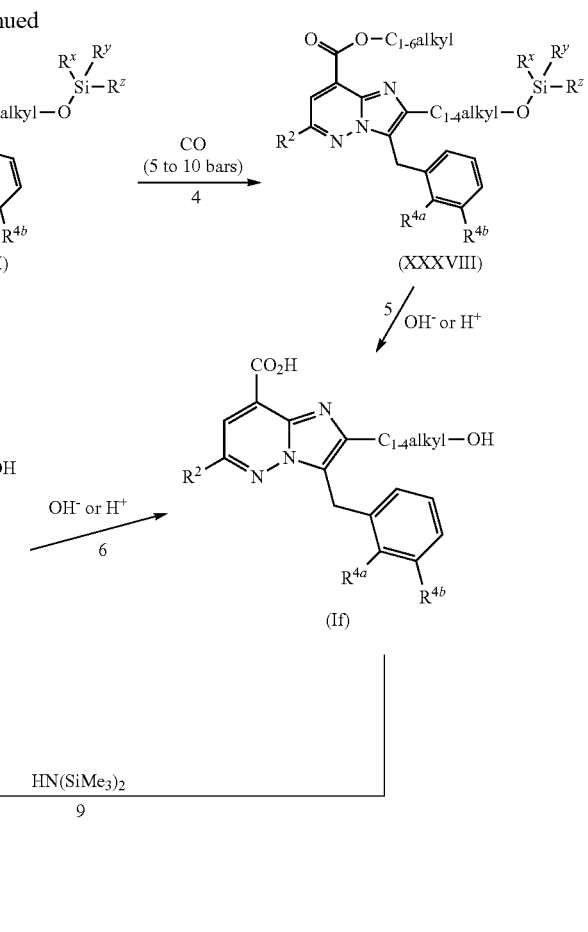

In Scheme 7, the following reaction conditions apply:

1: in the presence of a suitable activating agent such as for example imidazole and a suitable solvent such as for example N,N-dimethylformamide;

2: in the presence of a suitable base, such as for example lithium diisopropylamide, and a suitable solvent such as for example tetrahydrofuran (THF), at a suitable temperature such as for example at −70° C.;

3: in the presence of a suitable catalyst such as for example $Pd(PPh_3)_4$, and a suitable solvent such as a for example N,N-dimethylformamide (DMF), at a suitable temperature such as for example at 95° C.;

4: in the presence of a suitable catalyst such as for example $Pd(PPh_3)_4$, a suitable base such as for example triethylamine ($Et_3N$), and a suitable solvent such as for example methanol or ethanol, at a suitable temperature such as for example at 100° C. or 120° C.;

5: in the presence of a suitable base such as lithium hydroxide monohydrate, and a suitable solvent or a mixture of solvents such as for example a mixture of THF/water or MeOH/water optionally followed by the use of a suitable deprotecting agent such as for example tetrabutylammonium fluoride, in the presence of a suitable solvent such as for example THF;

Alternatively, in the presence of a suitable acid such as for example hydrochloric acid, and a suitable solvent such as for example THF;

6: in the presence of a suitable base such as lithium hydroxide monohydrate, and a suitable solvent or a mixture of solvents such as for example a mixture of THF/water or MeOH/water;

Alternatively, in the presence of a suitable acid such as for example hydrochloric acid, and a suitable solvent such as for example THF;

7: in the presence of a suitable acid such as for example sulphuric acid, and a suitable solvent such as methanol, at a suitable temperature such as for example at 100° C.;

8: in the presence of a suitable catalyst such as for example hydrido(dimethylphosphinous acid-kP)[hydrogen bis(dimethylphosphinito-kP)]platinum(II), and a suitable solvent or a mixture of solvents such as for example a mixture of THF/water, at a suitable temperature such as for example at 95° C.;

9: in the presence of a suitable peptidic coupling reagent such as 1-[bis(dimethylamino)methylene]-1H-[1,2,3]triazolo[4,5-b]pyridin-1-ium 3-oxide hexafluorophosphate (HATU), in the presence of a suitable base such as for example diisopropylamine, and a suitable solvent such as for example DMF;

In general, compounds of Formula (I) wherein $R^1$ is restricted to $R^{1a}$ being

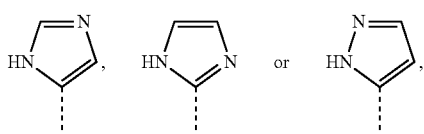

and wherein the other variables are as shown in Formula (Ig); and compounds of Formula (I) wherein $R^1$ is —$NH_2$, and wherein the other variables are as shown in Formula (Ih) can be prepared according to the following reaction Scheme 8 wherein all other variables are defined as above or according to the scope of the present invention.

In case of $R^{1a}$ (PG), first, in the presence of zinc chloride, a suitable deprotonating agent such as for example butyl lithium, a suitable solvent such as for example THF, at a suitable temperature such as for example −78° C., followed by addition (of/to) this solution (to) a mixture of intermediate (XXXVI), optionally in solution in THF, and a suitable catalyst such as for example Pd(PPh$_3$)$_4$, heating at a suitable temperature ranging from 60 to 100° C.;

3: in the presence of a suitable acid such as for example p-toluenesulfonic acid, hydrochloric acid or trifluoroacetic acid, in a suitable solvent such as for example dioxane, methanol or dichloromethane, at a suitable temperature such as for example 50 or 100° C.;

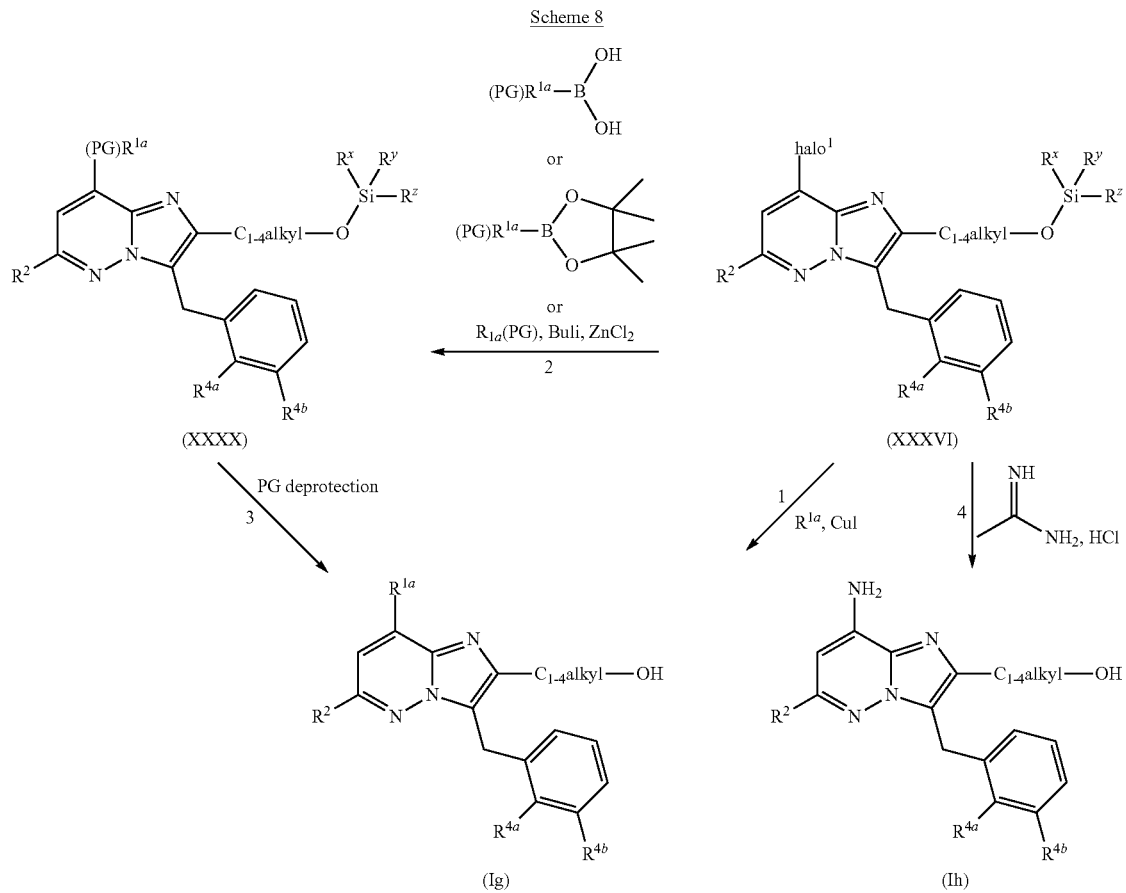

In Scheme 8, the following reaction conditions apply:
1: in the presence of copper iodide, a suitable catalyst such as for example palladium acetate, in a microwave, at a suitable temperature such as for example 185° C. followed by deprotection of the tert-Butyldimethylsilyl group with a suitable reagent such as tetrabutylammonium fluoride, hydrochloric acid or trifluoroacetic acid in a suitable solvent such as THF, dioxane or; dichloromethane;
2: in case of (PG)$R^{1a}$B(OH)$_2$ or (PG)$R^{1a}$ (4,4,5,5-tetramethyl-1,3,2-dioxaborolane), in the presence of a suitable catalyst such as for example 1,1'-bis(diphenylphosphino) ferrocene palladium(II)dichloride dichloromethane adduct, a suitable base such as for example potassium carbonate, and a suitable solvent such as for example a mixture of dioxane and water, at a suitable temperature such as for example at 100° C.;

4: in the presence of a suitable catalyst such as for example copper iodide, a suitable ligand such as for example L-proline, a suitable base such as for example cesium carbonate, a suitable solvent such as for example N,N-dimethylformamide, at a suitable temperature such as 110° C. in a sealed vessel followed by deprotection of the tert-Butyldimethylsilyl group with a suitable reagent such as tetrabutylammonium fluoride, hydrochloric acid or trifluoroacetic acid in a suitable solvent such as THF, dioxane or dichloromethane.

In general, compounds of Formula (I) wherein $R^1$ is a —C(=O)OH, and wherein the other variables are as shown in Formula (If), can be prepared according to the following reaction Scheme 9, wherein all other variables are defined as above or according to the scope of the present invention.

Scheme 9

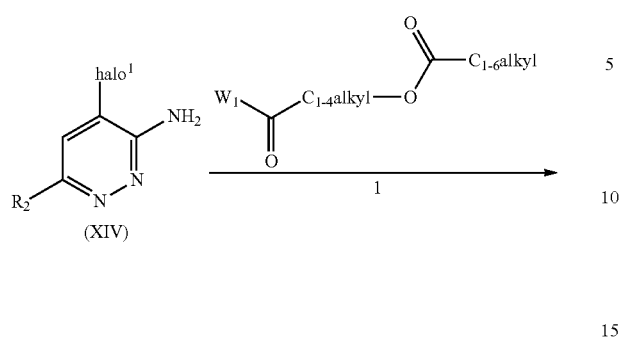
(XIV)

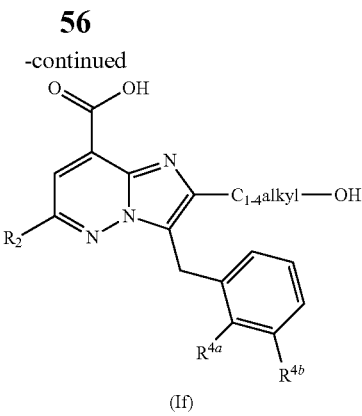
(If)

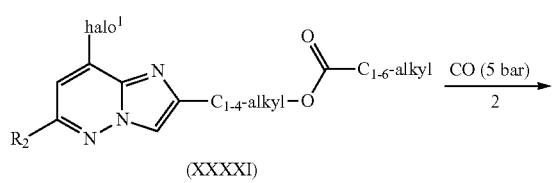
(XXXXI)

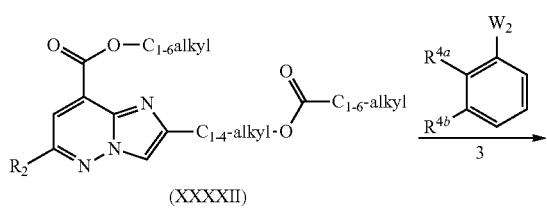
(XXXXII)

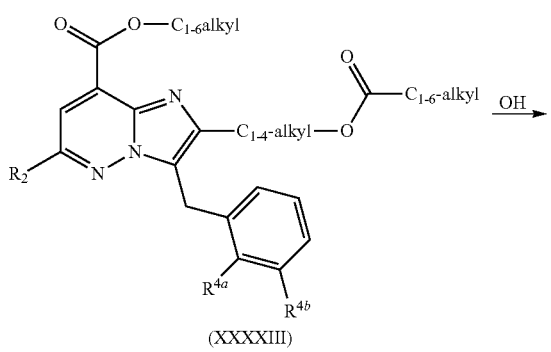
(XXXXIII)

In Scheme 9, the following reaction conditions apply:

1: at a suitable temperature such as for example 70° C. or 90° C., in the presence of a suitable solvent such as for example ethanol, N,N-dimethylformamide or dimethoxyethane;

2: in the presence of a suitable catalyst such as for example $Pd(PPh_3)_4$ or $Pd_2(OAc)_2$, optionally a suitable ligand such as for example 4,5-Bis(diphenylphosphino)-9,9-dimethylxanthene, a suitable base such as for example triethylamine ($Et_3N$), and a suitable solvent such as for example methanol or ethanol, at a suitable temperature such as for example at 100° C. or 120° C.;

3: in the presence of a suitable catalyst such as for example palladium acetate, a suitable ligand such as triphenylphosphine, a suitable base such as for example $K_2CO_3$, a suitable solvent such as for example dioxane, and a suitable temperature such as for example 100° C., optionally in a sealed vessel;

4: in the presence of a suitable base such as lithium hydroxide monohydrate, and a suitable solvent or a mixture of solvents such as for example a mixture of THF/water or MeOH/water.

In general, compounds of Formula (I) wherein $R^1$ is a —$NH_2$, and wherein the other variables are as shown in Formula (Ii); and compounds of Formula (I) wherein $R^1$ is restricted to $R^{1a}$ being

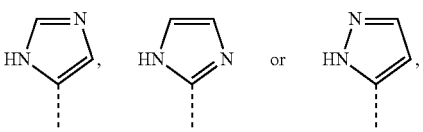

and wherein the other variables are as shown in Formula (Ij) can be prepared according to the following reaction Scheme 10. In scheme 10, $R^9$ is defined as H or $CH_3$, and $R^{10}$ is defined as —$C_{1-4}$alkyl-$SO_2$—$CH_3$ or —$C_{1-4}$alkyl-OH. All other variables in Scheme 10 are defined as above or according to the scope of the present invention.

Scheme 10
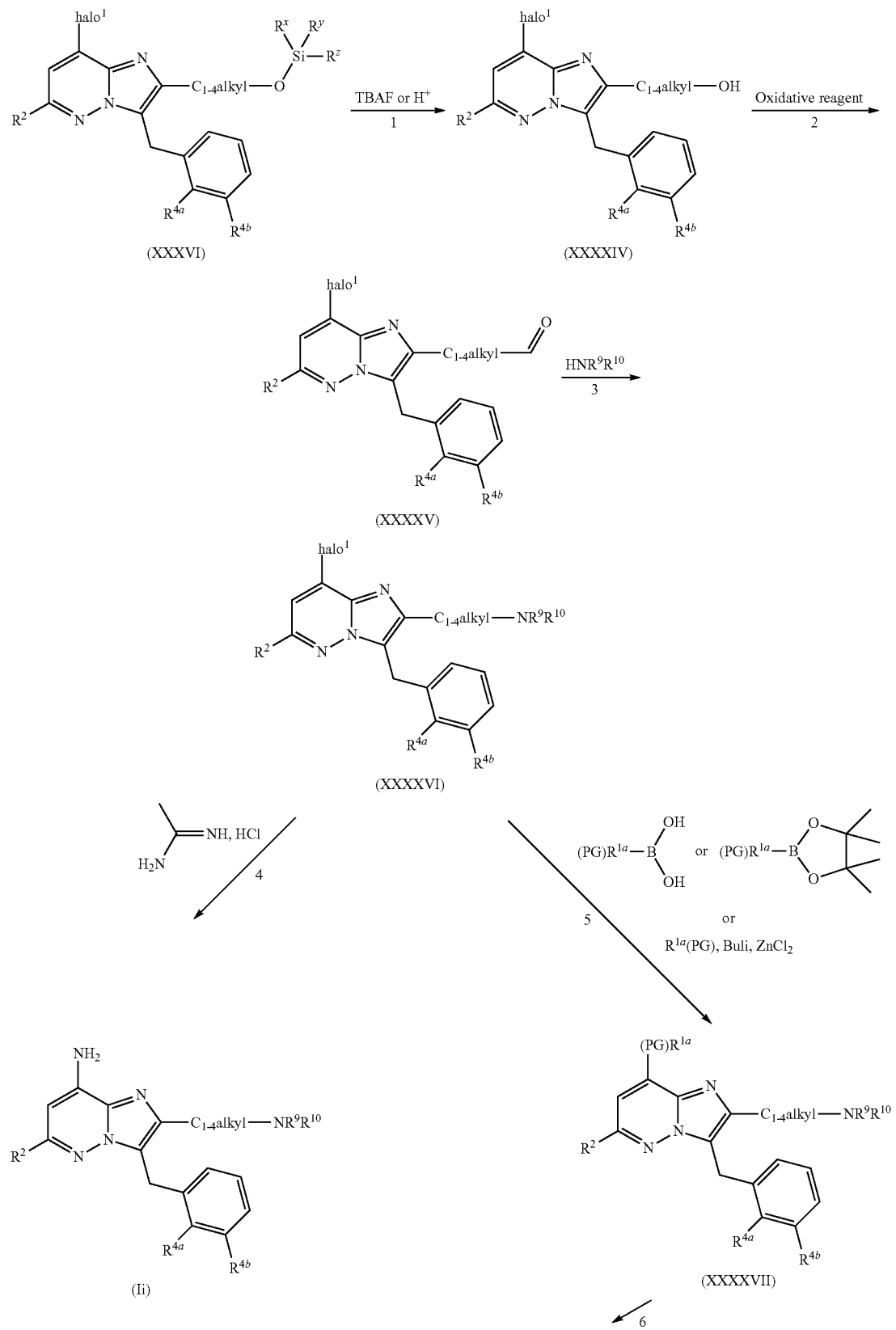

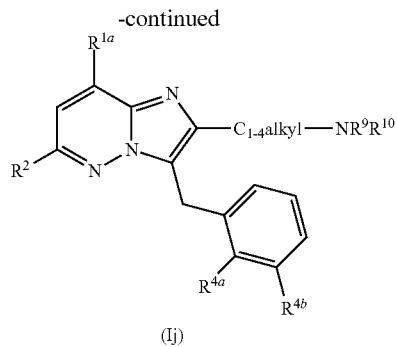

(Ij)

In Scheme 10, the following reaction conditions apply:
1: in the presence of a suitable reagent such as for example tetrabutylammonium fluoride, hydrochloric acid or trifluoroacetic acid in a suitable solvent such as THF, dioxane or dichloromethane;
2: at a suitable temperature such as for example 80° C., in the presence of a suitable oxidative reagent such as for example manganese dioxide, in a suitable solvent such as for example dioxane;
3: in the presence of a suitable reducing agent such as for example sodium triacetoxyborohydride, a suitable additive such as for example sodium acetate, and in a suitable solvent such as for example dichloromethane;
4: in the presence of a suitable catalyst such as for example copper iodide, a suitable ligand such as for example L-proline, a suitable base such as for example cesium carbonate, a suitable solvent such as for example N,N-dimethylformamide, at a suitable temperature such as 110° C., in a sealed vessel optionally followed by protecting groups cleavage with a suitable reagent such as tetrabutylammonium fluoride, hydrochloric acid or trifluoroacetic acid in a suitable solvent such as for example THF, dioxane or dichloromethane;
5: in case of (PG)R$^{1a}$B(OH)$_2$ or (PG)R$^{1a}$ (4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium carbonate, and a suitable solvent such as for example a mixture of dioxane and water, at a suitable temperature such as for example at 100° C.;

In case of R$^{1a}$ (PG), first, in the presence of zinc chloride, a suitable deprotonating agent such as for example butyl lithium, a suitable solvent such as for example THF, at a suitable temperature such as for example −78° C., followed by addition (of/to) this solution (to) a mixture of intermediate (XXXXVI), optionally in solution in THF, and a suitable catalyst such as for example Pd(PPh$_3$)$_4$, heating at a suitable temperature ranging from 60 to 100° C.;
6: in the presence of a suitable acid such as for example p-toluenesulfonic acid, hydrochloric acid or trifluoroacetic acid, in a suitable solvent such as for example dioxane, methanol or dichloromethane, at a suitable temperature such as for example 50 or 100° C.

In general, compounds of Formula (I) wherein R$^1$ is —NH$_2$, and wherein the other variables are as shown in Formula (Ik); and compounds of Formula (I) wherein R$^1$ is restricted to R$^{1a}$ being

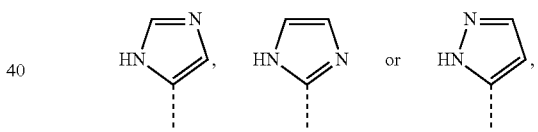

and wherein the other variables are as shown in Formula (Im) can be prepared according to the following reaction Scheme 11, wherein all other variables are defined as above or according to the scope of the present invention.

Scheme 11

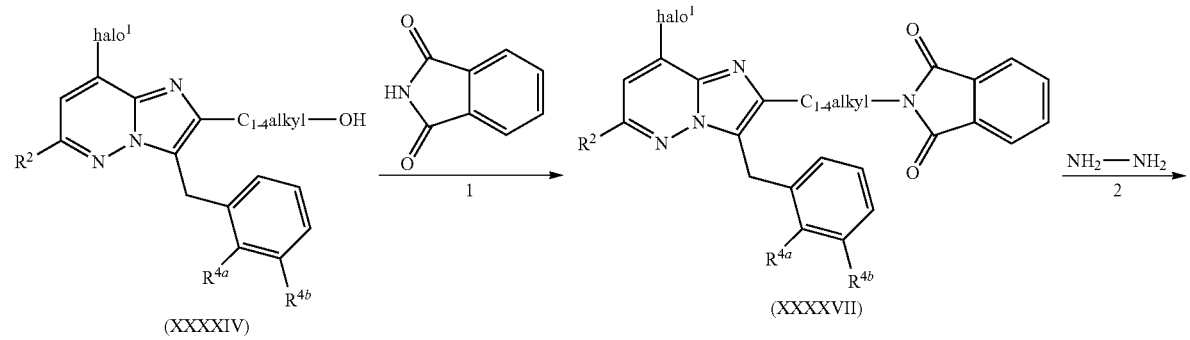

(XXXXIV)

(XXXXVII)

-continued
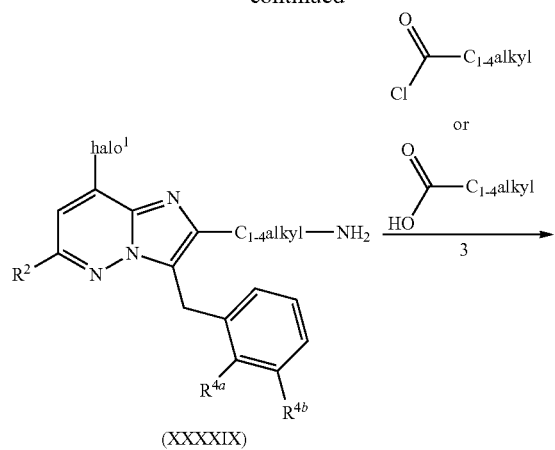
(XXXXIX)
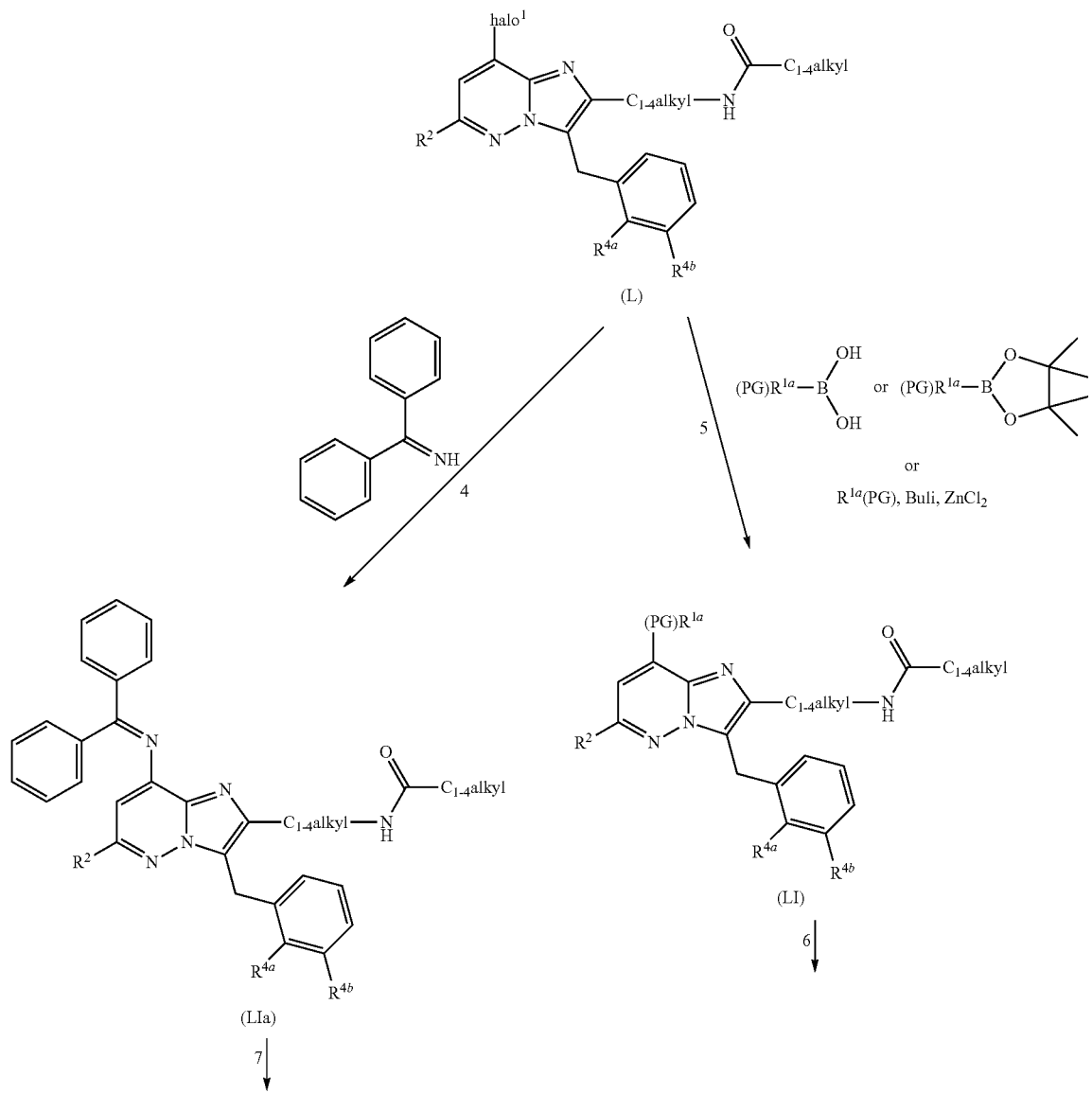

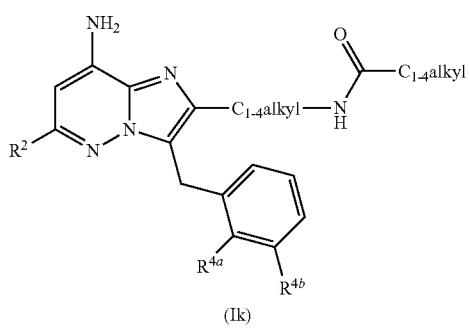

(Ik)

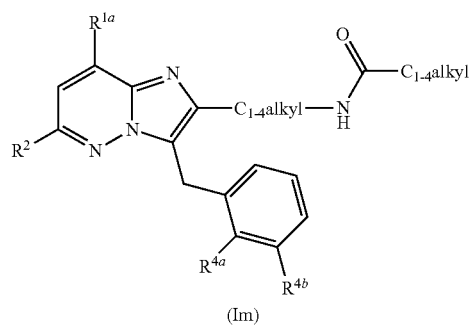

(Im)

-continued

In Scheme 11, the following reaction conditions apply:
1: in the presence of a suitable reagent such as for example di-tert-butyl azodicarboxylate, a suitable phosphine such as for example triphenylphosphine, and in a suitable solvent such as for example THF;
2: at a suitable temperature such as for example 80° C., in a suitable solvent such as for example ethanol;
3: in case of an acyl chloride, in the presence of a suitable base such as for example diisopropylethylamine, and in a suitable solvent such as for example dichloromethane in case of a carboxylic acid, in the presence of a suitable coupling reagent such as for example 1-(3-dimethyamino-propyl)-3-ethylcarbodiimide hydrochloride, a suitable additive such as for example 1-hydroxybenzotriazole, a suitable base such as for example triethylamine, and in a suitable solvent such as for example a mixture of THF and dichloromethane;
4: in the presence of a suitable catalyst such as for example palladium acetate, a suitable ligand such as for example 2,2'-bis(diphenylphosphino)-1,1'-binaphthyl, a suitable base such as for example cesium carbonate, a suitable solvent such as for example dioxane, at a suitable temperature such as 100° C., optionally in a sealed vessel;
5: in case of (PG)$R^{1a}$B(OH)$_2$ or (PG)$R^{1a}$ (4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium carbonate, and a suitable solvent such as for example a mixture of dioxane and water, at a suitable temperature such as for example at 100° C.;
In case of $R^{1a}$ (PG), first, in the presence of zinc chloride, a suitable deprotonating agent such as for example butyl lithium, a suitable solvent such as for example THF, at a suitable temperature such as for example −78° C., followed by addition (of/to) this solution (to) a mixture of intermediate (L), optionally in solution in THF, and a suitable catalyst such as for example Pd(PPh$_3$)$_4$, heating at a suitable temperature ranging from 60 to 100° C.;
6: in the presence of a suitable acid such as for example p-toluenesulfonic acid, hydrochloric acid or trifluoroacetic acid, in a suitable solvent such as for example dioxane, methanol or dichloromethane, at a suitable temperature such as for example 50 or 100° C.;
7: in the presence of a suitable acid such as for example hydrochloric acid or trifluoroacetic acid, in a suitable solvent such as for example tetrahydrofurane or dichloromethane, at a suitable temperature such as for example room temperature, 50° C. or 70° C.

In general, compounds of Formula (I) wherein $R^1$ is —NH$_2$, and wherein the other variables are as shown in Formula (In); and compounds of Formula (I) wherein $R^1$ is restricted to $R^{1a}$ being

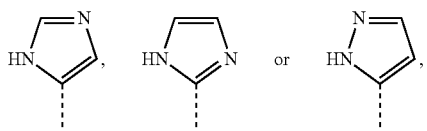

and wherein the other variables are as shown in Formula (Io) can be prepared according to the following reaction Scheme 12, wherein all other variables are defined as above or according to the scope of the present invention.

Scheme 12

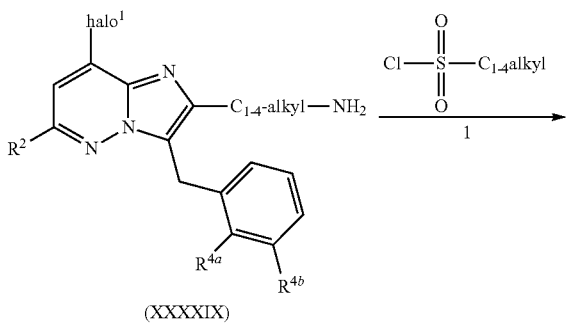

(XXXXIX)

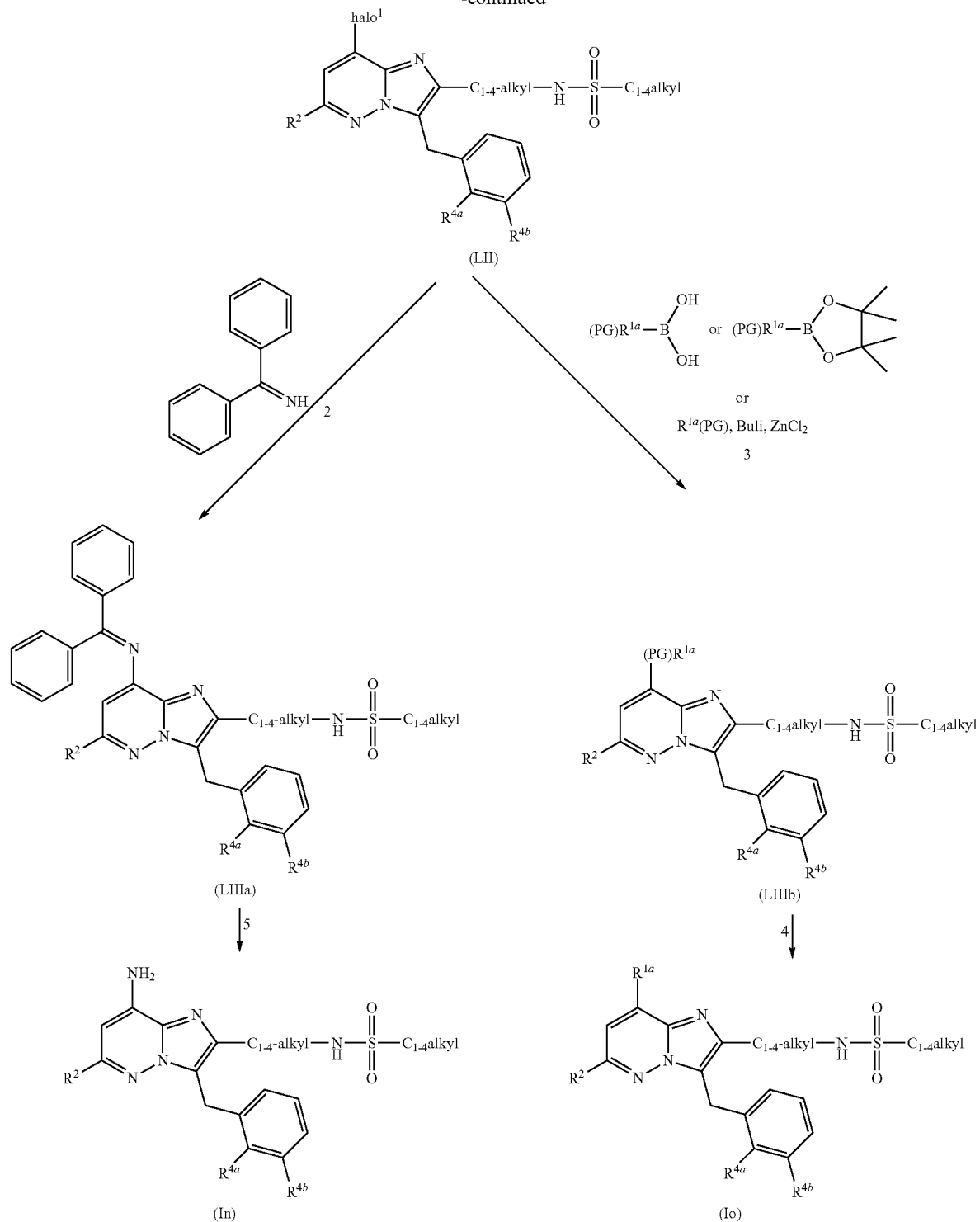

In Scheme 12, the following reaction conditions apply:
1: in the presence of a suitable base such as for example triethylamine; in a suitable solvent such as for example dichloromethane;
2: in the presence of a suitable catalyst such as for example palladium acetate, a suitable ligand such as for example 2,2'-bis(diphenylphosphino)-1,1'-binaphthyl, a suitable base such as for example cesium carbonate, a suitable solvent such as for example dioxane, at a suitable temperature such as 100° C., optionally in a sealed vessel;

3: in case of (PG)R$^{1a}$B(OH)$_2$ or (PG)R$^{1a}$ (4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium carbonate, and a suitable solvent such as for example a mixture of dioxane and water, at a suitable temperature such as for example at 100° C.;

In case of $R^{1a}$ (PG), first, in the presence of zinc chloride, a suitable deprotonating agent such as for example butyl lithium, a suitable solvent such as for example THF, at a suitable temperature such as for example −78° C., followed by addition (of/to) this solution (to) a mixture of intermediate (LII), optionally in solution in THF, and a suitable catalyst such as for example Pd(PPh$_3$)$_4$, heating at a suitable temperature ranging from 60 to 100° C.;

4: in the presence of a suitable acid such as for example p-toluenesulfonic acid, hydrochloric acid or trifluoroacetic acid, in a suitable solvent such as for example dioxane, methanol or dichloromethane, at a suitable temperature such as for example 50 or 100° C.;

5: in the presence of a suitable acid such as for example hydrochloric acid or trifluoroacetic acid, in a suitable solvent such as for example tetrahydrofurane or dichloromethane, at a suitable temperature such as for example room temperature, 50° C. or 70° C.

In general, compounds of Formula (I) wherein $R^1$ is —NH$_2$, and wherein the other variables are as shown in Formula (Ip); and compounds of Formula (I) wherein $R^1$ is restricted to $R^{1a}$ being

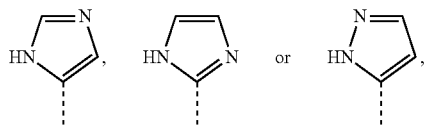

and wherein the other variables are as shown in Formula (Iq) can be prepared according to the following reaction Scheme 13, wherein halo$^{1a}$ is defined as Cl, Br and I, and all other variables are defined as above or according to the scope of the present invention.

Scheme 13

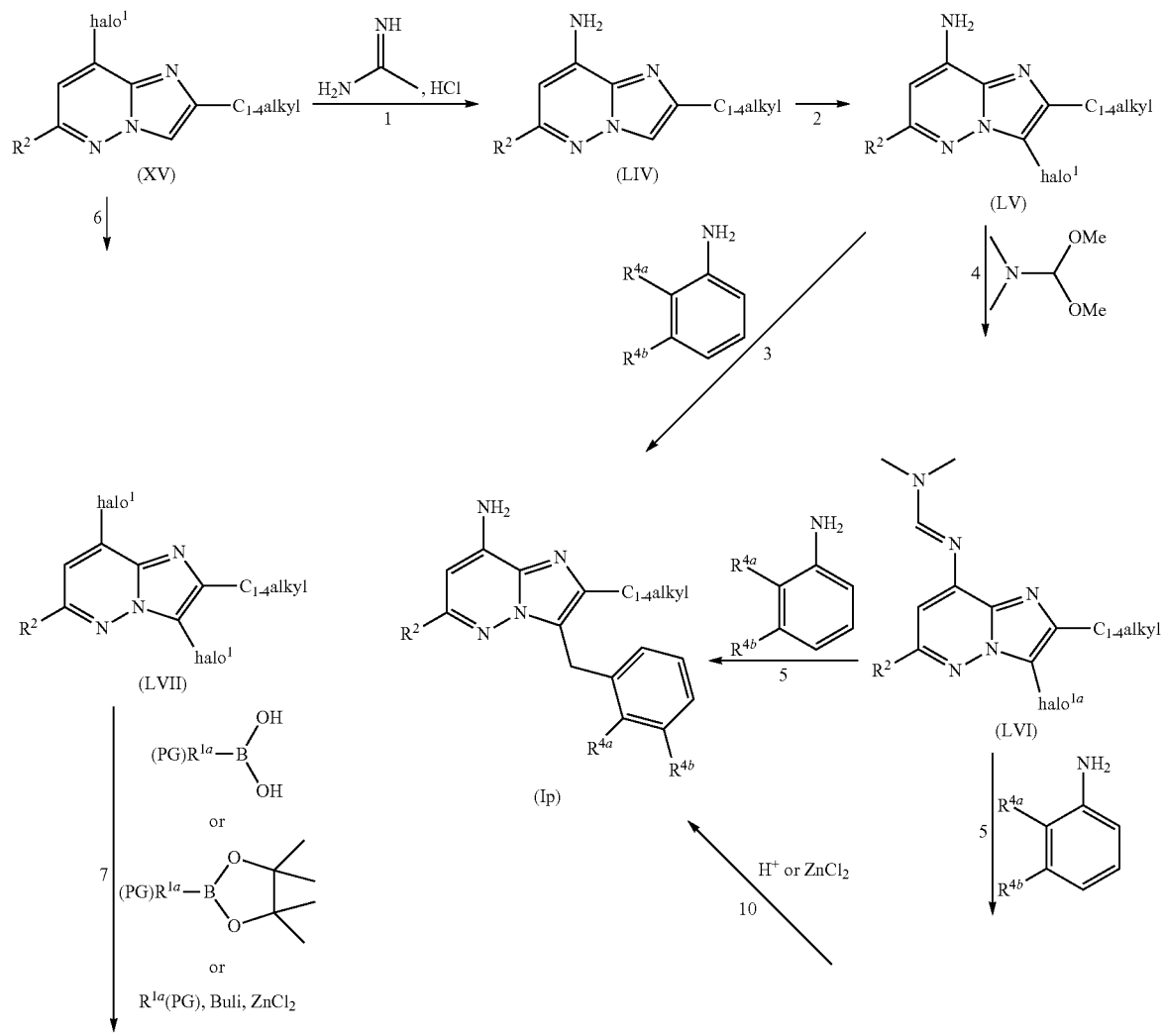

-continued

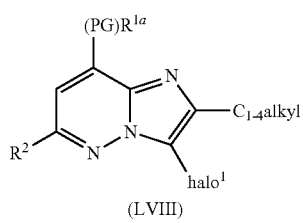

(LVIII)

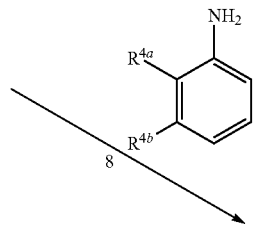
8

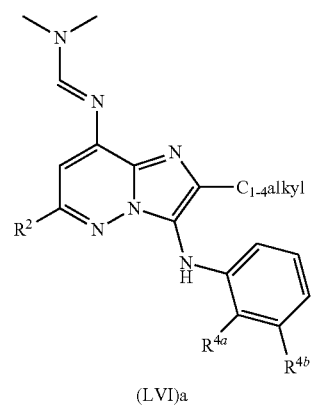

(LVI)a

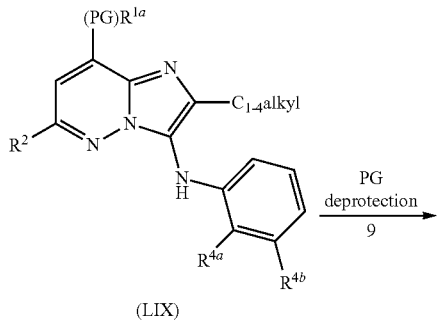

(LIX)

PG deprotection
9

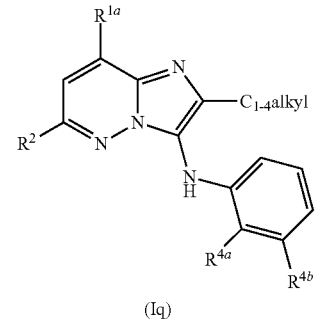

(Iq)

In Scheme 13, the following reaction conditions apply:

1: in the presence of a suitable catalyst such as for example copper iodide, a suitable ligand such as for example L-proline, a suitable base such as for example cesium carbonate, a suitable solvent such as for example N,N-dimethylformamide, at a suitable temperature such as 110° C., in a sealed vessel;

2: in the presence of a suitable brominating reagent such as for example N-bromosuccinimide, in a suitable solvent such as for example acetonitrile;

3: at a temperature such as 100° C. or in a microwave at a temperature of 140° C., in the presence of a suitable catalyst such as for example tris(dibenzylideneacetone)dipalladium (0), a suitable ligand such as for example 2-(di-t-butylphosphino)biphenyl, a suitable base such as for example sodium tert-butoxide, and in a suitable solvent such as for example dioxane;

4: at a temperature such as for example 120° C., in a suitable solvent such as for example toluene;

5: at a temperature such as 100° C. or in a microwave at a temperature of 140° C., in the presence of a suitable catalyst such as for example tris(dibenzylideneacetone)dipalladium (0), a suitable ligand such as for example 2-(di-t-butylphosphino)biphenyl, a suitable base such as for example sodium tert-butoxide, and in a suitable solvent such as for example dioxane, in a sealed vessel;

6: in the presence of a suitable brominating reagent such as for example N-bromosuccinimide, in a suitable solvent such as for example acetonitrile;

7: in case of $(PG)R^{1a}B(OH)_2$ or $(PG)R^{1a}$ (4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium carbonate, and a suitable solvent such as for example a mixture of dioxane and water, at a suitable temperature such as for example at 100° C.;

In case of $R^{1a}(PG)$, first, in the presence of zinc chloride, a suitable deprotonating agent such as for example butyl lithium, a suitable solvent such as for example THF, at a suitable temperature such as for example −78° C., followed by addition (of/to) this solution (to) a mixture of intermediate (LVII), optionally in solution in THF, and a suitable catalyst such as for example $Pd(PPh_3)_4$, heating at a suitable temperature ranging from 60 to 100° C.;

8: at a temperature such as 100° C. or in a microwave at a temperature of 140° C., in the presence of a suitable catalyst such as for example tris(dibenzylideneacetone)dipalladium (0), a suitable ligand such as for example 2-(di-t-butylphosphino)biphenyl, a suitable base such as for example sodium tert-butoxide, and in a suitable solvent such as for example dioxane;

9: in the presence of a suitable acid such as for example p-toluenesulfonic acid, hydrochloric acid or trifluoroacetic acid, in a suitable solvent such as for example dioxane, methanol or dichloromethane, at a suitable temperature such as for example 50 or 100° C.;

10: in the presence of a suitable acid such as for example hydrochloric acid or trifluoroacetic acid, in a suitable solvent such as for example tetrahydrofurane or dichloromethane, at a suitable temperature such as for example room temperature, 50° C. or 70° C.

Alternatively, in a suitable solvent such as for example EtOH, at a suitable temperature such as for example 90° C.

In general, compounds of Formula (I) wherein $R^1$ is a —$NH_2$, and wherein the other variables are as shown in Formula (Ip); compounds of Formula (I) wherein $R^1$ is restricted to $R^{1a}$ being

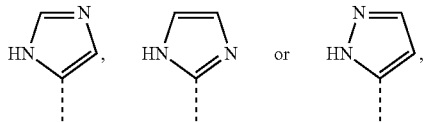

and wherein the other variables are as shown in Formula (Iq);
compounds of Formula (I) wherein $R^1$ is —C(=O)OH, and wherein the other variables are as shown in Formula (Ir); and compounds of Formula (I) wherein $R^1$ is —C(=O)$NH_2$, and wherein the other variables are as shown in Formula (Is); can be prepared according to the following reaction Scheme 14, wherein all other variables are defined as above or according to the scope of the present invention.

Scheme 14

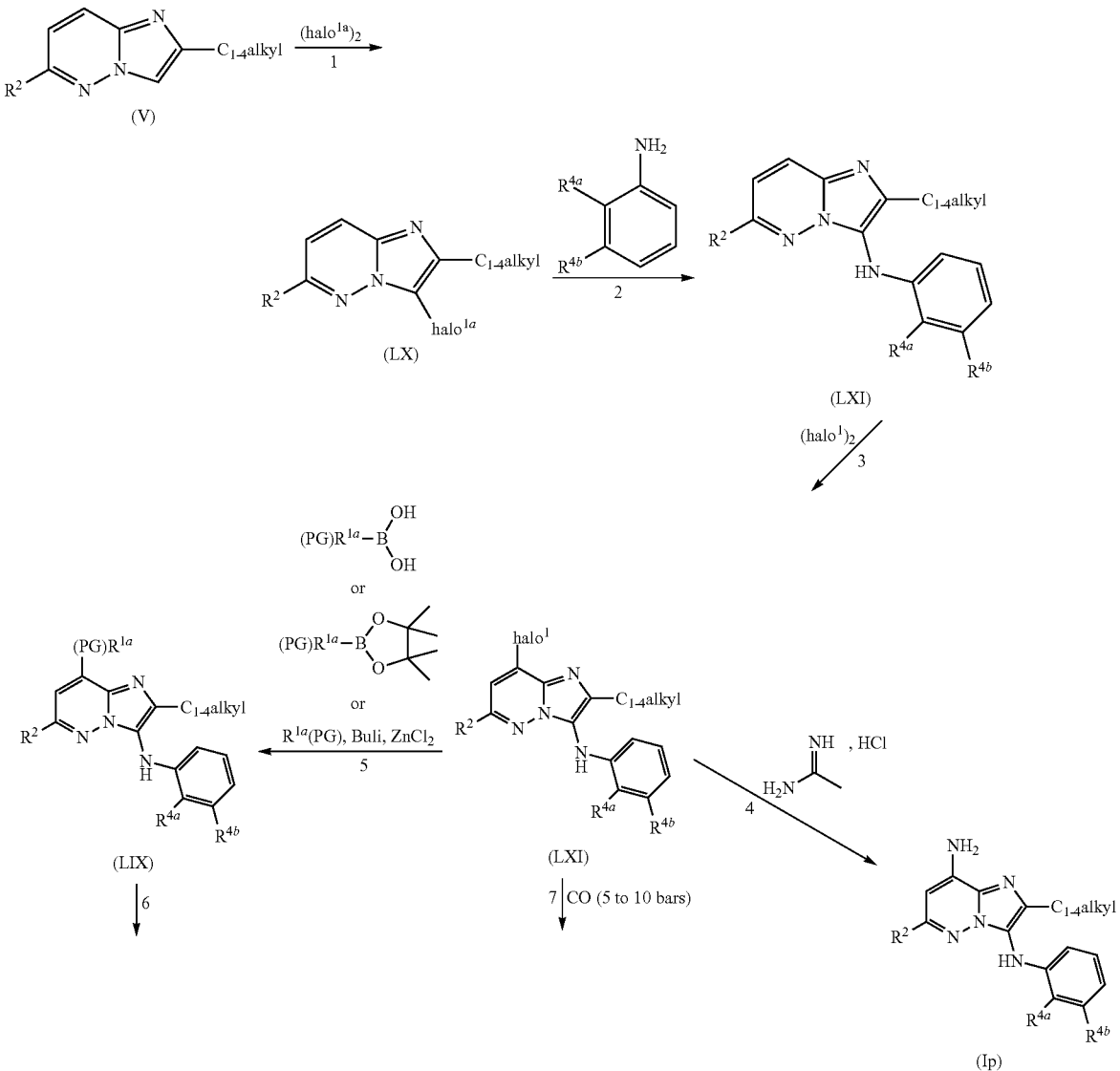

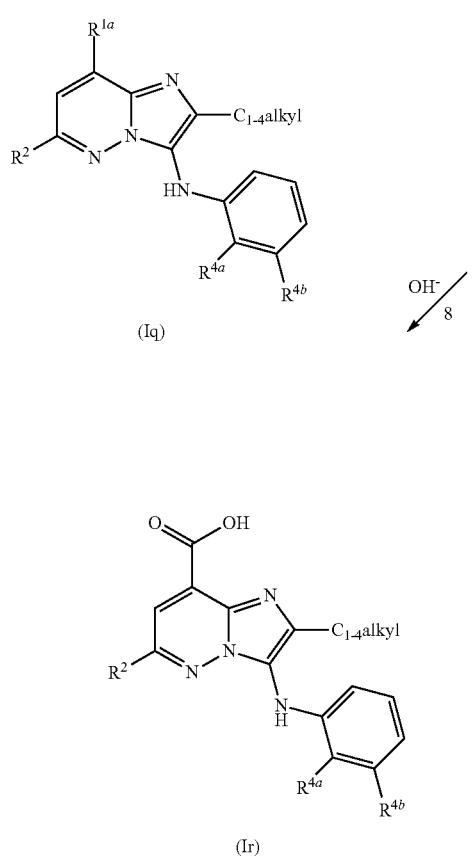

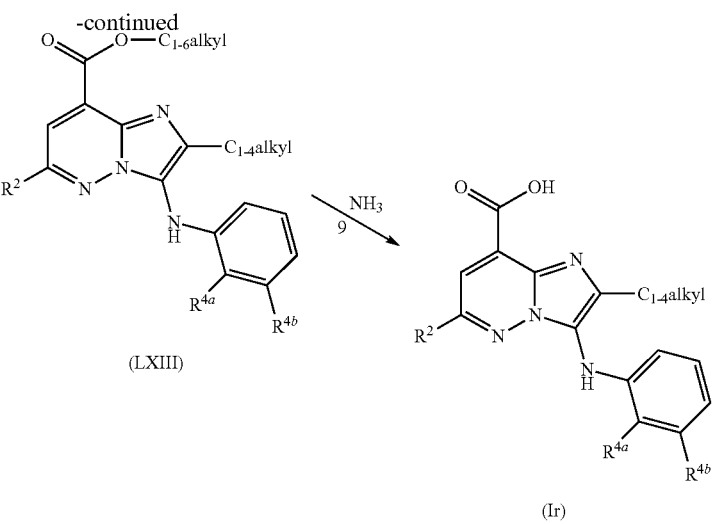

In Scheme 14, the following reaction conditions apply:

1: in the presence of a suitable brominating reagent such as for example N-bromosuccinimide, in a suitable solvent such as for example acetonitrile;

2: at a temperature such as 100° C. or in a microwave at a temperature of 140° C., in the presence of a suitable catalyst such as for example tris(dibenzylideneacetone)dipalladium (O), a suitable ligand such as for example 2-(di-t-butylphosphino)biphenyl, a suitable base such as for example sodium tert-butoxide, and in a suitable solvent such as for example dioxane;

3: in the presence of a suitable base, such as for example lithium diisopropylamide, and a suitable solvent such as for example tetrahydrofuran (THF), at a suitable temperature such as for example at −78° C.;

4: in the presence of a suitable catalyst such as for example copper iodide, a suitable ligand such as for example L-proline, a suitable base such as for example cesium carbonate, a suitable solvent such as for example N,N-dimethylformamide, at a suitable temperature such as 110° C., in a sealed vessel;

5: in case of (PG)$R^{1a}$B(OH)$_2$ or (PG)$R^{1a}$ (4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium carbonate, and a suitable solvent such as for example a mixture of dioxane and water, at a suitable temperature such as for example at 100° C.;

In case of $R^{1a}$ (PG), first, in the presence of zinc chloride, a suitable deprotonating agent such as for example butyl lithium, a suitable solvent such as for example THF, at a suitable temperature such as for example −78° C., followed by addition (of/to) this solution (to) a mixture of intermediate (LXII), optionally in solution in THF, and a suitable catalyst such as for example Pd(PPh$_3$)$_4$, heating at a suitable temperature ranging from 60 to 100° C.;

6: in the presence of a suitable acid such as for example p-toluenesulfonic acid, hydrochloric acid or trifluoroacetic acid, in a suitable solvent such as for example dioxane, methanol or dichloromethane, at a suitable temperature such as for example 50 or 100° C.;

7: in the presence of a suitable catalyst such as for example Pd(PPh$_3$)$_4$, a suitable base such as for example triethylamine (Et$_3$N), and a suitable solvent such as for example methanol or ethanol, at a suitable temperature such as for example at 100° C. or 120° C.;

8: in the presence of a suitable base such as lithium hydroxide monohydrate, and a suitable solvent or a mixture of solvents such as for example a mixture of THF/water or MeOH/water;

9: in a suitable solvent such as for example methanol, at a suitable temperature such as for example at 65° C. and, in a sealed vessel.

In general, compounds of Formula (I) wherein $R^1$ is restricted to $R^{1a}$ being

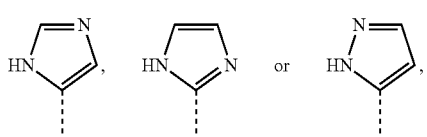

and wherein the other variables are as shown in Formula (Iu);
compounds of Formula (I) wherein $R^1$ is —C(=O)OH, and wherein the other variables are as shown in Formula (Iv); and $R^1$ compounds of Formula (I) wherein $R^1$ is —C(=O)NH$_2$, and wherein the other variables are as shown in Formula (Iw);
can be prepared according to the following reaction Scheme 15, wherein all other variables are defined as above or according to the scope of the present invention.

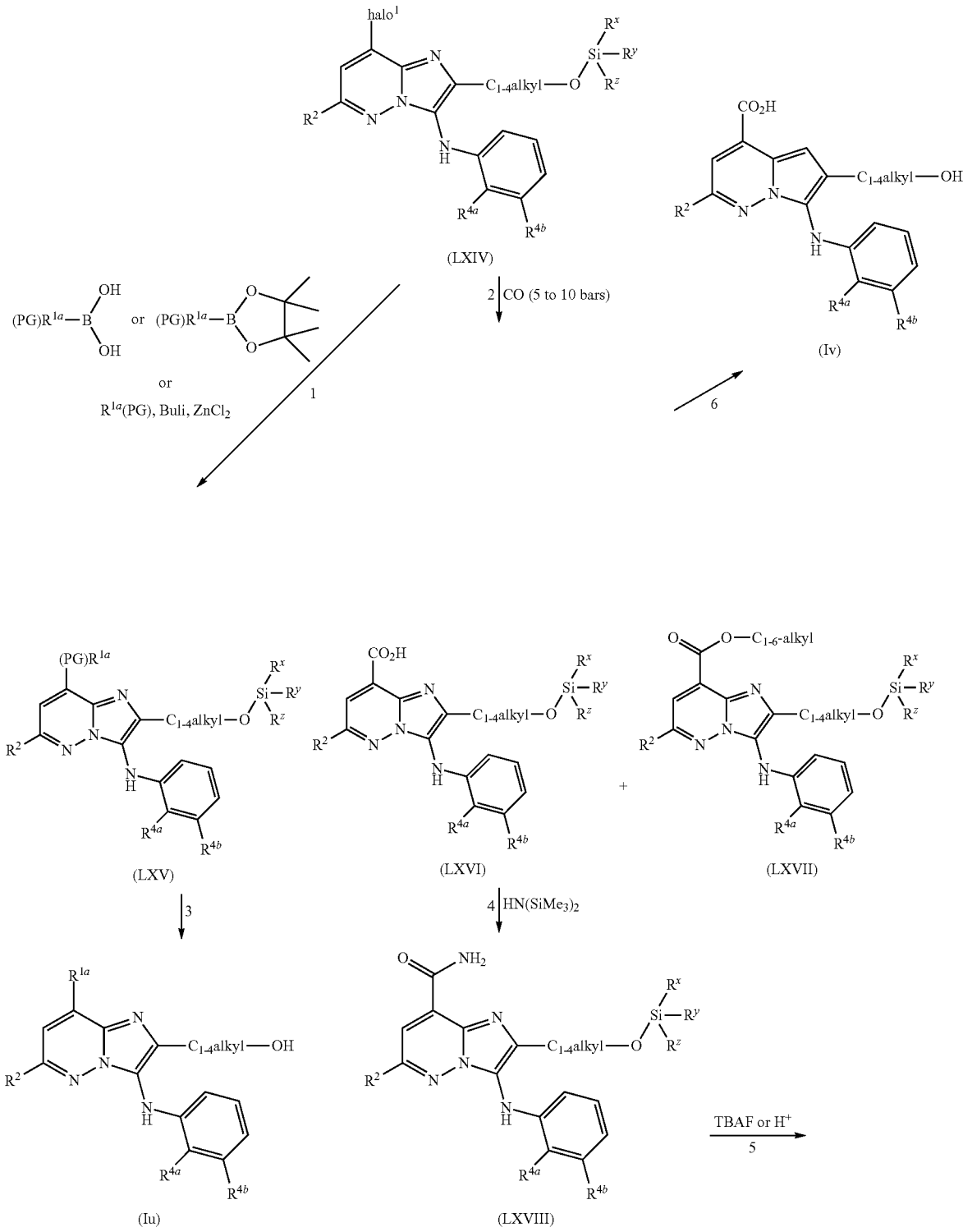

Scheme 15

-continued

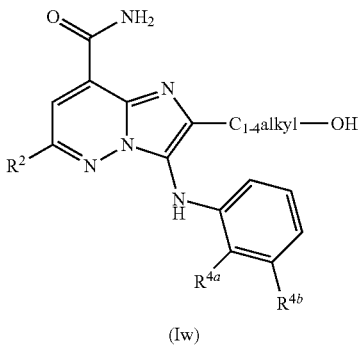

(Iw)

In Scheme 15, the following reaction conditions apply:
1: in case of (PG)R$^{1a}$B(OH)$_2$ or (PG)R$^{1a}$ (4,4,5,5-tetramethyl-1,3,2-dioxaborolane), in the presence of a suitable catalyst such as for example 1,1'-bis(diphenylphosphino) ferrocene palladium(II)dichloride dichloromethane adduct, a suitable base such as for example potassium carbonate, and a suitable solvent such as for example a mixture of dioxane and water, at a suitable temperature such as for example at 100° C.;
In case of R$^{1a}$(PG), first, in the presence of zinc chloride, a suitable deprotonating agent such as for example butyl lithium, a suitable solvent such as for example THF, at a suitable temperature such as for example −78° C., followed by addition (of/to) this solution (to) a mixture of intermediate (LXIV), optionally in solution in THF, and a suitable catalyst such as for example Pd(PPh$_3$)$_4$, heating at a suitable temperature ranging from 60 to 100° C.;
2: in the presence of a suitable catalyst such as for example Pd(PPh$_3$)$_4$, a suitable base such as for example triethylamine (Et$_3$N), and a suitable solvent such as for example methanol or ethanol, at a suitable temperature such as for example at 100° C. or 120° C.;
3: in the presence of a suitable acid such as for example p-toluenesulfonic acid, hydrochloric acid or trifluoroacetic acid, in a suitable solvent such as for example dioxane, methanol or dichloromethane, at a suitable temperature such as for example 50 or 100° C.;
4: in the presence of a suitable peptidic coupling reagent such as 1-[bis(dimethylamino)methylene]-1H-[1,2,3]triazolo[4,5-b]pyridin-1-ium 3-oxide hexafluorophosphate (HATU), in the presence of a suitable base such as for example diisopropylamine, and a suitable solvent such as for example DMF;
5: in the presence of a suitable deprotecting reagent such as for example tetrabutylammonium fluoride, in a suitable solvent such as for example THF;
6: in the presence of a suitable base such as lithium hydroxide monohydrate, and a suitable solvent or a mixture of solvents such as for example a mixture of THF/water or MeOH/water.

Intermediates of Formula (LXIV) used in the above Scheme 15 can be prepared according to the following reaction Scheme 16, wherein all other variables are defined as above or according to the scope of the present invention.

Scheme 16

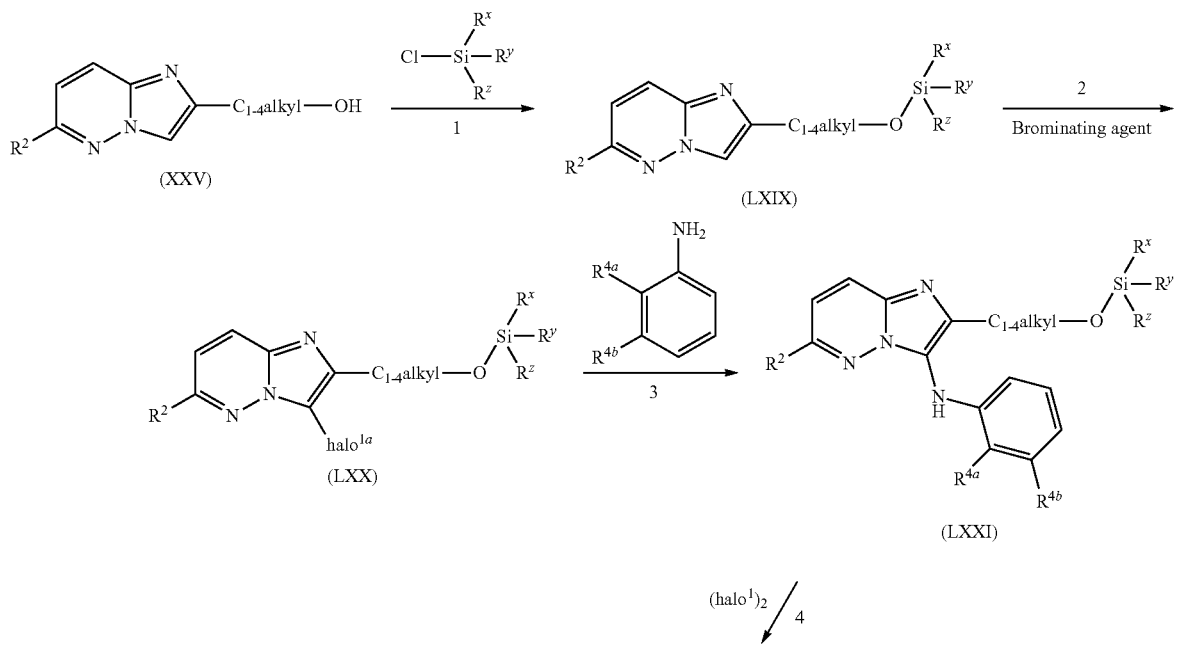

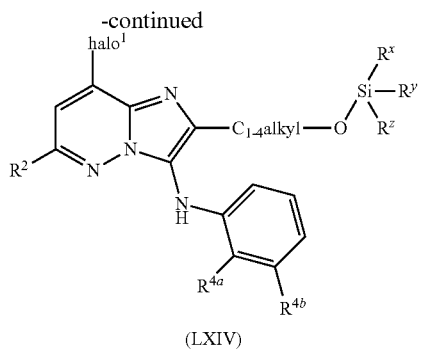

(LXIV)

In Scheme 16, the following reaction conditions apply:
1: in the presence of a suitable activating agent such as for example imidazole and a suitable solvent such as for example N,N-dimethylformamide;
2: in the presence of a suitable brominating reagent such as for example N-bromosuccinimide, in a suitable solvent such as for example acetonitrile;
3: at a temperature such as 100° C. or in a microwave at a temperature of 140° C., in the presence of a suitable catalyst such as for example tris(dibenzylideneacetone)dipalladium (0), a suitable ligand such as for example 2-(Dicyclohexylphosphino)-3,6-dimethoxy-2',4',6'-triisopropyl-1,1'-biphenyl, a suitable base such as for example cesium carbonate, and in a suitable solvent such as for example toluene;
4: in the presence of a suitable base, such as for example lithium diisopropylamide, and a suitable solvent such as for example tetrahydrofuran (THF), at a suitable temperature such as for example at −78° C.;

In general, compounds of Formula (I) wherein $R^1$ is —$NH_2$, and wherein the other variables are as shown in Formula (Ix); and compounds of Formula (I) wherein $R^1$ is restricted to $R^{1a}$ being

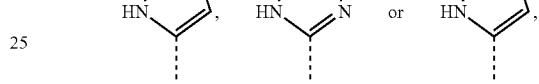

and wherein the other variables are as shown in Formula (Iy) can be prepared according to the following reaction Scheme 17, wherein m1 represents 0, 1, 2 or 3; n1 represents 0, 1, 2 or 3; provided that n1+m1≤3; and wherein all other variables are defined as above or according to the scope of the present invention.

Scheme 17

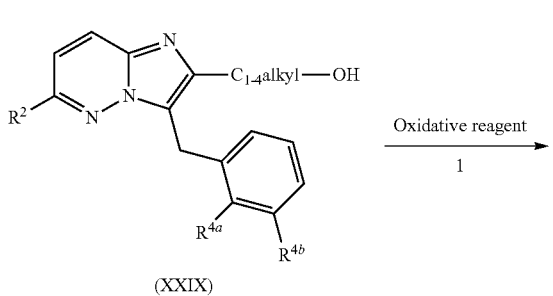

(XXIX)

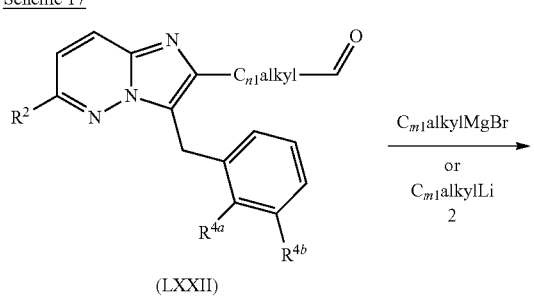

(LXXII)

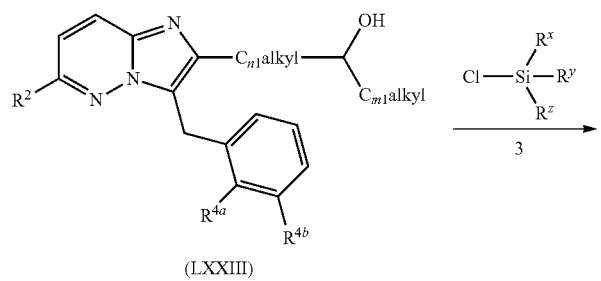

(LXXIII)

81   82

-continued

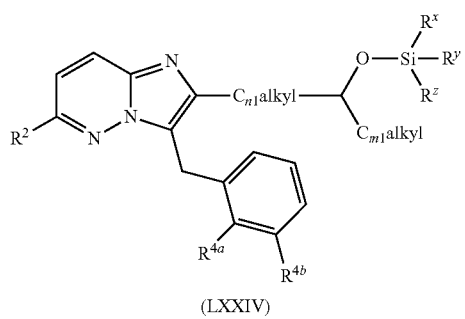

(LXXIV)

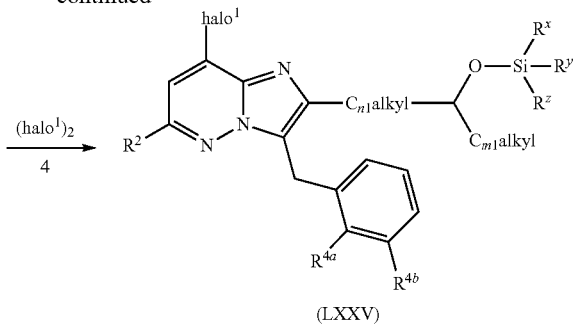

(LXXV)

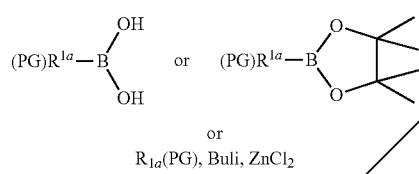

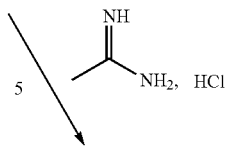

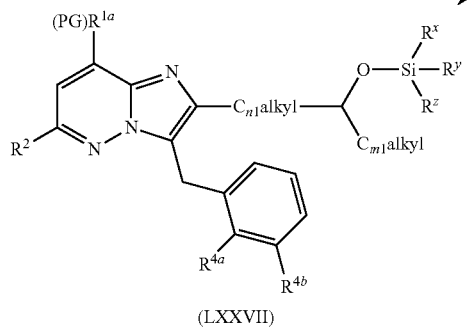

(LXXVII)

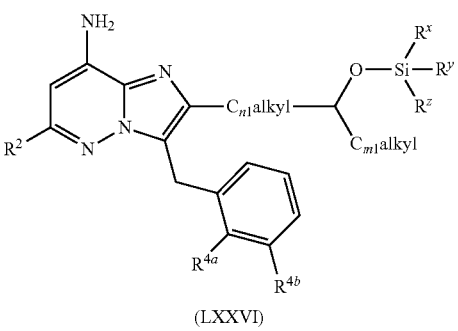

(LXXVI)

8 | PG deprotection

6 | TBAF or H⁺

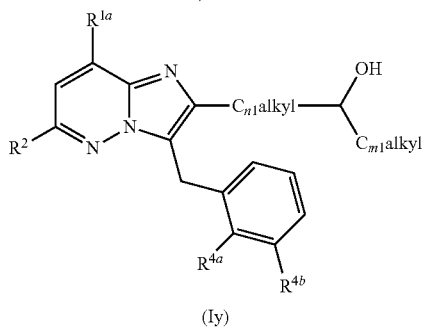

(Iy)

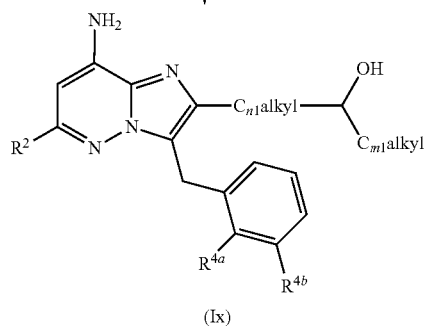

(Ix)

In Scheme 17, the following reaction conditions apply:
1: at a suitable temperature such as for example 80° C., in the presence of a suitable oxidative reagent such as for example manganese dioxide, in a suitable solvent such as for example dioxane;
2: at a suitable temperature such as for example 0° C. or −78° C., in a suitable solvent such as for example THF;
3: in the presence of a suitable activating agent such as for example imidazole and a suitable solvent such as for example N,N-dimethylformamide;
4: in the presence of a suitable base, such as for example lithium diisopropylamide, and a suitable solvent such as for example tetrahydrofuran (THF), at a suitable temperature such as for example at −70° C.;
5: in the presence of a suitable catalyst such as for example copper iodide, a suitable ligand such as for example L-proline, a suitable base such as for example cesium carbonate, a suitable solvent such as for example N,N-dimethylformamide, at a suitable temperature such as 110° C., in a sealed vessel;
6: in the presence of a suitable deprotecting reagent such as for example tetrabutylammonium fluoride, in a suitable solvent such as for example THF;
7: in case of $(PG)R^{1a}B(OH)_2$ or $(PG)R^{1a}$(4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium carbonate, and a suitable solvent such as for example a mixture of dioxane and water, at a suitable temperature such as for example at 100° C.;

In case of $R^{1a}$ (PG), first, in the presence of zinc chloride, a suitable deprotonating agent such as for example butyl lithium, a suitable solvent such as for example THF, at a suitable temperature such as for example −78° C., followed by addition (of/to) this solution (to) a mixture of intermediate (LXXV), optionally in solution in THF, and a suitable catalyst such as for example Pd(PPh$_3$)$_4$, heating at a suitable temperature ranging from 60 to 100° C.;

8: in the presence of a suitable acid such as for example p-toluenesulfonic acid, hydrochloric acid or trifluoroacetic acid, in a suitable solvent such as for example dioxane, methanol or dichloromethane, at a suitable temperature such as for example 50 or 100° C.

In general, compounds of Formula (I) wherein $R^1$ is —NH$_2$, and wherein the other variables are as shown in Formula (Iz) can be prepared according to the following reaction Scheme 18, wherein all other variables are defined as above or according to the scope of the present invention.

line, a suitable base such as for example cesium carbonate, a suitable solvent such as for example N,N-dimethylformamide, at a suitable temperature such as 110° C., in a sealed vessel.

In general, compounds of Formula (I) wherein $R^1$ is —C(=O)NH$_2$, and wherein the other variables are as shown in Formula (Iza) can be prepared according to the following reaction Scheme 19, wherein all other variables are defined as above or according to the scope of the present invention.

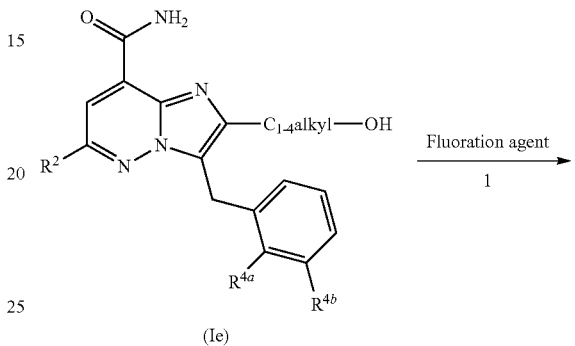

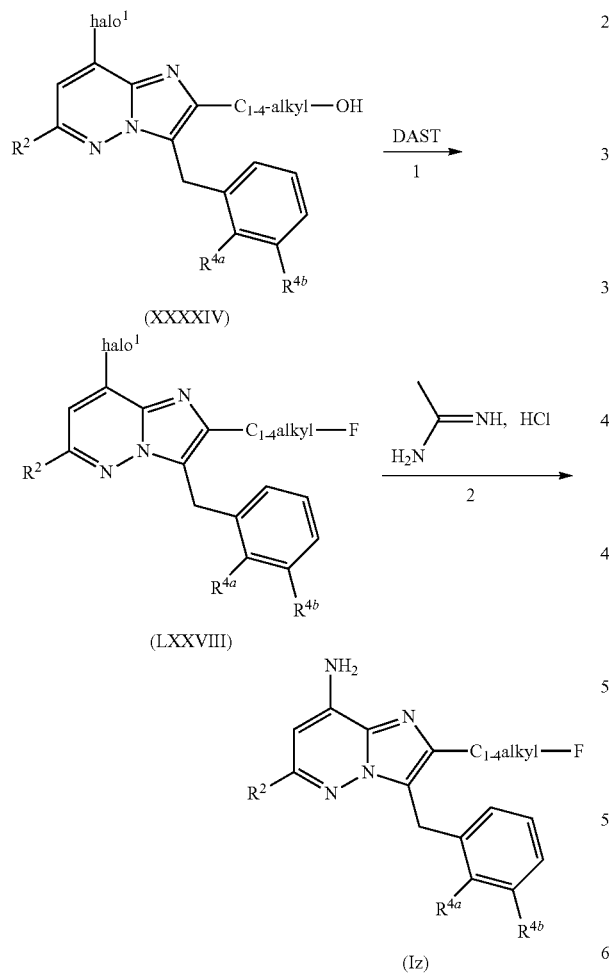

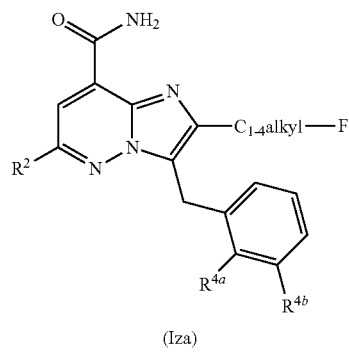

In Scheme 19, the following reaction conditions apply:
1: in a suitable solvent such as for example dichloromethane.

In general, compounds of Formula (I) wherein $R^1$ is —NH$_2$, and wherein the other variables are as shown in Formula (Ik) and (Ika) can be prepared or alternatively prepared according to the following reaction Scheme 20, wherein all other variables are defined as above or according to the scope of the present invention.

In Scheme 18, the following reaction conditions apply:
1: in a suitable solvent such as for example dichloromethane; 'DAST' means diethylaminosulfur trifluoride;
2: in the presence of a suitable catalyst such as for example copper iodide, a suitable ligand such as for example L-pro-

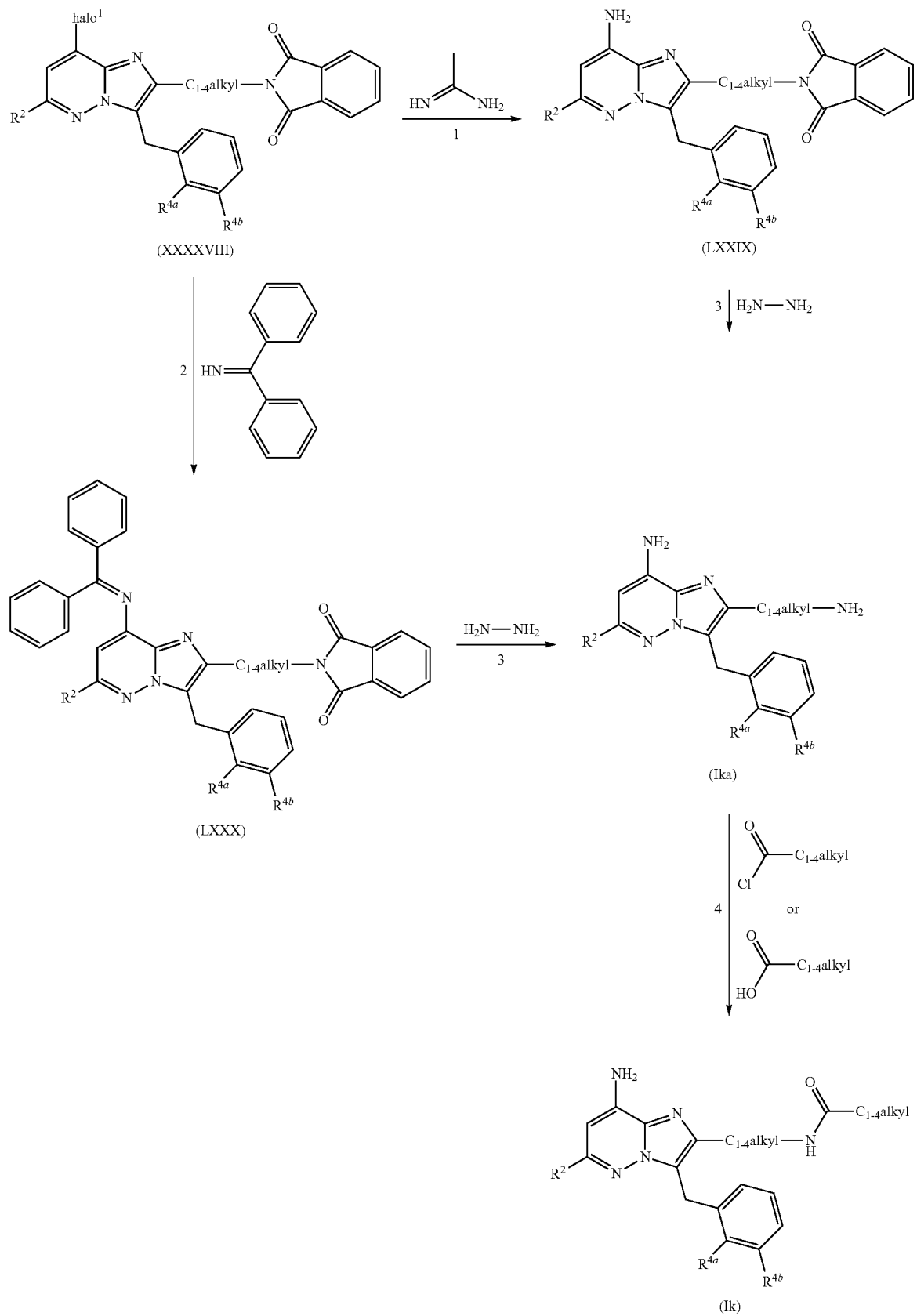

In Scheme 20, the following reaction conditions apply:

1: in the presence of a suitable catalyst such as for example copper iodide, a suitable ligand such as for example L-proline, a suitable base such as for example cesium carbonate, a suitable solvent such as for example N,N-dimethylformamide, at a suitable temperature such as 110° C., in a sealed vessel;

2: in the presence of a suitable catalyst such as for example palladium acetate, a suitable ligand such as for example 2,2'-bis(diphenylphosphino)-1,1'-binaphthyl, a suitable base such as for example cesium carbonate, a suitable solvent such as for example dioxane, at a suitable temperature such as 100° C.;

3: at a suitable temperature such as for example 80° C., in a suitable solvent such as for example ethanol;

4: in case of an acyl chloride, in the presence of a suitable base such as for example diisopropylethylamine, and in a suitable solvent such as for example dichloromethane in case of a carboxylic acid, in the presence of a suitable coupling reagent such as for example 1-(3-dimethyaminopropyl)-3-ethylcarbodiimide hydrochloride, a suitable additive such as for example 1-hydroxybenzotriazole, a suitable base such as for example triethylamine, and in a suitable solvent such as for example a mixture of THF and dichloromethane.

In general, compounds of Formula (I) wherein $R^1$ is $—NH_2$, and wherein the other variables are as shown in Formula (Ik) and (Ika) can alternatively be prepared according to the following reaction Scheme 21, wherein all other variables are defined as above or according to the scope of the present invention.

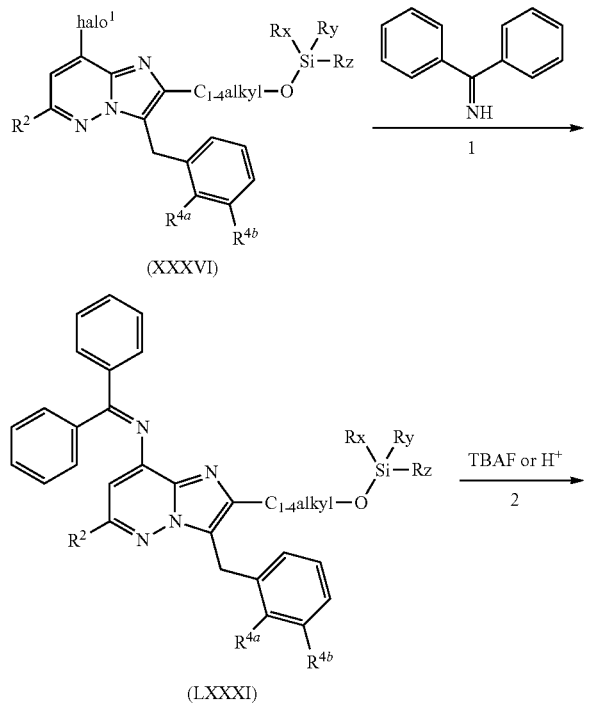

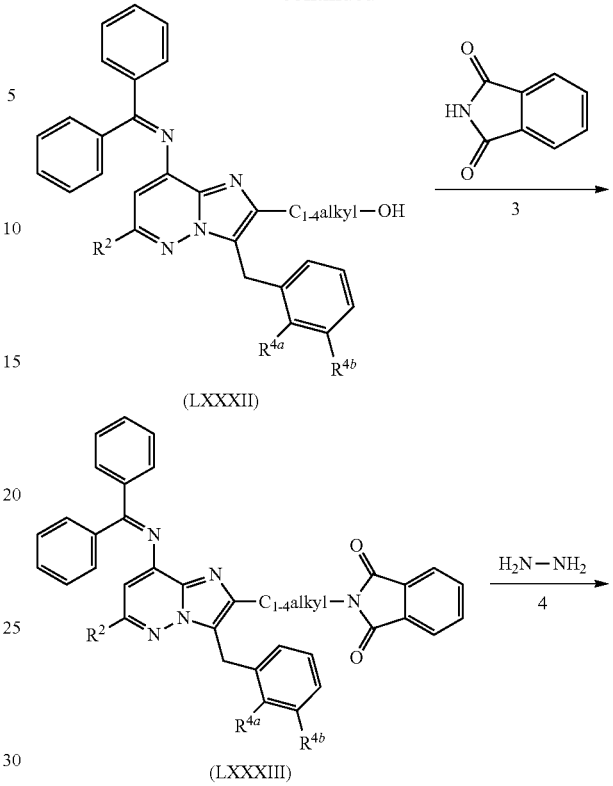

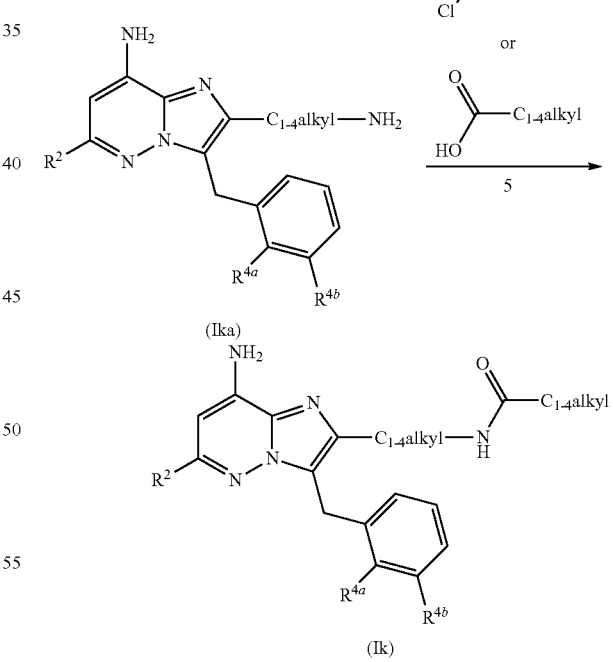

In Scheme 21, the following reaction conditions apply:
1: in the presence of a suitable catalyst such as for example palladium acetate, a suitable ligand such as for example 2,2'-bis(diphenylphosphino)-1,1'-binaphthyl, a suitable base such as for example cesium carbonate, a suitable solvent such as for example dioxane, at a suitable temperature such as 100° C.;

2: in the presence of a suitable reagent such as for example tetrabutylammonium fluoride (TBAF), hydrochloric acid or trifluoroacetic acid in a suitable solvent such as THF, dioxane or dichloromethane;
3: in the presence of a suitable reagent such as for example di-tert-butyl azodicarboxylate, a suitable phosphine such as for example triphenylphosphine, and in a suitable solvent such as for example THF;
4: in case of an acyl chloride, in the presence of a suitable base such as for example diisopropylethylamine, and in a suitable solvent such as for example dichloromethane in case of a carboxylic acid, in the presence of a suitable coupling reagent such as for example 1-(3-dimethyaminopropyl)-3-ethylcarbodiimide hydrochloride, a suitable additive such as for example 1-hydroxybenzotriazole, a suitable base such as for example triethylamine, and in a suitable solvent such as for example a mixture of THF and dichloromethane.

In general, compounds of Formula (I) wherein $R^1$ is —C(=O)NH$_2$, and wherein the other variables are as shown in Formula (Iea), compounds of Formula (I) wherein $R^1$ is restricted to $R^{1a}$ being

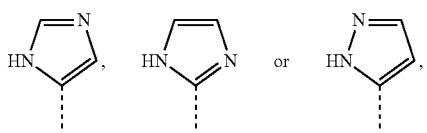

and wherein the other variables are as shown in Formula (Iga); and compounds of Formula (I) wherein $R^1$ is —NH$_2$, and wherein the other variables are as shown in Formula (Iha) can be prepared according to the following reaction Scheme 22 wherein all other variables are defined as above or according to the scope of the present invention.

Scheme 22

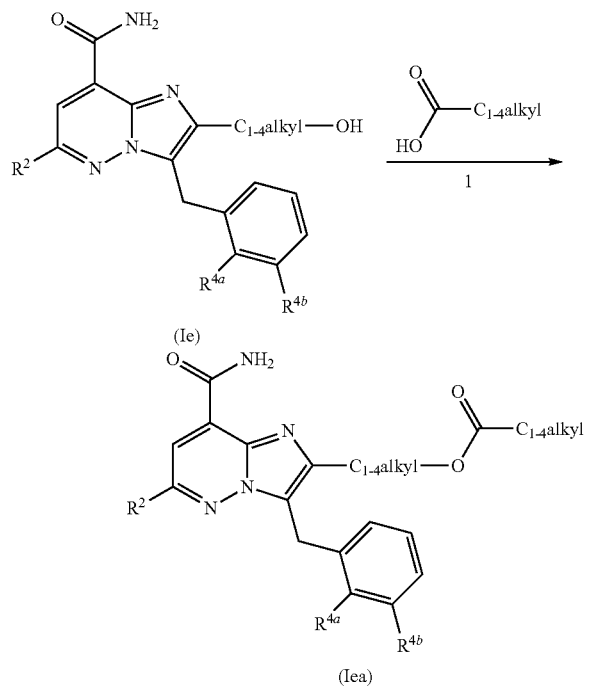

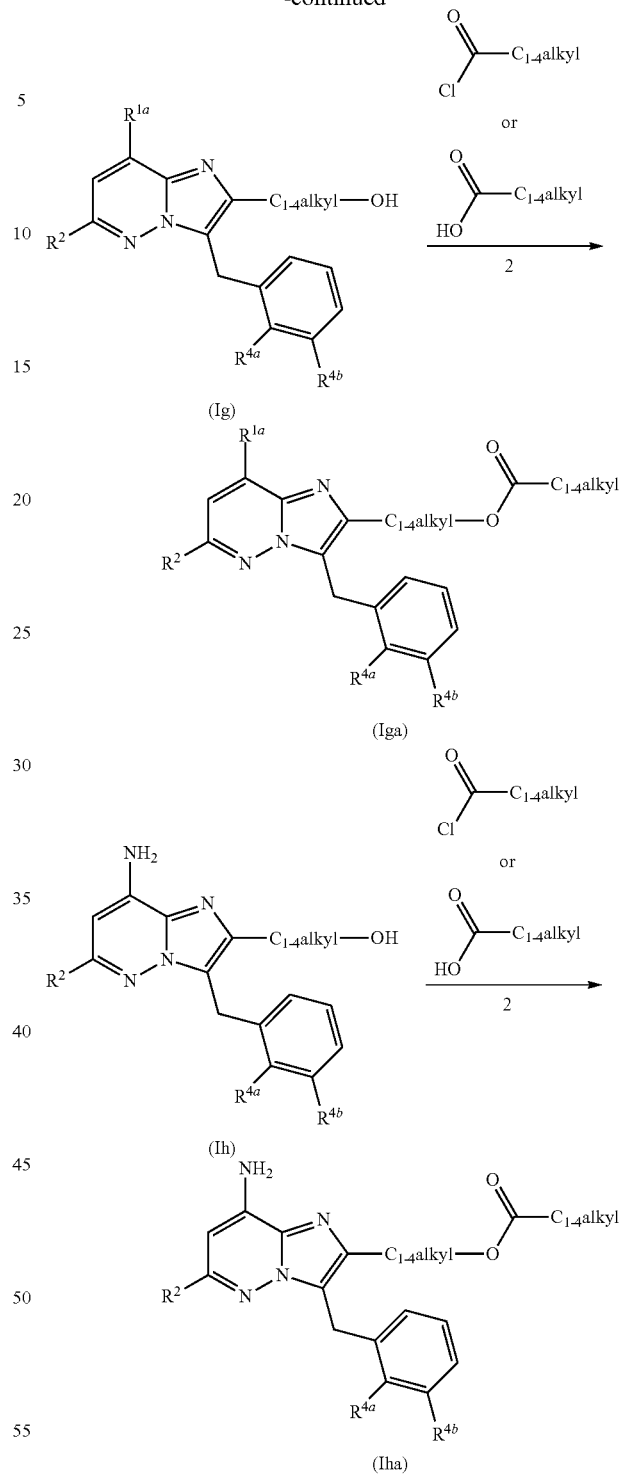

In Scheme 22, the following reaction conditions apply:
1: in the presence of a suitable base such as for example triethylamine, and in a suitable solvent such as for example dichloromethane
2: in case of an acyl chloride, in the presence of a suitable base such as for example triethylamine, and in a suitable solvent such as for example dichloromethane in case of a carboxylic acid, in the presence of a suitable coupling reagent such as for example 1-[bis(dimethylamino)

methylene]-1H-1,2,3-triazolo[4,5-b]pyridinium 3-oxide, a suitable additive such as for example dimethylaminopyridine, a suitable base such as for example diisopropylethylamine, and in a suitable solvent such as for example DMF.

In general, compounds of Formula (I) wherein $R^1$ is —C(=O)NH$_2$, and wherein the other variables are as shown in Formula (Ieb), compounds of Formula (I) wherein $R^1$ is restricted to $R^{1a}$ being

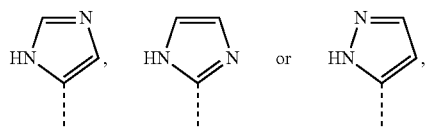

and wherein the other variables are as shown in Formula (Igb); and compounds of Formula (I) wherein $R^1$ is —NH$_2$, and wherein the other variables are as shown in Formula (Ihb) can be prepared according to the following reaction Scheme 23.

In scheme 23, $R^{11}$ represents —CH(NH$_2$)—C$_{1-4}$alkyl, —CH(NH$_2$)—C$_{1-4}$alkyl-Ar or

and PG$^1$ represent a protective group such as for example tert-butoxycarbonyl or benzyloxycarbonyl.

All other variables are defined as above or according to the scope of the present invention.

Scheme 23

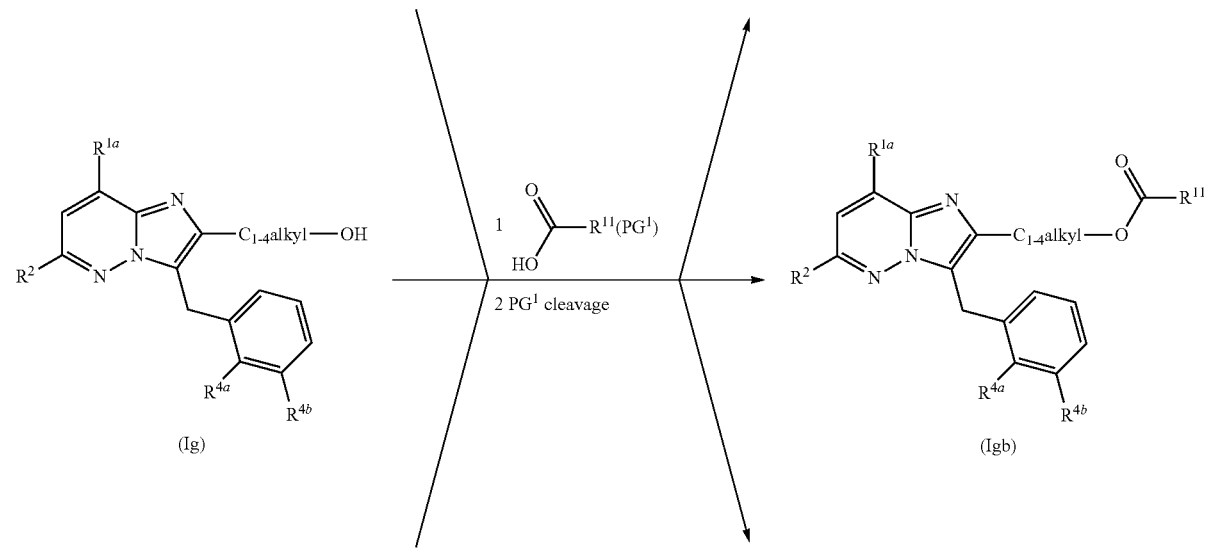

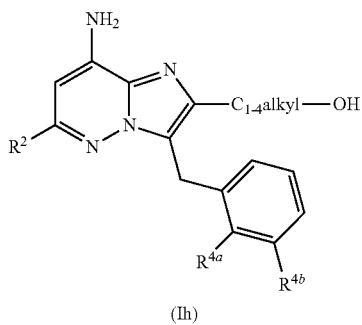

(Ih)

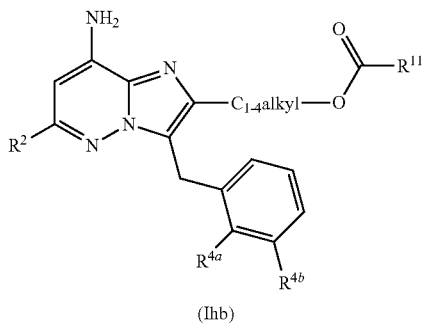

(Ihb)

In Scheme 23, the following reaction conditions apply:
1: in the presence of a suitable coupling reagent such as for example 1-[bis(dimethylamino)methylene]-1H-1,2,3-triazolo[4,5-b]pyridinium 3-oxide, a suitable additive such as for example dimethylaminopyridine, a suitable base such as for example diisopropylethylamine, and in a suitable solvent such as for example of DMF;
2: in the presence of an acide such as for example trifluoroacetic acid or hydrogen chloride in a suitable solvent such as for example dichloromethane or methanol. Alternatively, in the presence of palladium on charcoal, in a suitable solvent such as methanol under an atmosphere of hydrogen.

Intermediates of Formula (XXXV) (used in Scheme 7) can alternatively be prepared according to the following reaction Scheme 24, wherein all variables are defined as above or according to the scope of the present invention.

Scheme 24

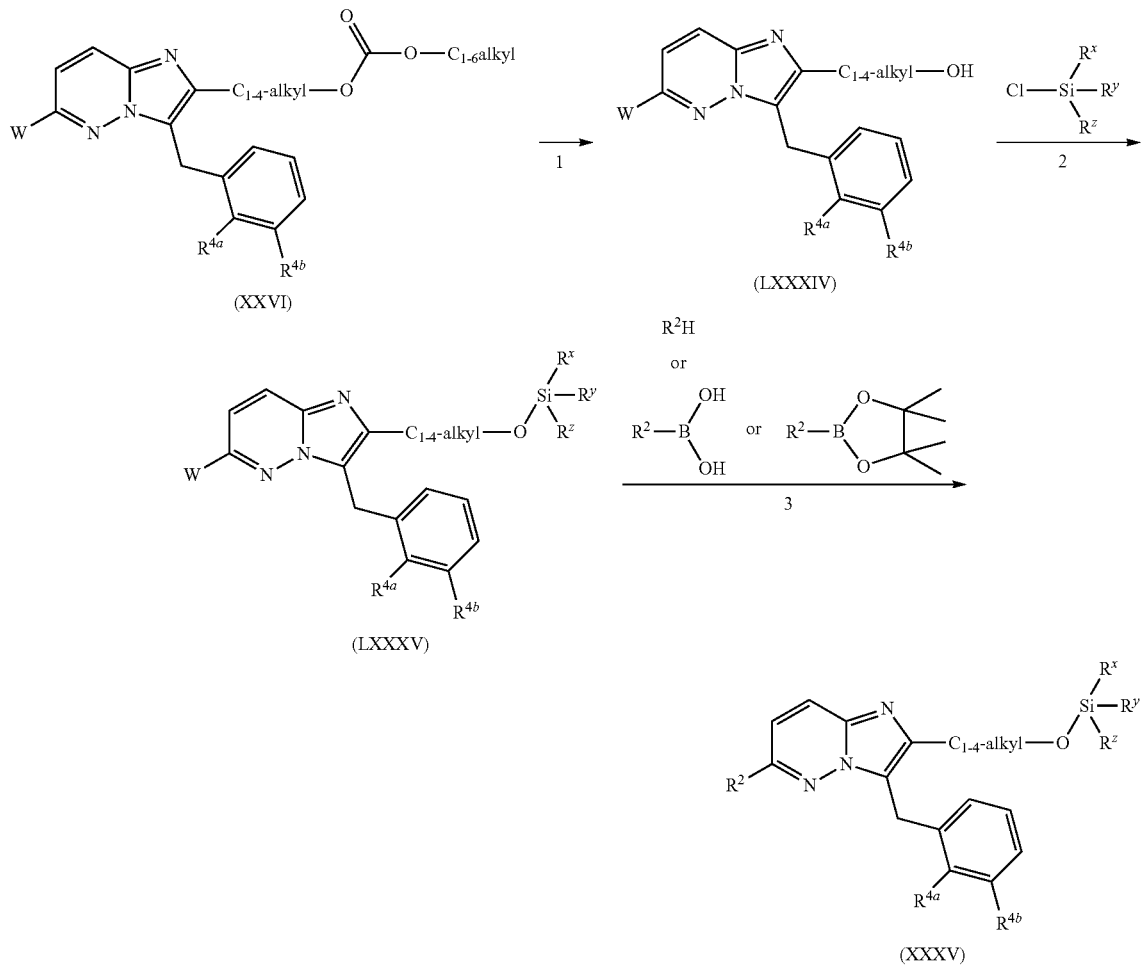

In Scheme 24 the following reaction conditions apply:
1: in the presence of a suitable base such as for example sodium hydroxide monohydrate, a suitable solvent such as for example a mixture of tetrahydrofuran and ethanol.
2: in the presence of a suitable activating agent such as for example imidazole and a suitable solvent such as for example N,N-dimethylformamide;
3: in case of $R_2H$:
Without any solvent at a suitable temperature such as 120° C.
Alternatively in the presence of a suitable ligand such as Ruphos, a suitable catalyst such as for example tris(dibenzylideneacetone)dipalladium ($Pd_2dba_3$), a suitable base such as for example $Cs_2CO_3$, and a suitable solvent such as for example 2-methyl-2-butanol, at a suitable temperature such as for example 80° C.;
in case of $R_2B(OH)_2$ or $R_2$(4,4,5,5-tetramethyl-1,3,2-dioxaborolane), in the presence of a suitable catalyst such as for example 1,1'-bis(diphenylphosphino)ferrocene palladium(II)dichloride dichloromethane adduct, a suitable base such as for example potassium phosphate, and a suitable solvent such as for example a mixture dioxane and water, at a suitable temperature such as for example at 80° C.

In general, compounds of Formula (I) wherein $R^1$ is —$NH_2$, and wherein the other variables are as shown in Formula (Iha) can be prepared according to the following reaction Scheme 25 wherein all other variables are defined as above or according to the scope of the present invention.

Scheme 25

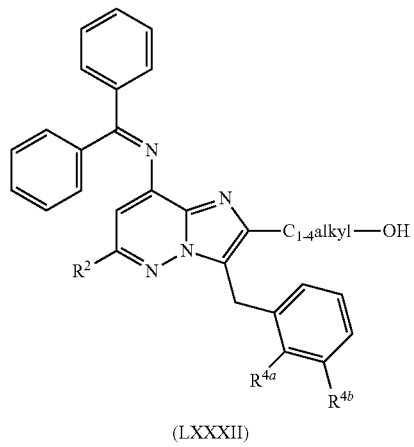

(LXXXII)

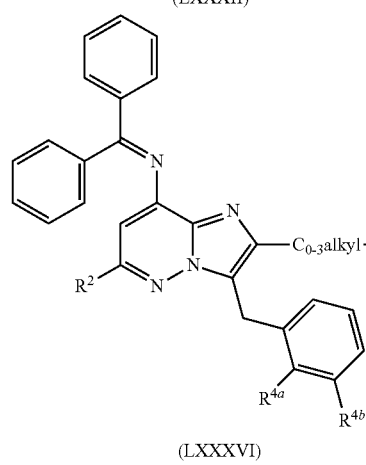

(LXXXVI)

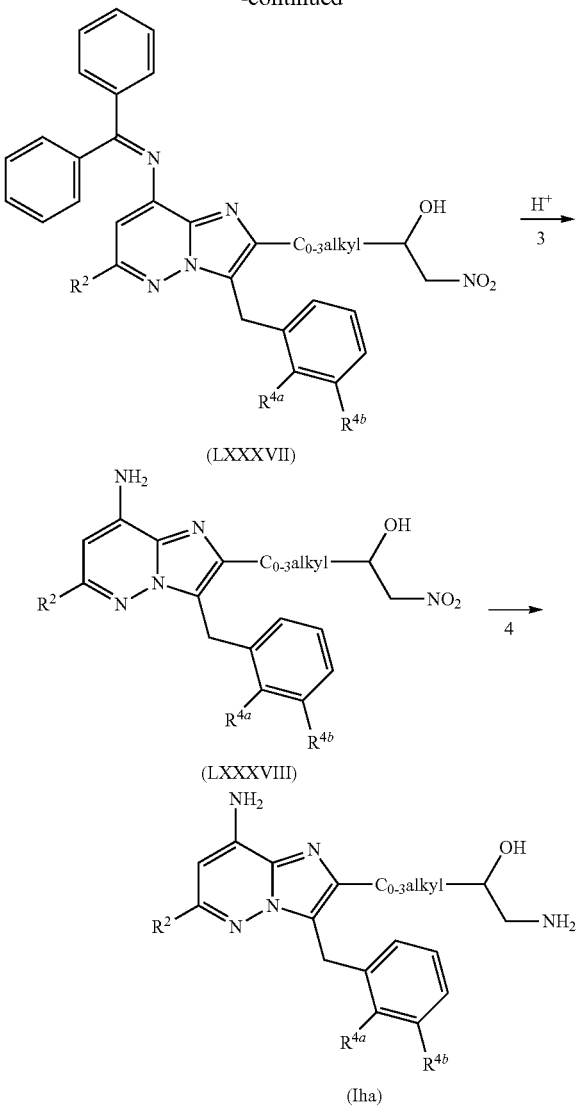

(LXXXVII)

(LXXXVIII)

(Iha)

In Scheme 25 the following reaction conditions apply:
1: at a suitable temperature such as for example 80° C., in the presence of a suitable oxidative reagent such as for example manganese dioxide, in a suitable solvent such as for example toluene;
2: at a suitable temperature such as for example room temperature, in the presence of a suitable base such as for example sodium hydroxide, in a suitable solvent such as for example tetrahydrofuran;
3: at a suitable temperature such as for example room temperature, in the presence of a suitable acid such as for example hydrochloric acid, in a suitable solvent such as for example tetrahydrofuran;
4: at a suitable temperature such as for example 0° C., in the presence of a suitable reducing agent such as for example sodium borohydride, in the presence of a suitable catalyst such as for example nickel (II) chloride, in a suitable solvent such as for example methanol.

In general, compounds of Formula (I) wherein $R^1$ is —$NH_2$, and wherein the other variables are as shown in Formula (Ih) can be alternatively prepared according to the following reaction Scheme 26 wherein all other variables are defined as above or according to the scope of the present invention.

Scheme 26

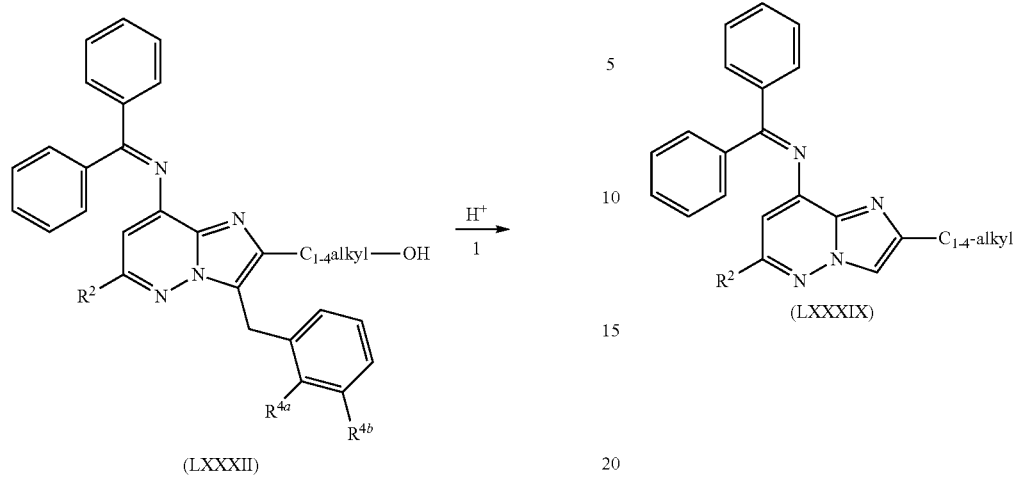

(LXXXII)

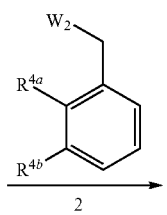

(LXXXIX)

(Ih)

(XC)

In Scheme 26 the following reaction conditions apply:

1: at a suitable temperature such as for example room temperature, in the presence of a suitable acid such as for example aqueous hydrochloric acid, in a suitable solvent such as for example tetrahydrofuran.

In general, compounds of Formula (I) wherein $R^1$ is —$NH_2$, and wherein the other variables are as shown in Formula (Id), can be alternatively prepared according to the following reaction Scheme 27. All other variables in Scheme 27 are defined according to the scope of the present invention.

Scheme 27

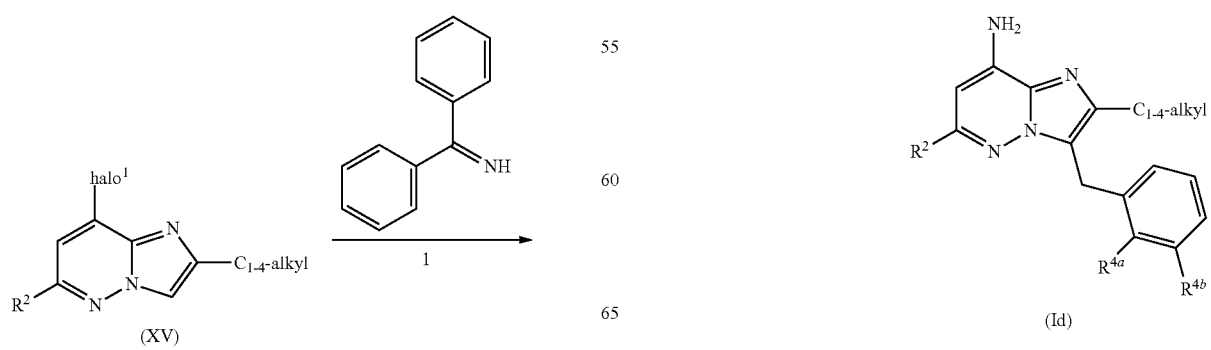

(XV)

(Id)

In Scheme 27 the following reaction conditions apply:

1: in the presence of a suitable catalyst such as for example palladium acetate, a suitable ligand such as for example 2,2'-bis(diphenylphosphino)-1,1'-binaphthyl, a suitable base such as for example cesium carbonate, a suitable solvent such as for example dioxane, at a suitable temperature such as 100° C., optionally in a sealed vessel;

2: in the presence of a suitable catalyst such as for example palladium acetate, a suitable ligand such as for example 2,2'-bis(diphenylphosphino)-1,1'-binaphthyl, a suitable base such as for example cesium carbonate, a suitable solvent such as for example dioxane, at a suitable temperature such as 115° C., in a sealed vessel;

3: at a suitable temperature such as for example 60° C., in the presence of a suitable acid such as for example aqueous hydrochloric acid, in a suitable solvent such as for example tetrahydrofuran;

In general, compounds of Formula (I) wherein $R^1$ is a —$NH_2$, and wherein the other variables are as shown in Formula (Ii) can be alternatively prepared according to the following reaction Scheme 28. In scheme 10, $R^9$ is defined as H or $CH_3$, and $R^{10}$ is defined as —$C_{1-4}$alkyl-$SO_2$—$CH_3$ or —$C_{1-4}$alkyl-OH. All other variables in Scheme 28 are defined as above or according to the scope of the present invention.

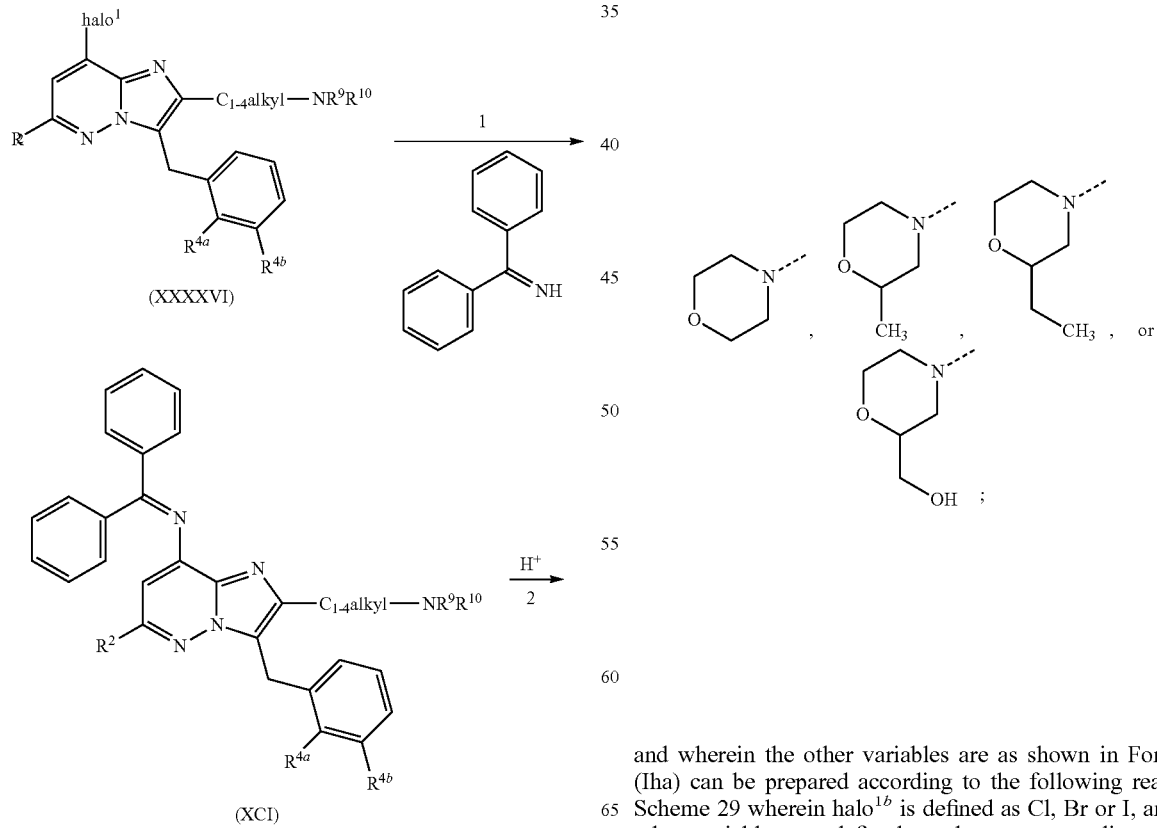

Scheme 28

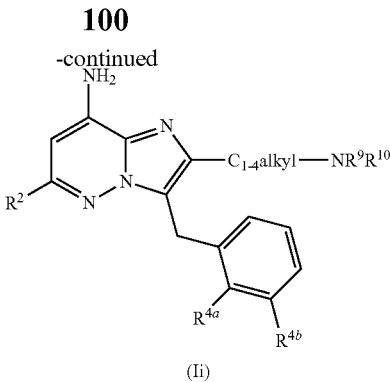

(Ii)

In Scheme 28 the following reaction conditions apply:

1: in the presence of a suitable catalyst such as for example palladium acetate, a suitable ligand such as for example 2,2'-bis(diphenylphosphino)-1,1'-binaphthyl, a suitable base such as for example cesium carbonate, a suitable solvent such as for example dioxane, at a suitable temperature such as 100° C., optionally in a sealed vessel;

2: at a suitable temperature such as for example room temperature, in the presence of a suitable acid such as for example aqueous hydrochloric acid, in a suitable solvent such as for example tetrahydrofuran;

In general, compounds of Formula (I) wherein $R^1$ is —$NH_2$, wherein $R^2$ is restricted to $R^{2a}$ being and wherein the other variables are as shown in Formula (Iha) can be prepared according to the following reaction Scheme 29 wherein $halo^{1b}$ is defined as Cl, Br or I, and all other variables are defined as above or according to the scope of the present invention.

Scheme 29
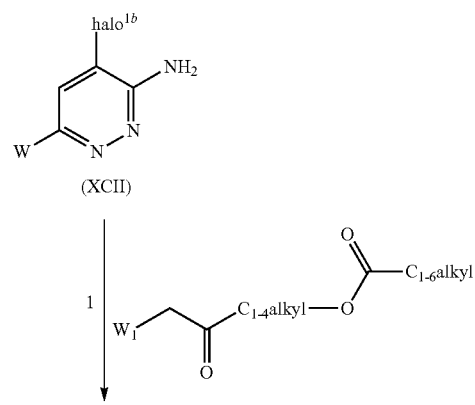
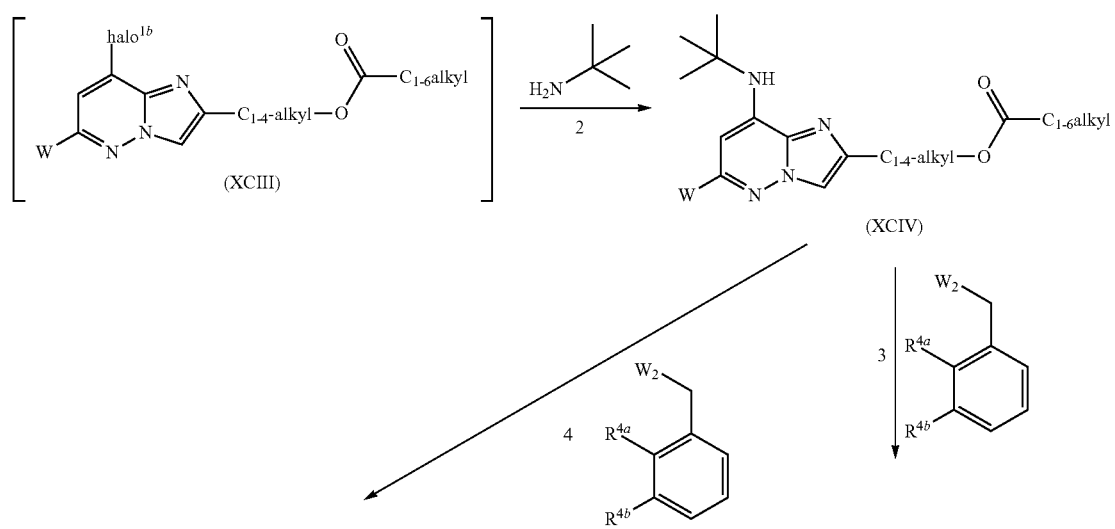
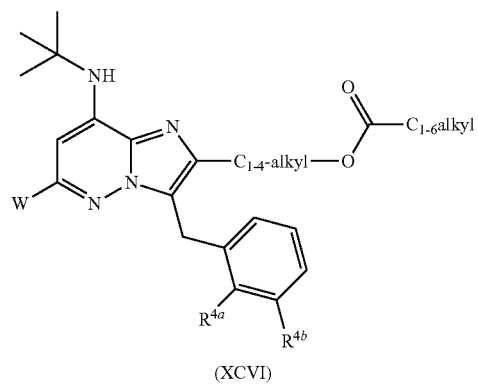
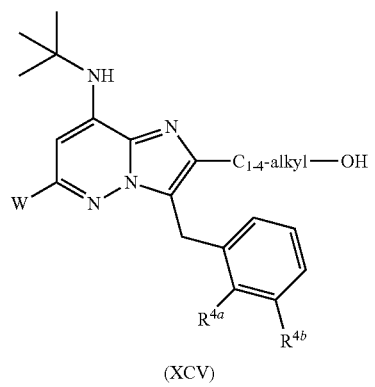

-continued

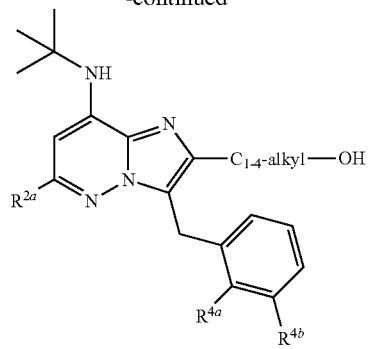

(XCVII)

6 | H⁺

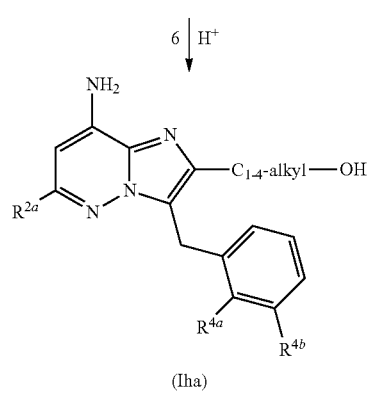

(Iha)

In Scheme 29 the following reaction conditions apply:
1: in a suitable solvent such as for example N-methyl-2-pyrrolidinone, at a suitable temperature ranged between 70° C. and 80° C., optionally in the presence of molecular sieve 4 Å,
2: in the presence of a suitable base such as for example diisopropylamine, in a suitable solvent such as for example N-methyl-2-pyrrolidinone, at a suitable temperature ranged between 80° C. and 90° C.;
3: in the presence of a suitable catalyst such as for example palladium acetate, a suitable ligand such as triphenylphosphine, a suitable base such as for example $K_2CO_3$, a suitable solvent such as for example dioxane, and a suitable temperature such as for example 120° C., optionally in a sealed vessel;
4: in the presence of a suitable catalyst such as for example palladium acetate, a suitable ligand such as triphenylphosphine, a suitable base such as for example $K_2CO_3$, a suitable solvent such as for example dioxane, and a suitable temperature such as for example 100° C., optionally in a sealed vessel;
5: In the presence of a suitable catalyst such as for example palladium acetate (Pd(Oac)₂), a suitable ligand such as for example 4,5-Bis(diphenylphosphino)-9,9-dimethylxanthene (Xantphos), a suitable base such as for example sodium phenoxide trihydrate or aqueous sodium hydroxide, in a suitable solvent such as for example dioxane, at a suitable temperature ranged between 100 to 120° C.;
6: In the presence of a suitable acid such as for example aqueous hydrochloric acid, in a suitable solvent such as for example methanol, at a suitable temperature such as for example 65° C. or solvent reflux.

In general, compounds of Formula (I) wherein $R^1$ is —$NH_2$, wherein $R^2$ is restricted to $R^{2a}$ being

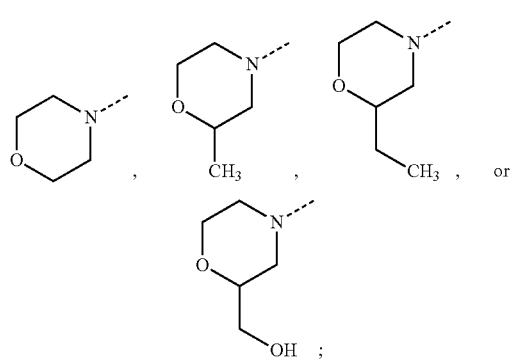

and wherein the other variables are as shown in Formula (Ida) can be prepared according to the following reaction Scheme 30 wherein halo$^{1b}$ is defined as Cl, Br or I, and all other variables are defined as above or according to the scope of the present invention.

Scheme 30

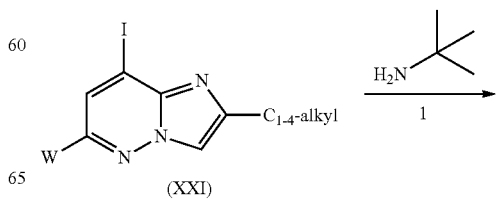

(XXI)

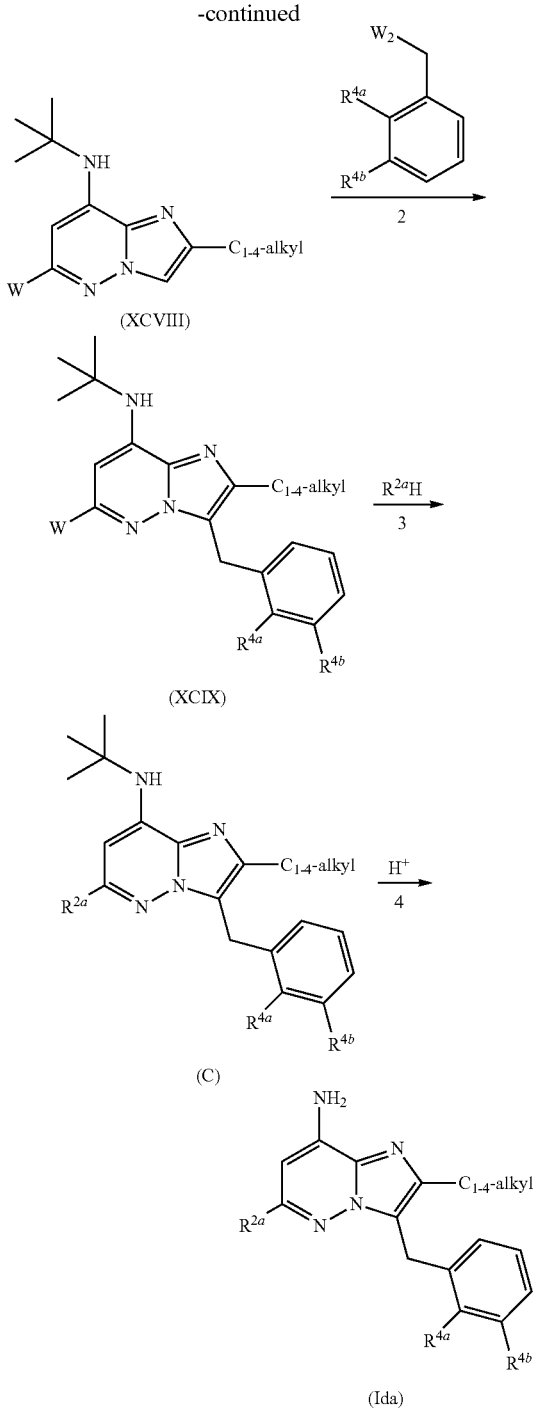

In Scheme 30 the following reaction conditions apply:

1: in the presence of a suitable base such as for example diisopropylamine, in a suitable solvent such as for example N-methyl-2-pyrrolidinone, at a suitable temperature ranged between 80° C. and 90° C.;

2: in the presence of a suitable catalyst such as for example palladium acetate, a suitable ligand such as triphenylphosphine, a suitable base such as for example K$_2$CO$_3$, a suitable solvent such as for example dioxane, and a suitable temperature such as for example 120° C., optionally in a sealed vessel;

3: in the presence of a suitable catalyst such as for example palladium acetate, a suitable ligand such as triphenylphosphine, a suitable base such as for example K$_2$CO$_3$, a suitable solvent such as for example dioxane, and a suitable temperature such as for example 100° C., optionally in a sealed vessel;

4: In the presence of a suitable catalyst such as for example palladium acetate (Pd(Oac)$_2$), a suitable ligand such as for example 4,5-Bis(diphenylphosphino)-9,9-dimethylxanthene (Xantphos), a suitable base such as for example sodium phenoxide trihydrate or aqueous sodium hydroxide, in a suitable solvant such as for example dioxane, at a suitable temperature ranged between 100 to 120° C.;

6: In the presence of a suitable acid such as for example aqueous hydrochloric acid, in a suitable solvent such as for example methanol, at a suitable temperature such as for example 65° C. or solvent reflux.

In all these preparations, the reaction products may be isolated from the reaction medium and, if necessary, further purified according to methodologies generally known in the art such as, for example, extraction, crystallization, trituration and chromatography.

The chirally pure forms of the compounds of Formula (I) form a preferred group of compounds. It is therefore that the chirally pure forms of the intermediates and their salt forms are particularly useful in the preparation of chirally pure compounds of Formula (I). Also enantiomeric mixtures of the intermediates are useful in the preparation of compounds of Formula (I) with the corresponding configuration.

Pharmacology

It has been found that the compounds of the present invention inhibit PI3Kβ kinase activity, and optionally also have PI3Kδ inhibitory activity. Some of the compounds of the present invention may undergo metabolism to a more active form in vivo (prodrugs).

It is therefore anticipated that the compounds according to the present invention or pharmaceutical compositions thereof may be useful for treating or preventing, in particular treating, of diseases such as cancer, autoimmune disorders, cardiovascular diseases, inflammatory diseases, neurodegenerative diseases, allergy, pancreatitis, asthma, multiorgan failure, kidney diseases, platelet aggregation, sperm motility, transplantation rejection, graft rejection, lung injuries and the like; in particular cancer.

Because the pharmaceutically active compounds of the present invention are active as PI3Kβ inhibitors, they exhibit therapeutic utility in treatment or prevention, in particular treatment, of susceptible neoplasms, particularly those neoplasms that exhibit a PTEN deficiency.

As used herein, the phrase "PTEN deficient" or "PTEN deficiency" shall describe tumors with deficiencies of the tumor suppressor function of PTEN (Phosphatase and Tensin Homolog). Such deficiency includes mutation in the PTEN gene, reduction or absence of PTEN proteins when compared to PTEN wild-type, or mutation or absence of other genes that cause suppression of PTEN function.

"Susceptible neoplasm" as used herein refers to neoplasms which are susceptible to treatment by a kinase inhibitor and particularly neoplasms that are susceptible to treatment by a PI3Kβ inhibitor. Neoplasms which have been associated with inappropriate activity of the PTEN phosphatase and particularly neoplasms which exhibit mutation of PTEN, or mutation of an upstream activator of PI3Kβ kinase or overexpression of an upstream activator of PI3Kβ kinase, and are therefore susceptible to treatment with an PI3Kβ inhibitor, are known in the art, and include both primary and metastatic tumors and cancers. According to an embodiment, description of the treatment of a susceptible neoplasm may be used interchangeably with description of the treatment of a cancer.

According to one embodiment, "susceptible neoplasms" include but are not limited to PTEN-deficient neoplasms listed as follows: brain (gliomas), glioblastomas, leukemias, Bannayan-Zonana syndrome, Cowden disease, Lhermitte-Duclos disease, breast cancer, inflammatory breast cancer, colorectal cancer Wilm's tumor, Ewing's sarcoma, Rhabdomyosarcoma, ependymoma, medulloblastoma, colon cancer, head and neck cancer, liver cancer, kidney cancer, lung cancer, melanoma, squamous cell carcinoma, ovarian cancer, pancreatic cancer, prostate cancer, sarcoma cancer, osteosarcoma, giant cell tumor of bone, thyroid cancer, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, Plasmacytoma, Immunoblastic large cell leukemia, Mantle cell leukemia, Multiple myeloma, Megakaryoblastic leukemia, Acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, cervical cancer, vulval cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), and testicular cancer.

According to an alternative embodiment, the term "susceptible neoplasm" includes and is limited to hormone refractory prostate cancer, non-small-cell lung cancer, endometrial cancer, gastric cancer, melanoma, head and neck cancer, breast cancer, including tripnegative breast cancer, and glioma.

In an embodiment, the term "susceptible neoplasm" includes and is limited to prostate cancer, in particular hormone refractory prostate cancer.

The compounds of the present invention may also have therapeutic applications in sensitising tumour cells for radiotherapy and chemotherapy.

Hence the compounds of the present invention may be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogoues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

The invention relates to compounds of Formula (I) and N-oxides, pharmaceutically acceptable addition salts, and solvates thereof, for use as a medicament.

The invention also relates to compounds of Formula (I) and N-oxides, pharmaceutically acceptable addition salts, and solvates thereof, for use in the inhibition of PI3Kβ kinase activity and optionally also for use in the inhibition of PI3Kδ.

The compounds of the present invention can be "anticancer agents", which term also encompasses "anti-tumor cell growth agents" and "anti-neoplastic agents".

The invention also relates to compounds of Formula (I) and N-oxides, pharmaceutically acceptable addition salts, and solvates thereof, for use in the treatment of diseases mentioned above.

The invention also relates to compounds of Formula (I) and N-oxides, pharmaceutically acceptable addition salts, and solvates thereof, for the treatment or prevention, in particular for the treatment, of said diseases.

The invention also relates to compounds of Formula (I) and N-oxides, pharmaceutically acceptable addition salts, and solvates thereof, for the treatment or prevention, in particular in the treatment, of PI3Kβ mediated diseases or conditions.

The invention also relates to compounds of Formula (I) and N-oxides, pharmaceutically acceptable addition salts, and solvates thereof, for the treatment or prevention, in particular in the treatment, of PI3Kβ and optionally PI3Kδ mediated diseases or conditions.

The invention also relates to the use of compounds of Formula (I) and N-oxides, pharmaceutically acceptable addition salts, and solvates thereof, for the manufacture of a medicament.

The invention also relates to the use of compounds of Formula (I) and N-oxides, pharmaceutically acceptable addition salts, and solvates thereof, for the manufacture of a medicament for the inhibition of PI3Kβ.

The invention also relates to the use of compounds of Formula (I) and N-oxides, pharmaceutically acceptable addition salts, and solvates thereof, for the manufacture of a medicament for the inhibition of PI3Kβ and optionally also for the inhibition of PI3Kδ.

The invention also relates to the use of compounds of Formula (I) and N-oxides, pharmaceutically acceptable addition salts, and solvates thereof, for the manufacture of a medicament for the treatment or prevention, in particular for the treatment, of any one of the disease conditions mentioned hereinbefore.

The invention also relates to the use of compounds of Formula (I) and N-oxides, pharmaceutically acceptable addition salts, and solvates thereof, for the manufacture of a medicament for the treatment of any one of the disease conditions mentioned hereinbefore.

The compounds of Formula (I) and N-oxides, pharmaceutically acceptable addition salts, and solvates thereof, can be administered to mammals, preferably humans for the treatment or prevention of any one of the diseases mentioned hereinbefore.

In view of the utility of the compounds of Formula (I) and N-oxides, pharmaceutically acceptable addition salts, and solvates thereof, there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I) or a N-oxide, a pharmaceutically acceptable addition salt, or a solvate thereof, to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent cancer or cancer-related conditions, may be administered alone or in combination with one or more additional therapeutic agents. Combination therapy includes administration of a single pharmaceutical dosage formulation which contains a compound of Formula (I), a N-oxide, a pharmaceutically acceptable addition salt, or a solvate thereof, and one or more additional therapeutic agents, as well as administration of the compound of Formula (I), a N-oxide, a pharmaceutically acceptable addition salt, or a solvate thereof, and each additional therapeutic agents in its own separate pharmaceutical dosage formulation. For example, a compound of Formula (I), a N-oxide, a pharmaceutically acceptable addition salt, or a solvate thereof, and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound of Formula (I), a N-oxide, a pharmaceutically acceptable addition salt, or a solvate thereof.

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds of Formula (I) and N-oxides, pharmaceutically acceptable addition salts, and solvates thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing a compound of Formula (I), a N-oxide, a pharmaceutically acceptable addition salt, or a solvate thereof, may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In order to enhance the solubility and/or the stability of the compounds of Formula (I) and N-oxides, pharmaceutically acceptable addition salts, and solvates thereof, in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), a N-oxide, a pharmaceutically acceptable addition salt, or a solvate thereof, and from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anti-cancer agent is envisaged, especially for use as a medicine, more specifically for use in the treatment of cancer or related diseases.

For the treatment of the above conditions, the compounds of the invention may be advantageously employed in combination with one or more other medicinal agents, more particularly, with other anti-cancer agents or adjuvants in cancer therapy.

Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetrarcin A;

glucocorticolden for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example antinomycin D, bleomycin, mitomycin C, dactinomycin, carminomycin, daunomycin, levamisole, plicamycin, mithramycin;

antimetabolites for example clofarabine, aminopterin, cytosine arabinoside or methotrexate, azacitidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

farnesyltransferase inhibitors for example tipifamib;

histone deacetylase (HDAC) inhibitors for example sodium butyrate, suberoylanilide hydroxamic acid (SAHA), depsipeptide (FR 901228), NVP-LAQ824, R306465, JNJ-26481585, trichostatin A, vorinostat;

Inhibitors of the ubiquitin-proteasome pathway for example PS-341, MLN 0.41 or bortezomib;

Yondelis;

Telomerase inhibitors for example telomestatin;

Matrix metalloproteinase inhibitors for example batimastat, marimastat, prinostat or metastat;

Recombinant interleukins for example aldesleukin, denileukin diftitox, interferon alfa 2a, interferon alfa 2b, peginterferon alfa 2b;

MAPK inhibitors;

Retinoids for example alitretinoin, bexarotene, tretinoin;

Arsenic trioxide;

Asparaginase;

Steroids for example dromostanolone propionate, megestrol acetate, nandrolone (decanoate, phenpropionate), dexamethasone;

Gonadotropin releasing hormone agonists or antagonists for example abarelix, goserelin acetate, histrelin acetate, leuprolide acetate;

Thalidomide, lenalidomide;

Mercaptopurine, mitotane, pamidronate, pegademase, pegaspargase, rasburicase;

BH3 mimetics for example ABT-737;

MEK inhibitors for example PD98059, AZD6244, CI-1040;

colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin;

a steroidal cytochrome P450 17alpha-hydroxylase-17,20-lyase inhibitor (CYP 17), e.g. abiraterone, abiraterone acetate;

Glycolysis inhibitors, such as 2-deoxyglucose;

mTOR inhibitors such as rapamycins and rapalogs, and mTOR kinase inhibitors;

PI3K inhibitors and dual mTOR/PI3K inhibitors;

autophagy inhibitors, such as chloroquine and hydroxychloroquine;

androgen receptor antagonist drugs, e.g. enzalutamide or ARN-509;

antibodies that re-activate the immune response to tumors, for example nivolumab (anti-PD-1), lambrolizumabi (anti-PD-1), ipilimumab (anti-CTLA4), and MPDL3280A (anti-PD-L 1).

The present invention further relates to a product containing as first active ingredient a compound according to the invention and as further active ingredient one or more anticancer agents, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m$^2$) of body surface area, for example 50 to 400 mg/m$^2$, particularly for cisplatin in a dosage of about 75 mg/m$^2$ and for carboplatin in about 300 mg/m$^2$ per course of treatment.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour *vinca* alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m²) of body surface area, for example 120 to 200 mg/m², particularly for cyclophosphamide in a dosage of about 100 to 500 mg/m², for chlorambucil in a dosage of about 0.1 to 0.2 mg/kg, for carmustine in a dosage of about 150 to 200 mg/m², and for lomustine in a dosage of about 100 to 150 mg/m² per course of treatment.

The anti-tumour anthracycline derivative is advantageously administered in a dosage of 10 to 75 mg per square meter (mg/m²) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m²) of body surface area, or as known in the art, if different. Trastuzumab is advantageously administered in a dosage of 1 to 5 mg per square meter (mg/m) of body surface area, particularly 2 to 4 mg/m² per course of treatment.

These dosages may be administered for example once, twice or more per course of treatment, which may be repeated for example every 7, 14, 21 or 28 days.

The following examples illustrate the present invention. In case no specific stereochemistry is indicated for a stereocenter of a compound, this means that the compound was obtained as a mixture of the R and the S enantiomers.

EXAMPLES

Hereinafter, the term 'DCM' means dichloromethane, 'Me' means methyl, 'Et' means ethyl, 'MeOH' means methanol, 'DMF' means dimethylformamide, 'Et₂O' means diethyl ether, 'EtOAc' means ethyl acetate, 'THF' means tetrahydrofuran, 'ACN' means acetonitrile, 'EtOH' means ethanol, 'DME' means 1,2-dimethoxyethane, 'SFC' means supercritical fluid chromatography, 'MgSO₄' means magnesium sulfate, 'q.s.' means quantum sufficit, 'M.P.' means melting point, 'iPrNH₂' means isopropylamine, 'DIPE' means diisopropylether, 'K₂CO₃' means potassium carbonate, 'Ruphos' means 2-dicyclohexylphosphino-2',6'-diisopropoxbiphenyl, 'Celite®' means diatomaceous earth, 'NH₄Cl' means ammonium chloride, 'Na₂S₂O₃' means sodium thiosulfate, 'Pd₂dba₃' means Tris(dibenzylideneacetone)dipalladium(0), 'Pd(Ph₃)₄' means tetrakis-(triphenylphosphine)palladium(0), 'HATU' means N-[dimethylamino)-(3H-[1,2,3]triazolo-[4,5-B]pyridin-3-yloxy)methylidene]-N-methylmethylaminium hexafluorophosphate, 'BrettPhos' means 2-(dicyclohexylphosphino)3,6-dimethoxy-2',4',6'-triisopropyl-1,1'-biphenyl, 'PdCl₂dppf.DCM' means (1,1'-bis(diphenylphosphino)ferrocene)dichloropalladium-dichloromethane (1:1), 'iPrOH' means isopropanol, 'TFA' means trifluoroacetic acid, 'rt' means room temperature, 'PPh₃' means triphenylphosphine, 'DMAP' means dimethylaminopyridine, 'Pd/C' means palladium on carbon, 'TBAF' means tetrabutylammonium fluoride, 'MTBE' means methyl tert-butyl ether, 'Me-THF' means 2-methyltetrahydrofuran, 'Boc' means t-butoxycarbonyl, 'Ms' means methanesulfonyl (mesyl), 'MsO' means mesylate, 'DIPEA' means diisopropylethylamine, 'Xantphos' means (9,9-dimethyl-9H-xanthene-4,5-diyl)bis[diphenylphosphine], 'XPhos' means dicyclohexyl [2',4',6'-tris(1-methylethyl)[1,1'-biphenyl]-2-yl]-phosphine, 'NMP' means N-methyl-2-pyrrolidone, 'HPLC' means high performance liquid chromatography.

For intermediates that were used in a next reaction step as a crude or as a partially purified intermediate, theoretical mol amounts are indicated in the reaction protocols described below.

A. Preparation of the Intermediate Compounds

Note: in some preparations of intermediate compounds, final compounds were also obtained during the reaction.

Example A1

Preparation of Intermediate 1

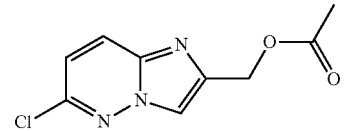

3-Amino-6-chloropyridazine (50 g; 386 mmol) was dissolved in DMF (500 mL). 1-acetoxy-3-chloroacetone was added (80 mL; 680 mmol) and the mixture was heated at 90° C. for 15 hours. The reaction was cooled to room temperature, poured into cooled water and EtOAc, basified with K₂CO₃ powder (pH=10-11). The organic layer was dried over MgSO₄, filtered and evaporated to dryness.

The residue was purified by chromatography over silica gel (irregular SiOH, 50 g; mobile phase: 99% DCM, 1% MeOH). The fractions containing the product were collected and evaporated to dryness yielding 38 g (44%) of intermediate 1.

Alternative Route:

3-Amino-6-chloropyridazine (40 g; 309 mmol) was dissolved in DME (1200 mL). 1-acetoxy-3-chloroacetone (80 mL; 680 mmol) and molecular sieves 4A (40 g) were added. Then the mixture was heated at 90° C. for 15 hours. The reaction was cooled to room temperature, DCM was added and the mixture was filtered over a pad of Celite®. The filtrate was poured into cooled water, basified with K₂CO₃ powder (pH=10-11). The organic layer was separated dried over MgSO₄, filtered and evaporated to dryness.

The residue (51 g) was purified by chromatography over silica gel (irregular SiOH, 900 g; mobile phase: 60% Heptane, 5% MeOH, 35% EtOAc). The fractions containing the product were collected and evaporated to dryness to afford 26.3 g (38%) of intermediate 1.

Preparation of Intermediate 2

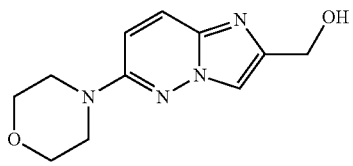 [SMILES: OCc1cn2nc(N3CCOCC3)ccc2n1]

A mixture of intermediate 1 (29.8 g; 132 mmol) and morpholine (330 mL; 375 mmol) was heated at 105° C. for 20 hours. The mixture was cooled and the solvent was evaporated, the residue was poured into cooled water, basified with $K_2CO_3$ powder and DCM was added. The organic layer was separated, dried over $MgSO_4$, filtered and evaporated to dryness.

The residue was crystallized from DCM. The precipitate was filtered and dried to afford 18.8 g (61%) of intermediate 2.

The filtrate was purified by chromatography over silica gel (irregular SiOH, 550 g; gradient from 100% DCM to 90% DCM 10% $CH_3OH$ 0.1% $NH_4OH$). The fractions containing the product were collected and evaporated to dryness yielding 17.3 g (54%) of intermediate 2.

Alternative Route:

Lithium aluminum hydride (7.7 g; 202.7 mmol) was added portionwise to a solution of intermediate 103 (28 g; 101.3 mmol) in THF (300 mL) at 0° C. The reaction mixture was stirred overnight at room temperature. The reaction was quenched with water (7.7 mL) then an aqueous solution of sodium hydroxide 1N (7.7 mL). The precipitate was filtered over a pad of Celite® The filtrate was evaporated to afford 20 g of intermediate 2.

Preparation of Intermediate 3

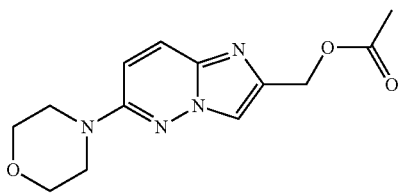 [SMILES: CC(=O)OCc1cn2nc(N3CCOCC3)ccc2n1]

Acetyl chloride (6.8 mL; 96.2 mmol) was added dropwise to a solution of intermediate 2 ((18.8 g; 80.2 mmol), triethylamine (16.8 mL; 0.12 mmol) in DCM (350 mL) at 5° C.

The reaction mixture was stirred for 2 hours at room temperature. The solution was poured into water and the organic layer was separated then dried over $MgSO_4$, filtered and evaporated until dryness.

The residue (23 g) was purified by chromatography over silica gel (irregular SiOH, 330 g; gradient from 100% DCM to 95% DCM 5% $CH_3OH$ 0.1% $NH_4OH$). The fractions containing the product were collected and evaporated to dryness yielding 19.4 g (88%) of intermediate 3

Preparation of Intermediate 4

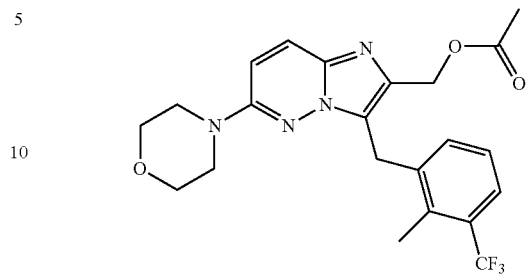

A mixture of intermediate 3 (15.5 g; 56.1 mmol), 1-(chloromethyl)-2-methyl-3-(trifluoromethyl)benzene (14 g; 67.3 mmol) and potassium carbonate (11.6 g; 84 mmol) in dioxane (210 mL) was degassed under nitrogen then triphenylphosphine (2.94 g; 11.2 mmol) and palladium acetate (1.4 g; 6.2 mmol) was added and the reaction mixture was heated at 100° C. for 15 hours. The mixture was cooled down to room temperature, poured into water, basified with $K_2CO_3$ solid and extracted with EtOAc. The organic layer was dried over $MgSO_4$, filtered and evaporated to dryness.

The residue was purified by chromatography over silica gel (irregular SiOH, 550 g; gradient from 100% DCM to 95% DCM 5% $CH_3OH$ 0.1% $NH_4OH$). The fractions containing the product were collected and evaporated to dryness yielding 21.1 g (84%) of intermediate 4.

Preparation of Intermediate 5

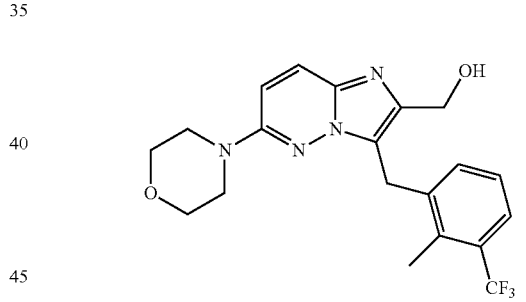

Lithium hydroxide monohydrate (9.8 g; 234 mmol) was added to a mixture of intermediate 4 (21 g; 47 mmol) in methanol (175 mL) and water (56 mL). Then the reaction was stirred at room temperature for 15 hours and the solvent was evaporated.

The residue was taken up with water. The precipitate was filtered, then washed twice with water and dried to afford 43.4 g (98%) intermediate 5

Alternative Route:

A mixture of intermediate 25 (96 g; 241 mmol) and morpholine (500 mL) was heated at 120° C. overnight. After cooling to room temperature, the reaction mixture was concentrated. The residue was washed with a saturated solution of sodium hydrogenocarbonate. The precipitate was filtered, washed with ACN and dried to afford 70 g (71%) of intermediate 5.

Alternative Route:

Under nitrogen, lithium aluminum hydride (0.13 g; 3.3 mmol) was added portionwise to a solution of intermediate 104 (1.25 g; 2.8 mmol) in THF (30 mL) at 0° C. The reaction mixture was stirred for 2 hours at room temperature. The reaction was quenched carefully with water (0.5 mL) then DCM was added. The reaction mixture was dried over MgSO₄, filtered and evaporated. The residue (1.2 g) was solubilized in DCM. The insoluble part was filtered off, washed with DCM and dried to give 0.39 g (34%) of intermediate 5. The filtrate was purified by chromatography over silica gel (irregular SiOH 40 g; gradient from 100% DCM to 95% DCM 5% CH₃OH 0.1% NH₄OH). The fractions containing the product were collected and evaporated to dryness yielding 0.12 g (10%) of intermediate 5 and 0.091 g of intermediate 104.

Preparation of Intermediate 6

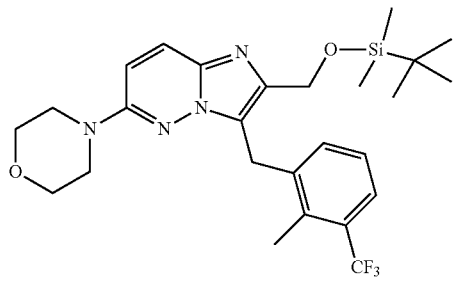 [SMILES: Cc1c(Cc2c(CO[Si](C)(C)C(C)(C)C)nc3ccc(N4CCOCC4)nn23)cccc1C(F)(F)F]

Imidazole (5.34 g; 35.4 mmol) was added to a mixture of intermediate 5 (7.2 g; 17.7 mmol), tert-butyldimethylchlorosilane (5 g; 74.3 mmol) in DMF (25 mL) and the reaction was stirred at room temperature for 15 hours. The mixture was poured into water and extracted with DCM. The organic layer was dried over MgSO₄, filtered and evaporated to dryness.

The residue (12 g) was purified by chromatography over silica gel (irregular SiOH 120 g; gradient from 100% DCM to 95% DCM 5% CH₃OH 0.1% NH₄OH). The fractions containing the product were collected and evaporated to dryness yielding 9.1 g (99%) of intermediate 6.

Preparation of Intermediate 7

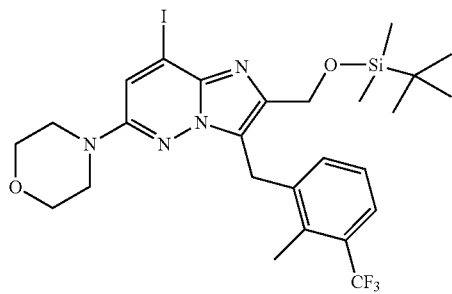 [SMILES: Cc1c(Cc2c(CO[Si](C)(C)C(C)(C)C)nc3c(I)cc(N4CCOCC4)nn23)cccc1C(F)(F)F]

Under nitrogen at −70° C., n-butyllithium 1.6 M in THF (20.6 mL; 33 mmol) was added dropwise to a solution of diisopropylamine (4.5 mL; 31.7 mmol) in THF (35 mL). The solution was stirred at −70° C. for 20 minutes and a solution of intermediate 6 (6.6 g; 12.7 mmol) in THF (70 mL) was added dropwise and the reaction was stirred at −70° C. for 30 minutes. A solution of iodine (3.5 g; 13.9 mmol) in THF (30 mL) was added dropwise and the reaction mixture was stirred 1 hour at −70° C. An aqueous solution of NH₄Cl (10%) was added and the reaction was extracted with EtOAc. The organic layer was separated, dried over MgSO₄, filtered and evaporated to dryness.

The residue (9 g) was purified by chromatography over silica gel (irregular SiOH, 40 g; gradient from 100% DCM to 95% DCM 5% CH₃OH 0.1% NH₄OH). The fractions containing the product were collected and evaporated to dryness yielding 5 g (61%) of intermediate 7.

Example A2

Preparation of Intermediate 8

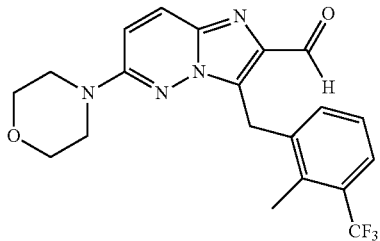 [SMILES: Cc1c(Cc2c(C=O)nc3ccc(N4CCOCC4)nn23)cccc1C(F)(F)F]

A mixture of intermediate 5 (28.1 g; 69.2 mmol) and manganese dioxide (60.2 g; 692 mmol) in dioxane (620 mL) was heated at 80° C. for 1 hour. The mixture was cooled, filtered through a pad of Celite®. The filtrate was evaporated to afford 24.7 g (88%) of intermediate 8.

Preparation of Intermediate 9

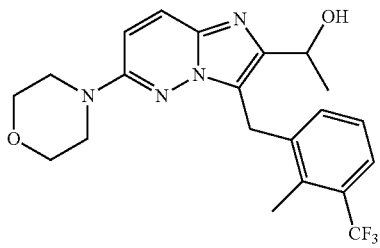 [SMILES: Cc1c(Cc2c(C(C)O)nc3ccc(N4CCOCC4)nn23)cccc1C(F)(F)F]

Methyl magnesium chloride (4.1 mL, 12 mmol) was added dropwise to a solution of intermediate 8 (2.0 g, 4.9 mmol) in dry THF (40 mL) at 0° C. The reaction mixture was stirred at 0° C. for 1 hour then room temperature overnight.

The reaction mixture was poured onto a saturated solution of NH₄Cl and extracted with DCM. The organic layer was separated, dried over MgSO₄, filtered and evaporated to afford 2.1 g (98%) of intermediate 9 which was directly used in the next reaction step without any further treatment.

Preparation of Intermediate 10

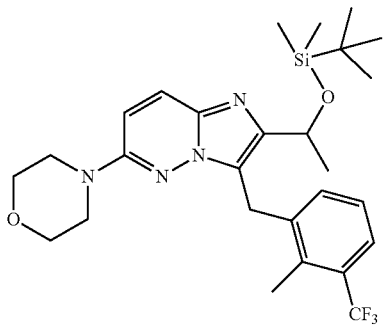 [SMILES: Cc1c(Cc2c(C(C)O[Si](C)(C)C(C)(C)C)nc3ccc(N4CCOCC4)nn23)cccc1C(F)(F)F]

Intermediate 10 was prepared according to an analogous procedure as described for the synthesis of intermediate 6, using intermediate 9 as starting material (99%).

Preparation of Intermediate 11

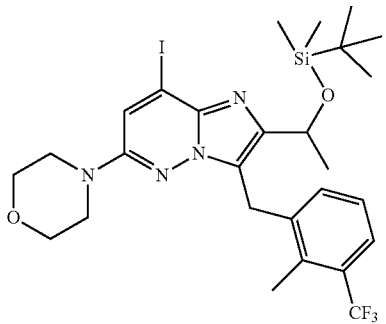 [SMILES: Cc1c(Cc2c(C(C)O[Si](C)(C)C(C)(C)C)nc3c(I)cc(N4CCOCC4)nn23)cccc1C(F)(F)F]

Intermediate 11 was prepared according to an analogous procedure as described for the synthesis of intermediate 7, using intermediate 10 as starting material (50%).

Example A3

Preparation of Intermediate 12

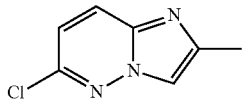

3-Amino-6-chloropyridazine (50 g; 386 mmol) in chloro-2-propanone (154 mL; 1930 mmol) was heated at 90° C. for 15 hours. The reaction was cooled to room temperature, poured into cooled water and EtOAc and basified with a saturated aqueous solution of hydrogenocarbonate. The organic layer was washed twice with water, dried over $MgSO_4$, filtered and evaporated to dryness. The residue was triturated in hexane. The precipitate was filtered, washed with pentane and dried to afford 31 g (48%) of intermediate 12.

Preparation of Intermediate 13

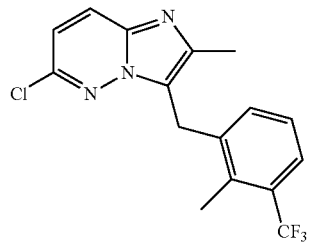 [SMILES: Cc1nc2ccc(Cl)nn2c1Cc1cccc(C(F)(F)F)c1C]

A mixture of intermediate 12 (6.8 g; 40.6 mmol), 1-(chloromethyl)-2-methyl-3-(trifluoromethyl)benzene (11 g; 52.7 mmol) and potassium carbonate (8.4 g; 60.9 mmol) in dioxane (170 mL) was degassed with nitrogen during 10 minutes. Then triphenylphosphine (2.2 g; 8.1 mmol) and palladium acetate (0.91 g; 4.1 mmol) were added and the reaction mixture was heated at 100° C. for 9 hours. The mixture was cooled, poured into water, and EtOAc added. The organic layer was separated, dried over $MgSO_4$, filtered and evaporated to dryness.

The residue was purified by chromatography over silica gel (irregular SiOH, 550 g; gradient from 100% DCM to 97% DCM 3% $CH_3OH$ 0.1% $NH_4OH$). The fractions containing the product were collected and evaporated to dryness yielding 11.2 g (81%) of intermediate 13.

Preparation of Intermediate 14

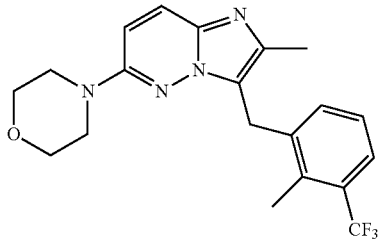 [SMILES: Cc1nc2ccc(N3CCOCC3)nn2c1Cc1cccc(C(F)(F)F)c1C]

A mixture of intermediate 13 (11 g; 32.3 mmol) and morpholine (60 mL; 683 mmol) was heated at 120° C. for 48 hours. The mixture was cooled, evaporated, the residue portioned between water and DCM. The organic layer was dried over $MgSO_4$, filtered and evaporated to dryness.

The residue (14 g) was purified by chromatography over silica gel (irregular SiOH, 330 g; gradient from 100% DCM to 95% DCM 5% $CH_3OH$ 0.1% $NH_4OH$). The fractions containing the product were collected and evaporated to dryness yielding 8.45 g (67%) of intermediate 14.
Alternative Route:

In a sealed tube, a mixture of intermediate 105 (5 g; 22.9 mmol), 1-(chloromethyl)-2-methyl-3-(trifluoromethyl)benzene (6.2 g; 29.8 mmol) and potassium carbonate (4.7 g; 34 mmol) in dioxane (78 mL) was degassed with nitrogen during 10 minutes. Then triphenylphosphine (1.2 g; 4.6 mmol) and palladium acetate (0.54 g; 2.3 mmol) were added and the reaction mixture was heated at 100° C. overnight. The mixture was cooled, solubilized in EtOAc. The organic layer was washed with brine, separated, dried over $MgSO_4$, filtered and evaporated to dryness.

The residue was purified by chromatography over silica gel (irregular SiOH, 300 g; gradient from 100% DCM to 98% DCM 2% CH₃OH 0.1% NH₄OH). The fractions containing the product were collected and evaporated. The residue (7.2 g) was purified by chromatography over silica gel (irregular SiOH, 200 g; gradient from 60% Heptane 5% MeOH 35% EtOAc). The fractions containing the product were collected and evaporated to afford 1.6 g (18%) of intermediate 14 and 1.8 g of intermediate 105.

Preparation of Intermediate 15

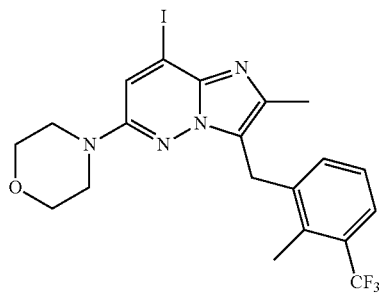 [SMILES: Cc1nc2c(I)cc(N3CCOCC3)nn2c1Cc1cccc(C(F)(F)F)c1C]

Under nitrogen at −70° C., lithium diisoprylamide in 2M in hexanes/THF (27 mL; 54 mmol) was added dropwise to a solution of intermediate 14 (8.4 g; 21.52 mmol) and iodine (5.7 g; 22.6 mmol) in THF (180 mL). The reaction mixture was stirred 1 hour. A 10% aqueous solution of NH₄Cl was added and the product was extracted with EtOAc.

The organic layer was dried over MgSO₄, filtered and evaporated to dryness.

The residue (11 g) was purified by chromatography over silica gel (irregular SiOH, 330 g; gradient from 100% DCM to 95% DCM 5% CH₃OH 0.1% NH₄OH). The fractions containing the product were collected and evaporated to dryness yielding 3.5 g (32%) of intermediate 15.

Example A4

Preparation of Intermediate 16

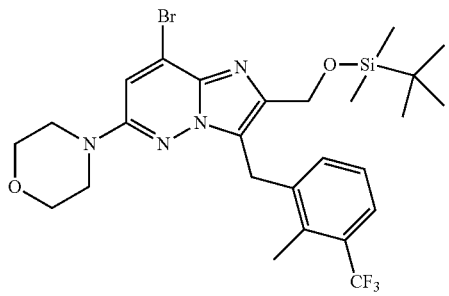 [SMILES: Cc1c(Cc2c(CO[Si](C)(C)C(C)(C)C)nc3c(Br)cc(N4CCOCC4)nn23)cccc1C(F)(F)F]

Under nitrogen at −70° C., n-butyllithium 1.6 M in THF (9.4 mL; 14.9 mmol) was added dropwise to a solution of diisopropylamine (2 mL; 14.4 mmol) in THF (35 mL). The solution was stirred for 20 minutes then a solution of intermediate 6 (3 g; 5.8 mmol) in THF (40 mL) was added dropwise and the reaction was stirred at −70° C. for 1 hour. A solution of bromine (0.36 mL; 6.9 mmol) in THF (30 mL) was added dropwise and the reaction mixture was allowed to warm to −20° C. The reaction mixture was quenched with a 10% aqueous solution of NH₄Cl and EtOAc was added. The organic layer was decanted, separated, washed with brine, dried over MgSO₄, filtered and evaporated to dryness.

The residue (9 g) was purified by chromatography over silica gel (irregular SiOH, 40 g; gradient from 100% DCM to 95% DCM 5% CH₃OH 0.1% NH₄OH). The fractions containing the product were collected and evaporated to dryness yielding 1 g (30%) of intermediate 16.

Preparation of Intermediate 17

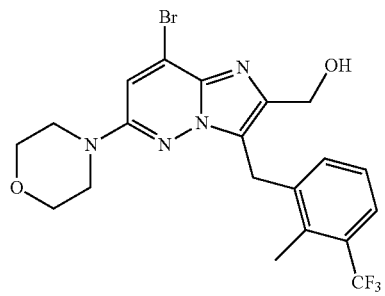 [SMILES: Cc1c(Cc2c(CO)nc3c(Br)cc(N4CCOCC4)nn23)cccc1C(F)(F)F]

Intermediate 17 was prepared according to an analogous procedure as described for the synthesis of intermediate 33, using intermediate 16 as starting material (71%).

Example A5

Preparation of Intermediate 18

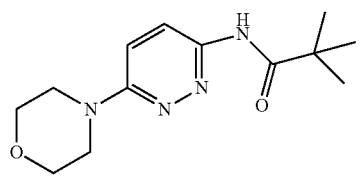 [SMILES: CC(C)(C)C(=O)Nc1ccc(N2CCOCC2)nn1]

A mixture of N-(6-chloro-3-pyridazinyl)-2,2-dimethyl-propanamide (65.3 g; 305.6 mmol) and morpholine (538 mL; 6.1 mmol) was heated at 120° C. for 24 hours. The mixture was cooled and evaporated. The residue was poured into cooled water, basified with K₂CO₃ powder and DCM was added. The organic layer was separated, dried over MgSO₄, filtered and evaporated to dryness.

The residue was crystallized from Et₂O. The precipitate was filtered and dried to afford 69.3 g (87%) of intermediate 18.

Preparation of Intermediate 19

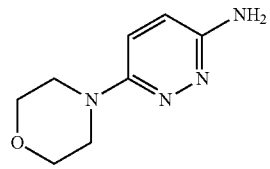 [SMILES: Nc1ccc(N2CCOCC2)nn1]

Intermediate 18 (70 g; 264.8 mmol) in HCl 6N (132 mL; 0.8 mmol) and dioxane (1500 mL) were heated at 70° C. overnight. The reaction was cooled to room temperature, then concentrated and the residue was poured into water. The mixture was basified and saturated with K₂CO₃ powder, and was extracted several times with DCM. The organic layer was dried over MgSO₄, filtered and evaporated until dryness to afford 43.1 g (91%) of intermediate 19.

Preparation of Intermediate 20

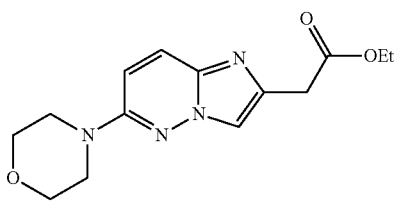 [SMILES: CCOC(=O)Cc1cn2nc(N3CCOCC3)ccc2n1]

Ethyl-4-chloroacetate (45.3 mL; 333 mmol) was added dropwise to a suspension intermediate 19 (24 g; 133 mmol) in EtOH (720 mL). Then, the mixture was heated at 80° C. for 15 hours. The solution was cooled to room temperature and concentrated. The residue was taken up with DCM. The precipitate was filtered off given 11 g of intermediate 19. The filtrate was evaporated to dryness. The residue (60 g) was purified by chromatography over silica gel (irregular SiOH, 1000 g; mobile phase 42% Heptane 8% CH₃OH (0.1% NH₄OH), 50% EtOAc). The fractions containing the product were collected and evaporated to dryness. An intermediate residue (16 g) which was crystallized from Et₂O. The red precipitate was filtered, rinced with Et₂O and dried vaccum to afford 13 g (39%) of intermediate 20.

Preparation of Intermediate 21

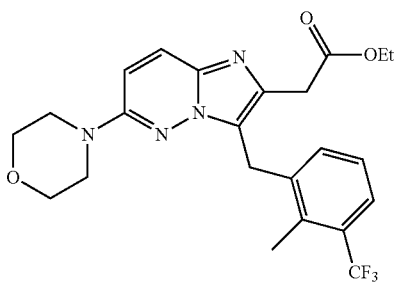 [SMILES: CCOC(=O)Cc1nc2ccc(N3CCOCC3)nn2c1Cc1cccc(C(F)(F)F)c1C]

The experiment was done twice on the same quantities of intermediate 7 (7 g) and, for the work-up and the purification, both experiments were combined.

In a sealed tube, to a mixture of intermediate 20 (7 g; 24.11 mmol), 1-(chloromethyl)-2-methyl-3-(trifluoromethyl)benzene (6.04 g; 28.93 mmol) and potassium carbonate (5 g; 36.17 mmol) in dioxane (105 mL) degassed under nitrogen were added triphenylphosphine (1.3 g; 4.82 mmol) and palladium acetate (0.54 g; 2.41 mmol).

The reactions mixtures were heated to 100° C. for 15 hours. The reactions were cooled to room temperature, combined, poured into water and extracted with EtOAc. The organic layer was washed with brine, dried over MgSO₄, filtered and evaporated until dryness. The product was taken-up with Et₂O, the precipitate was filtered off and dried under vaccum to give 9 g (40%) of intermediate 21.

The filtrate was evaporated to dryness. The residue (18 g) was purified by chromatography over silica gel (irregular SiOH, 450 g; mobile phase 40% Heptane 10% CH₃OH, 50% EtOAc). The fractions containing the product were collected and evaporated to dryness yielding 2.8 g (13%) of intermediate 21.

Preparation of Intermediate 22

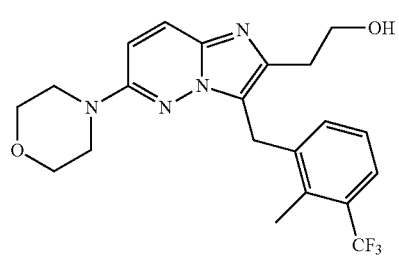 [SMILES: Cc1c(Cc2c(CCO)nc3ccc(N4CCOCC4)nn23)cccc1C(F)(F)F]

Intermediate 21 (5 g; 10.8 1 mmol) in THF (250 mL) was refluxed and then, potassium borohydride (2.33 g; 43.2 5 mmol) followed by lithium chloride (1.83 g; 43.25 mmol) were added portion wise. The reaction was heated at reflux for 7 hours. The reaction mixture was cooled to room temperature. Then the mixture was poured into ice water and extracted with DCM. The organic layer was dried over MgSO₄, filtered and evaporated. The residue was taken-up with Et₂O and the grey precipitate was filtered off to afford 2.5 g (55%) of intermediate 22.

Preparation of Intermediate 23

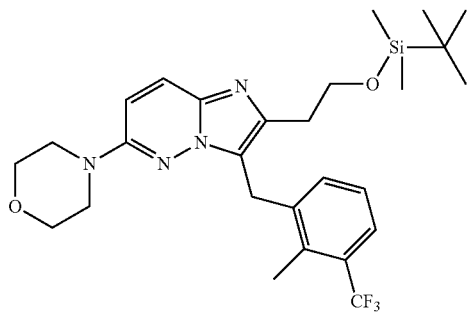 [SMILES: Cc1c(Cc2c(CCO[Si](C)(C)C(C)(C)C)nc3ccc(N4CCOCC4)nn23)cccc1C(F)(F)F]

Intermediate 23 was prepared according to an analogous procedure as described for the synthesis of intermediate 6, using intermediate 22 as starting material (68%).

Preparation of Intermediate 24

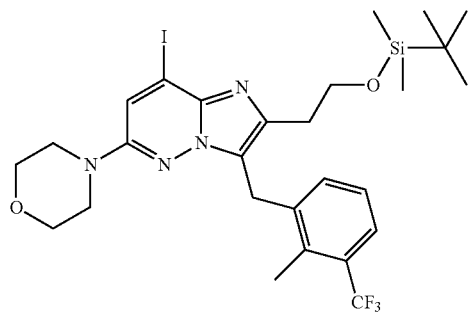 [SMILES: Cc1c(Cc2c(CCO[Si](C)(C)C(C)(C)C)nc3c(I)cc(N4CCOCC4)nn23)cccc1C(F)(F)F]

Under nitrogen, n-butyllithium 1.6 M in THF (7.4 mL; 11.8 mmol) was added dropwise to a solution of diisopropylamine (1.7 mL; 11.8 mmol) in THF (10 mL) at −70° C. The solution was stirred for 20 minutes. Then, a solution of intermediate 23 (2.1 g; 4.0 mmol) in THF (30 mL) was added dropwise and stirred at −70° C. for 30 minutes. A solution of iodine (2 g; 7.9 mmol) in THF (10 mL) was added dropwise and the reaction mixture was stirred 1 hour at −70° C. An aqueous solution of $NH_4Cl$ 10% was added followed by EtOAc. The organic layer was dried over $MgSO_4$, filtered and evaporated to dryness.

The residue (9 g) was purified by chromatography over silica gel (irregular SiOH, 80 g; mobile phase 99% DCM 1% $CH_3OH$). The fractions containing the product were collected and evaporated to dryness yielding 1.5 g (59%) of intermediate 24.

Example A6

Preparation of Intermediate 25

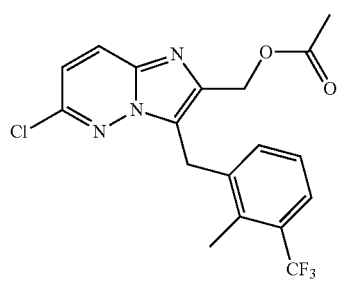 [SMILES: CC(=O)OCc1nc2ccc(Cl)nn2c1Cc1cccc(C(F)(F)F)c1C]

Intermediate 25 was prepared according to an analogous procedure as described for the synthesis of intermediate 4, using intermediate 1 as starting material (55%).

Preparation of Intermediate 26

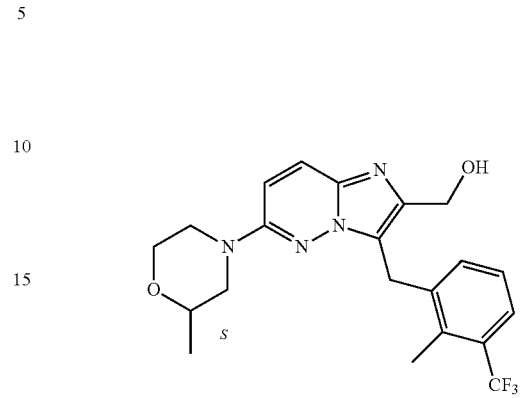

In a sealed tube, a mixture of intermediate 25 (1.3 g; 3.27 mmol), S-(2-methylmorpholine) (0.66 g; 6.54 mmol) and cesium carbonate (2.13 g; 6.54 mmol) in 2-methyl-2-butanol (13 mL) was carefully degassed with nitrogen. Then, dicyclohexyl(2′,6′-diisopropoxy-[1,1′-biphenyl]-2-yl)phosphine (0.153 g; 0.33 mmol) and $Pd_2dba_3$ (0.3 g; 0.33 mmol) were added and the mixture was heated at 110° C. overnight. The mixture was poured into water, filtered through a pad of Celite® and extracted with EtOAc. The organic layer was dried over $MgSO_4$, filtered and evaporated until dryness. The residue (2 g) was purified by chromatography over silica gel (irregular SiOH, 80 g; mobile phase 95% DCM 5% $CH_3OH$ 0.1% $NH_4OH$). The fractions containing the product were collected and evaporated to dryness yielding 1.15 g (84%) of intermediate 26 (S enantiomer)

Preparation of Intermediate 27

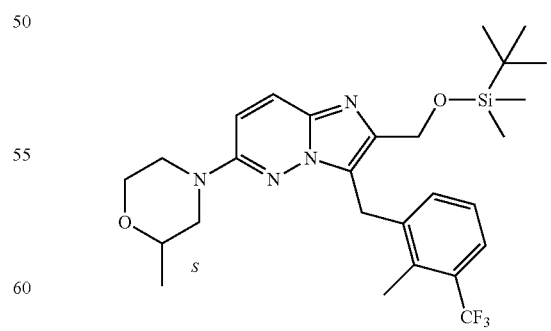

Intermediate 27 (S-enantiomer) was prepared according to an analogous procedure as described for the synthesis of intermediate 6, using intermediate 26 as starting material (42%).

Preparation of Intermediate 28

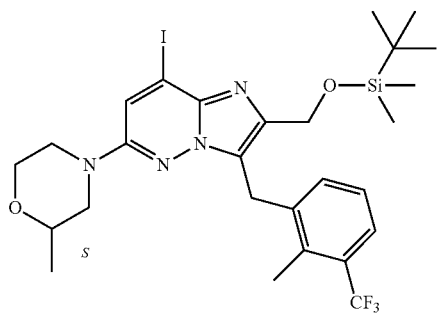

Intermediate 28 (S-enantiomer) was prepared according to an analogous procedure as described for the synthesis of intermediate 7, using intermediate 27 as starting material (30%).

Example A7

Preparation of Intermediate 29

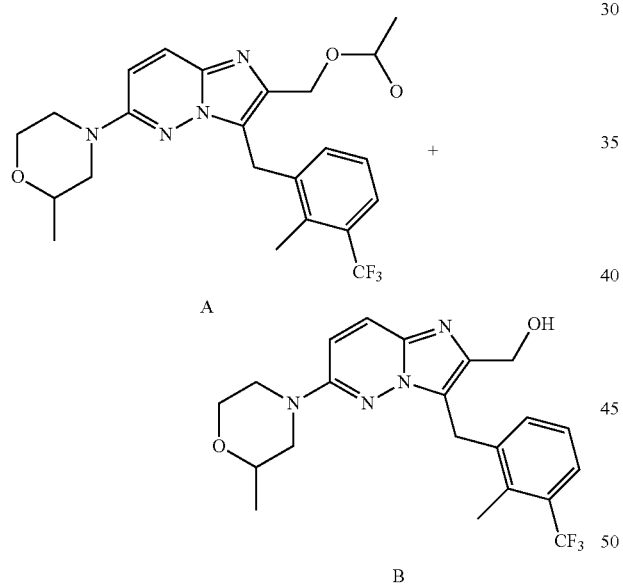

The reaction was splitted into 2 parts of intermediate 25 (4 g; 10 mmol).

In a sealed tube, a mixture of intermediate 25 (8 g; 20.1 mmol), racemic-2-methylmorpholine (4 g; 40.2 mmol) and cesium carbonate (13.1 g; 40.2 mmol) in dry 2-methyl-2-butanol (80 mL) was previously degassed. Then, RuPhos (0.47 g; 1 mmol) and $Pd_2dba_3$ (0.92 g; 1 mmol) were added and the reaction was heated at 110° C. overnight. The mixture was poured into water, filtered through a pad of Celite® and washed with EtOAc. The organic layer was separated, dried over $MgSO_4$, filtered and evaporated until dryness to give 13.1 g of intermediate 29 which used it in the next step without any further purification.

Preparation of Intermediate 30

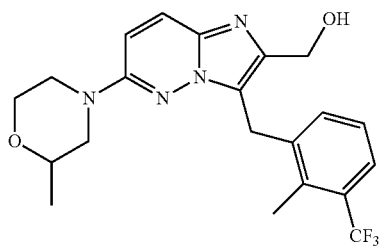 [SMILES: Cc1c(Cc2c(CO)nc3ccc(N4CCOC(C)C4)nn23)cccc1C(F)(F)F]

Intermediate 30 was prepared according to an analogous procedure as described for the synthesis of intermediate 5, using intermediate 29 as starting material (67%).

Preparation of Intermediate 31

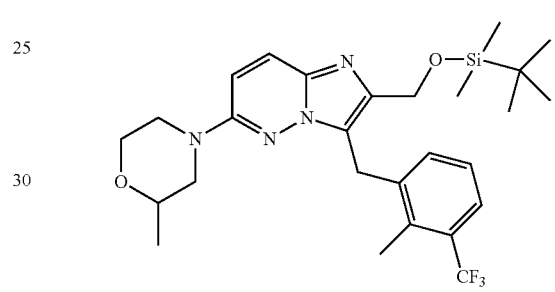

Intermediate 31 was prepared according to an analogous procedure as described for the synthesis of intermediate 6, using intermediate 30 as starting material (94%).

Preparation of Intermediate 32

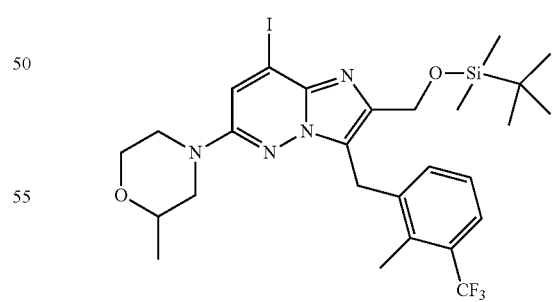

Intermediate 32 was prepared according to an analogous procedure as described for the synthesis of intermediate 7, using intermediate 31 as starting material (46%).

Example A8

Preparation of Intermediate 33

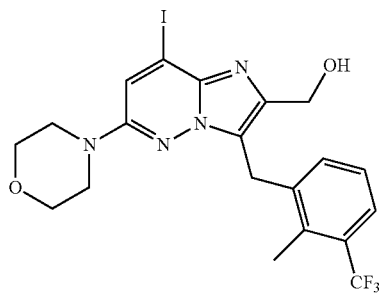

Tetrabutylammonium fluoride (2.3 mL; 2.3 mmol) was added dropwise to a solution of intermediate 7 (1.5 g; 2.3 mmol) in THF (23 mL). The reaction mixture was stirred overnight at room temperature. The reaction mixture was concentrated, taken up with MeOH and the precipitate was filtered and dried to give 0.63 g (51%) of intermediate 33. The filtrate was purified by chromatography over silica gel (irregular SiOH, 24 g; gradient from 99% DCM 1% CH$_3$OH 0.1% NH$_4$OH. to 98% DCM 2% CH$_3$OH 0.1% NH$_4$OH). The fractions containing the product were collected and evaporated to dryness yielding 0.6 g (43%) of intermediate 33.

Example A9

Preparation of Intermediate 34

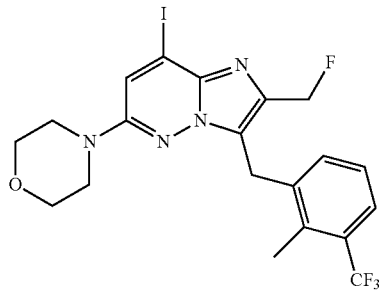

Diethylaminosulfur trifluoride (0.49 mL; 3.8 mmol) was added dropwise to a mixture of intermediate 33 (0.4 g, 0.75 mmol) in DCM (10 mL). The reaction mixture was stirred 48 hours at room temperature. A 10% aqueous solution of K$_2$CO$_3$ was added and stirred for 20 minutes. The organic layer was separated, dried over MgSO$_4$, filtered and evaporated. The residue was purified by chromatography over silica gel (Irregular SiOH, 15-40 µm, 24 g, gradient from 100% DCM to 98% DCM 2% CH$_3$OH 0.1% NH$_4$OH). The fractions containing the product were collected and evaporated to dryness to afford 0.022 g (55%) of intermediate 34.

Example A10

Preparation of Intermediate 35

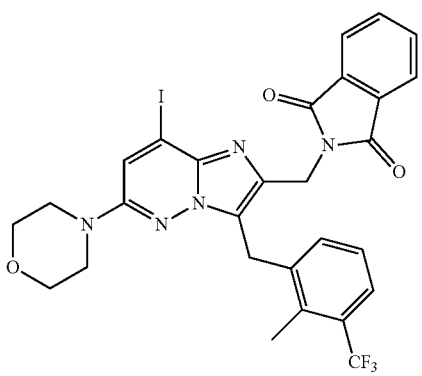 [SMILES: Cc1c(Cc2c(CN3C(=O)c4ccccc4C3=O)nc3c(I)cc(N4CCOCC4)nn23)cccc1C(F)(F)F]

Di-tert-butyl azodicarboxylate (0.454 g; 1.97 mmol) was added portionwise to a solution of intermediate 33 (0.7 g; 1.32 mmol), phtalimide (0.23 g; 1.58 mmol) and triphenylphosphine (0.52 g; 1.97 mmol) in THF (20 mL) at room temperature under nitrogen. The reaction mixture was stirred at room temperature overnight. The reaction mixture was diluted with DCM and washed with a 10% aqueous solution of K$_2$CO$_3$. The organic layer was dried over MgSO$_4$, filtered and evaporated. The residue was taken up with Et$_2$O, filtered and dried to afford 0.83 mg of intermediate 35.

Preparation of Intermediate 36

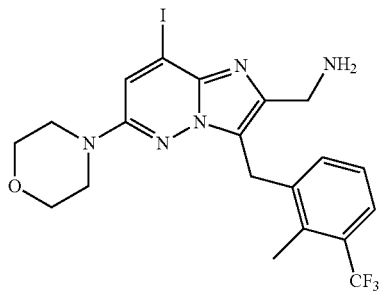 [SMILES: Cc1c(Cc2c(CN)nc3c(I)cc(N4CCOCC4)nn23)cccc1C(F)(F)F]

Hydrazine monohydrate (0.17 mL; 2.84 mmol) was added to a suspension of intermediate 35 (0.51 g; 0.78 mmol) in EtOH (11 mL) at room temperature. The reaction mixture was heated at 80° C. overnight. The mixture was cooled down to room temperature, then DCM was added and the mixture was stirred at room temperature for 10 minutes. The insoluble was filtered and washed with DCM. The filtrate was evaporated to give 0.25 g (61%) of intermediate 36.

Preparation of Intermediate 37

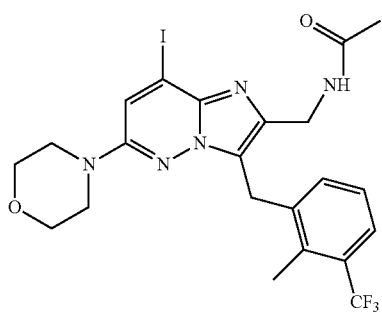 [SMILES: CC(=O)NCc1nc2c(I)cc(N3CCOCC3)nn2c1Cc1cccc(C(F)(F)F)c1C]

Diisopropylamine (0.203 mL; 1.18 mmol) was added to a solution of intermediate 36 (0.250 g; 0.47 mmol) and acetyl chloride (0.037 mL; 0.52 mmol) in DCM (4.5 mL). The reaction mixture was stirred at room temperature for 4 hours. Water and DCM were added, the mixture was filtered with DCM over Chromabond® and the aqueous layer was washed three times with DCM. The organic layer was evaporated. The residue (0.225 g) was recrystallized with ACN/diethylether. The precipitate was filtered and dried to give 0.085 g (32%) of intermediate 37. M.P.: 172° C. (Köfler).

Example A11

Preparation of Intermediate 38

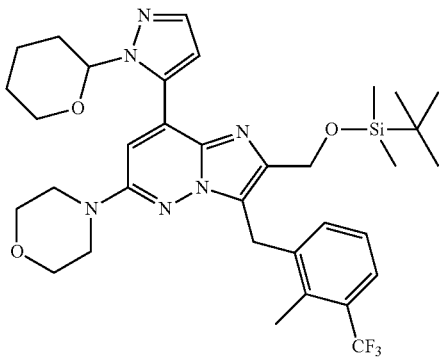 [SMILES: Cc1c(Cc2c(CO[Si](C)(C)C(C)(C)C)nc3c(-c4ccnn4C4CCCCO4)cc(N4CCOCC4)nn23)cccc1C(F)(F)F]

In a sealed tube and under nitrogen, PdCl$_2$dppf.DCM (0.019 g; 0.023 mmol) was added to a mixture of intermediate 7 (0.151 g; 0.23 mmol), 1-(tetrahydropyran-2-yl)1H-pyrazole-5-boronic acid pinacol ester (0.076 g; 0.28 mmol) and potassium carbonate (0.64 g; 0.47 mmol) in dioxane (4 mL) and water (1 mL). Then the mixture was heated at 95° C. for 4 hours. The reaction mixture was cooled to room temperature, poured onto water and DCM was added. The suspension was filtered over a pad of Celite®. The organic layer was decanted, dried over MgSO$_4$, filtered and evaporated to dryness. The residue was purified by chromatography over silica gel (irregular SiOH, 24 g; gradient from 100% DCM to 95% DCM 5% CH$_3$OH 0.1% NH$_4$OH). The fractions containing the product were collected and evaporated to dryness yielding 0.1 g (64%) of intermediate 38.

Preparation of Intermediate 39

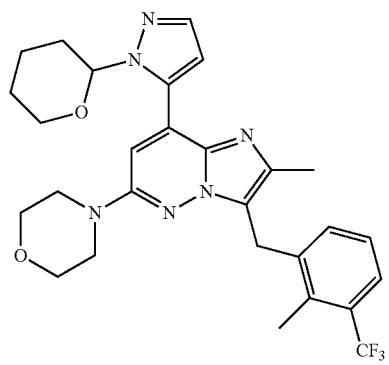 [SMILES: Cc1nc2c(-c3ccnn3C3CCCCO3)cc(N3CCOCC3)nn2c1Cc1cccc(C(F)(F)F)c1C]

Intermediate 39 was prepared according to an analogous procedure as described for the synthesis of intermediate 38, using intermediate 15 as starting material (49%).

Example A12

Preparation of Intermediate 40

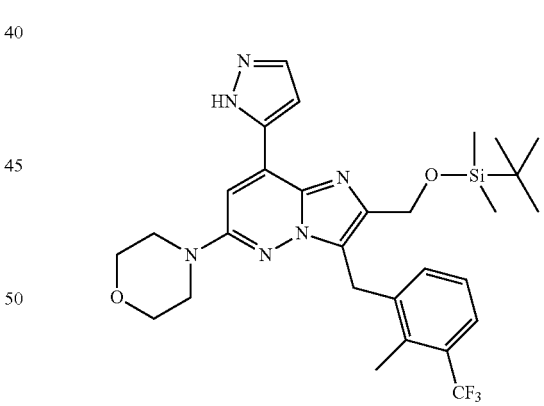

Intermediate 38 (0.1 g, 0.15 mmol) and p-toluenesulfonic acid (0.005 g, 0.03 mmol) in MeOH (5 mL) were heated at 50° C. for 2 hours. The mixture was poured into water, basified with an aqueous solution of K$_2$CO$_3$ (10%) and extracted with DCM. The organic layer was separated, dried over MgSO$_4$, filtered and evaporated to afford 0.13 g of intermediate 40 which was directly used in the next step without any further treatment

Example A13

Preparation of Intermediate 41

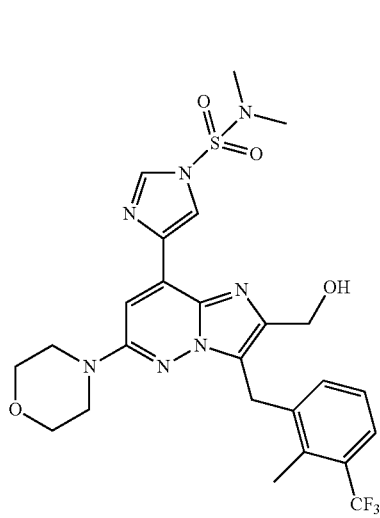 [SMILES: Cc1c(Cc2c(CO)nc3c(-c4cn(S(=O)(=O)N(C)C)cn4)cc(N4CCOCC4)nn23)cccc1C(F)(F)F]

In a sealed tube and under nitrogen, PdCl₂dppf.DCM (0.084 g; 0.103 mmol) was added to a mixture of intermediate 17 (0.5 g; 1.0 mmol), N,N-dimethyl-4-(4,4,5,5-tetramethyl-1,3,2-dioxaborolan-2-yl)-1H-imidazole-1-sulfonamide (0.43 g; 1.44 mmol) and potassium carbonate (0.29 g; 2.1 mmol) in dioxane (16 mL) and water (4 mL). The reaction mixture was heated at 100° C. for 4 hours, then cooled to room temperature and poured into water. DCM was added. The suspension was filtered over a pad of Celite®. The organic layer was decanted, dried over MgSO₄, filtered and evaporated to dryness. The residue was crystallized from ACN. The precipitate was filtered and dried to afford 0.525 g (80%) of intermediate 41.

Preparation of Intermediate 42

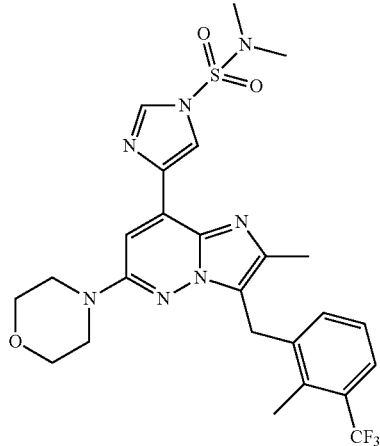 [SMILES: Cc1nc2c(-c3cn(S(=O)(=O)N(C)C)cn3)cc(N3CCOCC3)nn2c1Cc1cccc(C(F)(F)F)c1C]

Intermediate 42 was prepared according to an analogous procedure as described for the synthesis of intermediate 41, using intermediate 15 as starting material, and intermediate 42 was directly used in the next step without any further treatment.

Preparation of Intermediate 43

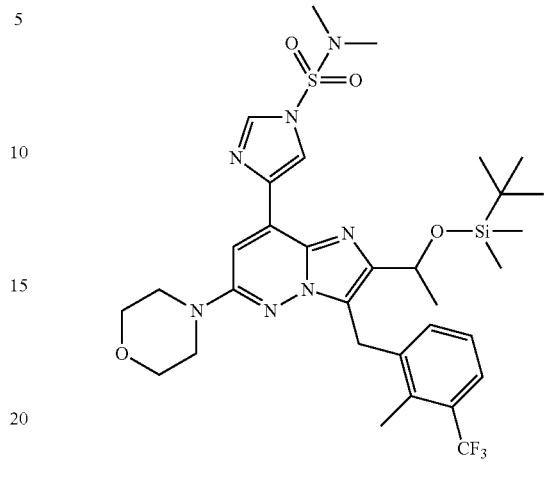

Intermediate 43 was prepared according to an analogous procedure as described for the synthesis of intermediate 41, using intermediate 11 as starting material (84%).

Preparation of Intermediate 44

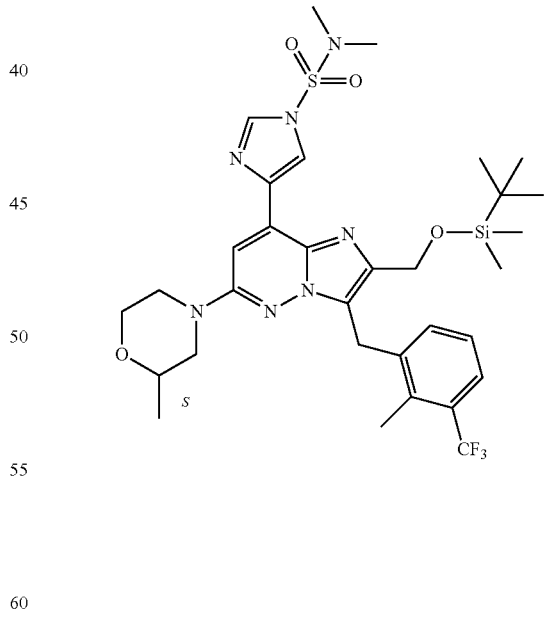

Intermediate 44 (S-enantiomer) was prepared according to an analogous procedure as described for the synthesis of intermediate 41, using intermediate 28 as starting material, and intermediate 44 was directly used in the next step without any further purification.

Preparation of Intermediate 45

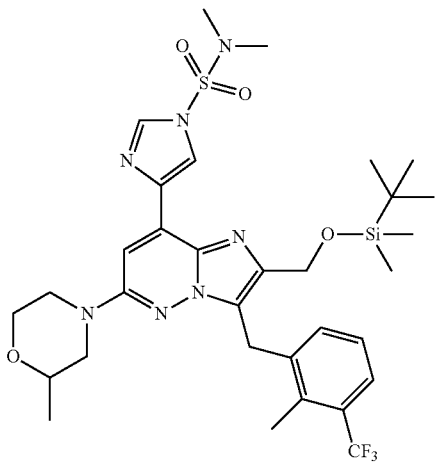 [SMILES: Cc1c(Cc2c(CO[Si](C)(C)C(C)(C)C)nc3c(-c4cn(S(=O)(=O)N(C)C)cn4)cc(N4CCOC(C)C4)nn23)cccc1C(F)(F)F]

Intermediate 45 was prepared according to an analogous procedure as described for the synthesis of intermediate 41, using intermediate 32 as starting material, and intermediate 45 was directly used in the next step without any further purification.

Preparation of Intermediate 46

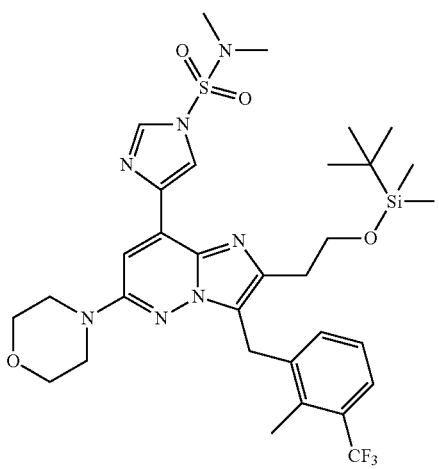 [SMILES: Cc1c(Cc2c(CCO[Si](C)(C)C(C)(C)C)nc3c(-c4cn(S(=O)(=O)N(C)C)cn4)cc(N4CCOCC4)nn23)cccc1C(F)(F)F]

Intermediate 46 was prepared according to an analogous procedure as described for the synthesis of intermediate 41, using intermediate 24 as starting material, and intermediate 46 was directly used in the next step without any further purification.

Example 14

Preparation of Intermediate 47

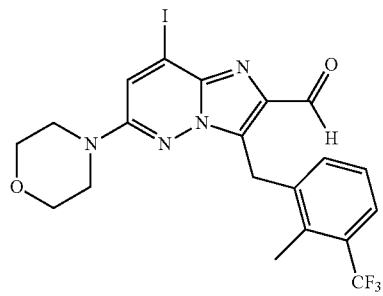 [SMILES: Cc1c(Cc2c(C=O)nc3c(I)cc(N4CCOCC4)nn23)cccc1C(F)(F)F]

Intermediate 47 was prepared according to an analogous procedure as described for the synthesis of intermediate 8, using intermediate 33 as starting material (73%).

Example 15

Preparation of Intermediate 48

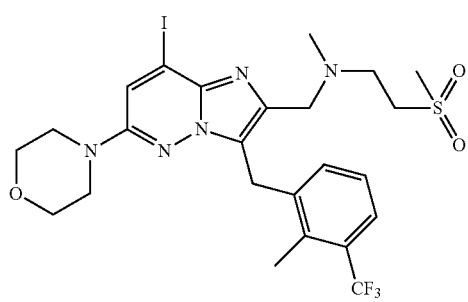 [SMILES: Cc1c(Cc2c(CN(C)CCS(C)(=O)=O)nc3c(I)cc(N4CCOCC4)nn23)cccc1C(F)(F)F]

Sodium triacetoxyborohydride (0.18 g; 0.85 mmol) was added to a mixture of intermediate 47 (0.3 g; 0.57 mmol), 2-(methylamino)-1-(methylsulfonyl)-ethane (0.085 g; 0.62 mmol) and acetic acid sodium salt (0.070 g; 0.85 mmol) in dichloroethane (15 mL). The reaction mixture was stirred overnight at room temperature. The solution was poured into an aqueous solution of sodium hydrogenocarbonate and the product was extracted with DCM. The organic layer was separated, dried over $MgSO_4$, filtered and evaporated to dryness.

The residue (1.3 g) was purified by chromatography over silica gel (Irregular SiOH, 15-40 μm, 24 g, gradient from 99% DCM 1% $CH_3OH$ 0.1% $NH_4OH$ to 97% DCM 3% $CH_3OH$ 0.1% $NH_4OH$). The fractions containing the product were collected and evaporated to dryness to afford 0.304 g (83%) of intermediate 48.

Preparation of Intermediate 49

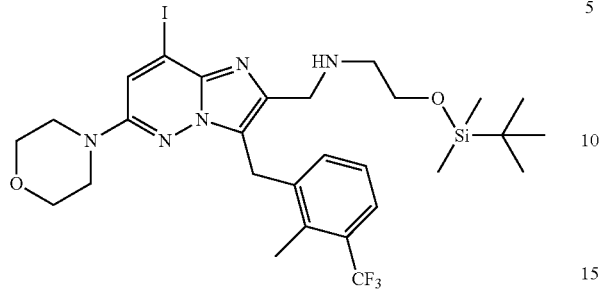

Intermediate 49 was prepared according to an analogous procedure as described for the synthesis of intermediate 48, using intermediate 47 as starting material and 2-(tert-butyldimethylsilyloxy)ethanamine (82%).

Preparation of Intermediate 50

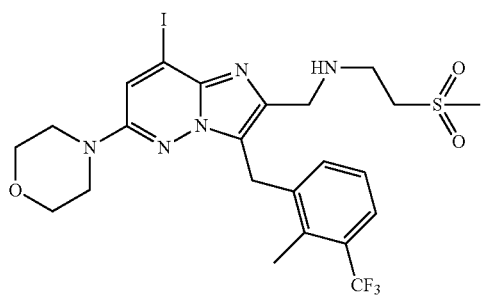 [SMILES: Cc1c(Cc2c(CNCCS(C)(=O)=O)nc3c(I)cc(N4CCOCC4)nn23)cccc1C(F)(F)F]

Intermediate 50 was prepared according to an analogous procedure as described for the synthesis of intermediate 48, using intermediate 47 as starting material and 2-aminoethylmethyl sulfone (16%).

Preparation of Intermediate 51

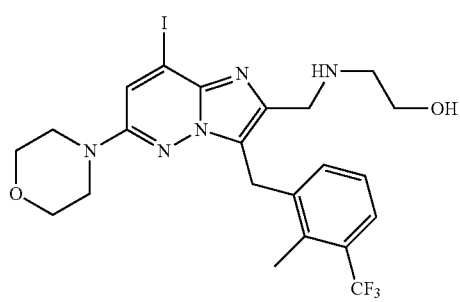 [SMILES: Cc1c(Cc2c(CNCCO)nc3c(I)cc(N4CCOCC4)nn23)cccc1C(F)(F)F]

Intermediate 51 was prepared according to an analogous procedure as described for the synthesis of intermediate 48, using intermediate 47 as starting material and ethanolamine (40%).

Example A16

Preparation of Intermediate 52

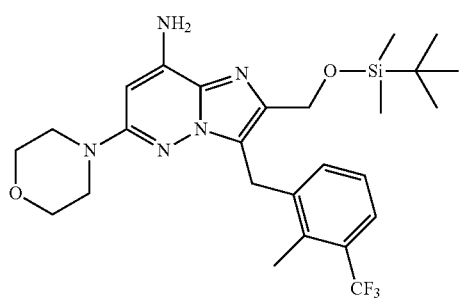 [SMILES: Cc1c(Cc2c(CO[Si](C)(C)C(C)(C)C)nc3c(N)cc(N4CCOCC4)nn23)cccc1C(F)(F)F]

In a sealed tube and under nitrogen, acetamidine hydrochloride (0.35 g; 3.72 mmol) was added to a mixture of intermediate 7 (2 g; 3.1 mmol), L-proline (0.071 g; 0.62 mmol), cesium carbonate (3 g; 9.3 mmol) and copper iodide (0.059 g; 0.31 mmol) in DMF (12 mL). The reaction mixture was heated at 110° C. overnight. The solution was poured onto cooled water and EtOAc. The organic layer was washed with brine, dried over MgSO$_4$, filtered and evaporated to dryness.

The residue was purified by chromatography over silica gel (Irregular SiOH, 15-40 μm, 40 g, gradient from 99% DCM 1% CH$_3$OH 0.1% NH$_4$OH, to 97% DCM 3% CH$_3$OH 0.1% NH$_4$OH). The fractions containing the product were collected and evaporated to dryness to afford 1.3 g (47%) of intermediate 52.

Preparation of Intermediate 53

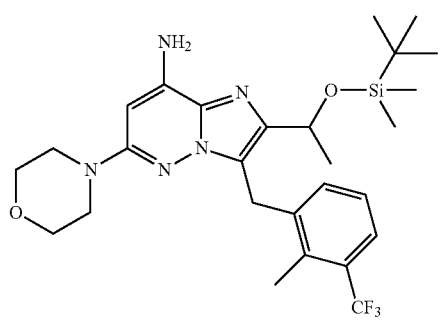 [SMILES: Cc1c(Cc2c(C(C)O[Si](C)(C)C(C)(C)C)nc3c(N)cc(N4CCOCC4)nn23)cccc1C(F)(F)F]

Intermediate 53 was prepared according to an analogous procedure as described for the synthesis of intermediate 55, using intermediate 11 as starting material (67%).

Preparation of Intermediate 54

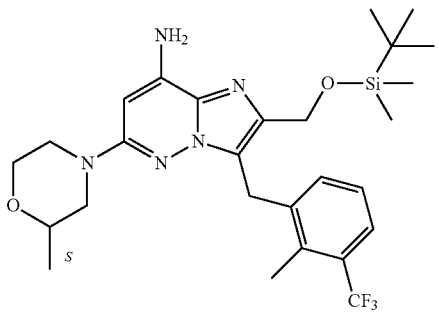

Intermediate 54 (S-enantiomer) was prepared according to an analogous procedure as described for the synthesis of intermediate 55, using intermediate 28 as starting material (54%).

Preparation of Intermediate 55

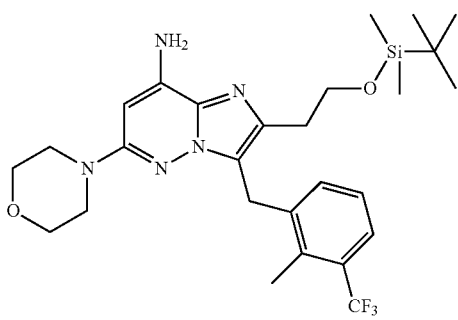 [SMILES: Cc1c(Cc2c(CCO[Si](C)(C)C(C)(C)C)nc3c(N)cc(N4CCOCC4)nn23)cccc1C(F)(F)F]

In a sealed tube and under nitrogen, acetamidine hydrochloride (0.138 g; 1.45 mmol) was added to a mixture of intermediate 24 (0.8 g; 1.21 mmol), L-proline (0.0028 g; 0.024 mmol), carbonate cesium (0.138 g; 1.45 mmol) and cooper iodure (0.0023 g; 0.012 mmol) in DMF (5 mL). The reaction mixture was heated at 110° C. overnight. The solution was poured into cooled water and EtOAc was added. The organic layer was washed with brine, dried over MgSO₄, filtered and evaporated to dryness.

The residue was purified by chromatography over silica gel (Irregular SiOH, 15-40 μm, 300 g, gradient from 99% DCM 1% CH₃OH. to 99% DCM 1% CH₃OH 0.1% NH₄OH).

The fractions containing the product were collected and evaporated to dryness to afford 0.111 g (17%) of intermediate 55.

Example A17

Preparation of Intermediate 56

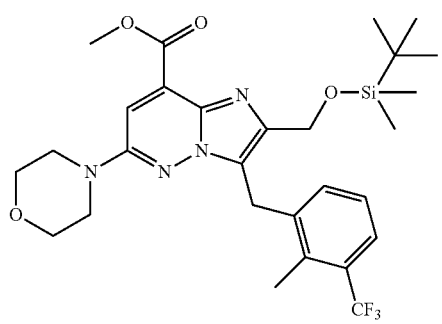 [SMILES: COC(=O)c1cc(N2CCOCC2)nn2c(Cc3cccc(C(F)(F)F)c3C)c(CO[Si](C)(C)C(C)(C)C)nc12]

In sealed tube, to a mixture of intermediate 7 (0.5 g, 0.77 mmol), triethylamine (1.5 mL, 11 mmol) in MeOH (9.4 mL) previously purged with N₂ then was added Pd(PPh₃)₄ (0.089 g, 0.077 mmol). The reaction was then purged for 5 additional minutes and carbon monoxide was added (5 bars) the reaction was stirred overnight at 120° C. and then concentrated. The residue was purified by chromatography over silica gel (Irregular SiOH, 15-40 μm, 24 g, mobile phase: 99% DCM 1% CH₃OH 0.1% NH₄OH). The fractions containing the product were collected and evaporated to dryness to afford 0.16 g (36%) of intermediate 56.

Example A18

Preparation of Intermediate 57

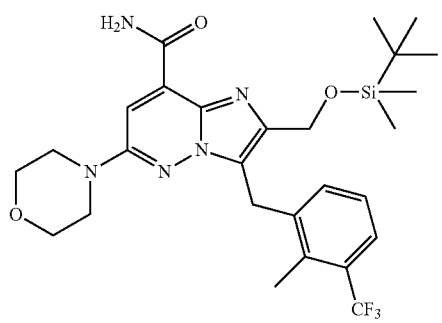 [SMILES: Cc1c(Cc2c(CO[Si](C)(C)C(C)(C)C)nc3c(C(N)=O)cc(N4CCOCC4)nn23)cccc1C(F)(F)F]

In a sealed tube, intermediate 56 (0.16 g, 0.28 mmol) in ammonia in MeOH 7N (1.6 mL) was stirred overnight at 100° C. The mixture was concentrated to afford 0.156 g (100%) of intermediate 57

Alternative Route:

In a sealed tube, a mixture of intermediate 106 (1 g; 1.84 mmol) in THF (16 mL) and water (0.7 mL) was degassed with nitrogen for 10 minutes. Then, hydrido(dimethylphosphinous acid-kP)[hydrogen bis(dimethylphosphinito-kP)] platinum(II) (0.16 g, 0.37 mmol) was added. The resulting mixture was heated at 95° C. for 2 hours. The mixture was poured into water and extracted with EtOAc. The organic layer was separated, dried over MgSO₄, filtered and evaporated to dryness to give 1.06 g of intermediate 57, which was directly used for the next step without any further treatment.

Example A19

Preparation of Intermediate 58

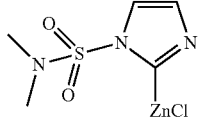

N-butillithium (9.4 mL (1.6 M in hexanes); 15 mmol) was added dropwise at −78° C. to a solution of N,N-Dimethyl-imidazole-1-sulfonamide (2.63 g; 15 mmol) in THF (45 mL) and the reaction mixture was stirred for 30 minutes. A solution of zinc chloride (30 mL (1 M in THF); 30 mmol) was added and the reaction mixture was allowed to warm to room temperature over 30 minutes. The reaction mixture containing intermediate 58 [c=0.18 M] was directly used in the next reaction step without any further treatment.

Preparation of Intermediate 59

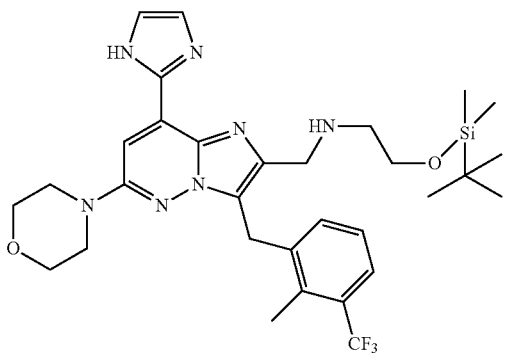 [SMILES: Cc1c(Cc2c(CNCCO[Si](C)(C)C(C)(C)C)nc3c(-c4ncc[nH]4)cc(N4CCOCC4)nn23)cccc1C(F)(F)F]

Intermediate 58 (16 mL; 2.89 mmol; 0.18 M) was added dropwise a previously degassed mixture of intermediate 49 (0.398 g; 0.58 mmol) and Pd(PPh$_3$)$_4$ (0.067 g; 0.058 mmol) in THF (2 mL). The reaction mixture was heated at 100° C. for 1 hour. Additional intermediate 58 (16 mL; 2.89 mmol; 0.18 M) was added and stirring was pursued overnight at 100° C. The reaction mixture was cooled to room temperature, diluted with DCM and quenched with a 10% aqueous solution of K$_2$CO$_3$. The mixture was filtered through a pad of Celite® which was washed with EtOAc. The filtrate was extracted with EtOAc. The organic layer was washed with brine, dried over MgSO$_4$, filtered and the solvent was evaporated. The residue (1.4 g) was purified by chromatography over silica gel (Irregular SiOH, 15-40 µm, 40 g, mobile phase 97% DCM 3% CH$_3$OH 0.1% NH$_4$OH). The fractions containing the product were collected and evaporated to dryness 0.098 g (27%) of intermediate 59.

Preparation of Intermediate 60

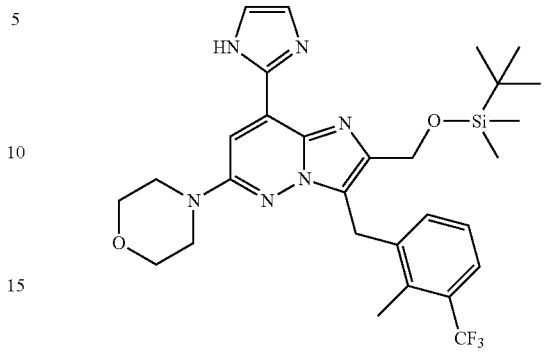

Intermediate 58 (12.6 mL; 2.27 mmol; 0.18 M) was added dropwise a previously degassed mixture of intermediate 11 (0.3 g; 0.45 mmol) and Pd(PPh$_3$)$_4$ (0.052 g; 0.045 mmol). The reaction mixture was heated at 100° C. for 1 hour. Additional intermediate 58 (16 mL; 2.89 mmol; 0.18 M) was added and stirring was pursued overnight at 100° C. The reaction mixture was cooled to room temperature, diluted with DCM and quenched with a 10% aqueous solution of K$_2$CO$_3$. The mixture was filtered through a pad of Celite® which was washed with DCM. The filtrate was extracted with DCM. The organic layer was washed with brine, dried over MgSO$_4$, filtered and the solvent was evaporated. The residue (1.1 g) was purified by chromatography over silica gel (Irregular SiOH, 15-40 µm, 50 g, mobile phase from 98% DCM 2% CH$_3$OH 0.1% NH$_4$OH to 90% DCM 10% CH$_3$OH 1% NH$_4$OH). The fractions containing the product were collected and evaporated to dryness, yielding 0.238 g of intermediate 60 (87%).

Example A20

Preparation of Intermediate 61

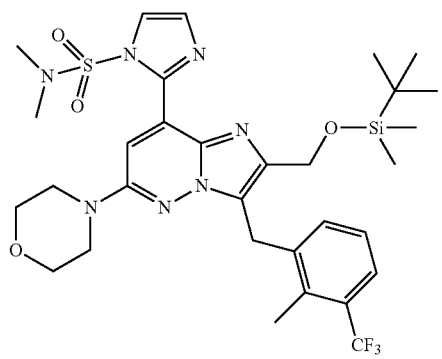 [SMILES: Cc1c(Cc2c(CO[Si](C)(C)C(C)(C)C)nc3c(-c4nccn4S(=O)(=O)N(C)C)cc(N4CCOCC4)nn23)cccc1C(F)(F)F]

Under nitrogen, at −78° C., n-butyllithium (0.97 mL 1.6M in hexanes, 1.55 mmol) was added to a solution of intermediate 58 (0.271 g, 1.55 mol) in THF (6 mL) and the mixture was stirred at 0° C. for 30 minutes. A solution of zinc chloride (3 mL 1M in THF; 3 mmol) was added and the reaction mixture was allowed to warm to room temperature over 30 minutes. The solution was added to a previously degassed mixture of intermediate 7 (0.2 g; 0.31 mmol) and Pd(PPh$_3$)$_4$ (0.036 g; 0.031 mmol) in sealed tube and the reaction mixture was heated between 100° C. and 60° C. for 1h30 (pre-heated oil bath, heating stopped immediately). The reaction mixture was cooled to room temperature, diluted with DCM and quenched with a 10% aqueous solution of K$_2$CO$_3$. The organic layer was separated, dried over MgSO$_4$, filtered and evaporated to dryness to afford 0.440 g which was directly used in the next reaction step without any further treatment Example A21

Preparation of Intermediate 62

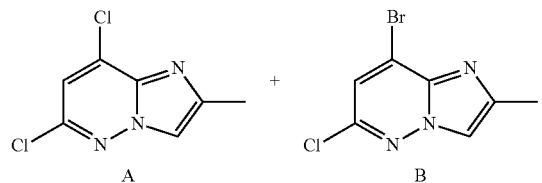

3-Amino-4-bromo-6-chloropyridazine (23.65 g; 113.46 mmol) in chloro-2-propanone (70.9 mL; 891 mmol) and the mixture was heated at 90° C. for 15 hours. The reaction was cooled to room temperature and Et$_2$O was added. The precipitate was filtered, washed with Et$_2$O and dried. The residue was stirred with DCM. The precipitate was filtered and dried to afford 41.1 g of a mixture intermediate 62 (A/B: 75/25 based on $^1$H NMR).

Preparation of Intermediate 63

Triethylamine (100 mL; 0.72 mmol) was added to a solution of intermediate 62 ((41.1 g; 0.14 mmol) in DCM (1 L). The reaction mixture was stirred at room temperature for 20 minutes. The mixture was poured into water, the organic layer was separated, dried over MgSO$_4$, filtered and evaporated till dryness. The residue (26.7 g) was purified by chromatography over silica gel (irregular SiOH, 330 g; gradient from 100% DCM to 95% DCM 5% CH$_3$OH 0.1% NH$_4$OH). The fractions containing the product were collected and evaporated to dryness yielding 21.1 g (72%) of intermediate 63.

Preparation of Intermediate 64

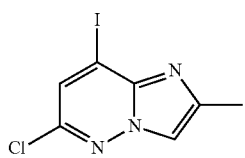

The experiment was realized in 8 batches. For each batch, hydriodic acid (0.23 mL, 1.8 mmol) was added to a solution of intermediate 63 ((2.5 g, 8.8 mmol) and sodium iodide (3.8 g, 26 mmol) in ACN (16 mL) in a sealed tube. The mixture was heated at 160° C. using one single mode microwave (Biotage Initiator EXP 60) with a power output ranging from 0 to 400 W for 40 minutes.

The 8 batches were combined for the work up.

The reaction mixture was poured into water and a 10% aqueous solution of K$_2$CO$_3$ was added and the solution was extracted with DCM. The insoluble was filtered, washed with water then DCM and dried to afford 0.55 g (2%) of intermediate 64 (The organic layer was separated, dried over MgSO$_4$, filtered and evaporated. The residue (28.45 g) was crystallized in acetone. The precipitate was filtered and dried to give 17 g (58%) of intermediate 64.

The filtrate was concentrated and the residue (11.45 g) was purified by chromatography over silica gel (Irregular SiOH, 15-40 µm, 120 g, gradient 90% heptane 10% EtOAc to 70% heptane 30% EtOAc). The fractions containing the product were collected and evaporated to dryness to afford 9.4 g (33%) of intermediate 64.

Preparation of Intermediate 65

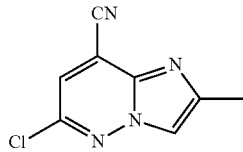

Under nitrogen, a mixture of intermediate 64 ((20 g, 68 mmol), zinc cyanide (12 g, 102 mmol) and Pd(PPh$_3$)$_4$ (7.9 g, 6.8 mmol) in dry DMF (260 ml) was heated at 80° C. overnight. The mixture was concentrated, poured into water and 500 mL of EtOAc was added. The organic layer was washed with brine dried over MgSO$_4$, filtrated and dried. The residue was purified by chromatography over silica gel (Irregular SiOH, 15-40 µm, 120 g, mobile phase 80% heptane 20% EtOAc). The fractions containing the product were collected and evaporated to dryness to afford 6.4 g (49%) of intermediate 65 and 6.8 g of impure fractions which was purified by achiral SFC (Stationary phase: 2-Ethylpyridine 5 µm 150*30 mm), Mobile phase: 95% CO$_2$, 5% MeOH). The fractions containing the product were collected and evaporated to dryness to afford additional 1.15 g (9%) of intermediate 65.

Preparation of Intermediate 66

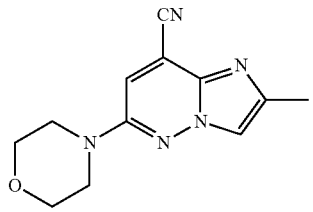 [SMILES: Cc1cn2nc(N3CCOCC3)cc(C#N)c2n1]

A mixture of intermediate 65 (5.2 g, 27 mmol) and morpholine (47 mL, 0.54 mmol) was stirred at 25° C. for 4 days. The mixture was concentrated at room temperature and the residue was taken in MeOH. The solid was filtrated, washed with MeOH, then Et$_2$O, filtered and dried to give 2.49 g (38%) of intermediate 66.

Preparation of Intermediate 67

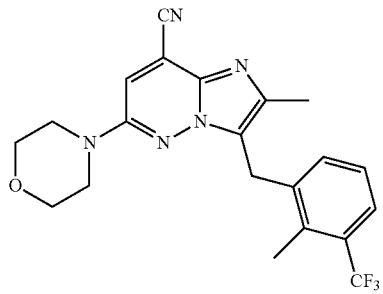 [SMILES: Cc1nc2c(C#N)cc(N3CCOCC3)nn2c1Cc1cccc(C(F)(F)F)c1C]

A mixture of intermediate 66 (1.5 g; 6.16 mmol), 1-(chloromethyl)-2-methyl-3-(trifluoromethyl)benzene (1.5 g; 7.4 mmol) and potassium carbonate (1.3 g; 9.3 mmol) in dioxane (21 mL) was degassed under nitrogen, and triphenylphosphine (0.33 g; 1.24 mmol) and palladium acetate (0.14 g; 0.62 mmol) were added. The reaction mixture was heated at 100° C. overnight, cooled to room temperature and solubilized with EtOAc. The organic layer was washed twice with brine, dried over MgSO$_4$, filtered and concentrated. The residue was purified by chromatography over silica gel (irregular SiOH 80 g; gradient from 100% DCM to 99% DCM 1% CH$_3$OH 0.1% NH$_4$OH). The fractions containing the product were collected and evaporated to dryness yielding 1.5 g (59%) of intermediate 67.

Alternative Route:

Intermediate 15 (0.54 g; 1.1 mmol), zinc cyanide (0.184 g; 1.6 mmol) and Pd(PPh$_3$)$_4$ (0.121 g; 0.1 mmol) in DMF (4 mL) were heated at 100° C. overnight. The reaction mixture was cooled, water and EtOAc were added. The organic layer was separated, dried over MgSO$_4$, filtered and evaporated. The residue was purified by chromatography over silica gel (irregular SiOH, 24 g; mobile phase: 97% DCM 3% CH$_3$OH). The fractions containing the product were collected and evaporated to dryness yielding 0.14 g (33%) of intermediate 67 and 0.122 g (27%) of compound 10.

Alternative Route:

Intermediate 107 (0.050 g; 0.14 mmol), morpholine (0.036 mL; 0.41 mmol) and potassium phosphate tribasic (0.058 g, 0.27 mmol) in toluene (0.58 mL) was degassed under nitrogen then, Pd$_2$dba$_3$ (0.013 g; 0.014 mmol) and 2-(di-t-butylphosphino)biphenyl (0.008 g; 0.027 mmol) were added. The reaction mixture was heated at 100° C. overnight. The mixture was solubilized in EtOAc and washed with brine. The organic layer was separated, dried over MgSO$_4$, filtered and evaporated.

The residue was purified by chromatography over silica gel (irregular SiOH, 25 g; mobile phase gradient from: 80% heptane 20% EtOAc to 60% heptane 40% EtOAc). The fractions containing the product were collected and evaporated to dryness yielding 0.008 g (14%) of intermediate 67 and 0.030 g (60%) of intermediate 107.

Preparation of Intermediate 68

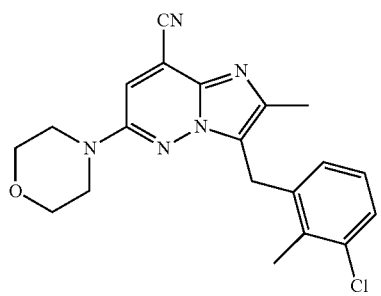 [SMILES: Cc1nc2c(C#N)cc(N3CCOCC3)nn2c1Cc1cccc(Cl)c1C]

Intermediate 68 was prepared according to an analogous procedure as described for the synthesis of intermediate 67, using intermediate 66 as starting material and 1-chloro-3-(chloromethyl)-2-methylbenzene (68%).

Preparation of Intermediate 69

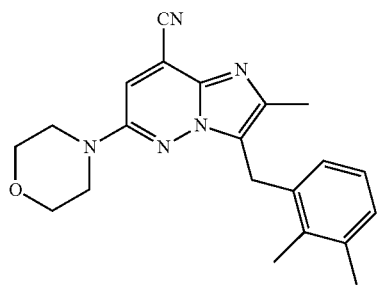 [SMILES: Cc1cccc(Cc2c(C)nc3c(C#N)cc(N4CCOCC4)nn23)c1C]

Intermediate 69 was prepared according to an analogous procedure as described for the synthesis of intermediate 67, using intermediate 66 as starting material and 1-(chloromethyl)-2,3-dimethylbenzene (69%).

Preparation of Intermediate 70

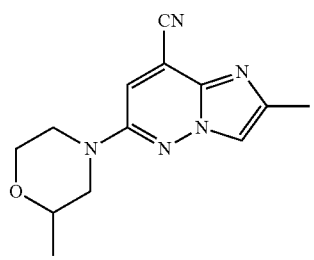 [SMILES: Cc1cn2nc(N3CCOC(C)C3)cc(C#N)c2n1]

Intermediate 70 was prepared according to an analogous procedure as described for the synthesis of intermediate 66, using intermediate 65 as starting material (8%).

Preparation of Intermediate 71

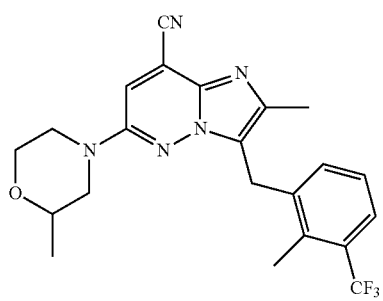 [SMILES: Cc1nc2c(C#N)cc(N3CCOC(C)C3)nn2c1Cc1cccc(C(F)(F)F)c1C]

Intermediate 71 was prepared according to an analogous procedure as described for the synthesis of intermediate 67, using intermediate 70 as starting material (50%).

Example A22

Preparation of Intermediate 72

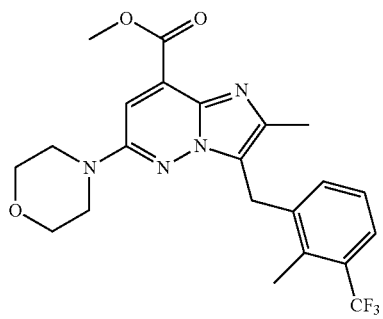 [SMILES: COC(=O)c1cc(N2CCOCC2)nn2c(Cc3cccc(C(F)(F)F)c3C)c(C)nc12]

In a sealed tube, to a solution of intermediate 67 (1.5 g, 3.6 mmol) in MeOH (29 mL) was added sulfuric acid (9.6 mL). The reaction mixture was heated to 100° C. overnight. The mixture was concentrated, diluted in a saturated solution of hydrogen carbonate and extracted with EtOAc. The organic layer was washed with brine, dried over $MgSO_4$ and evaporated. The residue was purified by chromatography over silica gel (Irregular SiOH, 15-40 µm, 40 g, gradient from 100% DCM, to 98% DCM 2% $CH_3OH$ 0.1% $NH_4OH$). The fractions containing the product were collected and evaporated to dryness to afford 1.6 g (96%) of intermediate 72.

Alternative Route:

In a sealed tube, a mixture of intermediate 108 (1.5 g; 5.4 mmol), 1-(chloromethyl)-2-methyl-3-(trifluoromethyl)benzene (1.4 g; 6.5 mmol) and potassium carbonate (1.1 g; 8.2 mmol) in dioxane (25 mL) was degassed under nitrogen and then triphenylphosphine (0.28 g; 1.1 mmol) and palladium acetate (0.13 g; 0.54 mmol) were added. The reaction mixture was heated at 100° C. for 20 hours. The mixture was cooled down to room temperature, poured into water, basified with $K_2CO_3$ solid and extracted with EtOAc. The organic layer was dried over $MgSO_4$, filtered and evaporated to dryness. The residue was purified by chromatography over silica gel (irregular SiOH, 80 g; gradient from 100% DCM to 95% DCM 5% $CH_3OH$ 0.1% $NH_4OH$). The fractions containing the product were collected and evaporated to dryness yielding 1.07 g (71%) of intermediate 72.

Preparation of Intermediate 73

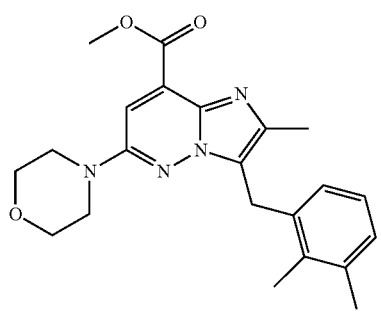 [SMILES: COC(=O)c1cc(N2CCOCC2)nn2c(Cc3cccc(C)c3C)c(C)nc12]

Intermediate 73 was prepared according to an analogous procedure as described for the synthesis of intermediate 72, using intermediate 69 as starting material (84%).

Preparation of Intermediate 74

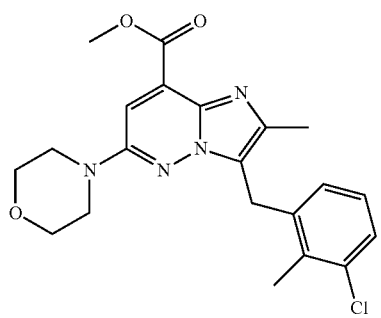 [SMILES: COC(=O)c1cc(N2CCOCC2)nn2c(Cc3cccc(Cl)c3C)c(C)nc12]

Intermediate 74 was prepared according to an analogous procedure as described for the synthesis of intermediate 72, using intermediate 68 as starting material, and intermediate 74 was directly used in the next step without any further treatment.

Preparation of Intermediate 75

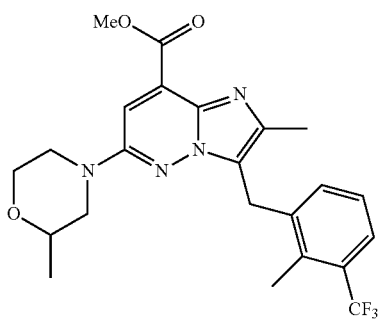 [SMILES: COC(=O)c1cc(N2CCOC(C)C2)nn2c(Cc3cccc(C(F)(F)F)c3C)c(C)nc12]

Intermediate 75 was prepared according to an analogous procedure as described for the synthesis of intermediate 72, using intermediate 71 as starting material (70%).

Preparation of Intermediate 76

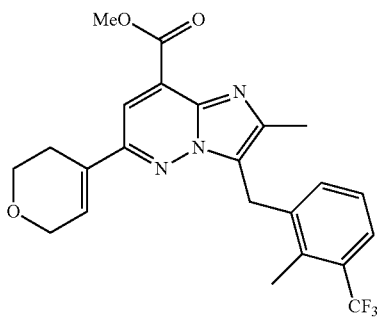 [SMILES: COC(=O)c1cc(C2=CCOCC2)nn2c(Cc3cccc(C(F)(F)F)c3C)c(C)nc12]

Intermediate 76 was prepared according to an analogous procedure as described for the synthesis of intermediate 72, using intermediate 88 as starting material (47%).

Example A23

Preparation of Intermediate 77

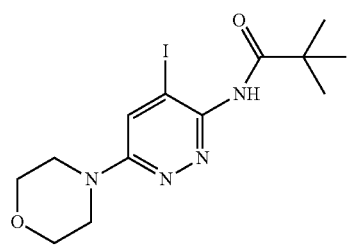 [SMILES: CC(C)(C)C(=O)Nc1nnc(N2CCOCC2)cc1I]

Under nitrogen, at −78° C., n-butyllithium (250 mL 1.6M in hexanes, 0.4 mol) was added to a solution of 2,2,6,6-tetramethylpiperidine (68.1 mL, 0.405 mol) in THF (265 mL) and the solution was stirred at 0° C. for 30 minutes. After cooling to −78° C., a solution of intermediate 18 ((13.2 g, 50 mmol) in THF (265 mL) was added dropwise and the mixture was stirred at −78° C. for 1 hour. Iodine (104.06 g, 0.41 mol) in THF (120 mL) was added dropwise and the reaction mixture was stirred at −78° C. for 2 hours. The reaction mixture was poured into water and basified with NH₄Cl powder. Then, the aqueous layer was extracted with EtOAc. The organic layer was taken up with an aqueous solution of Na₂S₂O₃, separated, dried over MgSO₄, filtered and evaporated. The residue (26 g) was purified by chromatography over silica gel (irregular SiOH, 300 g; gradient from 100% DCM to 90% DCM 10% CH₃OH 0.1% NH₄OH). The fractions containing the product were collected and evaporated to dryness yielding 15.3 g (79%) of intermediate 77.

Preparation of Intermediate 78

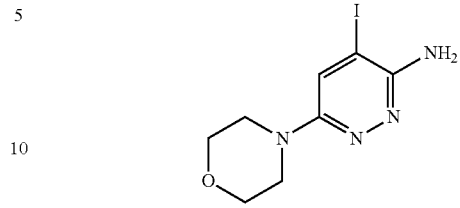

Intermediate 78 was prepared according to an analogous procedure as described for the synthesis of intermediate 19, using intermediate 77 as starting material (90%).

Preparation of Intermediate 79

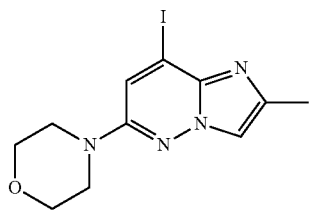 [SMILES: Cc1cn2nc(N3CCOCC3)cc(I)c2n1]

Intermediate 78 (51 g; 166.6 mmol) in chloro-2-propanone (225 g; 2432 mmol) was heated at 90° C. for 5 hours. The reaction mixture was poured into ice water, basified with a solution of Na₂CO₃ (2M) (pH=8). The product was extracted three times with EtOAc. The organic layers were combined, washed with brine, dried over MgSO₄, filtered and evaporated till dryness. The residue (40 g) was purified by chromatography over silica gel (irregular SiOH; gradient from 100% petroleum ether to 50% EtOAc 50% petroleum ether). The fractions containing the product were collected and evaporated to dryness yielding 35 g (60%) of intermediate 79.

Preparation of Intermediate 80

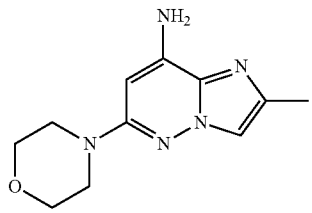 [SMILES: Cc1cn2nc(N3CCOCC3)cc(N)c2n1]

Intermediate 80 was prepared according to an analogous procedure as described for the synthesis of compound 33, using intermediate 79 as starting material (9%).

Preparation of Intermediate 81

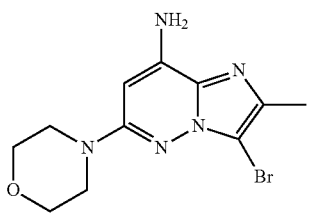 [SMILES: Cc1nc2c(N)cc(N3CCOCC3)nn2c1Br]

To a solution of intermediate 80 (0.2 g; 0.86 mmol) in ACN (4.5 mL) was added portionwise N-bromosuccinimide (0.15 g; 0.86 mmol) at room temperature. The solution was stirred overnight. EtOAc and a saturated aqueous solution of brine were added to the reaction mixture. The organic layer was washed, separated, dried over MgSO$_4$, filtered and evaporated to afford 0.23 g (86%) of intermediate 81.

Example A24

Preparation of Intermediate 82

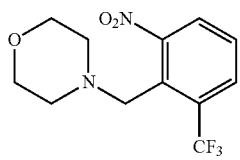 [SMILES: O=[N+]([O-])c1cccc(C(F)(F)F)c1CN1CCOCC1]

Triethylamine (4.6 mL, 32.4 mmol) and morpholine (1.7 mL, 19.4 mmol) were added to a solution of 2-(bromomethyl)-1-nitro-3-(trifluoromethyl)benzene (4.6 g, 16.195 mmol) in DCM (50 mL) and the reaction mixture was stirred at room temperature for 48 hours. Then, it was poured into ice water and EtOAc was added. The aqueous layer was extracted with EtOAc, dried over MgSO$_4$, filtered and evaporated till dryness.

The residue (4.3 g) was purified by chromatography over silica gel (irregular SiOH; 120 g, gradient from 70% Heptane 30% EtOAc to 60% Heptane 40% EtOAc). The fractions containing the product were collected and evaporated to dryness yielding 2 g (43%) of intermediate 82.

Preparation of Intermediate 83

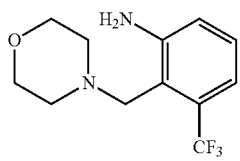

A solution of intermediate 82 (2 g, 6.9 mmol), iron powder (1.9 g, 34.5 mmol) and iron (II) sulfate heptahydrate (0.58 g, 2.1 mmol) in a mixture of a saturated solution of NH$_4$Cl (20 mL) and MeOH (40 mL) was stirred at 80° C. overnight. The mixture was filtered over a pad of Celite® and the filtrate was concentrated under reduce pressure. The residue was poured into brine and extracted with DCM. The organic layer was washed 2× with brine, dried and concentrated to afford (1.4 g, 78%) of intermediate 83.

Example A25

Preparation of Intermediate 84

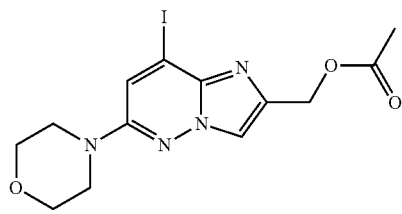 [SMILES: CC(=O)OCc1cn2nc(N3CCOCC3)cc(I)c2n1]

Intermediate 84 was prepared according to an analogous procedure as described for the synthesis of intermediate 1, using intermediate 77 as starting material (9%).

Preparation of Intermediate 85

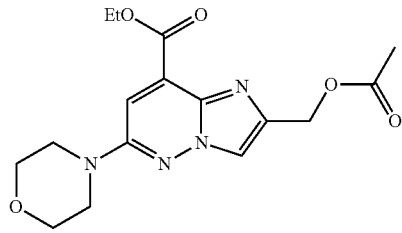 [SMILES: CCOC(=O)c1cc(N2CCOCC2)nn2cc(COC(C)=O)nc12]

In a sealed tube, a mixture of intermediate 84 (0.57 g, 1.4 mmol), triethylamine (2.76 mL, 19.8 mmol) in EtOH (10 mL) was degassed with nitrogen. Then, palladium acetate (0.031 g, 0.14 mmol) and 4,5-bis(diphenylphosphino)-9,9-dimethylxanthene (0.16 g, 0.28 mmol) were added and the reaction mixture was purged for 5 minutes. Carbon monoxide was added (5 bars) and the reaction was stirred for 15 hours at 100° C. The mixture was poured into water and basified with K$_2$CO$_3$ powder. Then EtOAc was added. The organic layer was extracted, dried over MgSO$_4$, filtered and evaporated until dryness. The residue (0.474 g) was purified by chromatography over silica gel (irregular SiOH, 24 g; gradient from 100% DCM to 80% DCM 20% CH$_3$OH 0.1% NH$_4$OH). The fractions containing the product were collected and evaporated to dryness yielding 0.116 g (24%) of intermediate 85.

Preparation of Intermediate 86

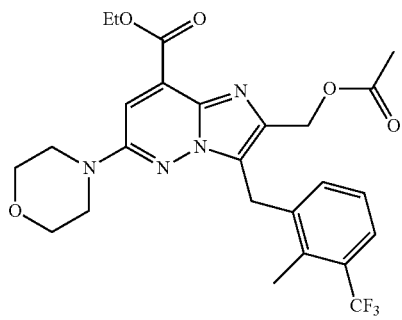 [SMILES: CCOC(=O)c1cc(N2CCOCC2)nn2c(Cc3cccc(C(F)(F)F)c3C)c(COC(C)=O)nc12]

Intermediate 86 was prepared according to an analogous procedure as described for the synthesis of intermediate 4, using intermediate 85 as starting material (32%).

Example A26

Preparation of Intermediate 87

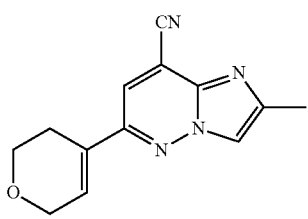 [SMILES: Cc1cn2nc(C3=CCOCC3)cc(C#N)c2n1]

A mixture of intermediate 65 (0.5 g; 2.6 mmol), 3,6-dihydro-2H-pyran-4-boronic acid pinacol ester (0.55 g; 2.6 mmol), potassium phosphate (1.6 g; 7.8 mmol) in dioxane (11 mL) and water (4 mL) was carefully purged with nitrogen. PdCl₂dppf.DCM (0.21 g; 0.26 mmol) was added and the reaction mixture was purged once again with nitrogen. The reaction mixture was heated at 80° C. overnight. The reaction mixture was diluted with EtOAc and washed with water and with brine. The organic layer was dried over MgSO₄, filtered and evaporated. The residue was purified by chromatography over silica gel (irregular SiOH, 25 g; gradient from 100% DCM to 99% DCM 1% CH₃OH 0.1% NH₄OH). The fractions containing the product were collected and evaporated to dryness. The residue was purified by chromatography over silica gel (irregular SiOH, 25 g; mobile phase from 100% DCM). The fractions containing the product were collected and evaporated to dryness to afford 0.15 g (24%) of intermediate 87.

Preparation of Intermediate 88

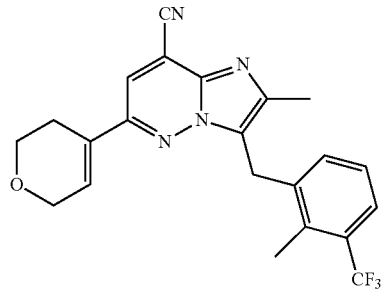 [SMILES: Cc1nc2c(C#N)cc(C3=CCOCC3)nn2c1Cc1cccc(C(F)(F)F)c1C]

Intermediate 88 was prepared according to an analogous procedure as described for the synthesis of intermediate 67, using intermediate 87 as starting material (43%).

Example A27

Preparation of Intermediate 89

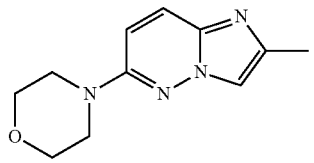 [SMILES: Cc1cn2nc(N3CCOCC3)ccc2n1]

Intermediate 89 was prepared according to an analogous procedure as described for the synthesis of intermediate 2, using intermediate 12 as starting material (59%).

Preparation of Intermediate 90

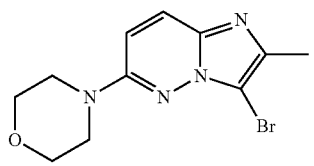 [SMILES: Cc1nc2ccc(N3CCOCC3)nn2c1Br]

To a solution of intermediate 89 (6.0 g; 27 mmol) in ACN (143 mL) was added portionwise N-bromosuccinimide (5.1 g; 29 mmol) at room temperature. The solution was stirred overnight. EtOAc and a saturated aqueous solution of brine were added to the mixture. The organic layer was washed, separated, dried over MgSO₄, filtered and evaporated. The residue was purified by chromatography over silica gel (irregular SiOH, 120 g; mobile phase 98% DCM 2% CH₃OH 0.1% NH₄OH). The fractions containing the product were collected and evaporated to dryness to afford 4.7 g (58%) of intermediate 90.

Preparation of Intermediate 91

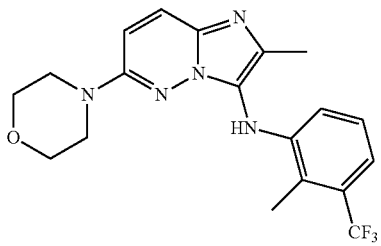

Under nitrogen, in a sealed tube, to a mixture of intermediate 90 (2.0 g, 6.7 mmol), 2-methyl-3-(trifluoromethyl)aniline (1.4 g, 8.1 mmol) and sodium tert-butoxide (1.3 g, 13 mmol) in toluene (28 mL) degassed with nitrogen, were added Pd$_2$dba$_3$ (0.62 g, 0.67 mmol) and 2-(di-t-butylphosphino)biphenyl (0.4 g, 1.3 mmol). The reaction mixture was heated at 100° C. overnight. EtOAc and a saturated aqueous solution of brine were added to the mixture. The organic layer was washed, separated, dried on MgSO$_4$, filtered and evaporated. The residue was purified by chromatography over silica gel (irregular SiOH, 120 g; mobile phase gradient from 98% DCM 2% CH$_3$OH to 98% DCM 2% CH$_3$OH 0.1% NH$_4$OH). The fractions containing the product were collected and evaporated to dryness to afford 1.7 g (65%) of intermediate 91.

Preparation of Intermediate 92

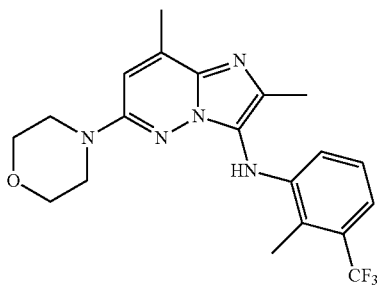 [SMILES: Cc1nc2c(C)cc(N3CCOCC3)nn2c1Nc1cccc(C(F)(F)F)c1C]

Under nitrogen, at −78° C. iodine (1 g; 4 mmol) was added dropwise to a solution of intermediate 91 (1.5 g; 3.8 mmol) in THF (31 mL). The reaction mixture was stirred 10 minutes and lithium diisopropylamide 1.6 M in hexanes/THF (6 mL; 9.6 mmol) was added. The reaction was stirred for 1 hour at −78° C. EtOAc and a saturated aqueous solution of brine were added to the reaction. The organic layer was washed, separated, dried over MgSO$_4$, filtered and evaporated to dryness. The residue was purified by chromatography over silica gel (irregular SiOH 40 g; mobile phase 98% DCM 2% CH$_3$OH 0.1% NH$_4$OH). The fractions containing the product were collected and evaporated to dryness yielding 0.64 g (32%) of intermediate 92

Example A28

Preparation of Intermediate 93

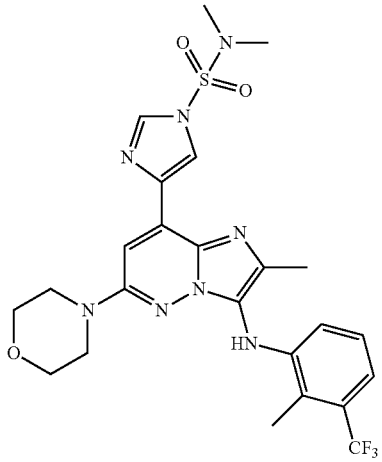 [SMILES: Cc1nc2c(-c3cn(S(=O)(=O)N(C)C)cn3)cc(N3CCOCC3)nn2c1Nc1cccc(C(F)(F)F)c1C]

In a sealed tube, under nitrogen, PdCl$_2$dppf.DCM (0.032 g; 0.039 mmol) was added to a mixture of intermediate 92 (0.2 g; 0.39 mmol), N,N-dimethyl-4-(4,4,5,5-tetramethyl-1,3,2-dioxaborolan-2-yl)-1H-imidazole-1-sulfonamide (0.16 g; 0.54 mmol) and potassium carbonate (0.11 g; 0.78 mmol) in dioxane (6 mL) and water (1.5 mL). The reaction mixture was heated at 100° C. overnight. The reaction mixture was cooled to room temperature, poured into water and DCM was added. The suspension was filtered over a pad of Celite®. The organic layer was decanted, dried over MgSO$_4$, filtered and evaporated to dryness yielding 0.36 g of intermediate 93 which was directly used in the next reaction step without any further treatment.

Example A29

Preparation of Intermediate 94

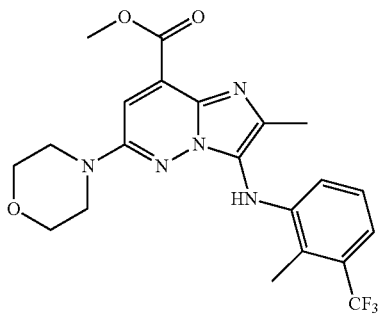 [SMILES: COC(=O)c1cc(N2CCOCC2)nn2c(Nc3cccc(C(F)(F)F)c3C)c(C)nc12]

In a sealed tube, a mixture of intermediate 92 (0.75 g, 1.4 mmol) and triethylamine (2.83 mL, 20.3 mmol) in MeOH (18 mL) was degassed with nitrogen. Pd(PPh$_3$)$_4$ (0.17 g, 0.45 mmol) was added and the reaction was purged for 5 minutes. Carbon monoxide was added (5 bars) and the reaction was stirred for 15 hours at 120° C. The mixture was concentrated and the residue was purified by chromatography over silica gel (irregular SiOH, 40 g; gradient from 99% DCM 1% CH$_3$OH 0.1% NH$_4$OH to 97% DCM 3% CH$_3$OH 0.1% NH₄OH). The fractions containing the product were collected and evaporated to dryness yielding 0.35 g (25%) of intermediate 94.

Preparation of Intermediate 95/Intermediate 96

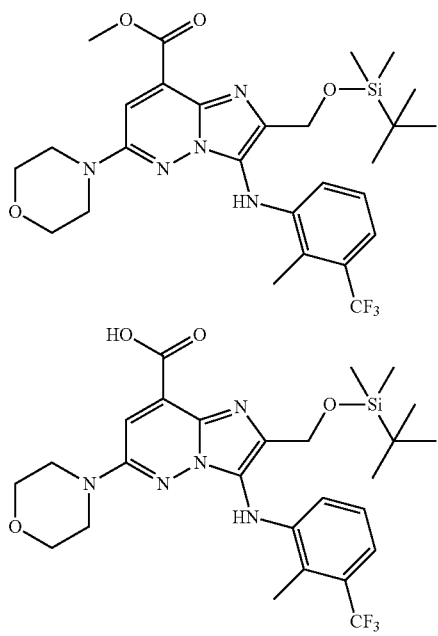

In a sealed tube, a mixture of intermediate 100 (0.25 g, 0.39 mmol) and triethylamine (0.75 mL, 5.4 mmol) in MeOH (5 mL) was degassed with nitrogen. Pd(PPh₃)₄ (0.089 g, 0.077 mmol) was added and the reaction was purged for 5 minutes. Carbon monoxide was added (5 bars) and the reaction was stirred for 15 hours at 120° C. The mixture was concentrated and the residue was purified by chromatography over silica gel (irregular SiOH, 24 g; gradient from 97% DCM 3% CH₃OH to 85% DCM 15% CH₃OH). The fractions containing the product were collected and evaporated to dryness yielding 0.08 g (36%) of intermediate 95 and 0.114 g (52%) of intermediate 96.

Example A30

Preparation of Intermediate 97

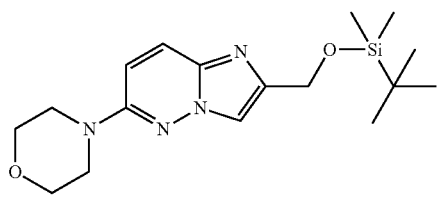 [SMILES: CC(C)(C)[Si](C)(C)OCc1cn2nc(N3CCOCC3)ccc2n1]

Intermediate 97 was prepared according to an analogous procedure as described for the synthesis of intermediate 6 using intermediate 2 as starting material (72%).

Preparation of Intermediate 98

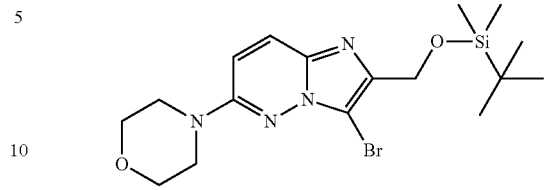

Intermediate 98 was prepared according to an analogous procedure as described for the synthesis of intermediate 90 using intermediate 97 as starting material (95%).

Preparation of Intermediate 99

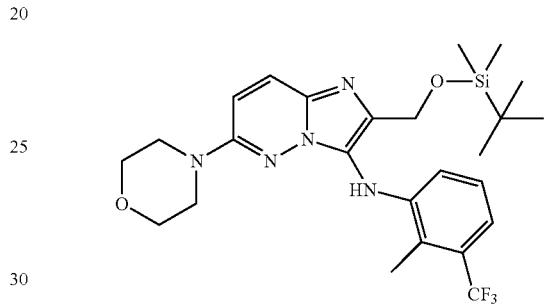

Under nitrogen, to a mixture of intermediate 98 (15 g, 35.1 mmol), 2-methyl-3-(trifluoromethyl)aniline (7.4 g, 42.1 mmol), Pd₂dba₃ (3.21 g; 3.51 mmol) and cesium carbonate (22.9 g, 70.2 mmol) in toluene (250 mL) was degassed with nitrogen for 10 minutes, then BrettPhos was added (3.8 g, 7.1 mmol). The reaction mixture was heated at 85° C. overnight. The reaction was filtered and the filtrate was concentrated. The residue was purified by chromatography over silica gel mobile phase 50% petroleum ether 50% EtOAc). The fractions containing the product were collected and evaporated to dryness. The residue (10 g; 33%) by high performance liquid chromatography (C18 SiO₂, 250*50 mm*10 μm, gradient from 40% NH₄HCO₃ water 60% Acetonitrile to 15% NH₄HCO₃ water to 85% Acetonitrile in 25 min). The fractions containing the product were collected and evaporated to dryness to afford 5.2 g (25%) of intermediate 99

Preparation of Intermediate 100

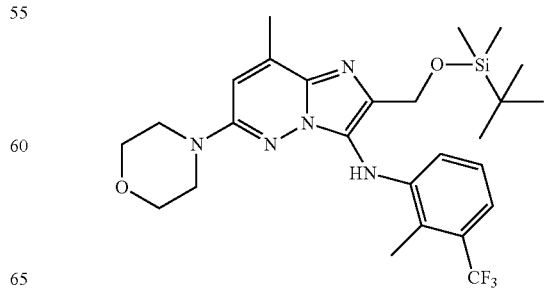

Under nitrogen at 0° C., n-butyllithium 2.5 M in THF (17.4 mL; 43.5 mmol) was added dropwise to a solution of diisopropylamine (4.28 g; 42.3 mmol) in THF (50 mL). Intermediate 99 (6.3 g; 12.1 mmol) in THF (45 mL) was added dropwise and the reaction was stirred at −78° C. for 30 minutes. A solution of iodine (3.4 g; 13.3 mmol) in THF (25 mL) was added dropwise and the reaction mixture was stirred 1 hour at −78° C. A saturated solution of NH$_4$Cl (80 mL) was added and the reaction was extracted with EtOAc. The organic layer was separated, dried over MgSO$_4$, filtered and evaporated to dryness. The residue (7 g) was purified by chromatography over silica gel (mobile phase: 50% petroleum ether 50% EtOAc). The fractions containing the product were collected, evaporated to dryness and washed with ACN to afford 1.27 g (16%) of intermediate 100 and 1.75 g impure product. This impure product was purified by high performance liquid chromatography (C18 SiO$_2$ 250*50 mm*10 μm, gradient from 40% NH$_4$HCO$_3$ water 60% Acetonitrile to 15% NH$_4$HCO$_3$ water 85% Acetonitrile in 25 min). The fractions containing the product were collected and evaporated to dryness to afford 0.88 g (11%) of intermediate 100.

Example A31

Preparation of Intermediate 101

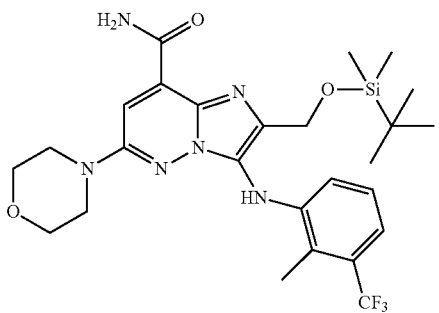 [SMILES: Cc1c(Nc2c(CO[Si](C)(C)C(C)(C)C)nc3c(C(N)=O)cc(N4CCOCC4)nn23)cccc1C(F)(F)F]

Diisopropylamine (0.168 mL; 0.97 mmol) was added to a solution of intermediate 96 (0.11 g; 0.19 mmol), 1,1,1,3,3,3-hexamethyldisilazane (0.053 mL; 0.25 mmol) and HATU (0.096 g; 0.25 mmol) in DMF (3.5 mL) and the reaction mixture was stirred at room temperature for 18 hours.

The reaction mixture was diluted with EtOAc and a 10% aqueous solution of K$_2$CO$_3$ was added. The organic layer was decanted, washed with water then brine, dried over MgSO$_4$, filtered and evaporated to dryness. The residue was purified by chromatography over silica gel (Irregular SiOH, 15-40 μm, 10 g, gradient from 97% DCM 3% CH$_3$OH to 95% DCM 5% CH$_3$OH). The fractions containing the product were collected and evaporated to dryness to afford 0.117 g (62%) of intermediate 101.

Example A32

Preparation of Intermediate 102

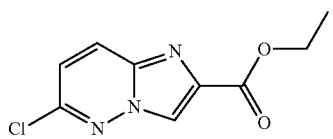

3-amino-6-chloropyridazine (20 g; 154.4 mmol) and ethyl bromopyruvate (38.9 mL; 308.8 mmol) in EtOH (90 mL) were refluxed overnight. The reaction mixture was cooled to room temperature, water and DCM were added. The organic layer was separated, dried over MgSO$_4$, filtered and evaporated. The residue was purified by chromatography over silica gel (Irregular SiOH, 15-40 μm, 300 g, gradient from 97% heptane 30% EtOAc to 50% Heptane 50% EtOAc). The fractions containing the product were collected and evaporated to dryness to afford 13.5 g (39%) of intermediate 102.

Preparation of Intermediate 103

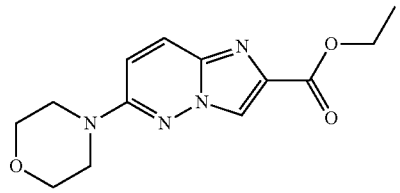 [SMILES: CCOC(=O)c1cn2nc(N3CCOCC3)ccc2n1]

A mixture of intermediate 102 and morpholine (84 mL; 0.96 mmol) was heated at 90° C. for 4 hours. The reaction mixture was cooled to room temperature and the solvent was evaporated, the residue was poured into water and DCM was added. The organic layer was separated, dried over MgSO$_4$, filtered and evaporated. DCM was added then the solution was stirred overnight. The precipitate was filtered to eliminate morpholine excess. The filtrate was purified by chromatography over silica gel (Irregular SiOH, 15-40 μm, 300 g, gradient from 99% DCM 1% CH$_3$OH 0.1% NH$_4$OH to 97% DCM 3% CH$_3$OH 0.1% NH$_4$OH). The fractions containing the product were collected and evaporated to dryness to afford 6.9 g (71%) of intermediate 103.

Preparation of Intermediate 104

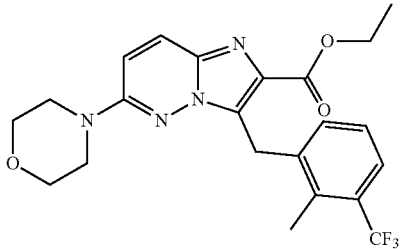 [SMILES: CCOC(=O)c1nc2ccc(N3CCOCC3)nn2c1Cc1cccc(C(F)(F)F)c1C]

A mixture of intermediate 103 (2 g; 7.2 mmol), 1-(chloromethyl)-2-methyl-3-(trifluoromethyl)benzene (1.7 g; 7.96 mmol) and potassium carbonate (1.5 g; 10.9 mmol) in dioxane (29 mL) was degassed under nitrogen then triphenylphosphine (0.38 g; 1.45 mmol) and palladium acetate (0.16 g; 0.72 mmol) was added and the reaction mixture was heated at 100° C. for 15 hours. The mixture was cooled down to room temperature, poured into water, basified with K$_2$CO$_3$ solid and extracted with EtOAc. The organic layer was dried over MgSO$_4$, filtered and evaporated to dryness. The residue (6 g) was purified by chromatography over silica gel (irregular SiOH, 550 g; gradient from 100% DCM to 95% DCM 5% CH$_3$OH 0.1% NH$_4$OH). The fractions containing the product were collected, evaporated to dryness and crystallized in acetone. The precipitate was filtered and dried to give 1.5 g (46%) of intermediate 104.

Example A33

Preparation of Intermediate 105

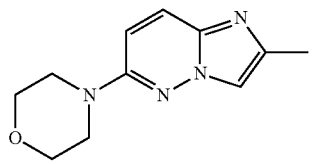 [SMILES: Cc1cn2nc(N3CCOCC3)ccc2n1]

A mixture of intermediate 12 (53 g; 0.32 mmol) and morpholine (550 mL; 6.25 mmol) was heated at 120° C. for 20 hours. The mixture was cooled and the solvent was evaporated, the residue was taken up with DCM and water. The organic layer was separated, dried over MgSO$_4$, filtered and evaporated to dryness. The residue (57 g) was purified by chromatography over silica gel (irregular SiOH, 550 g; gradient from 100% DCM to 90% DCM 10% CH$_3$OH 0.1% NH$_4$OH). The fractions containing the product were collected and evaporated to dryness yielding 12.7 g (24%) of intermediate 12 and 33.7 g (49%) of intermediate 105.

Example A34

Preparation of Intermediate 106

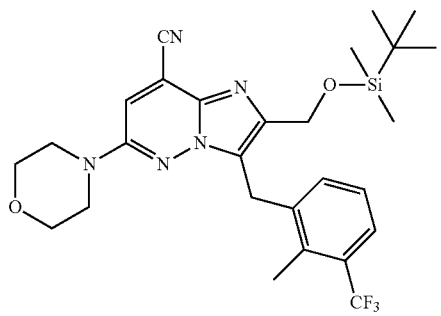 [SMILES: Cc1c(Cc2c(CO[Si](C)(C)C(C)(C)C)nc3c(C#N)cc(N4CCOCC4)nn23)cccc1C(F)(F)F]

In sealed tube, Intermediate 7 (3 g; 4.6 mmol), zinc cyanide (0.82 g; 7 mmol) and Pd(PPh$_3$)$_4$ (0.54 g; 0.4 mmol) in DMF (20 mL) were heated at 100° C. overnight. The reaction mixture was cooled, poured into water and DCM was added. The organic layer was separated, dried over MgSO$_4$, filtered and evaporated. The residue (3 g) was purified by chromatography over silica gel (irregular SiOH, 80 g; mobile phase, gradient from 100% DCM to 90% DCM 10% CH$_3$OH 0.1% NH$_4$OH). The fractions containing the product were collected and evaporated to dryness yielding 1 g (42%) of intermediate 106 and 0.76 g (29%) of intermediate 57.

Example A35

Preparation of Intermediate 107

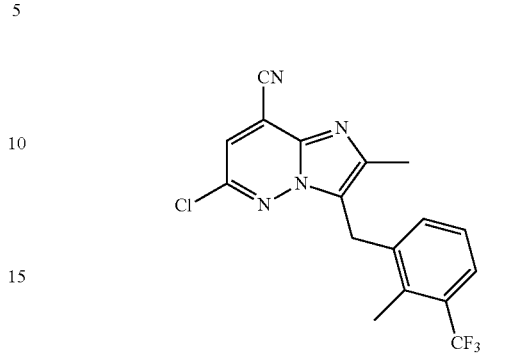

A mixture of intermediate 65 (0.1 g; 0.52 mmol), 1-(chloromethyl)-2-methyl-3-(trifluoromethyl)benzene (0.16 g; 0.78 mmol) and potassium carbonate (0.108 g; 0.78 mmol) in dioxane (1.8 mL) was degassed under nitrogen then triphenylphosphine (0.027 g; 0.104 mmol) and palladium acetate (0.012 g; 0.052 mmol) was added and the reaction mixture was heated at 100° C. for 15 hours. The mixture was cooled down to room temperature, solubilized in EtOAc. The organic layer was washed with brine, separated, dried over MgSO$_4$, filtered and evaporated to dryness. The residue (6 g) was purified by chromatography over silica gel (irregular SiOH, 25 g; 85% Heptane 15% EtOAc). The fractions containing the product were collected and evaporated to afford 0.050 g (26%) of intermediate 107.

Example A36

Preparation of Intermediate 108

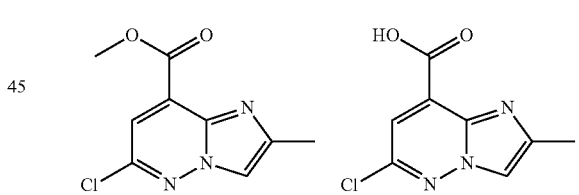

In sealed tube, to a mixture of intermediate 79 (5 g, 14.5 mmol), triethylamine (28.3 mL, 203.4 mmol) in MeOH (50 mL) previously purged with N$_2$ then was added Pd(PPh$_3$)$_4$ (0.004 g, 0.0029 mmol). The reaction was then purged for 5 additional minutes and carbon monoxide was added (6 bars) the reaction was stirred for 2 hours at 110° C. The reaction was poured into water, basified with K$_2$CO$_3$ powder and extracted with EtOAc. The organic layer was filtered and the insoluble was washed with EtOAc and dried to give 1.7 g of intermediate 108. The organic layer was extracted of filtrate, dried over MgSO$_4$, filtered and evaporated. The residue (7 g) was purified by chromatography over silica gel (Irregular SiOH, 15-40 µm, 330 g, mobile phase gradient: 100% DCM to 90% DCM 10% CH$_3$OH 0.1% NH$_4$OH). The fractions containing the product were collected and evaporated to dryness to afford 2 g (50%) of intermediate 108.

Example A37

Preparation of Intermediate 109

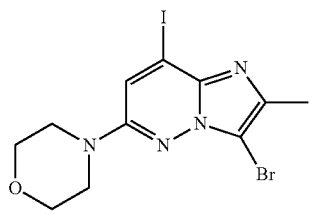 [SMILES: Cc1nc2c(I)cc(N3CCOCC3)nn2c1Br]

Intermediate 109 was prepared according to an analogous procedure as described for the synthesis of intermediate 81, using intermediate 79 as starting material (90).

Preparation of Intermediate 110

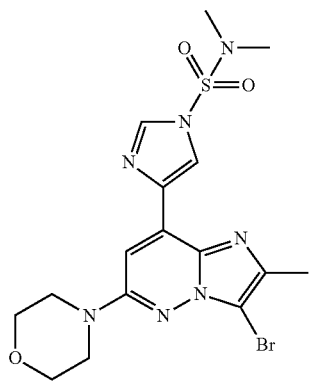 [SMILES: Cc1nc2c(-c3cn(S(=O)(=O)N(C)C)cn3)cc(N3CCOCC3)nn2c1Br]

In a sealed tube, under nitrogen, PdCl₂dppf.DCM (0.38 g; 0.47 mmol) was added to a mixture of intermediate 109 (2 g; 4.7 mmol), N,N-dimethyl-4-(4,4,5,5-tetramethyl-1,3,2-dioxaborolan-2-yl)-1H-imidazole-1-sulfonamide (2 g; 6.6 mmol) and potassium carbonate (1.3 g; 9.5 mmol) in dioxane (60 mL) and water (20 mL). The reaction mixture was heated at 100° C. for 3 hours. The reaction mixture was cooled to room temperature, poured into water and DCM was added. The suspension was filtered over a pad of Celite®. The organic layer was decanted, dried over MgSO₄, filtered and evaporated to dryness. The resulting residue was taken up with ACN, the precipitate was filtered and dried to afford 1.63 g of intermediate 110 (73%).

Preparation of Intermediate 111 (and Compound 41)

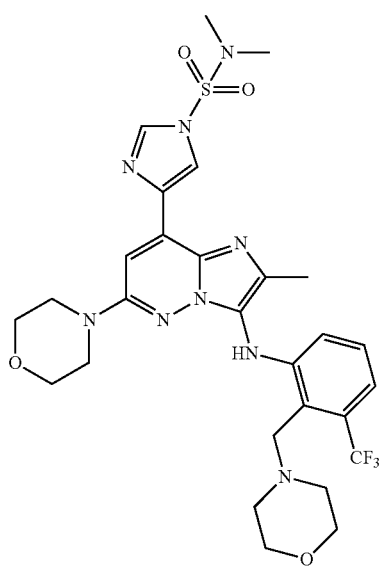

intermediate 111

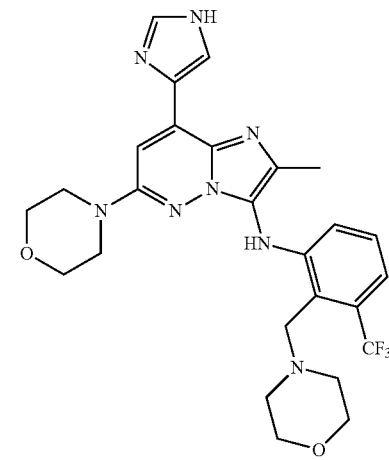

compound 41

Under nitrogen, in a sealed tube, to a mixture of intermediate 110 (0.2 g, 0.42 mmol), intermediate 83 ((0.133 g, 0.51 mmol) and sodium tert-butoxide (0.080 g, 0.85 mmol) in dioxane (2.5 mL), previously degassed with nitrogen then were added Pd₂dba₃ (0.039 g, 0.042 mmol) and 2-(di-t-butylphosphino)biphenyl (0.025 mg, 0.085 mmol). The reaction mixture was at 140° C. for 30 min using one single mode microwave with a power output ranging from 0 to 400 W. The reaction mixture was poured into water and DCM was added. The organic layer was separated, dried over MgSO₄, filtered and evaporated. The residue (0.250 g) was purified by chromatography over silica gel (Irregular SiOH, 15-40 μm, 12 g, gradient from 98% DCM 2% CH₃OH to 90% DCM 10% CH₃OH). The fractions containing the product were collected and evaporated to dryness to afford 0.114 g (34%) of intermediate 111 and 0.053 g (89% of purity based on LCMS; 20%) of compound 41.

Preparation of Intermediate 112

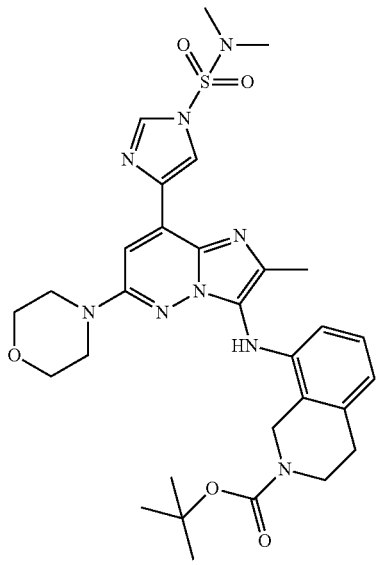 [SMILES: Cc1nc2c(-c3cn(S(=O)(=O)N(C)C)cn3)cc(N3CCOCC3)nn2c1Nc1cccc2c1CN(C(=O)OC(C)(C)C)CC2]

Intermediate 112 was prepared according to an analogous procedure as described for the synthesis of intermediate 111, using intermediate 110 as starting material and tert-butyl-8-amino-3,4-dihydroisoquinoline-2(1H)-carboxylate, which directly used for the next step without any further treatment.

Preparation of Intermediate 120 and Intermediate 121

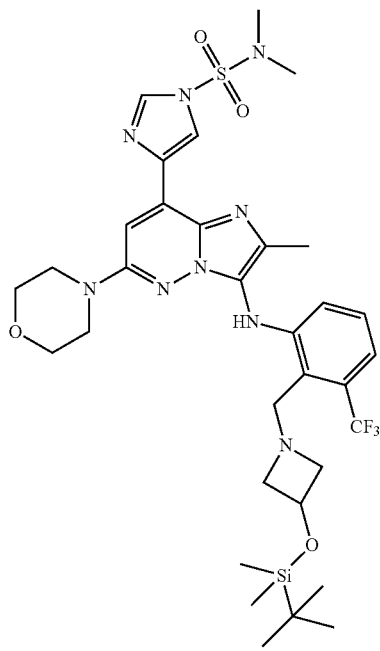

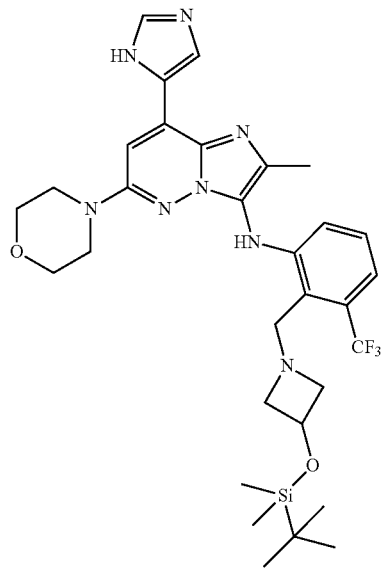

In a sealed tube, a mixture of intermediate 110 (400 mg; 0.85 mmol), intermediate 119 (306 mg; 0.85 mmol) and sodium tert-butoxide (163 mg; 1.70 mmol) in 1,4-dioxane (8 mL) was purged with $N_2$. $Pd_2(dba)_3$ (78 mg; 0.085 mmol) and 2-(di-t-butylphosphino)biphenyl (51 mg; 0.17 mmol) were added. The reaction mixture was purged with $N_2$ and heated at 100° C. for 5 hours. The reaction mixture was cooled to room temperature, diluted with DCM and quenched with water. The reaction mixture was filtered through a pad of Celite® and the organic layer was decanted, separated, washed with water, dried over $MgSO_4$, filtered and evaporated to dryness yielding 613 mg of a mixture of intermediate 120 and intermediate 121 which was used as such without purification in the next reaction step.

Preparation of Intermediate 130 (and Compound 50)

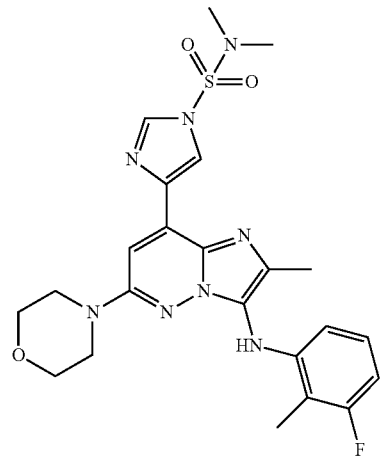

-continued

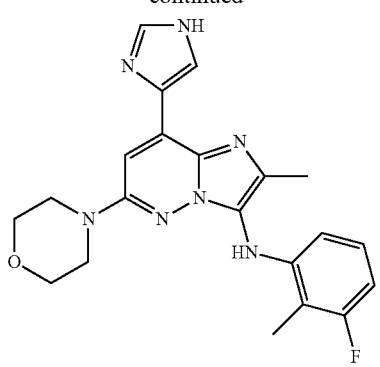

Intermediate 130 was prepared according to an analogous procedure as described for the synthesis of intermediate 111, using intermediate 110 and 3-fluoro-2-methylaniline as starting materials. Intermediate 130 was obtained as a mixture together with compound 50. The mixture was directly used as such for the next reaction step without purification.

Preparation of Intermediate 151 (and Compound 57)

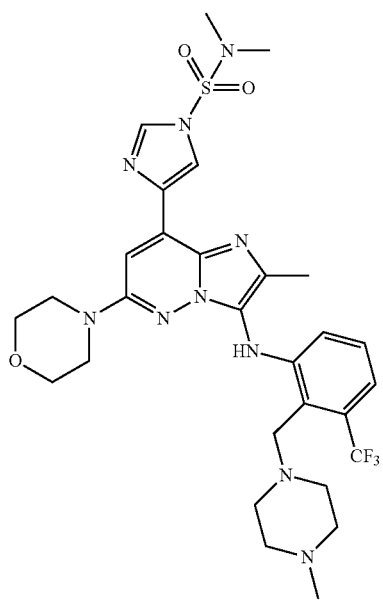

-continued

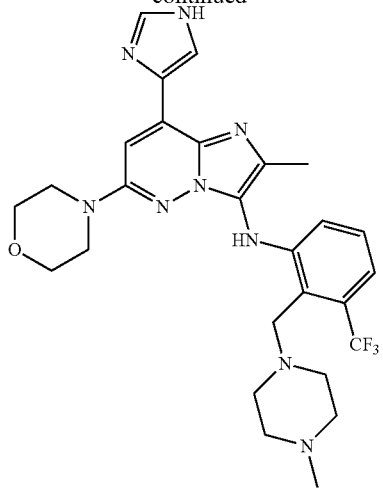

Intermediate 151 and compound 57 were prepared according to an analogous procedure as described for the synthesis of intermediate 111, using intermediate 110 and intermediate 150 as starting materials. The mixture of intermediate 151 and compound 57 was directly used as such in the next reaction step without purification.

Example A38

Preparation of Intermediate 113

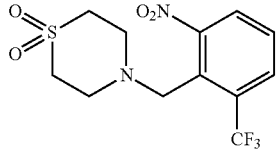 [SMILES: O=[N+]([O-])c1cccc(C(F)(F)F)c1CN1CCS(=O)(=O)CC1]

Triethylamine (2 mL, 14.1 mmol) and thiomorpholine-1,1-dioxide (1.1 mL, 8.4 mmol) were added to a solution of 2-(bromomethyl)-1-nitro-3-(trifluoromethyl)benzene (2 g, 7.0 mmol) in DCM (20 mL) and the reaction mixture was stirred at room temperature overnight. Then, it was poured into ice water and DCM was added. The aqueous layer was extracted with DCM, dried over MgSO$_4$, filtered and evaporated till dryness. The residue (2 g) was purified by chromatography over silica gel (irregular SiOH; 120 g, gradient from 80% Heptane 20% EtOAc to 60% Heptane 40% EtOAc). The fractions containing the product were collected and evaporated to dryness yielding 0.35 g (15%) of intermediate 113.

Preparation of Intermediate 114

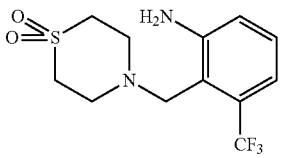 [SMILES: Nc1cccc(C(F)(F)F)c1CN1CCS(=O)(=O)CC1]

A solution of intermediate 113 (0.56 g, 1.6 mmol), Raney nickel 50% in water (0.6 g, 10.2 mmol) in EtOH (20 mL) was hydrogenated (2 atmosphere) at room temperature for 2 hours. The mixture was filtered over a pad of Celite®, washed with DCM and the filtrate was concentrated (reduce pressure) to afford (0.47 g, 92%) of intermediate 114.

Preparation of Intermediate 118

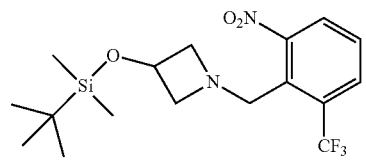 [SMILES: CC(C)(C)[Si](C)(C)OC1CN(Cc2c([N+](=O)[O-])cccc2C(F)(F)F)C1]

Intermediate 118 was prepared according to an analogous procedure as described for the synthesis of intermediate 113, using 2-(bromomethyl)-1-nitro-3-(trifluoromethyl)benzene and 3-[[(1,1-dimethylethyl)dimethylsilyl]oxy]-azetidine as starting materials (30%).

Preparation of Intermediate 119

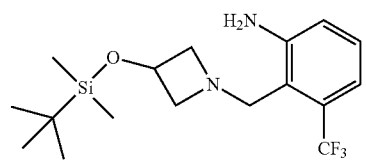

A mixture of intermediate 118 (1.24 g; 3.18 mmol) and Raney Nickel (1.2 g; 21.51 mmol) in MeOH (30 mL) was hydrogenated at room temperature under atmospheric pressure of $H_2$ for 2 hours. The catalyst was removed by filtration over Celite® and the filtrate was evaporated to dryness yielding 1.08 g (94%) of intermediate 119.

Preparation of Intermediate 122

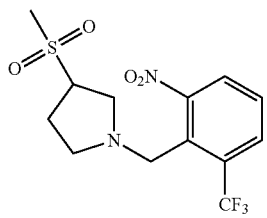

Intermediate 122 was prepared according to an analogous procedure as described for the synthesis of intermediate 113, using 2-(bromomethyl)-1-nitro-3-(trifluoromethyl)benzene and 3-(methylsulfony)pyrrolidine as starting material (85%).

Preparation of Intermediate 123

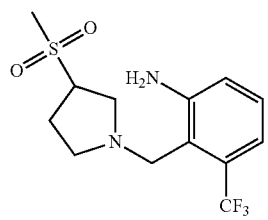 [SMILES: CS(=O)(=O)C1CCN(Cc2c([N+](=O)[O-])cccc2C(F)(F)F)C1]

Intermediate 123 was prepared according to an analogous procedure as described for the synthesis of intermediate 114, using intermediate 122 as starting material (100%).

Preparation of Intermediate 124

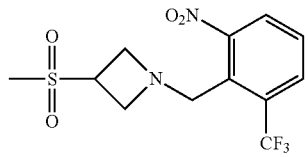 [SMILES: CS(=O)(=O)C1CN(Cc2c([N+](=O)[O-])cccc2C(F)(F)F)C1]

Intermediate 124 was prepared according to an analogous procedure as described for the synthesis of intermediate 113, using 2-(bromomethyl)-1-nitro-3-(trifluoromethyl)benzene and 3-(methylsulfonyl)-azetidine hydrochloride as starting material (78%).

Preparation of Intermediate 125

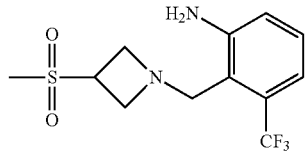

Intermediate 125 was prepared according to an analogous procedure as described for the synthesis of intermediate 114, using intermediate 124 as starting material (97%).

Preparation of Intermediate 127

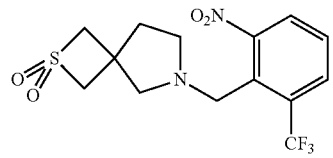 [SMILES: O=[N+]([O-])c1cccc(C(F)(F)F)c1CN1CCC2(C1)CS(=O)(=O)C2]

Intermediate 127 was prepared according to an analogous procedure as described for the synthesis of intermediate 113, using 2-(bromomethyl)-1-nitro-3-(trifluoromethyl)benzene and 2-thia-6-azaspiro[3.4]octane 2,2-dioxide hemioxalate as starting materials (34%).

Preparation of Intermediate 128

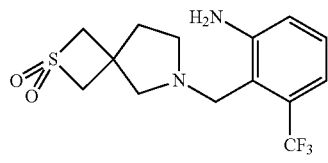

Intermediate 128 was prepared according to an analogous procedure as described for the synthesis of intermediate 114, using intermediate 127 as starting material (100%).

Preparation of Intermediate 136

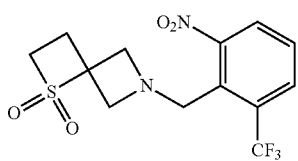 [SMILES: Nc1cccc(C(F)(F)F)c1CN1CC2(CCS2(=O)=O)C1]

Intermediate 136 was prepared according to an analogous procedure as described for the synthesis of intermediate 113, using 2-(bromomethyl)-1-nitro-3-(trifluoromethyl)benzene and 1-Thia-6-azaspiro[3.3]heptane, 1,1-dioxide hydrochloride as starting materials (78%).

Preparation of Intermediate 137

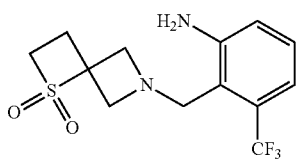

Intermediate 137 was prepared according to an analogous procedure as described for the synthesis of intermediate 114, using intermediate 136 as starting material (23%).

Preparation of Intermediate 139

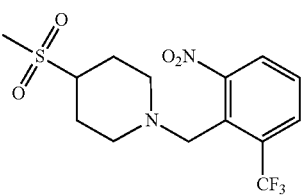 [SMILES: CS(=O)(=O)C1CCN(Cc2c([N+](=O)[O-])cccc2C(F)(F)F)CC1]

Intermediate 139 was prepared according to an analogous procedure as described for the synthesis of intermediate 113, using 2-(bromomethyl)-1-nitro-3-(trifluoromethyl)benzene and 4-(methylsulfonyl)-piperidine as starting material (100%).

Preparation of Intermediate 140

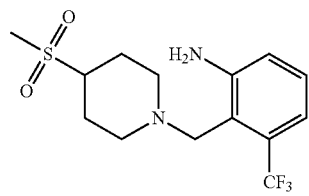 [SMILES: CS(=O)(=O)C1CCN(Cc2c(N)cccc2C(F)(F)F)CC1]

Intermediate 140 was prepared according to an analogous procedure as described for the synthesis of intermediate 114, using intermediate 139 as starting material (96%).

Preparation of Intermediate 142

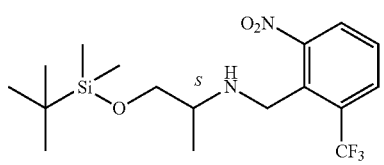

Intermediate 142 was prepared according to an analogous procedure as described for the synthesis of intermediate 113, using 2-(bromomethyl)-1-nitro-3-(trifluoromethyl)benzene and (2S)-1-[[(1,1-dimethylethyl)dimethylsilyl]oxy]-2-propanamine as starting material (49%).

Preparation of Intermediate 143

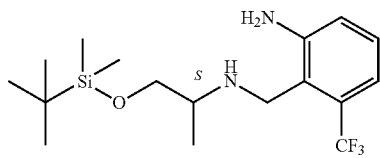

Intermediate 143 was prepared according to an analogous procedure as described for the synthesis of intermediate 119, using intermediate 142 as starting material (99%).

Preparation of Intermediate 145

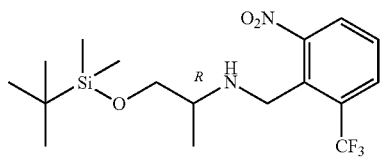

Intermediate 145 was prepared according to an analogous procedure as described for the synthesis of intermediate 113, using 2-(bromomethyl)-1-nitro-3-(trifluoromethyl)benzene and (2R)-1-[[(1,1-dimethylethyl)dimethylsilyl]oxy]-2-propanamine as starting material (37%).

Preparation of Intermediate 146

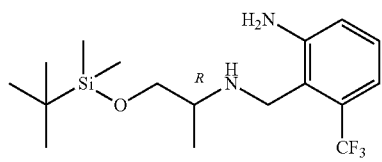

Intermediate 146 was prepared according to an analogous procedure as described for the synthesis of intermediate 119, using intermediate 145 as starting material (100%).

Preparation of Intermediate 149

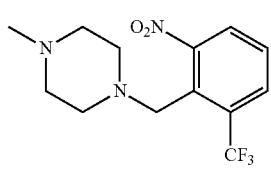

Intermediate 149 was prepared according to an analogous procedure as described for the synthesis of intermediate 113, using 2-(bromomethyl)-1-nitro-3-(trifluoromethyl)benzene and 1-methylpiperazine as starting material (48%).

Preparation of Intermediate 150

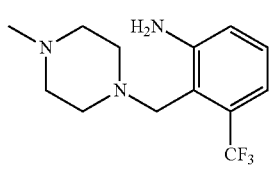 [SMILES: CN1CCN(Cc2c([N+](=O)[O-])cccc2C(F)(F)F)CC1]

Intermediate 150 was prepared according to an analogous procedure as described for the synthesis of intermediate 119, using intermediate 149 as starting material (98%).

Preparation of Intermediate 160

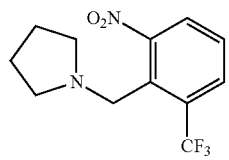

Intermediate 160 was prepared according to an analogous procedure as described for the synthesis of intermediate 113, using 2-(bromomethyl)-1-nitro-3-(trifluoromethyl)benzene and pyrrolidine as starting material (83%).

Preparation of Intermediate 161

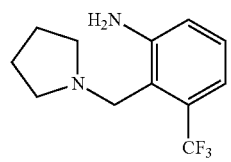 [SMILES: Nc1cccc(C(F)(F)F)c1CN1CCCC1]

Intermediate 161 was prepared according to an analogous procedure as described for the synthesis of intermediate 114, using intermediate 160 as starting material (36%).

Preparation of Intermediate 183

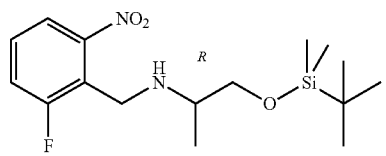

Intermediate 183 was prepared according to an analogous procedure as described for the synthesis of intermediate 113, using 2-fluoro-6-nitrobenzyl bromide and (2R)-1-[[(1,1-dimethylethyl)dimethylsilyl]oxy]-2-propanamine as starting material without purification for the next step (100%).

Preparation of Intermediate 184

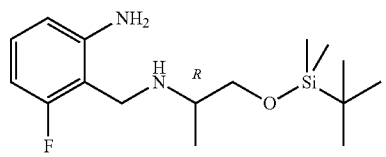

Intermediate 184 was prepared according to an analogous procedure as described for the synthesis of intermediate 114, using intermediate 183 as starting material with purification over silica gel (27%).

Example A39

Preparation of Intermediate 115

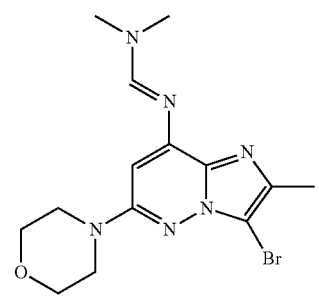 [SMILES: Cc1nc2c(/N=C/N(C)C)cc(N3CCOCC3)nn2c1Br]

A mixture of intermediate 81 (1 g; 3.2 mmol) and N,N-dimethylformamide dimethyl acetal (1.3 mL; 9.6 mmol) in toluene (45 mL) was heated at 120° C. for 2 hours. The reaction mixture was cooled and was concentrated to give 1.2 g of intermediate 115 (directly used for the next step without any further treatment).

Preparation of Intermediate 116 (and Compound 43)

Intermediate 116

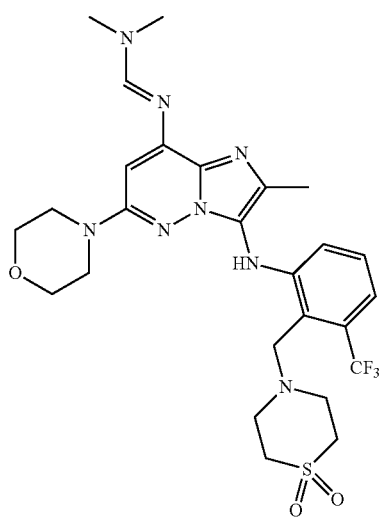

compound 43

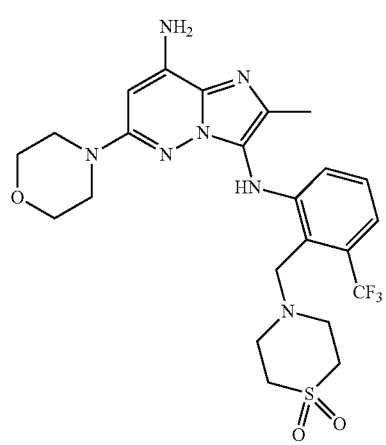

Under nitrogen, in a sealed tube, to a mixture of intermediate 115 (0.2 g, 0.252 mmol), intermediate 114 (0.25 g, 0.82 mmol) and sodium tert-butoxide (0.105 g, 1.1 mmol) in toluene (3 mL), previously degassed with nitrogen then were added $Pd_2dba_3$ (0.050 g, 0.055 mmol) and 2-(di-t-butylphosphino)biphenyl (0.032 mg, 0.11 mmol). The reaction mixture was heated to 100° C. for overnight. The reaction mixture was poured into water and DCM was added. The organic layer was separated, dried over $MgSO_4$, filtered and evaporated. The residue (0.450 g) was purified by chromatography over silica gel (Irregular SiOH, 15-40 μm, 25 g, gradient from 98% DCM 2% $CH_3OH$ 0.1% $NH_4OH$ to 90% DCM 10% $CH_3OH$ 0.5% $NH_4OH$). The fractions containing the products were collected and evaporated to dryness to afford 0.045 g (14%) of intermediate 116 and 190 mg of a second fraction which was taken up with $Et_2O$. The precipitate was filtered and dried to afford 90 mg (31%) of compound 43. M.P: 167° C. (kofler)

Preparation of Intermediate 117 (and Compound 38)

intermediate 117

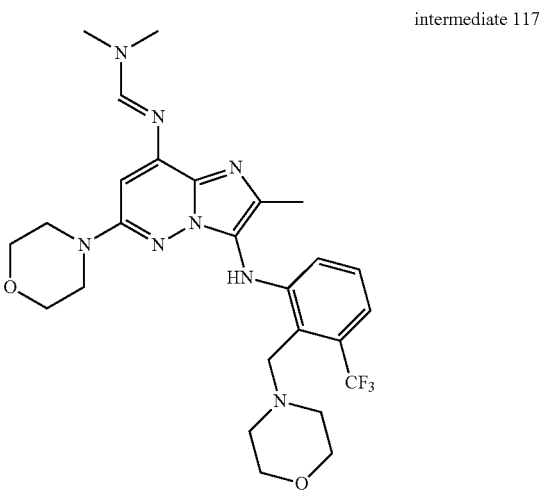

Compound 38

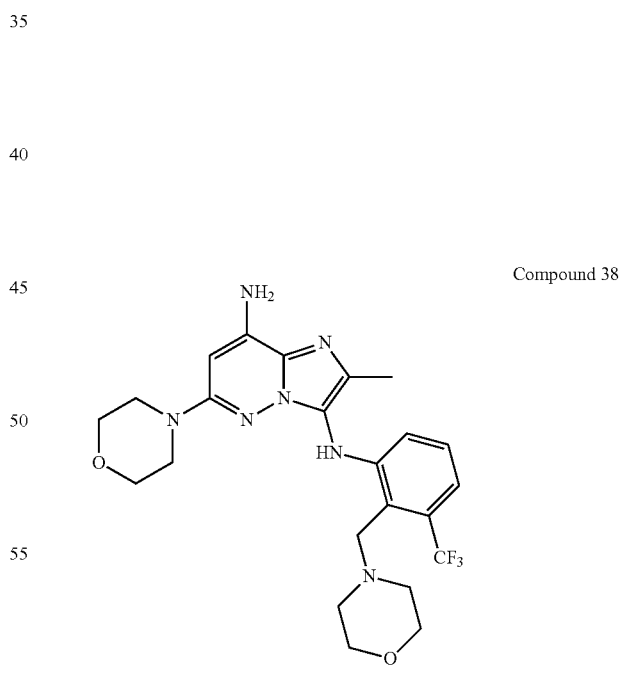

Intermediate 117 (and compound 38) were prepared according to an analogous procedure as described for the synthesis of intermediate 116, using intermediate 115 and intermediate 83 as starting materials.

(22% yield for intermediate 117; 4% yield for compound 38).

Preparation of Intermediate 126 (and Compound 48)

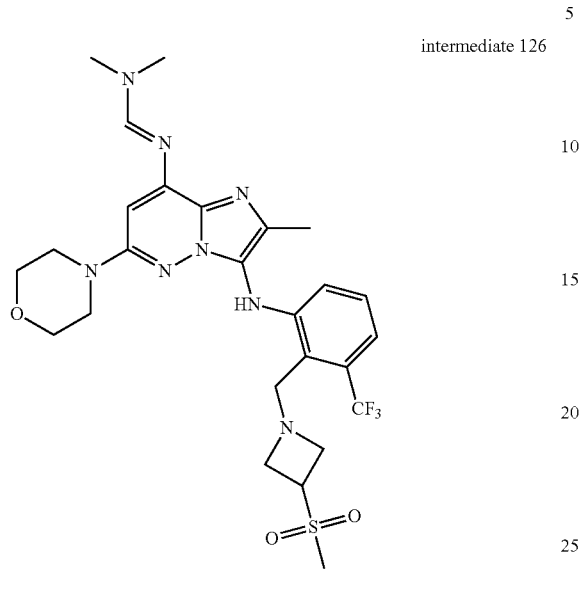

intermediate 126

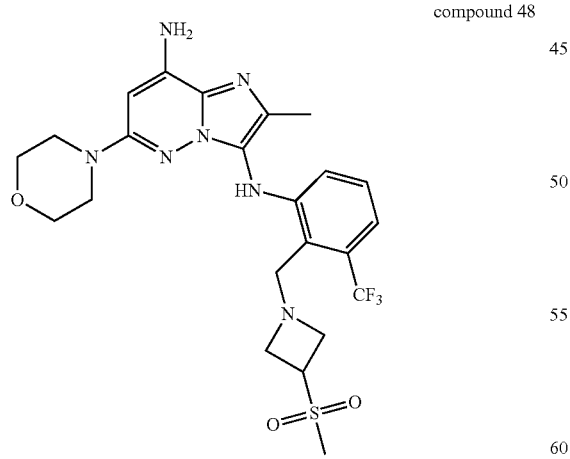

compound 48

Intermediate 126 (and compound 48) were prepared according to an analogous procedure as described for the synthesis of intermediate 116, using intermediate 125 and intermediate 115 as starting materials. (14% yield for intermediate 126; 49% yield for compound 48).

Preparation of Intermediate 129

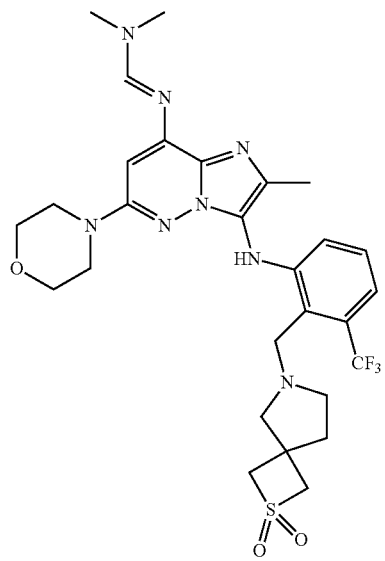 [SMILES: Cc1nc2c(/N=C/N(C)C)cc(N3CCOCC3)nn2c1Nc1cccc(C(F)(F)F)c1CN1CCC2(C1)CS(=O)(=O)C2]

Intermediate 129 was prepared according to an analogous procedure as described for the synthesis of intermediate 116, using intermediate 128 and intermediate 115 as starting materials (50%).

Preparation of Intermediate 132 and Intermediate 133

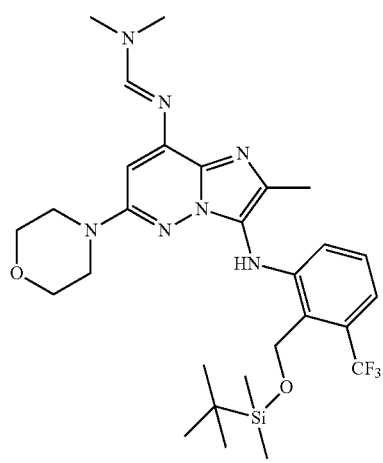

181
-continued

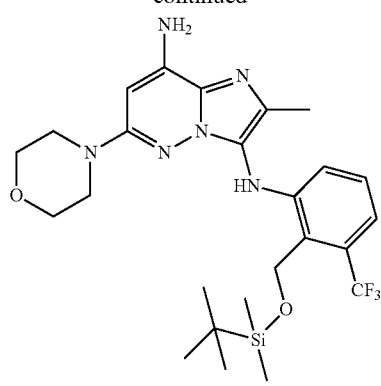

Intermediate 132 and intermediate 133 were prepared according to an analogous procedure as described for the synthesis of intermediate 116, using intermediate 131 and intermediate 115 as starting material (16% yield for intermediate 132; 17% yield for intermediate 133).

Preparation of Intermediate 134 and Intermediate 135

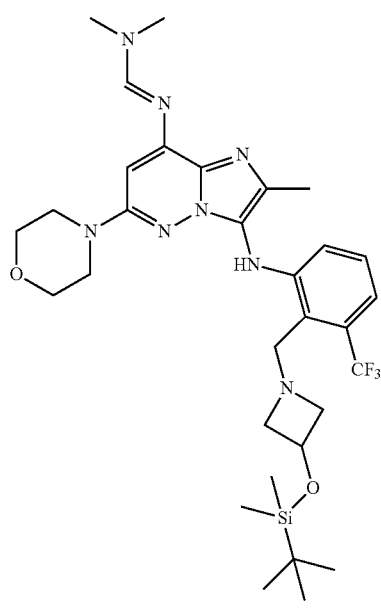

182
-continued

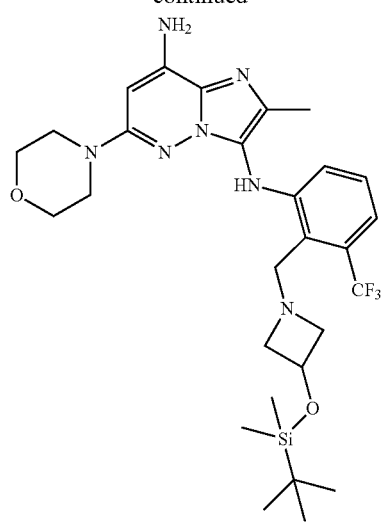

Intermediate 134 and intermediate 135 were prepared according to an analogous procedure as described for the synthesis of intermediate 116, using intermediate 119 and intermediate 115 as starting material (11% yield for intermediate 134; 29% yield for intermediate 135).

Preparation of Intermediate 138 (and Compound 53)

intermediate 138

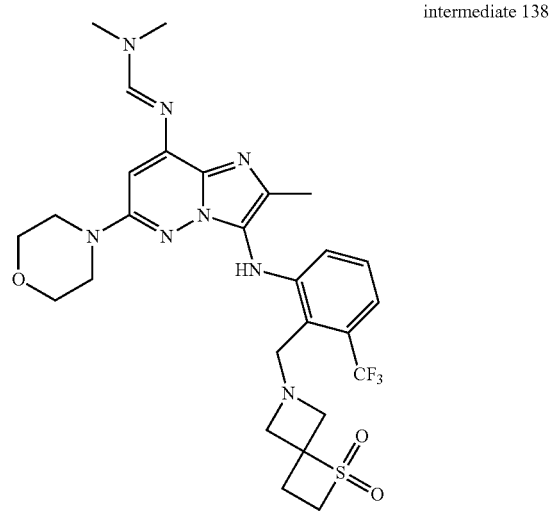

compound 53

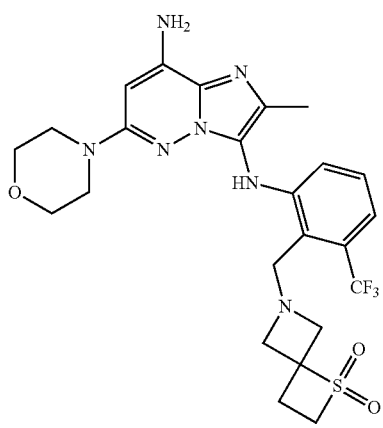

compound 54

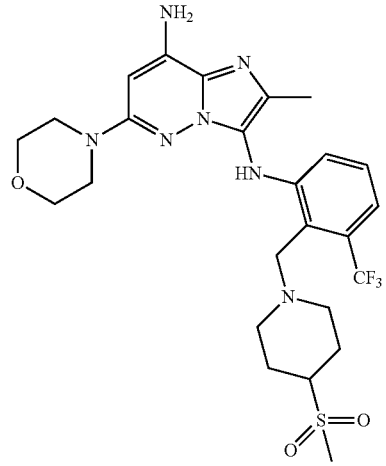

Intermediate 138 (and compound 53) were prepared according to an analogous procedure as described for the synthesis of intermediate 116, using intermediate 137 and intermediate 115 as starting materials.

(34% yield for intermediate 138; 24% yield for compound 53).

Preparation of Intermediate 141 (and Compound 54)

Intermediate 141 (and compound 54) were prepared according to an analogous procedure as described for the synthesis of intermediate 116, using intermediate 140 and intermediate 115 as starting materials. A mixture of intermediate 141 and compound 54 (ratio 47/53 evaluated by LC/MS) was obtained.

Preparation of Intermediate 144 intermediate 141

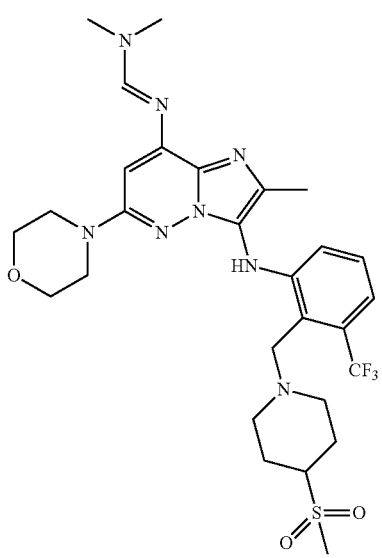

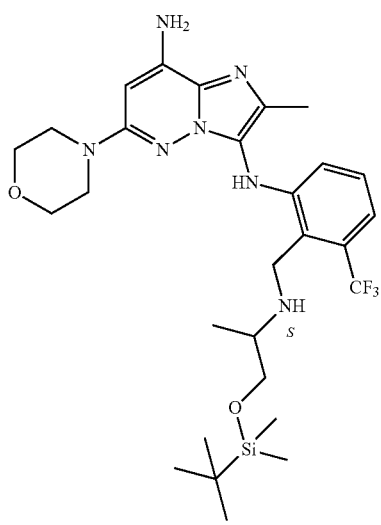

Intermediate 144 was prepared according to an analogous procedure as described for the synthesis of intermediate 116, using intermediate 143 and intermediate 115 as starting materials (40%).

185

Preparation of Intermediate 147 and Intermediate 148

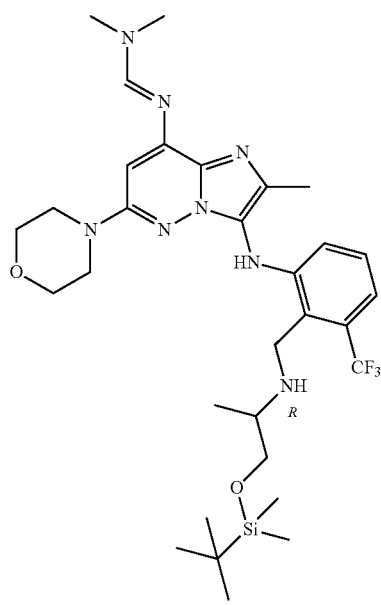

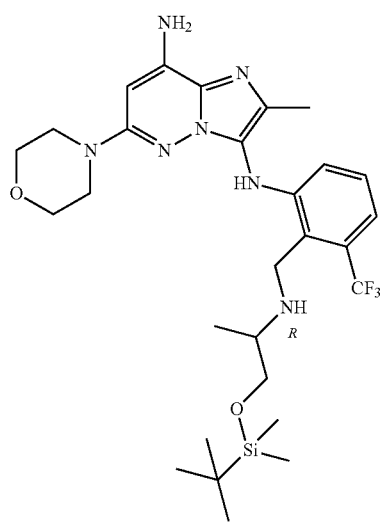

Intermediate 147 and intermediate 148 were prepared according to an analogous procedure as described for the synthesis of intermediate 116, using intermediate 146 and intermediate 115 as starting materials (51% yield for intermediate 147; 22% yield for intermediate 148).

186

Preparation of Intermediate 154 and Intermediate 155

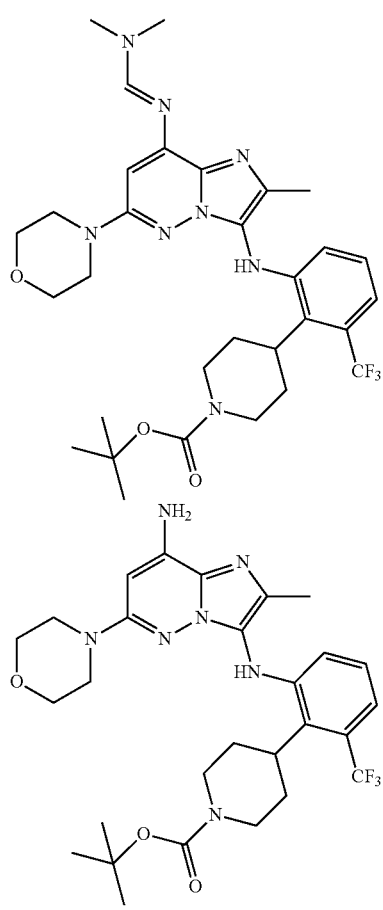

Intermediate 154 and intermediate 155 was prepared according to an analogous procedure as described for the synthesis of intermediate 116, using intermediate 153 and intermediate 115 as starting materials (39% yield for intermediate 154; 13% yield for intermediate 155).

Preparation of Intermediate 159

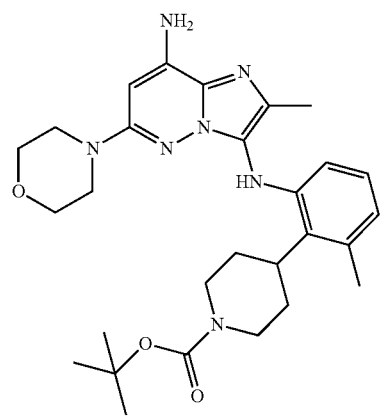 [SMILES: Cc1cccc(Nc2c(C)nc3c(N)cc(N4CCOCC4)nn23)c1C1CCN(C(=O)OC(C)(C)C)CC1]

Intermediate 159 was prepared according to an analogous procedure as described for the synthesis of intermediate 116, using intermediate 158 and intermediate 115 as starting materials (18%).

Preparation of Intermediate 162 (and Compound 62)

intermediate 162

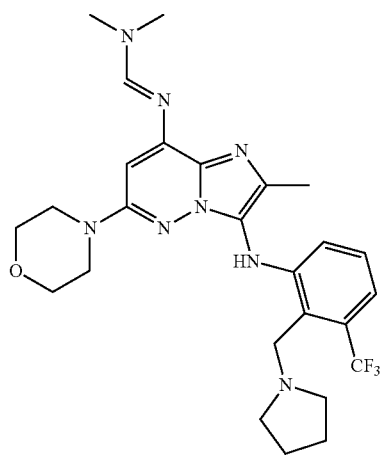

compound 62

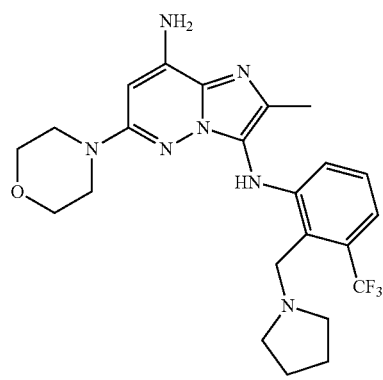

Intermediate 162 (and compound 62) were prepared according to an analogous procedure as described for the synthesis of intermediate 116, using intermediate 161 and intermediate 115 as starting materials. A mixture of intermediate 162 and compound 62 (ratio 58/31 evaluated by LC/MS) was obtained.

Preparation of Intermediate 163 (and Compound 63)

intermediate 163

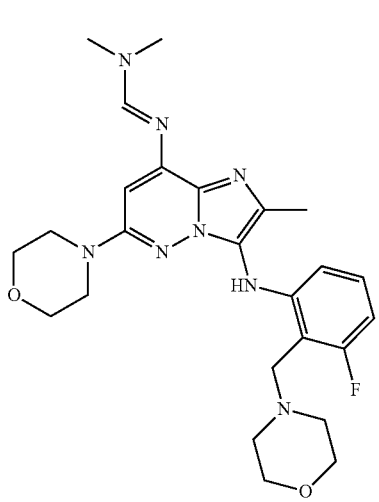

compound 63

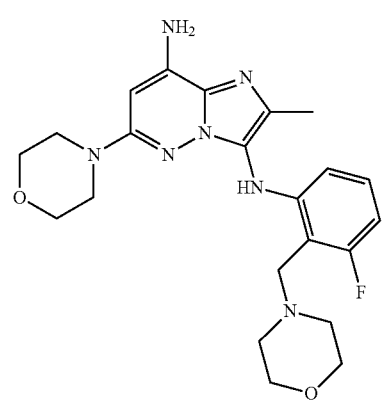

Intermediate 163 (and compound 63) were prepared according to an analogous procedure as described for the synthesis of intermediate 116, using 3-fluoro-2-(4-morpholinylmethyl)-benzenamine and intermediate 115 as starting materials. A mixture of intermediate 163 and compound 63 was obtained.

Preparation of Intermediate 164

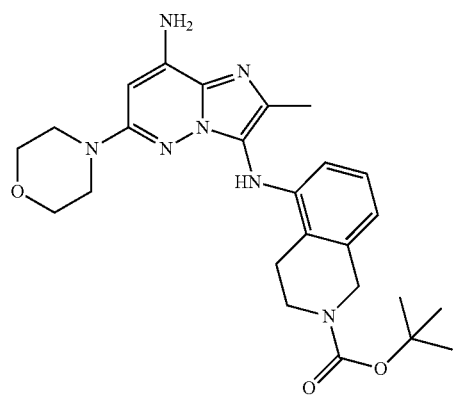 [SMILES: Cc1nc2c(N)cc(N3CCOCC3)nn2c1Nc1cccc2c1CCN(C(=O)OC(C)(C)C)C2]

Intermediate 164 was prepared according to an analogous procedure as described for the synthesis of intermediate 116, using 5-amino-3,4-dihydro-1,1-dimethylethyl ester 2(1H)-Isoquinolinecarboxylic acid and intermediate 115 as starting materials (68%).

Preparation of Intermediate 179 (and Compound 69)

intermediate 179

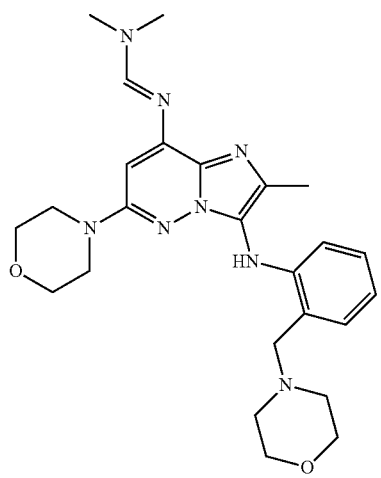

compound 69

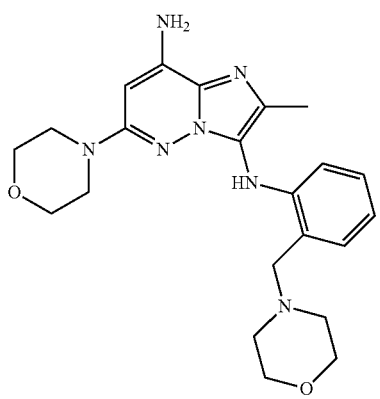

Intermediate 179 (and compound 69) were prepared according to an analogous procedure as described for the synthesis of intermediate 116, using 2-(morpholin-4-ylm-ethyl)aniline and intermediate 115 as starting material (26% yield for intermediate 179; 10% yield for compound 69).

Preparation of Intermediate 185a and Intermediate 185b

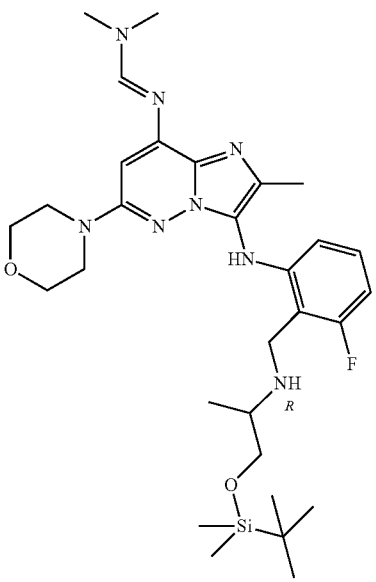

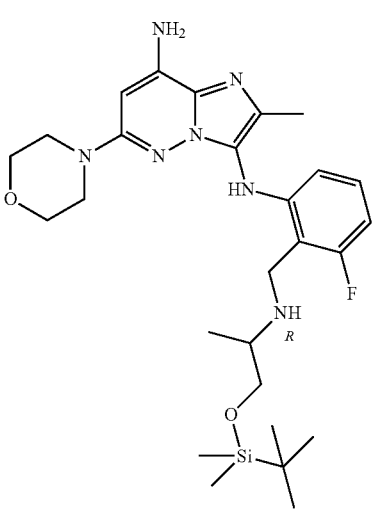

Intermediate 185a and intermediate 185b were prepared according to an analogous procedure as described for the synthesis of intermediate 116, using intermediate 184 and intermediate 115 as starting materials. A mixture of intermediate 185a and intermediate 185b was obtained and used as such in the next reaction step.

Preparation of Intermediate 199

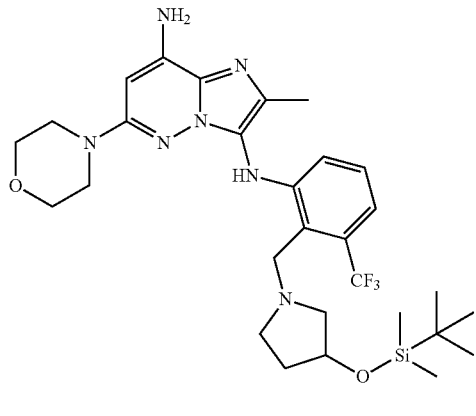 [SMILES: Cc1nc2c(N)cc(N3CCOCC3)nn2c1Nc1cccc(C(F)(F)F)c1CN1CCC(O[Si](C)(C)C(C)(C)C)C1]

Intermediate 199 was prepared according to an analogous procedure as described for the synthesis of intermediate 116, using intermediate 190 and intermediate 198 as starting material (32%).

Example A40

Preparation of Intermediate 131

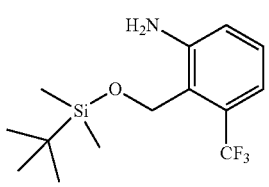 [SMILES: CC(C)(C)[Si](C)(C)OCc1c(N)cccc1C(F)(F)F]

Chloro tert-butyldimethylsilane (1.19 g; 7.91 mmol) was added to a solution of 2-amino-6-(trifluoromethyl)-benzenemethanol (1.26 g; 6.59 mmol) and imidazole (1.34 g; 19.78 mmol) in DCM (25 mL) at room temperature. The reaction mixture was stirred overnight, diluted with DCM and washed with a 10% aqueous solution of $K_2CO_3$. The organic layer was decanted, dried over $MgSO_4$, filtered and evaporated to dryness. The crude residue was purified by chromatography over silica gel (irregular SiOH, 40 g; gradient from 0% EtOAc, 100% heptane to 40% EtOAc, 60% heptane). The pure fractions were collected and evaporated to dryness yielding 1.06 g (53%) of intermediate 131.

Example A41

Preparation of Intermediate 133

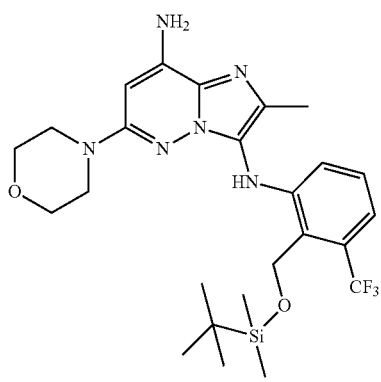 [SMILES: Cc1nc2c(N)cc(N3CCOCC3)nn2c1Nc1cccc(C(F)(F)F)c1CO[Si](C)(C)C(C)(C)C]

Intermediate 133 was prepared according to an analogous procedure as described for the synthesis of compound 45, using intermediate 132 as starting material (100%).

Preparation of Intermediate 135

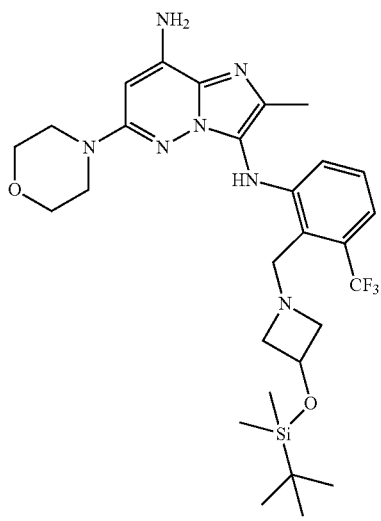 [SMILES: Cc1nc2c(N)cc(N3CCOCC3)nn2c1Nc1cccc(C(F)(F)F)c1CN1CC(O[Si](C)(C)C(C)(C)C)C1]

Intermediate 135 was prepared according to an analogous procedure as described for the synthesis of compound 45, using intermediate 134 as starting material (100%).

Preparation of Intermediate 148

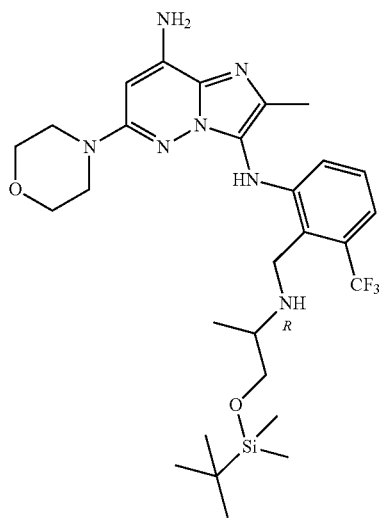

Intermediate 148 was prepared according to an analogous procedure as described for the synthesis of compound 45, using intermediate 147 as starting material (100%).

Preparation of Intermediate 156

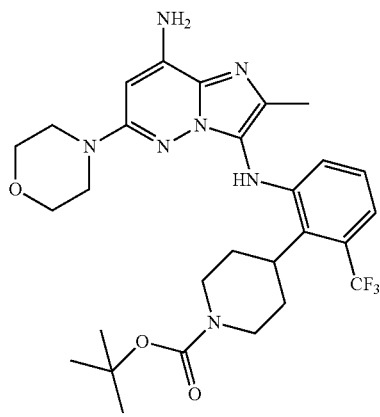 [SMILES: Cc1nc2c(N)cc(N3CCOCC3)nn2c1Nc1cccc(C(F)(F)F)c1C1CCN(C(=O)OC(C)(C)C)CC1]

Intermediate 156 was prepared according to an analogous procedure as described for the synthesis of compound 45, using intermediate 154 as starting material (89%).

Preparation of Intermediate 186

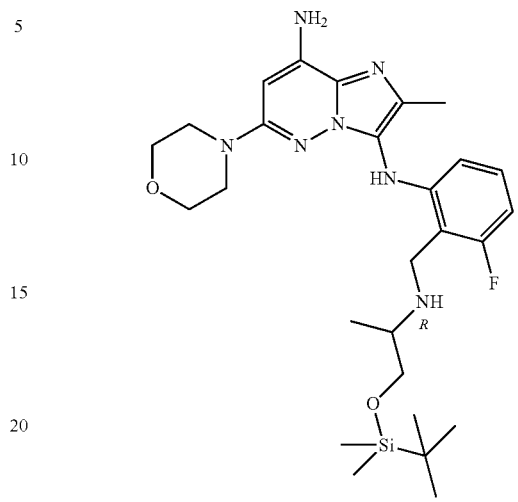

A mixture of intermediate 185a and 185b (0.37 g, 0.62 mmol) and zinc chloride (0.505 g, 3.71 mmol) in EtOH (10 mL) was heated at 90° C. overnight. The mixture was poured out into water and filtered through a pad of Celite®. The organic layer was extracted with DCM, separated, dried over MgSO$_4$, filtered and concentrated to dryness. The residue (0.570 g) was purified by chromatography over silica gel (Irregular SiOH 15-40 μm, 40 g; gradient: from 98% DCM, 20% MeOH to 94% DCM, 6% MeOH, 0.1% NH$_4$OH). The pure fractions were collected and the solvent was evaporated until dryness to give 0.145 g of intermediate 186.

Example A42

Preparation of Intermediate 152

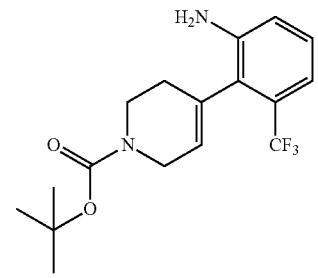

A mixture of 2-bromo-3-(trifluoromethyl)benzenamine (9.6 g; 40 mmol), 3,6-dihydro-4-(4,4,5,5-tetramethyl-1,3,2-dioxaborolan-2-yl)-1,1-dimethylethylester-1(2H)-pyridinecarboxylic acid (14.84 g; 48 mmol), [1,1'-bis[bis(1,1-dimethylethyl)phosphino]ferrocene]dichloro-palladium (652 mg; 1 mmol) and sodium carbonate (16.96 g; 160 mmol) in water (100 mL) and THF (300 mL) was heated at reflux overnight. The solvent was removed under reduced pressure and the residue was solubilized with EtOAc and H$_2$O. The organic layer was separated, dried over MgSO$_4$, filtered and evaporated. The residue was purified by chromatography over silica gel (eluent: from 100% petrol ether to 50% petrol ether, 50% EtOAc). The pure fractions were collected and the solvent was evaporated to give 12 g (95%, white crystals) of intermediate 152.

Preparation of Intermediate 153

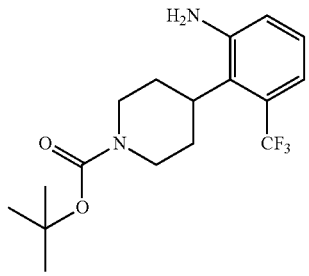 [SMILES: CC(C)(C)OC(=O)N1CCC(c2c(N)cccc2C(F)(F)F)CC1]

A mixture of intermediate 152 (13 g; 37.97 mmol) in EtOH (200 mL) was hydrogenated (50 psi) at 45° C. with 10% Pd/C (13 g. After consumption of hydrogen (1 equivalent, 18 hours), the catalyst was filtered off and the filtrate was evaporated. The residue (13 g) was purified by reverse phase HPLC (Column: SYNERGI, Flow Fate: 80 mL/min, Mobile Phase A: Purified water (containing 0.1% TFA), Mobile Phase B: ACN, Gradient: 65% phase A 35% phase B to 25% phase A 75% phase B). The pure fractions were collected and the pH of the solvent was adjusted to 8 with a 10% aqueous solution of NaHCO$_3$. The organic layer was evaporated and EtOAc was added. The organic layer was decanted, dried with Na$_2$SO$_4$ and evaporated to give 6.1 g (45%) of intermediate 153.

Preparation of Intermediate 157

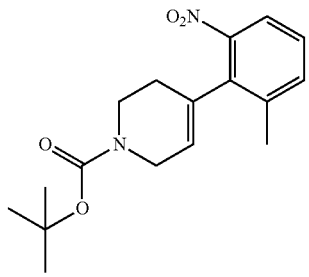 [SMILES: Cc1cccc([N+](=O)[O-])c1C1=CCN(C(=O)OC(C)(C)C)CC1]

A mixture of 2-bromo-1-methyl-3-nitrobenzene (12.96 g; 60 mmol), 3,6-dihydro-4-(4,4,5,5-tetramethyl-1,3,2-dioxaborolan-2-yl)-1,1-dimethylethylester-1(2H)-pyridinecarboxylic acid (22.26 g, 72 mmol), Pd(PPh$_3$)$_4$ (6.9 g; 6 mmol) and sodium carbonate (25.44 g; 240 mmol) in water (100 mL) and 1,4-dioxane (400 mL) was heated to reflux overnight. The solvent was removed under reduced pressure and the residue was partitioned between EtOAc and H$_2$O. The organic layer was separated, dried over MgSO$_4$, filtered and evaporated. The residue was purified by chromatography over silica gel (eluent: from 100% petrol ether to 50% petrol ether, 50% EtOAc). The pure fractions were collected and the solvent was evaporated to give 15 g (75%) of a yellowish solid intermediate 157.

Preparation of Intermediate 158

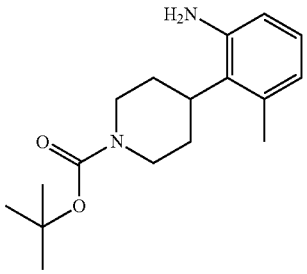 [SMILES: Cc1cccc(N)c1C1CCN(C(=O)OC(C)(C)C)CC1]

A mixture of intermediate 158 (10 g; 31.41 mmol) in EtOH (150 mL) was hydrogenated (45 psi) at 45° C. with 10% Pd/C (10 g). After consumption of H$_2$ (4 eq), the catalyst was filtered off and the filtrate was evaporated. The residue was dissolved again in EtOH (150 mL) and hydrogenated (50 psi) at 65° C. with 10% Pd/C (10 g). After consumption of H$_2$, the catalyst was filtered off and the filtrate was evaporated. The residue (9 g) was purified by chromatography over silica gel (eluent: 75% petrol ether, 25% EtOAc). The pure fractions were collected and the solvent was evaporated to give 3.4 g (34%) of intermediate 158.

Example A43

Preparation of Intermediate 166

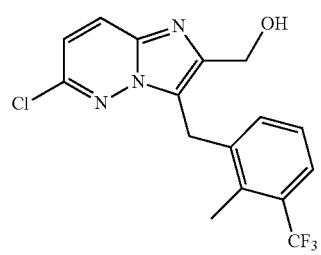 [SMILES: Cc1c(Cc2c(CO)nc3ccc(Cl)nn23)cccc1C(F)(F)F]

NaOH (1M in water) (26.6 mL; 26.6 mmol) was added dropwise to a solution of intermediate 25 (5.3 g; 13.3 mmol) in THF (65 mL) and EtOH (65 mL). The reaction mixture was stirred at rt for 2 hours. The mixture was evaporated under vacuum and the residue was taken up in DCM and water. The layers were separated and the aqueous layer was extracted with DCM. The combined organic layers were dried over MgSO$_4$, filtered off and evaporated under vacuum to give 4.54 g (95%; brown solid) of intermediate 166.

Preparation of Intermediate 167

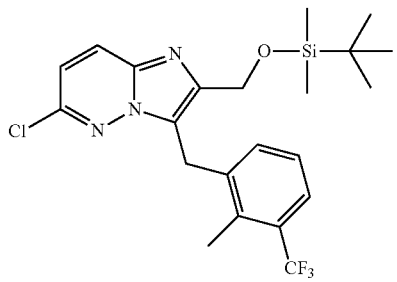 [SMILES: Cc1c(Cc2c(CO[Si](C)(C)C(C)(C)C)nc3ccc(Cl)nn23)cccc1C(F)(F)F]

Imidazole (2.58 g; 37.9 mmol) and tert-butyldimethylchlorosilane (3.81 g; 25.3 mmol) were added to a solution of intermediate 166 (4.54 g; 12.6 mmol) in DMF (65 mL). The reaction mixture was stirred at rt overnight. The mixture was evaporated under vacuum and the residue was taken-up in EtOAc. A 10% aqueous solution of NaHCO$_3$ was added and the layers were separated. The aqueous layer was extracted with EtOAc. The combined organic layers was washed with brine (3×), dried over MgSO$_4$, filtered off and evaporated under vacuum. The residue (6.39 g; beige solid) was purified by chromatography over silica gel (regular SiOH 30 μm, 200 g, gradient: from 100% DCM to 90% DCM, 10% EtOAc). The pure fractions were collected and the solvent was evaporated to give 4.94 g (83%; off-white solid) of intermediate 167.

Preparation of Intermediate 168

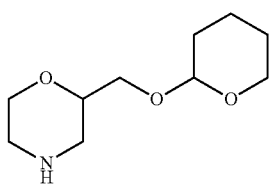 [SMILES: C1CCC(OCC2CNCCO2)OC1]

Pyridinium p-toluenesulfonate (82 mg; 0.33 mmol) and 3,4-dihydro-2H-pyran (0.595 mL; 6.51 mmol) were added to a solution of 2-morpholinemethanol (500 mg, 3.26 mmol) in DCM (32 mL). The reaction mixture was stirred at rt over the weekend. The reaction mixture was refluxed overnight. Then, a 10% aqueous solution of NaHCO$_3$ was added and the layers were separated. The aqueous layer was acidified with NH$_4$Cl (solid) until pH=7 and extracted with DCM (4×). The combined organic layers were dried over MgSO$_4$, filtered off and evaporated under vacuum. The residue (755 mg, pale yellow oil) was purified by chromatography over silica gel (regular SiOH, 30 μm, 40 g, gradient: from 100% DCM to 90% DCM, 1006 MeOH, 1% NH$_4$OH). The pure fractions were collected and the solvent was evaporated to give 558 mg (85%, yellow oil) of intermediate 168.

Preparation of Intermediate 169

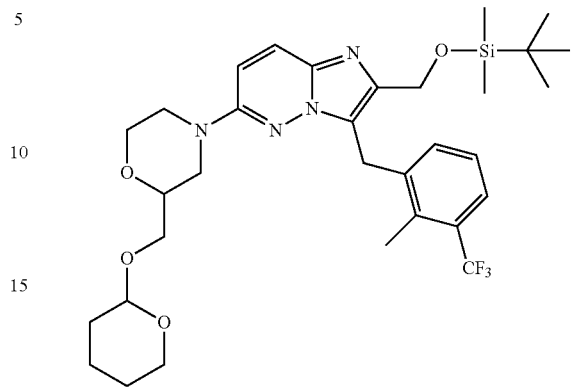

In sealed tube, intermediate 168 (514 mg; 2.55 mmol) and Cs$_2$CO$_3$ (1.66 g; 5.11 mmol) were added to a solution of intermediate 167 (800 mg; 1.70 mmol) in 2-methyl-2-butanol (17 mL). The reaction mixture was carefully degassed under vacuum and back-filled with N$_2$ (3×). Then, Pd$_2$(dba)$_3$ (78 mg; 0.09 mmol) and Ruphos (79 mg; 0.17 mmol) were added and the mixture was carefully degassed under vacuum and back-filled with N$_2$ (3×). The reaction mixture was stirred at 80° C. overnight. The mixture was filtered through a pad of Celite®. The cake was washed with DCM/MeOH (9:1) and the filtrate was evaporated under vacuum. The residue was taken-up in DCM and water. The layers were separated and the aqueous layer was extracted with DCM. The combined organics layers were dried over MgSO$_4$, filtered off and evaporated in vacuum. The residue (1.49 g, orange oil) was purified by chromatography over silica gel (irregular SiOH, 15-30 μm, 50 g, gradient: from 100% DCM to 97% DCM, 3% MeOH). The pure fractions were collected and the solvent was evaporated to give 985 mg (86%, orange oil) of intermediate 169.

Preparation of Intermediate 170

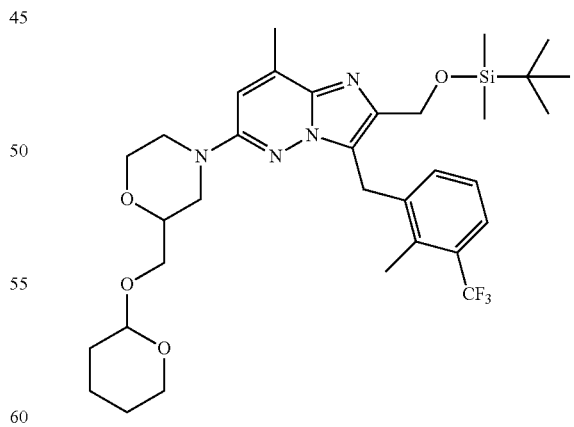

In a Schlenck reactor, n-butyllithium (1.49 mL; 1.6 M, 2.38 mmol) was added to a solution of diisopropylamine (0.323 mL; 2.28 mmol) in THF (5 mL) at −78° C. under N$_2$. The reaction mixture was stirred at −40° C. for 20 min and then, cooled down to −78° C. A solution of intermediate 169 (580 mg; 0.91 mmol) in THF (5 mL) was added dropwise and the mixture was stirred at −78° C. for 30 min. Then, a solution of iodine (255 mg; 1.01 mmol) in THF (5 mL) was added dropwise and the mixture was stirred at −78° C. for 1h30. The reaction mixture was raised to rt, slowly quenched with 10% aqueous solution of NH₄Cl and EtOAc was added. The layers were separated and the aqueous layer was extracted with EtOAc. The combined organics layers were dried over MgSO₄, filtered off and evaporated under vacuum. The residue (840 mg, brown foam) was purified by chromatography over silica gel (irregular SiOH 15-40 μm, 30 g, gradient: from 100% DCM to 85% DCM, 15% EtOAc). The pure fractions were collected and the solvent was evaporated to give 495 mg (53%, pale orange foam) of intermediate 170.

Preparation of Intermediate 171

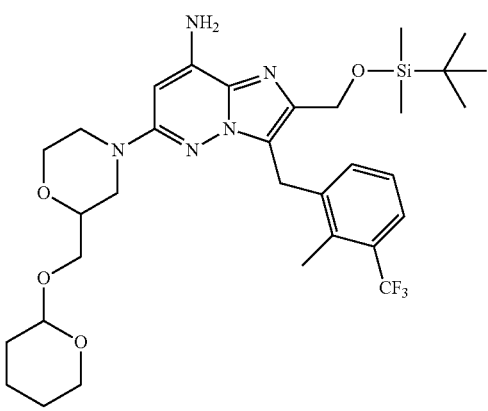 [SMILES: Cc1c(Cc2c(CO[Si](C)(C)C(C)(C)C)nc3c(N)cc(N4CCOC(COC5CCCCO5)C4)nn23)cccc1C(F)(F)F]

In sealed tube, L-proline (6.05 mg; 0.05 mmol), acetamidine hydrochloride (30 mg; 0.32 mmol) and Cs₂CO₃ (257 mg; 0.79 mmol) were added to a solution of intermediate 170 (200 mg; 0.263 mmol) in DMF (1 mL). The reaction mixture was carefully degassed under vacuum and back-filled with N₂ (3×). Then, CuI (5 mg; 0.03 mmol) was added and the mixture was again degassed under vacuum and back-filled with N₂ (3×). The reaction mixture was stirred at 110° C. overnight. The mixture was evaporated under vacuum. The residue was taken up in EtOAc, washed with 10% aqueous solution of NaHCO₃, brine (3×), dried over MgSO₄, filtered off and evaporated under vacuum. The residue (220 mg, brown oil) was purified by chromatography over silica gel (regular SiOH, 30 μm, 12 g, gradient: from 100% DCM to 96% DCM, 4% MeOH, 0.4% NH₄OH). The pure fractions were collected and the solvent was evaporated to give 111 mg (52%, off-white foam) of intermediate 171.

Example A44

Preparation of Intermediate 172

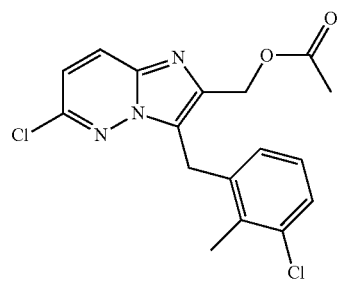 [SMILES: CC(=O)OCc1nc2ccc(Cl)nn2c1Cc1cccc(Cl)c1C]

The reaction was performed 3 times on 6 g (27.33 mmol) of 1-(bromomethyl)-3-chloro-2-methyl benzene:

Palladium(II) acetate (613 mg; 2.73 mmol) was added to a mixture of 1-(bromomethyl)-3-chloro-2-methyl benzene (6 g; 27.33 mmol), intermediate 1 (9.8 g; 37.17 mmol) and PPh₃ (1.42 g; 5.4 mmol) in 1,4-dioxane (200 mL) under N₂. The reaction mixture was heated at 100° C. for 16 hours. The 3 mixtures were combined for the treatment, then filtered a through a pad of Celite® and the filtrate was evaporated. The residue (29.7 g) was purified by chromatography over silica gel (eluent: from 90% petrol ether, 10% EtOAc to 50% petrol ether, 50% EtOAc). The pure fractions were collected and the solvent was evaporated to give 26 g (87%; 60% of purity based on LC/MS) of intermediate 172.

Preparation of Intermediate 173

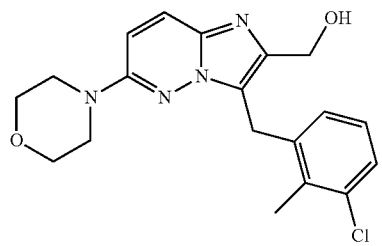

A mixture of intermediate 172 (26 g; 42.83 mmol) and morpholine (500 mL) was heated at 120° C. overnight. After cooling down to room temperature, the mixture was evaporated to remove morpholine. The mixture was washed with a 10% aqueous solution of NaHCO₃ and water. The precipitate was filtered and dried under vacuum to give 14.6 g of intermediate 173.

Preparation of Intermediate 175

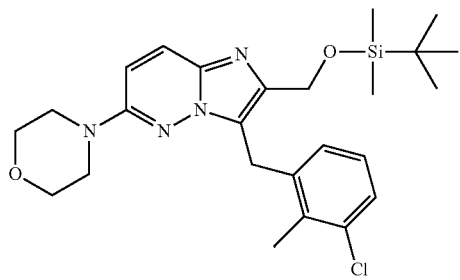 [SMILES: Cc1c(Cl)cccc1Cc1c(CO[Si](C)(C)C(C)(C)C)nc2ccc(N3CCOCC3)nn12]

1,1,1-trifluoro-(1,1-dimethylethyl)dimethylsilyl ester methanesulfonic acid (9.4 g; 35.4 mmol) and imidazole (5.06 g; 74.34 mmol) were added to a solution of intermediate 173 (6.6 g; 17.70 mmol) in DMF (150 mL) at room temperature. The mixture was poured into 10% aqueous solution of $NaHCO_3$ and extracted with DCM. The organic layer was separated, dried over $Na_2SO_4$, filtered and the solvent was evaporated. The residue (5 g) was purified by chromatography over silica gel (eluent: from 100% petrol ether to 75% petrol ether, 25% EtOAc). The pure fractions were collected and the solvent was evaporated to give 3.41 g (40%) of intermediate 175.

Preparation of Intermediate 176

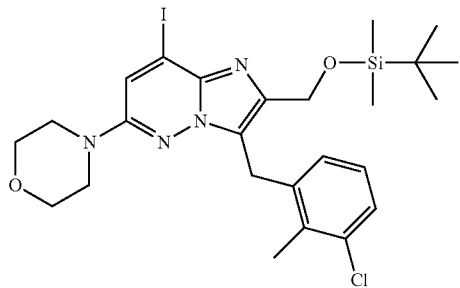 [SMILES: Cc1c(Cl)cccc1Cc1c(CO[Si](C)(C)C(C)(C)C)nc2c(I)cc(N3CCOCC3)nn12]

N-butyllithium (1.6 M in hexane) (1.7 mL; 2.67 mmol) was added dropwise to a solution of diisopropylamine (363 µL; 2.57 mmol) in THF (5.5 mL) at −78° C. under $N_2$. The reaction mixture was stirred 20 min at −78° C. A solution of intermediate 175 (500 mg; 1.03 mmol) in THF (6 mL), previously under $N_2$, was added dropwise in 2 min and the reaction mixture was stirred for 30 min (30 min: addition+reaction time) at −78° C. A solution of iodine (287 mg; 1.13 mmol) in THF (5.5 mL), previously under $N_2$, was added dropwise in 4 min and the reaction mixture was stirred at −78° C. for 1h10 (1h10: addition+reaction time). The mixture was poured into a 10% aqueous solution of $NH_4Cl$ and immediately extracted with EtOAc (3×). The organic layer was washed with brine, dried over $MgSO_4$, filtered and the solvent was evaporated. The residue (687 mg, brown oil) was purified by chromatography over silica gel (30 g, eluent: from 85% heptane, 15% EtOAc to 75% heptane, 25% EtOAc). The pure fractions were collected and the solvent was evaporated to give 283 mg (45%, brown solid) of intermediate 176.

Preparation of Intermediate 177

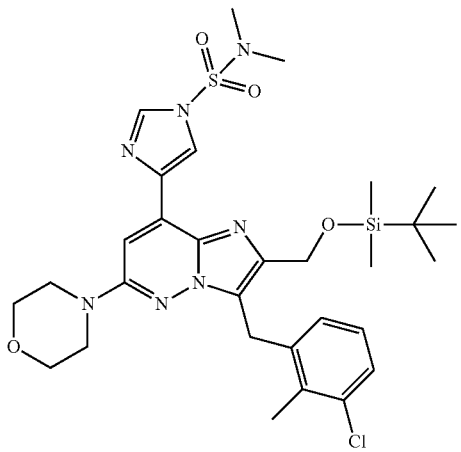 [SMILES: Cc1c(Cl)cccc1Cc1c(CO[Si](C)(C)C(C)(C)C)nc2c(-c3cn(S(=O)(=O)N(C)C)cn3)cc(N3CCOCC3)nn12]

Intermediate 177 was prepared according to an analogous procedure as described for the synthesis of intermediate 41, using intermediate 176 as starting material which was directly used in the next step without any further treatment.

Preparation of Intermediate 178

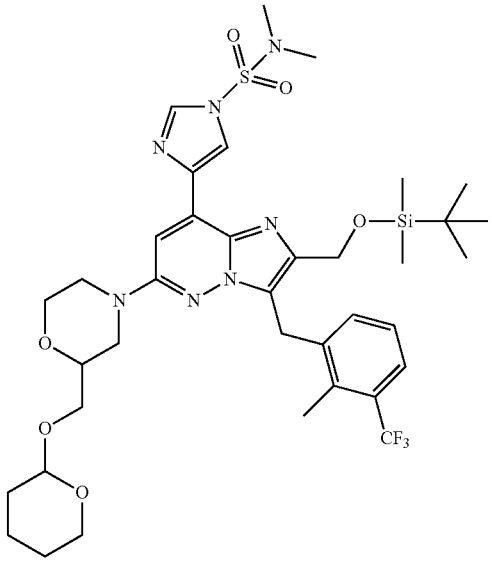 [SMILES: Cc1c(Cc2c(CO[Si](C)(C)C(C)(C)C)nc3c(-c4cn(S(=O)(=O)N(C)C)cn4)cc(N4CCOC(COC5CCCCO5)C4)nn23)cccc1C(F)(F)F]

In sealed tube, N,N-dimethyl-4-(4,4,5,5-tetramethyl-1,3,2-dioxaborolan-2-yl)-1H-imidazole-1-sulfonamide (81 mg; 0.27 mmol) and potassium phosphate (163 mg; 0.77 mmol) were added to a solution of intermediate 170 (195 mg, 0.26 mmol) in 1,4-dioxane (1.82 mL) and water (0.54 mL). The mixture was carefully degassed under vacuum and back-filled with $N_2$ (3×). Then, $PdCl_2dppf).DCM$ (21 mg; 0.026 mmol) was added and the mixture was degassed again under vacuum and back-filled with $N_2$ (3×). The mixture was stirred at 80° C. for 2 hours. The mixture was cooled down to room temperature Then EtOAc and water were added. A 10% aqueous solution of $NaHCO_3$ was added and the layers were separated. The organic layer was dried over $MgSO_4$, filtered off and evaporated under vacuum. The residue (300 mg, brown oil). was purified by chromatography over silica gel (regular SiOH, 30 μm, 12 g, gradient: from 100% DCM to 96% DCM, 4% MeOH (+10% aq. NH$_4$OH)). The pure fractions were collected and the solvent was evaporated to give 235 mg (90%, pale yellow foam) of intermediate 178.

Example A45

Preparation of Intermediate 189

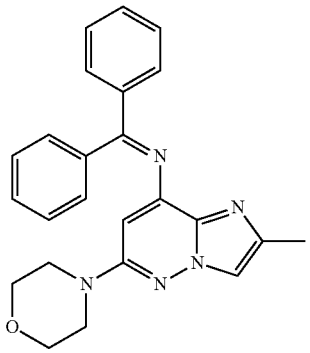 [SMILES: Cc1cn2nc(N3CCOCC3)cc(N=C(c3ccccc3)c3ccccc3)c2n1]

The reaction was performed twice on 15 g (43.59 mmol) of intermediate 79.

A mixture of intermediate 79 (7.5 g; 21.79 mmol), benzophenone imine (5.49 mL; 32.69 mmol), Cs$_2$CO$_3$ (21.3 g; 65.38 mmol) in 1,4-dioxane (80 mL) was degassed under nitrogen for 15 mn. 2,2'-bis(diphenylphosphino)-1,1'-binaphtyl (679 mg; 1.09 mmol) and palladium(II) acetate (245 mg; 1.09 mmol) were added and the reaction mixture was heated at 100° C. under nitrogen atmosphere overnight in sealed tube. The reaction mixtures were mixed, poured into water and the product was extracted with EtOAc. The organic layer was washed with a saturated solution of NaCl, dried over MgSO$_4$, filtered and the solvent was evaporated. The residue (30 g) was purified by chromatography over silica gel (Irregular SiOH 15-40 μm; 2*330 g; gradient: from 80/20 to 60/40 heptane/EtOAc).

The pure fractions were collected and the solvent was evaporated until dryness to give 16.1 g (93%) of intermediate 189.

Preparation of Intermediate 190

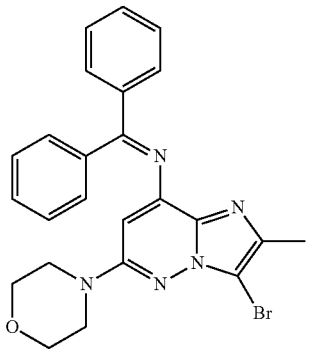 [SMILES: Cc1nc2c(N=C(c3ccccc3)c3ccccc3)cc(N3CCOCC3)nn2c1Br]

The reaction was performed 3 times on 5.37 g (13.53 mmol) of intermediate 189 and the different reaction mixtures were mixed for the work-up.

To a solution of intermediate 189 (5.37 g; 13.50 mmol) in ACN (480 mL) was added portionwise N-bromosuccinimide (1.92 g; 10.80 mmol) at rt. The solution was stirred at rt for 1.25 hour. A precipitate (pale yellow solid) was filtered off then, washed with pentane, dried under vacuo to give 11.5 g (60%) of intermediate 190.

The mother layer was stirred for 18 hours at rt and then, poured onto water and extracted with DCM. The resulting organic layer was dried over MgSO$_4$, filtered and concentrated. The resulting crude was mixed with another crude coming from a reaction performed on 5 g of intermediate 189. The material was purified by silica gel chromatography (Stationary phase: Irregular SiOH 20-45 μm, 450 g, Mobile phase: 70% heptane, 30% EtOAc). The fractions containing the product were mixed and the solvent was concentrated to afford an additional amount (3.2 g) of intermediate 190.

Preparation of Intermediate 191

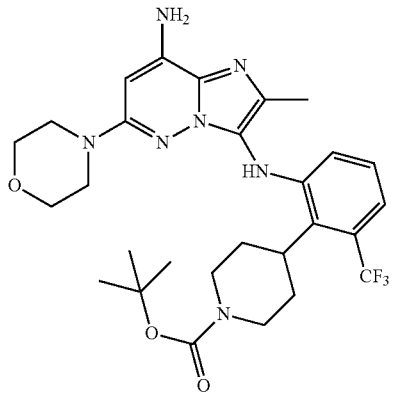 [SMILES: Cc1nc2c(N)cc(N3CCOCC3)nn2c1Nc1cccc(C(F)(F)F)c1C1CCN(C(=O)OC(C)(C)C)CC1]

The reaction was performed 3 times respectively on 1 g (2.1 mmol) of intermediate 190 and the different reaction mixtures were mixed for the work-up.

Under nitrogen, in a sealed tube, a mixture of intermediate 190 (1 g; 2.1 mmol), intermediate 153 (1.08 g; 3.15 mmol) and sodium tert-butoxide (403 mg; 4.20 mmol) in toluene (15 mL) was degassed under N$_2$. Then, Pd$_2$(dba)$_3$ (192 mg; 0.21 mmol) and 2-(di-t-butylphosphino)biphenyl (125 mg; 0.42 mmol) were added. The reaction mixture was heated at 100° C. overnight. The mixture was poured onto water and filtered through a pad of Celite®. The organic layer was extracted with DCM, separated, dried over MgSO$_4$, filtered and evaporated to dryness. The residue (8 g) was purified by chromatography over silica gel (Irregular SiOH 20-45 μm; 120 g; gradient: from 98/2/0.1 DCM/MeOH/NH$_4$OH to 95/5/0.1 DCM/MeOH/NH$_4$OH). The pure fractions were collected and the solvent was evaporated until dryness to give 900 mg (25%) of intermediate 191.

Preparation of Intermediate 192

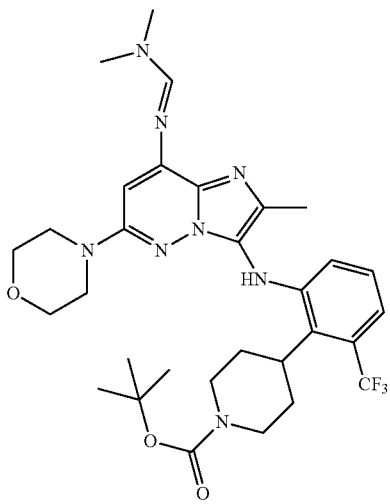 [SMILES: Cc1nc2c(/N=C/N(C)C)cc(N3CCOCC3)nn2c1Nc1cccc(C(F)(F)F)c1C1CCN(C(=O)OC(C)(C)C)CC1]

A mixture of intermediate 191 (1.9 g; 3.30 mmol) and N,N-dimethylformamide dimethyl acetal (1.32 mL; 9.90 mmol) in toluene (50 mL) was heated at 120° C. for 2 h. After cooling down to rt, the reaction mixture was concentrated under vacuum and the crude was taken up with diethyl ether, filtered off, washed with diethyl ether and dried to afford 1.1 g (53%) of intermediate 192. The product was used without purification in the next step.

Preparation of Intermediate 193

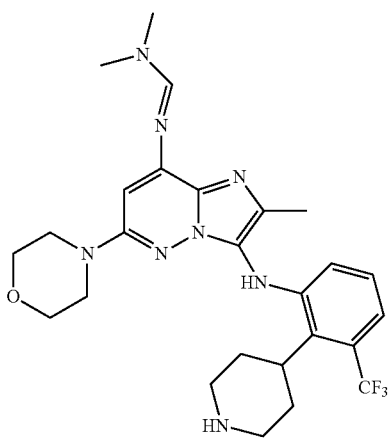 [SMILES: Cc1nc2c(/N=C/N(C)C)cc(N3CCOCC3)nn2c1Nc1cccc(C(F)(F)F)c1C1CCNCC1]

TFA (8.05 mL; 114.07 mmol) was added dropwise to a solution of intermediate 192 (1.05 g; 1.67 mmol) in DCM (50 mL) at 0° C. The mixture was stirred from 0° C. to rt for 1.5 h. The reaction mixture was concentrated under vacuum. This crude (2 g) was purified by chromatography over silica gel (SiOH 20-45 μm; 40 g; gradient: 98/2/0.5 DCM/MeOH/NH$_4$OH to 90/10/0.5 DCM/MeOH/NH$_4$OH). The fractions containing the product were collected and the solvent was evaporated to give 1.5 g of intermediate 193.

Preparation of Intermediate 194 and Intermediate 195

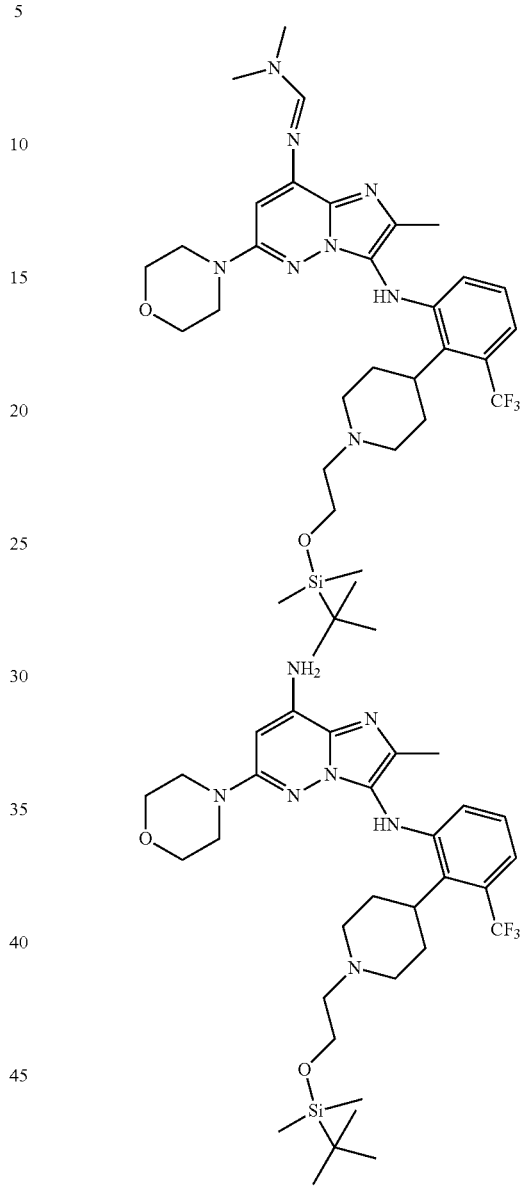

(Tert-butyldimethylsilyloxy)acetaldehyde (1.04 mL; 5.47 mmol) and acetic acid (0.64 mL) were successively added to a solution of intermediate 193 (1.45 g; 2.73 mmol) in anhydrous MeOH (30 mL). The reaction mixture was stirred at rt for 15 min. Then, sodium cyanoborohydride (515 mg; 8.20 mmol) was added. The reaction mixture was stirred at rt for 18 h. The reaction mixture was poured onto a 10% aqueous solution of K$_2$CO$_3$ and extracted with DCM. The organic layer was dried over MgSO$_4$, filtered off and the solvent was evaporated. The residue (1.8 g) was purified by chromatography over silica gel (SiOH 20-45 μm; 40 g; gradient: 98/2/0.1 DCM/MeOH/NH$_4$OH to 90/10/0.1 DCM/MeOH/NH$_4$OH). The pure fractions were collected and the solvent was evaporated to give 585 mg of a mixture intermediates 194 and 195. The mixture was directly used without purification in the next step.

Example A46

Preparation of Intermediate 196

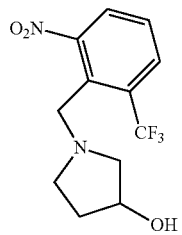 [SMILES: O=[N+]([O-])c1cccc(C(F)(F)F)c1CN1CCC(O)C1]

Intermediate 196 was prepared according to an analogous procedure as described for the synthesis of intermediate 113, using 2-(bromomethyl)-1-nitro-3-(trifluoromethyl)benzene and 3-pyrrolidinol as starting materials (89%; directly used without purification in the next step).

Preparation of Intermediate 197

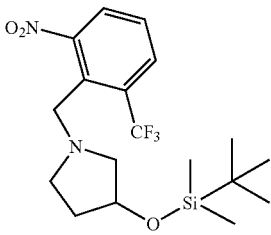

Tert-butyldimethylchlorosilane (1.87 g; 12.40 mmol) was added to a solution of intermediate 196 (1.8 g; 6.20 mmol) and imidazole (1.69 g; 24.81 mmol) in DCM (20 mL) at room temperature. The reaction mixture was stirred at rt overnight. The reaction mixture was poured into a 10% aqueous solution of $K_2CO_3$ and extracted with DCM. The organic layer was decanted, dried over $MgSO_4$, filtered and evaporated to dryness. The residue (3.3 g) was purified by chromatography over silica gel (irregular SiOH; 80 g; gradient: from 20% DCM, 80% heptane to 40% DCM, 60% heptane). The desired fractions were collected and evaporated to give 2.3 g (92%) of intermediate 197.

Preparation of Intermediate 198

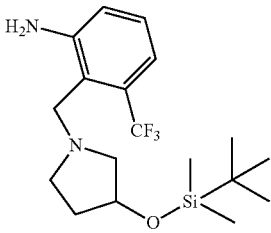 [SMILES: CC(C)(C)[Si](C)(C)OC1CCN(Cc2c([N+](=O)[O-])cccc2C(F)(F)F)C1]

Intermediate 198 was prepared according to an analogous procedure as described for the synthesis of intermediate 119, using intermediate 197 as starting material (95%). The hydrogenation was stirred for 4 h.

Example A47

Preparation of Intermediate 205

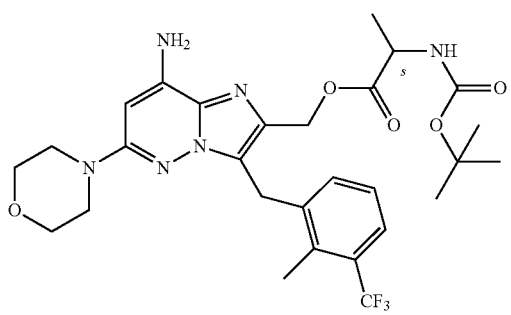 [SMILES: Cc1c(Cc2c(COC(=O)C(C)NC(=O)OC(C)(C)C)nc3c(N)cc(N4CCOCC4)nn23)cccc1C(F)(F)F]

Under $N_2$, DMAP (3 mg; 0.03 mmol), HATU (0.45 g; 1.2 mmol) and diisopropylethylamine (0.41 mL; 2.4 mmol) were added to a solution of Boc-L-alanine (0.23 g; 1.9 mmol) in DMF (6 mL) at rt. After 10 min, compound 14 (0.2 g; 0.47 mmol) was added and the solution was stirred at rt for 24 hours. The solution was poured out into cooled water and EtOAc was added. The organic layer was extracted, washed with $H_2O$, dried over $MgSO_4$ and evaporated to dryness. The residue (0.4 g) was purified by chromatography over silica gel (irregular SiOH 15-40 µm 30 g, eluent: 97% DCM, 3% MeOH, 0.1% $NH_4OH$). The pure fractions were collected and the solvent was evaporated to give 191 mg of intermediate 205 (68%).

Preparation of Intermediate 206

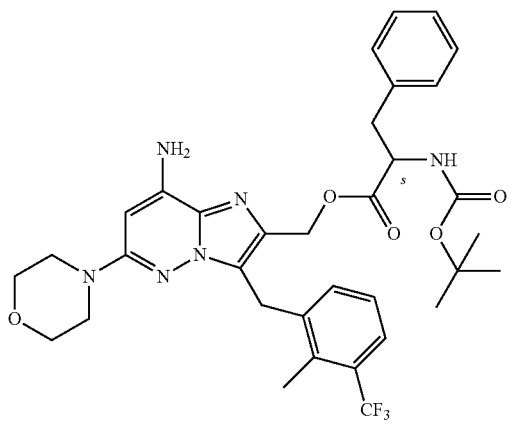 [SMILES: Cc1c(Cc2c(COC(=O)C(Cc3ccccc3)NC(=O)OC(C)(C)C)nc3c(N)cc(N4CCOCC4)nn23)cccc1C(F)(F)F]

Intermediate 206 was prepared according to an analogous procedure as described for the synthesis of intermediate 205, using compound 14 and Boc-L-phenylalanine as starting materials (49%; 155 mg).

Preparation of Intermediate 207

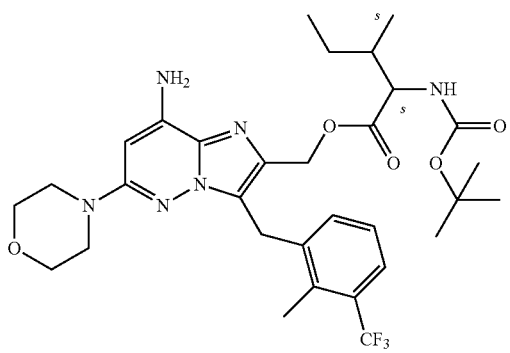 [SMILES: CCC(C)C(NC(=O)OC(C)(C)C)C(=O)OCc1nc2c(N)cc(N3CCOCC3)nn2c1Cc1cccc(C(F)(F)F)c1C]

Intermediate 207 was prepared according to an analogous procedure as described for the synthesis of intermediate 205, using compound 14 and N-Boc-L-isoleucine as starting materials (52%; 158 mg.

Preparation of Intermediate 208

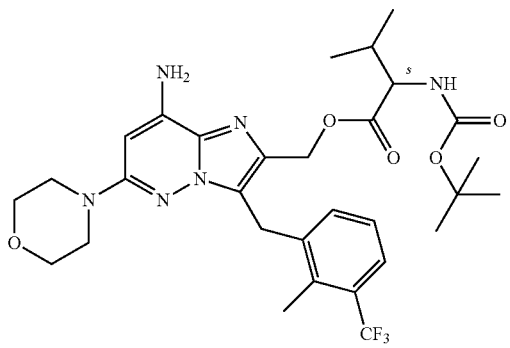 [SMILES: Cc1c(Cc2c(COC(=O)C(NC(=O)OC(C)(C)C)C(C)C)nc3c(N)cc(N4CCOCC4)nn23)cccc1C(F)(F)F]

Intermediate 208 was prepared according to an analogous procedure as described for the synthesis of intermediate 205, using compound 14 and Boc-L-valine as starting materials (55%; 162 mg).

Preparation of Intermediate 209

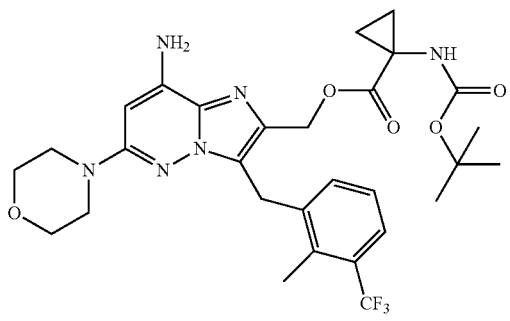 [SMILES: Cc1c(Cc2c(COC(=O)C3(NC(=O)OC(C)(C)C)CC3)nc3c(N)cc(N4CCOCC4)nn23)cccc1C(F)(F)F]

Intermediate 209 was prepared according to an analogous procedure as described for the synthesis of intermediate 205, using compound 14 and 1-tert-butoxycarbonylamino-cyclopropanecarboxylic acid as starting materials (46%; 100 mg).

Preparation of Intermediate 210

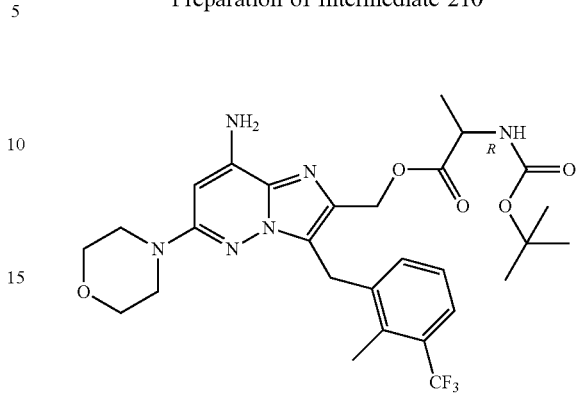

Intermediate 210 was prepared according to an analogous procedure as described for the synthesis of intermediate 205, using compound 14 and Boc-D-alanine as starting materials (98%; 552 mg).

Example A48

Preparation of Intermediate 211

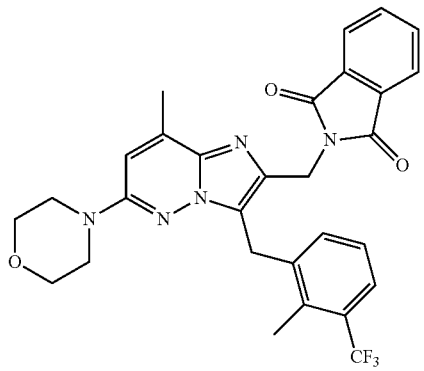 [SMILES: Cc1c(Cc2c(CN3C(=O)c4ccccc4C3=O)nc3c(C)cc(N4CCOCC4)nn23)cccc1C(F)(F)F]

Di-tert-butyl azodicarboxylate (12.98 g; 56.35 mmol) was added dropwise to a solution of intermediate 33 (20 g; 37.57 mmol), phtalimide (6.63 g; 45.08 mmol), PPh$_3$ (14.78 g; 56.35 mmol) in THF (300 mL) at room temperature under N$_2$. The reaction mixture was stirred at room temperature overnight. The mixture was poured into 10% aqueous solution of K$_2$CO$_3$ and extracted with EtOAc. The separated organic layer was dried over Na$_2$SO$_4$, filtered and the solvent was evaporated. The residue was washed with MTBE and was evaporated under vacuum to give 14.6 g (57%) of intermediate 211.

Preparation of Intermediate 212

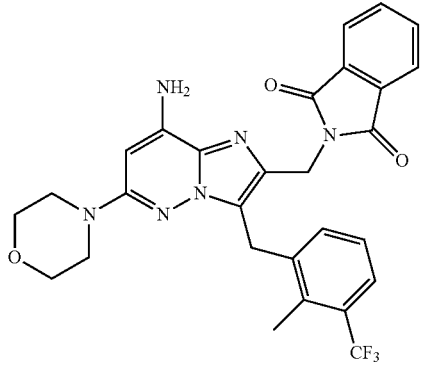 [SMILES: Cc1c(Cc2c(CN3C(=O)c4ccccc4C3=O)nc3c(N)cc(N4CCOCC4)nn23)cccc1C(F)(F)F]

In sealed tube, acetamidine hydrochloride (86 mg; 0.91 mmol) was added under $N_2$ to a mixture of copper(I) iodide (14 mg; 0.08 mmol), L-proline (17 mg, 0.15 mmol), intermediate 211 (0.5 g; 0.76 mmol) and $Cs_2CO_3$ (0.74 g; 2.27 mmol) in DMF (2.9 mL). The reaction mixture was stirred at 110° C. overnight. The mixture was concentrated, then solubilized in EtOAc and washed fifth times with brine. The organic layer was dried and evaporated. The residue (beige solid) was purified by chromatography over silica gel (SiOH; 30 µm; 24 g; mobile phase: from 99% DCM, 1% MeOH 0.1% $NH_4OH$ to 96% DCM, 4% MeOH 0.1% $NH_4OH$). The pure fractions were collected and the solvent was evaporated to give 76 mg (18%, white solid) of intermediate 212.

Alternative Pathway:

Di-tert-butyl azodicarboxylate (446 mg; 1.94 mmol) was added portionwise to a solution of compound 14 (371 mg; 0.88 mmol), phtalimide (155 mg; 1.06 mmol), $PPh_3$ (508 mg; 1.94 mmol) in DMF (12 mL) at room temperature under $N_2$. The reaction mixture was stirred at rt for 2 h. The crude was combined for the treatment with a batch coming from a reaction performed on 50 mg of compound 14. Water and EtOAc were added. The mixture was extracted with EtOAc (3×). The organic layer was washed with brine (2×), dried over $MgSO_4$, filtered and the solvent was evaporated. The residue (1.95 g, brown oil) was purified by chromatography over silica gel (irregular bare silica 150 g; mobile phase: 98% DCM, 2% MeOH, 0.1% $NH_4OH$). The pure fractions were collected and the solvent was evaporated to give 137 mg (25%, yellow foam) of intermediate 212.

Example A49

Preparation of Intermediate 213

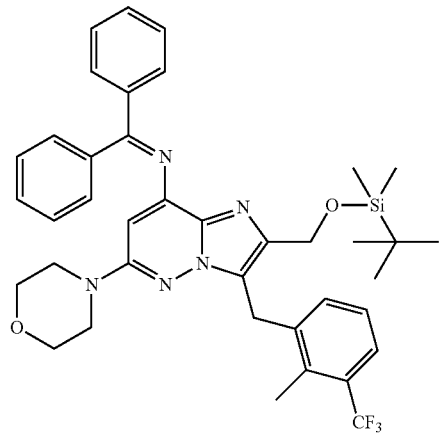 [SMILES: Cc1c(Cc2c(CO[Si](C)(C)C(C)(C)C)nc3c(N=C(c4ccccc4)c4ccccc4)cc(N4CCOCC4)nn23)cccc1C(F)(F)F]

The reaction was performed twice respectively on 8 g (12.37 mmol) and 10 g (5.65 mmol) of intermediate 7:

In a sealed vessel with good stirring, $N_2$ was bubbled in a mixture of intermediate 7 (18 g; 27.84 mmol) and benzophenone imine (7 mL; 41.76 mmol) in 1,4-dioxane (145 mL). Then, $Cs_2CO_3$ (27.2 g; 83.52 mmol) was added and the reaction mixture was degassed with $N_2$. Finally, rac-bis (diphenylphosphino)-1,1'-binaphtyl ((867 mg; 1.39 mmol) and palladium(II) acetate (312 mg; 1.39 mmol) were added and the reaction mixture was heated at 100° C. for 18 h. The reaction mixtures were combined for the work-up and partitioned between water and EtOAc. The organic layer was decanted, washed with brine, dried over $MgSO_4$, filtered and evaporated to dryness. The residue (29.6 g) was purified by successive chromatography over silica gel (Irregular SiOH; 450 g; gradient: from 100% heptane to 80% heptane, 20% EtOAc). The pure fractions were collected and evaporated to dryness yielding respectively 16.7 g (85%) and 3.6 g (18%) of intermediate 213. The 2 batches were used directly in the next step.

Preparation of Intermediate 214

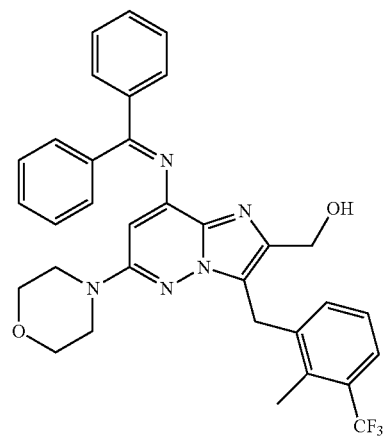 [SMILES: Cc1c(Cc2c(CO)nc3c(N=C(c4ccccc4)c4ccccc4)cc(N4CCOCC4)nn23)cccc1C(F)(F)F]

TBAF (1M in THF) (8.28 mL; 8.28 mmol) was added dropwise to a solution of intermediate 213 (5.8 g; 8.29 mmol) in THF (70 mL) at room temperature. The reaction mixture was stirred for 3 h at room temperature. The solution was poured into ice water, extracted with EtOAc and washed with brine. The organic layer was dried over $MgSO_4$, filtered and evaporated to dryness. The residue was crystallized from DIPE. The precipitate was filtered off and dried under vacuum to yield 2.7 g (55%) of intermediate 214. The filtrate was purified by chromatography over silica gel (irregular SiOH; 80 g; gradient: from 100% DCM to 90% DCM, 100/MeOH, 0.1% $NH_4OH$). The pure fractions were collected and evaporated to dryness to give 0.4 g (8%) of intermediate 214.

Preparation of Intermediate 215

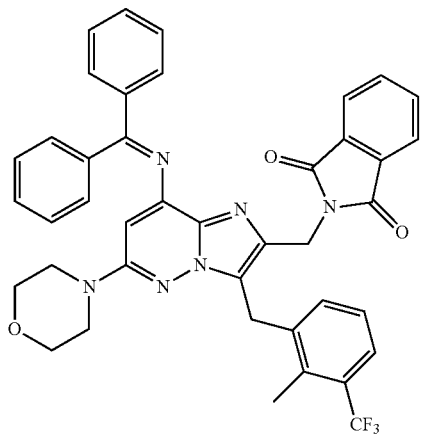 [SMILES: Cc1c(Cc2c(CN3C(=O)c4ccccc4C3=O)nc3c(N=C(c4ccccc4)c4ccccc4)cc(N4CCOCC4)nn23)cccc1C(F)(F)F]

Di-tert-butyl azodicarboxlate (337 mg; 1.46 mmol) was added portionwise to a solution of intermediate 214 (571 mg; 0.98 mmol), phtalimide (172 mg; 1.17 mmol), $PPh_3$ (384 mg; 1.463 mmol) in Me-THF (15 mL) at room temperature under $N_2$. The reaction mixture was stirred at room temperature overnight, diluted with DCM and washed with a 10% aqueous solution of $K_2CO_3$. The organic layer was decanted, dried over $MgSO_4$, filtered and evaporated to dryness. The residue was purified by chromatography over silica gel (irregular SiOH; 50 g; gradient: from 100% DCM to 95% DCM, 5% MeOH, 0.5% $NH_4OH$). The pure fractions were collected and evaporated to dryness yielding 800 mg of intermediate 215. The product was used without purification for the next step.

Example A50

Preparation of Intermediate 216

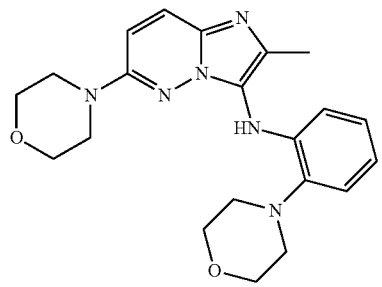 [SMILES: Cc1nc2ccc(N3CCOCC3)nn2c1Nc1ccccc1N1CCOCC1]

Intermediate 216 was prepared according to an analogous procedure as described for the synthesis of intermediate 91, using intermediate 90 and 2-as starting materials. The residue was purified by chromatography over silica gel (regular SiOH 30 µm; 40 g; gradient: from 98% DCM, 2% MeOH, 0.1% $NH_4OH$ to 96% DCM, 4% MeOH, 0.1% $NH_4OH$). The pure fractions were collected and evaporated to dryness to give 1.09 g (82%, yellow solid) of intermediate 216.

Preparation of Intermediate 217

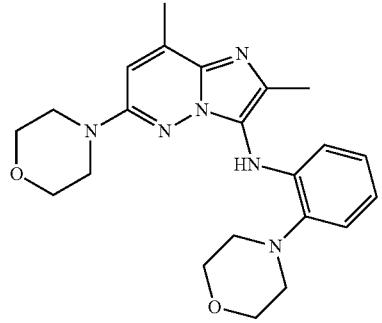 [SMILES: Cc1nc2c(C)cc(N3CCOCC3)nn2c1Nc1ccccc1N1CCOCC1]

N-butyllithium (6.2 mL; 9.95 mmol) was added dropwise to a solution of diisopropylamine (1.4 mL; 9.67 mmol) in THF (15 mL) at −78° C. under $N_2$. The reaction mixture was stirred for 20 min at −40° C. then cooled to −78° C. A solution of intermediate 216 (1.09 g; 2.76 mmol) in THF (15 mL) was added dropwise and stirred for 20 min. A solution of iodine (0.77 g; 3.04 mmol) in THF (15 mL) was added dropwise and stirred at −78° C. for 1 h20. The mixture was poured into a 10% aqueous solution of $NH_4Cl$ and allowed to reach rt. Then, it was extracted with EtOAc. The organic layer was dried over $MgSO_4$, filtered and evaporated until dryness. The residue was purified by chromatography over silica gel (40 g; SiOH 30 µm; gradient:from 70% heptane, 30% EtOAc to 55% heptane, 45% EtOAc). The pure fractions were collected and the solvent was evaporated to give 620 mg (43%, white solid) of intermediate 217.

Preparation of Intermediate 218

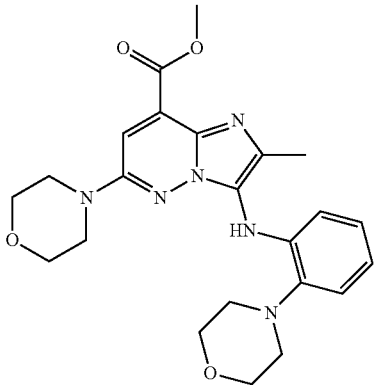 [SMILES: COC(=O)c1cc(N2CCOCC2)nn2c(Nc3ccccc3N3CCOCC3)c(C)nc12]

Intermediate 218 was prepared according to an analogous procedure as described for the synthesis of intermediate 94, using intermediate 217 and carbon monoxide as starting materials. The residue was purified by chromatography over silica gel (regular SiOH 30 μm; 25 g; gradient: from 99% DCM, 1% MeOH, 0.1% NH$_4$OH to 96% DCM, 4% MeOH, 0.1% NH$_4$OH). The pure fractions were collected and evaporated to dryness to give 272 mg (yellow solid) of intermediate 218.

Example A51

Preparation of Intermediate 219

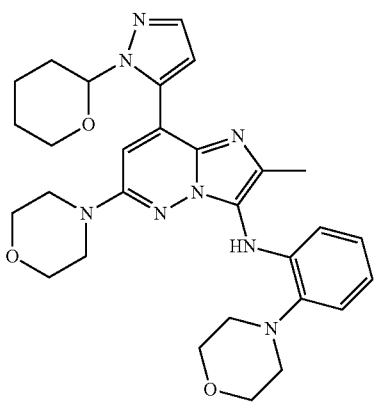 [SMILES: Cc1nc2c(-c3ccnn3C3CCCCO3)cc(N3CCOCC3)nn2c1Nc1ccccc1N1CCOCC1]

PdCl$_2$(dppf).DCM (24 mg; 0.03 mmol) was added to a solution of K$_2$CO$_3$ (80 mg; 0.58 mmol), 1-(tetrahydropyran-2-yl)-1H-pyrazole-5-boronic acid pinacol ester (96 mg; 0.35 mmol), intermediate 217 (150 mg; 0.29 mmol) in 1,4-dioxane (5.0 mL) and H$_2$O (1.2 mL). The reaction mixture was heated at 100° C. overnight in a sealed tube. The mixture was cooled down to room temperature, poured into brine and extracted with EtOAc. The organic layer was dried over MgSO$_4$, filtered and evaporated until dryness. The residue (160 mg, quant.) was used without purification in the next step.

Example A52

Preparation of Intermediate 221

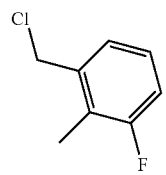

Lithium chloride (1.25 g; 29.55 mmol) was added to a solution of 3-fluoro-2-methylbenzyl bromide (1 g; 4.93 mmol) in DMF (5 mL) at rt. The reaction mixture was stirred at rt for 24 h, poured into water and extracted with Et$_2$O. The organic layer was decanted, washed with water and brine, dried over MgSO$_4$, filtered and evaporated to dryness to give 762 mg (97%) of intermediate 221.

Preparation of Intermediate 222

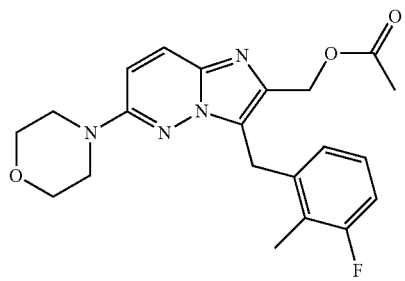 [SMILES: CC(=O)OCc1nc2ccc(N3CCOCC3)nn2c1Cc1cccc(F)c1C]

In a sealed tube, a mixture of intermediate 3 (300 mg; 1.09 mmol), intermediate 221 (206 mg; 1.30 mmol) and K$_2$CO$_3$ (225 mg; 1.63 mmol) in 1,4-dioxane (4 mL) was bubbled with N$_2$ for 15 min. Then, PPh$_3$ (57 mg; 0.22 mmol) and Palladium(II) acetate (27 mg; 0.12 mmol) were added. The reaction mixture was stirred at 100° C. overnight, cooled down to rt, poured onto water and extracted with DCM. The organic layer was decanted, dried over MgSO$_4$, filtered and evaporated to give 543 mg of mixture of intermediate 222 and intermediate 223 (1/1). The mixture of two products was used without purification in the next step.

Preparation of Intermediate 223

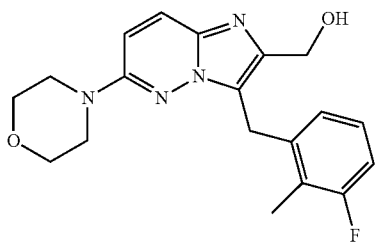 [SMILES: Cc1c(F)cccc1Cc1c(CO)nc2ccc(N3CCOCC3)nn12]

Lithium hydroxide monohydrate (228 mg; 5.43 mmol) (227 mg; 5.43 mmol) was added to a mixture of intermediate 222 (in mixture with 50% of intermediate 223) (432 mg;

1.09 mmol) in water (1.3 mL) and MeOH (4 mL) at rt. The reaction mixture was stirred at rt all over the week end and water was added to the mixture. The precipitate was filtered, washed with water (2×) and dissolved in DCM/MeOH. The organic layer was washed with water, dried over MgSO$_4$, filtered and evaporated to dryness. The residue was purified by chromatography over silica gel (irregular SiOH; 24 g; gradient: from 0.3% NH$_4$OH, 3% MeOH, 97% DCM to 0.6% NH$_4$OH, 6% MeOH, 94% DCM). The pure fractions were collected and evaporated to dryness. The residue (320 mg; 83%) was taken up with diethylether and the precipitate was filtered and dried to give 305 mg (79%) of intermediate 223. M.P.: 184° C. (Kofler).

Preparation of Intermediate 231

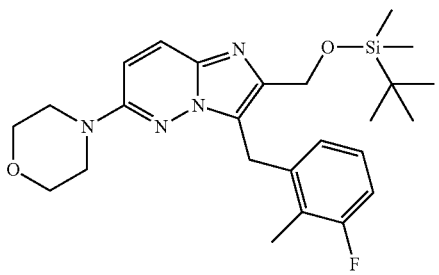 [SMILES: Cc1c(F)cccc1Cc1c(CO[Si](C)(C)C(C)(C)C)nc2ccc(N3CCOCC3)nn12]

Ter-butyldimethylsilyl chloride (4.4 g; 29.18 mmol) was added to a mixture of intermediate 223 (5.2 g; 14.59 mmol), imidazole (4 g; 58.36 mmol) in DMF (100 mL) at rt and the reaction mixture was stirred for 2 h at rt. The reaction mixture was poured into H$_2$O and extracted with EtOAc/diethylether. The organic layer was washed with H$_2$O, dried over MgSO$_4$, filtered and evaporated to dryness. The residue was purified by chromatography over silica gel (gradient: from 100% DCM to 0.3% NH$_4$OH, 3% MeOH, 97% DCM). The pure fractions were collected and evaporated to dryness. The residue (7 g) was purified by chromatography over silica gel (gradient: from 100% DCM to 7% MeOH, 93% DCM). The pure fractions were collected and evaporated to give 5.55 g (81%) of intermediate 231.

Preparation of Intermediate 232

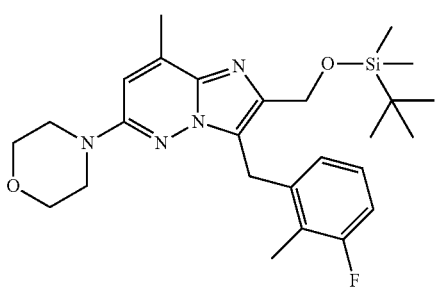 [SMILES: Cc1c(F)cccc1Cc1c(CO[Si](C)(C)C(C)(C)C)nc2c(C)cc(N3CCOCC3)nn12]

N-butyllithium (18.5 mL; 29.67 mmol) was added dropwise to a solution of diisopropyl amine (4 mL; 28.52 mmol) in Me-THF (54 mL) at −78° C. under N$_2$. The reaction mixture was stirred for 15 min at −78° C. Then, a solution of intermediate 231 (5.37 g; 11.41 mmol) in Me-THF (18 mL) was added dropwise (15 min) and the reaction mixture was stirred at this temperature for 30 min. A solution of iodine (3.18 g; 12.55 mmol) in Me-THF (18 mL) was added dropwise at −70° C. (15 min). The reaction mixture was stirred at this temperature for 30 min and poured onto a mixture of 10% aqueous solution of NH$_4$Cl. The reaction mixture was diluted with EtOAc. Then, the organic layer was decanted, washed with a saturated solution of sodium thiosulfate, water then brine, dried over MgSO$_4$, filtered and evaporated to dryness. The residue was purified by chromatography over silica gel (irregular SiOH; 80 g; gradient: from 15% EtOAc, 85% heptane to 40% EtOAc, 60% heptane). The pure fractions were collected and evaporated to give 2.46 g (36%) of intermediate 232.

Preparation of Intermediate 233

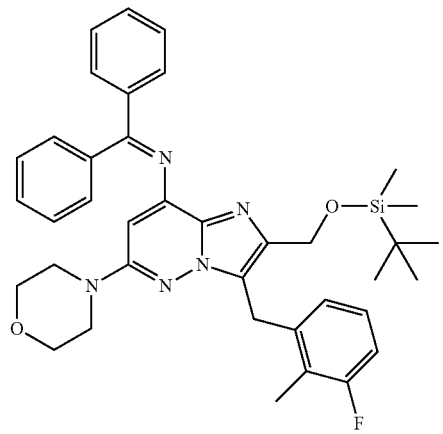 [SMILES: Cc1c(F)cccc1Cc1c(CO[Si](C)(C)C(C)(C)C)nc2c(N=C(c3ccccc3)c3ccccc3)cc(N3CCOCC3)nn12]

In a sealed vessel with good stirring, N$_2$ was bubbled in a mixture of intermediate 232 (1.2 g; 2.13 mmol) and benzophenone imine (0.535 mL; 3.19 mmol) in 1,4-dioxane (30 mL). Then, Cs$_2$CO$_3$ (2.08 g; 6.38 mmol) was added and the reaction mixture was degassed with N$_2$. Finally, racemic-2,2'-Bis(diphenylphosphino)-1,1'-binaphtyl (66 mg; 0.11 mmol) and Palladium(II) acetate (24 mg; 0.11 mmol) were added and the reaction mixture was heated at 100° C. for 18 h. The reaction mixture was partitioned between water and EtOAc. The organic layer was decanted, washed with brine, dried over MgSO$_4$, filtered and evaporated to dryness. The residue was purified by chromatography over silica gel (irregular SiOH; 40 g; gradient: from 100% heptane, to 70% heptane, 30% EtOAc). The pure fractions were collected and evaporated to give 180 mg (13%) of intermediate 233.

Preparation of Intermediate 226

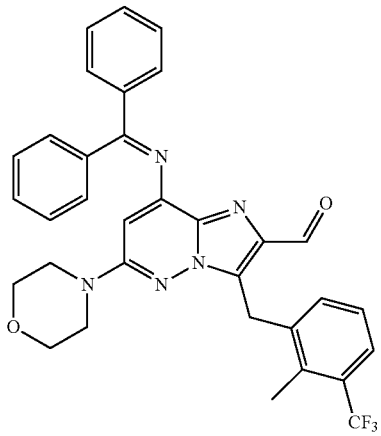 [SMILES: Cc1c(Cc2c(C=O)nc3c(N=C(c4ccccc4)c4ccccc4)cc(N4CCOCC4)nn23)cccc1C(F)(F)F]

A mixture of intermediate 214 (3.1 g; 2.29 mmol) and manganese oxide (3.2 g; 37.05 mmol) in toluene (50 mL) was heated at 80° C. for 1 h. The mixture was cooled down to rt, diluted in DCM and filtered through a pad of Celite® which was washed with DCM. The filtrate was evaporated until dryness. The residue (2.9 g) was purified immediately by chromatography over silica gel (irregular SiOH; 80 g; mobile phase: gradient from 100% DCM to 98% DCM, 2% MeOH). The pure fractions were collected and evaporated to dryness. The residue (2.24 g) was crystallized from DIPE. The precipitate was filtered off and dried under vacuum to give 1.66 g (54%) of intermediate 226.

Example A53

Preparation of Intermediate 227

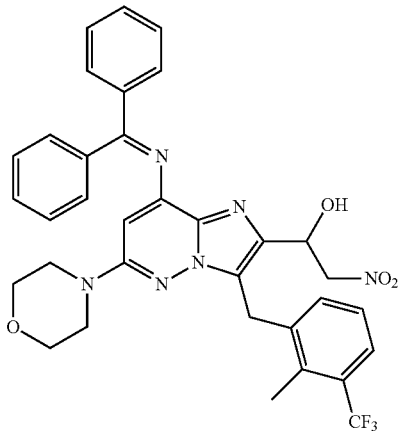 [SMILES: Cc1c(Cc2c(C(O)C[N+](=O)[O-])nc3c(N=C(c4ccccc4)c4ccccc4)cc(N4CCOCC4)nn23)cccc1C(F)(F)F]

At 0° C., nitromethane (0.406 mL; 7.45 mmol) was added to a mixture of intermediate 226 (0.87 g; 1.49 mmol) in THF (15 mL). NaOH (3N in $H_2O$) (0.497 mL; 1.49 mmol) was added dropwise and the mixture was allowed to stir at rt for 12 h. The reaction mixture was poured out into ice water and DCM was added. The organic layer was separated, dried over $MgSO_4$, filtered and the solvent was evaporated to give 0.878 g (73%, at 80% by NMR). This compound was used without any further purification in the next step.

Preparation of Intermediate 228

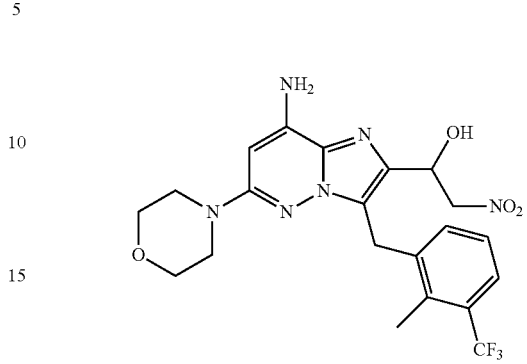

In a round bottom flask, intermediate 227 (0.878 g; 1.36 mmol) was diluted in THF (25 mL). Then, HCl (1M in $H_2O$) (13.62 mL; 13.62 mmol) was added and the reaction was stirred at rt for 2 h. The reaction mixture was poured onto iced water, neutralized with $K_2CO_3$ and the aqueous layer was extracted with EtOAc (3×). The organic layers were combined, dried over $MgSO_4$ and evaporated to dryness. The residue (0.792 g) was crystallized from DIPE. The precipitate was filtered off and dried under vacuum to give 0.392 g (68%).

Example A54

Preparation of Intermediate 234

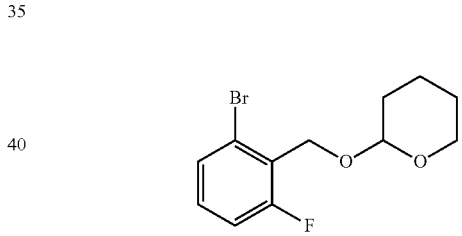

Pyridinium p-toluenesulfonate (0.612 g; 2.43 mmol) was added to a solution of 2-bromo-6-fluorobenzyl alcohol (5 g; 24.38 mmol) and 3,4-dihydro-2H-pyran (3.34 mL; 36.58 mmol) in DCM (50 mL) at rt. The reaction mixture was stirred at rt for 12 h. The mixture was washed with brine, dried over $MgSO_4$, filtered and evaporated to give 7.67 g (quant.) of intermediate 234. This compound was used in the next step without any purification.

Preparation of Intermediate 235

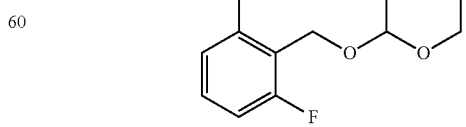

n-Butyllithium (17.1 mL; 27.39 mmol) was added dropwise to a solution of intermediate 234 (6.6 g; 22.83 mmol)

in THF (66 mL) at −78° C. The solution was stirred at −78° C. for 1 h and DMF (17.7 mL; 228.26 mmol) was added dropwise. The reaction mixture was stirred at −78° C. for 1 h and was allowed to warm to 0° C. The mixture was poured into water and the product was extracted with EtOAc. The organic layer was dried over MgSO$_4$, filtered and concentrated under vacuum to give 6.9 g of intermediate 235. This compound was used in the next step without any further purification.

Preparation of Intermediate 236

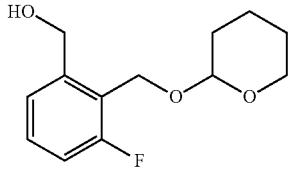 [SMILES: OCc1cccc(F)c1COC1CCCCO1]

Sodium borohydride (1.1 g; 28.96 mmol) was added portionwise to a solution of intermediate 235 (6.9 g; 28.96 mmol) in MeOH (100 mL) at 0° C. The solution was stirred at 0° C. for 2 h. The mixture was poured into water and the organic layer was extracted with DCM, separated, dried over MgSO$_4$, filtered and concentrated to dryness. The residue (7 g) was purified by chromatography over silica gel (Irregular SiOH; 15-40 µm; 40 g; gradient: from 90% heptane, 10% EtOAc to 60% heptane, 40% % EtOAc). The pure fractions were collected and the solvent was evaporated to give 3.4 g (49%) of intermediate 236.

Preparation of Intermediate 237

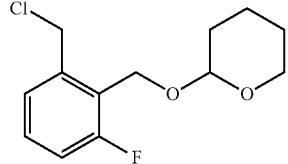 [SMILES: Fc1cccc(CCl)c1COC1CCCCO1]

Triethylamine (1.56 mL; 11.24 mmol) followed by methanesulfonyl chloride (0.87 mL; 11.24 mmol) was slowly added to a solution of intermediate 236 (1.8 g; 7.49 mmol) in DCM (20 mL) at 0° C. The reaction mixture was stirred at rt overnight Water was added and the product was extracted with DCM. The organic layer was dried over MgSO$_4$, filtered and evaporated. The residue (2.6 g) was purified by chromatography over silica gel (Irregular SiOH; 15-40 µm; 40 g; gradient: from 80% heptane, 20% EtOAc to 60% heptane, 40% EtOAc). The pure fractions were collected and the solvent was evaporated to give 14.6 g (82%) of intermediate 237.

Alternative Preparation of Intermediate 237

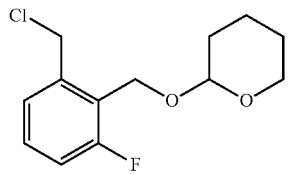 [SMILES: Fc1cccc(CCl)c1COC1CCCCO1]

and preparation of intermediate 237a

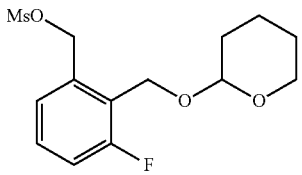 [SMILES: CS(=O)(=O)OCc1cccc(F)c1COC1CCCCO1]

To a solution of intermediate 236 (34.08 g; 140.42 mmol) in DCM (500 mL) cooled to 0° C., was added slowly Et$_3$N (29.36 mL; 210.632 mmol) followed by methanesulfonylchloride (16.3 mL; 210.632 mmol) and 4-(Dimethylamino) pyridine (DMAP) (171.55 mg; 1.4 mmol). The mixture was stirred at room temperature overnight. Water was added and the product was extracted with DCM. The organic layer was dried over MgSO$_4$, filtered and concentrated under vacuum.

The crude was purified by chromatography over silica gel (irregular SiOH, gradient from 100%6 n-heptane to 100% Ethyl acetate). The fractions containing the product were collected and evaporated to dryness yielding 24.67 g (67%) of intermediate 237 and 3.46 g (6%) of intermediate 237a.

Alternative for the Preparation of Intermediate 237

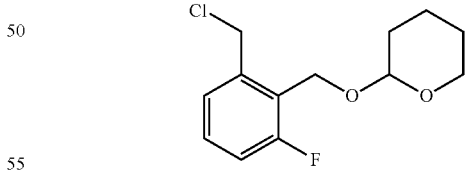

A mixture of intermediate 237a (3.46 g; 8.69 mmol) in THF (25 mL) was stirred at room temperature. LiCl (0.94 g; 21.74 mmol) was added and the mixture was refluxed for 1 h. The reaction mixture was poured into water and the organic layer was extracted with ethyl acetate. The organic phase was dried over MgSO$_4$, filtered, and the solvents were evaporated in vacuo to give 2.25 g (100%) of intermediate 237 as a clear oil.

Preparation of Intermediate 238

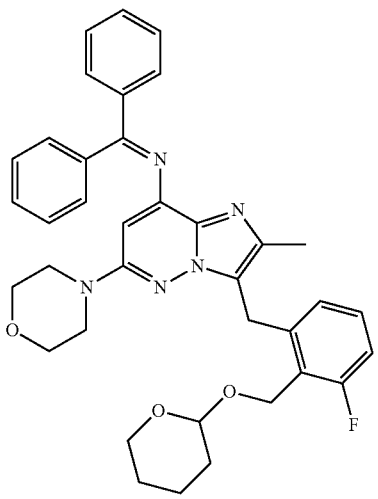 [SMILES: Cc1nc2c(N=C(c3ccccc3)c3ccccc3)cc(N3CCOCC3)nn2c1Cc1cccc(F)c1COC1CCCCO1]

In a sealed tube, intermediate 237 (97 mg; 0.38 mmol) and Cs₂CO₃ (0.24 g; 0.75 mmol) were added to a solution of intermediate 189 (0.1 g; 0.25 mmol) in 1,4-dioxane (1 mL). The mixture was carefully degassed under vacuum and back-filled with N₂ (3×). Then, racemic-2,2'-Bis(diphenylphosphino)-1,1'-binaphtyl (15 mg; 0.03 mmol) and palladium(II) acetate (6 mg; 0.03 mmol) were added and the mixture was carefully degassed under vacuum and back-filled with N₂ (3×). The reaction mixture was stirred at 115° C. overnight. The mixture was cooled down to rt and filtered through a pad of Celite®. The cake was washed with DCM/MeOH (1/1) and poured into water. The organic layer was extracted with DCM, separated, dried over MgSO₄, filtered and evaporated to dryness. The residue (200 mg) was purified by chromatography over silica gel (Irregular SiOH; 15-40 µm; 24 g, gradient: from 100% DCM to 95% DCM, 5% MeOH, 0.1% NH₄OH). The pure fractions were collected and the solvent was evaporated until dryness to give 80 mg (52%) of intermediate 238.

Example A55

Preparation of Intermediate 246

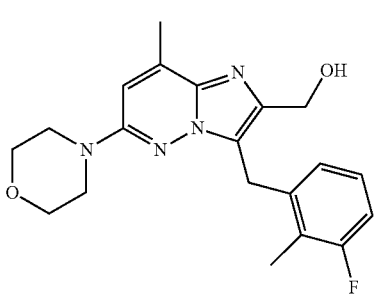 [SMILES: Cc1c(F)cccc1Cc1c(CO)nc2c(C)cc(N3CCOCC3)nn12]

Intermediate 246 was prepared according to an analogous procedure as described for the synthesis of intermediate 214, using intermediate 232 as starting material (1.27 g, 64%). The reaction mixture was performed in Me-THF.

Preparation of Intermediate 247

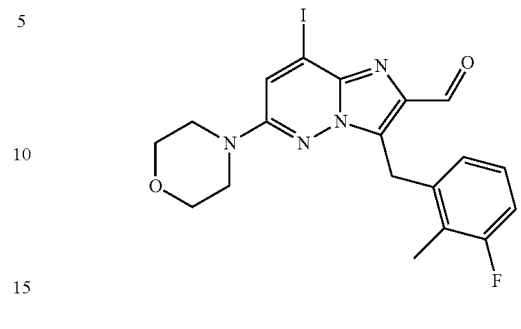

Intermediate 247 was prepared according to an analogous procedure as described for the synthesis of intermediate 226, using intermediate 246 as starting material (1.15 g).

The reaction was performed in 1,4-dioxane.

Preparation of Intermediate 250

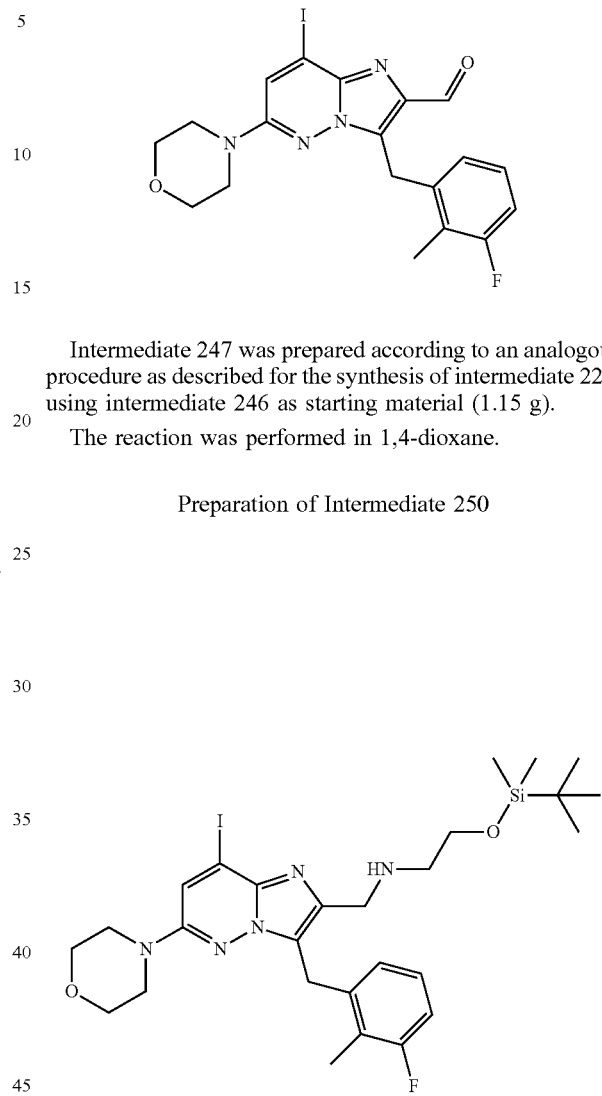

A mixture of intermediate 247 (255 mg; 0.531 mmol), 2-[[(1,1-dimethylethyl)dimethylsilyl]oxy]-ethanamine (465 mg; 2.655 mmol) in MeOH (5 mL) was stirred at room temperature overnight. Sodium triacetoxyborohydride (337 mg; 1.593 mmol) was added and stirred for 3 h. The reaction mixture was poured into water, basified with K₂CO₃ solid and extracted with EtOAc (3×). The organic layer was washed with brine, dried over MgSO₄, filtered and evaporated to dryness.

The residue was purified by chromatography over silica gel (irregular SiOH, 40 g; mobile phase: 0.1% NH₄OH, 97% DCM, 3% MeOH). The pure fractions were collected and evaporated to dryness yielding 230 mg (68%) of intermediate 250.

Preparation of Intermediate 251

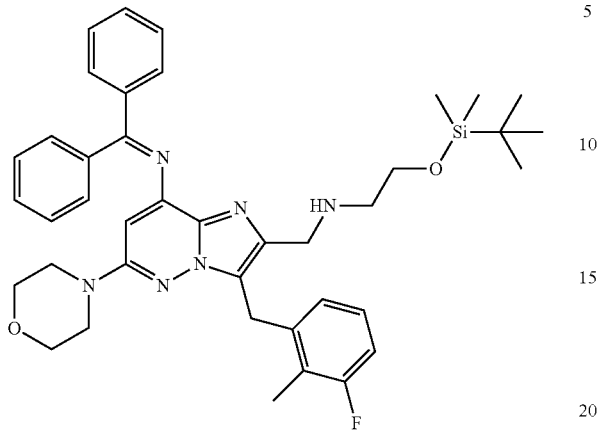

Intermediate 251 was prepared according to an analogous procedure as described for the synthesis of intermediate 201, using 250 and benzophenone imine as starting materials (183 mg, 73%).

Example A56

Preparation of Intermediate 239

n-butyllithium (188.4 mL; 471.05 mmol) was added to a solution of 2,2,6,6-tetramethylpiperidine (79.5 mL; 471.05 mmol) in THF (600 mL) at −20° C. 3-fluorobenzoic acid (30 g; 214.11 mmol) in THF (150 mL) was added dropwise at −50° C. and the mixture was stirred for 4 h at −50° C. Then, iodoethane (68.8 mL; 856.46 mmol) was added at −50° C. The reaction mixture was warmed to rt and stirred overnight. Subsequently, water (300 mL) was added. The aqueous layers were washed with MTBE (400 mL) and acidified with a 4M aqueous solution of HCl to pH 2. The mixture was separated and the aqueous layer was extracted with MTBE (2×400 mL). The combined organic layers were washed with brine and dried over MgSO$_4$. The solvent was removed under vacuum. The residue was purified by flash column chromatography over silica gel (eluent: from 100% petroleum ether from to 80% petroleum ether, 20% EtOAc). The pure fractions were collected and the solvent was evaporated to give 19 g (53%) of intermediate 239.

Preparation of Intermediate 240

Intermediate 239 (19.62 g; 116.67 mmol) was dissolved in THF (200 mL). Borane tetrahydrofuran complex (1M in THF) (233.3 mL; 233.34 mmol) was added dropwise at 0° C. The reaction mixture was stirred overnight at 50° C. The mixture was quenched with a saturated aqueous solution of NaHCO$_3$ (300 mL) and extracted with EtOAc (3×400 mL). The mixture was washed with brine and dried over Na$_2$SO$_4$. The solvent was evaporated under vacuum to give 17.9 g (100%) of intermediate 240.

Preparation of Intermediate 241

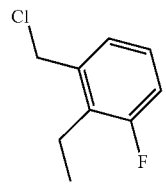

Thionyl chloride (12.6 mL; 174.15 mmol) was added to a solution of intermediate 240 (17.9 g; 116.10 mmol) in DCM (335 mL) at 0° C. The reaction mixture was warmed to rt and stirred overnight. The solvent was evaporated under vacuum. The residue was purified by preparative high-performance liquid chromatography (Phenomenex Synergi Max-RP; 250*50 mm*10 um; eluent: ACN/H$_2$O from 40% to 80%). The pure fractions were collected and the solvent was evaporated under vacuum. The residue was freeze-dried to give 6.7 g (32%) of intermediate 241.

Preparation of Intermediate 242

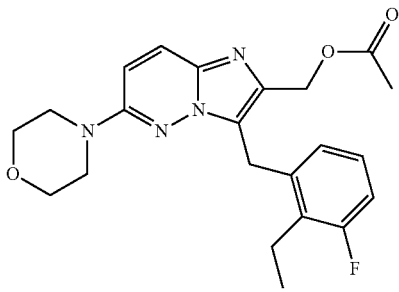 [SMILES: CCc1c(F)cccc1Cc1c(COC(C)=O)nc2ccc(N3CCOCC3)nn12]

Intermediate 242 was prepared according to an analogous procedure as described for the synthesis of intermediate 222, using intermediate 3 and intermediate 241 as starting materials (10.9 g). The product was used without purification for the next step.

Preparation of Intermediate 243

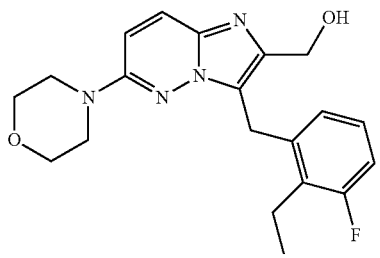 [SMILES: CCc1c(F)cccc1Cc1c(CO)nc2ccc(N3CCOCC3)nn12]

Intermediate 243 was prepared according to an analogous procedure as described for the synthesis of intermediate 223, using intermediate 242 as starting material (6.04 g, 90%). M.P.: 170° C. (Kofler).

Preparation of Intermediate 254

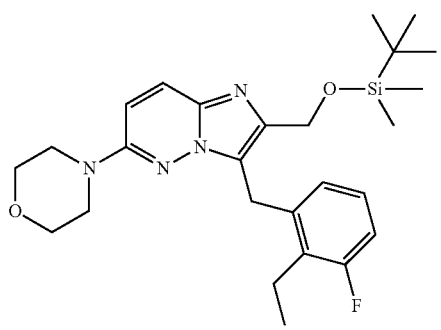 [SMILES: CCc1c(F)cccc1Cc1c(CO[Si](C)(C)C(C)(C)C)nc2ccc(N3CCOCC3)nn12]

Intermediate 254 was prepared according to an analogous procedure as described for the synthesis of intermediate 231, using intermediate 243 as starting material (6.6 g, 86%).

Preparation of Intermediate 255

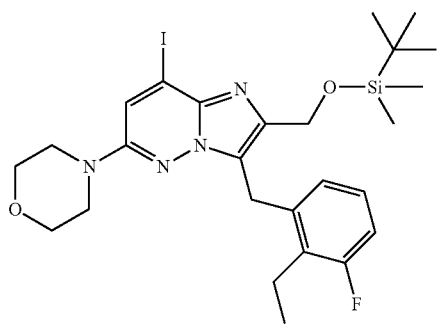 [SMILES: CCc1c(F)cccc1Cc1c(CO[Si](C)(C)C(C)(C)C)nc2c(I)cc(N3CCOCC3)nn12]

Intermediate 255 was prepared according to an analogous procedure as described for the synthesis of intermediate 232, using intermediate 254 as starting material (4.1 g, 51%).

Preparation of Intermediate 256

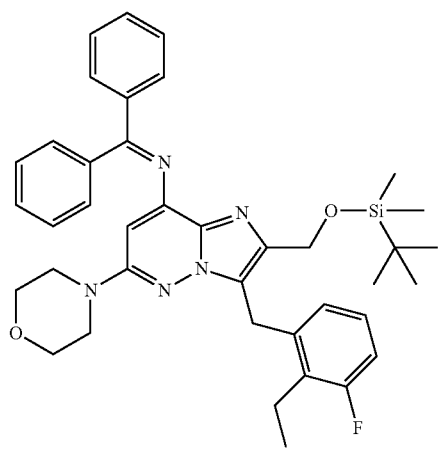 [SMILES: CCc1c(F)cccc1Cc1c(CO[Si](C)(C)C(C)(C)C)nc2c(N=C(c3ccccc3)c3ccccc3)cc(N3CCOCC3)nn12]

Intermediate 256 was prepared according to an analogous procedure as described for the synthesis of intermediate 233, using intermediate 255 as starting material (214 mg, 65%).

Preparation of Intermediate 257

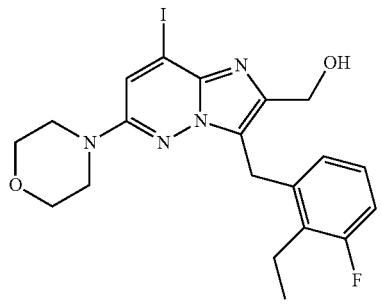 [SMILES: CCc1c(F)cccc1Cc1c(CO)nc2c(I)cc(N3CCOCC3)nn12]

Intermediate 257 was prepared according to an analogous procedure as described for the synthesis of intermediate 214, using intermediate 255 as starting material (2.39 g, 79%, M.P.: 198° C. (K)). The reaction mixture was performed in Me-THF.

Preparation of Intermediate 258

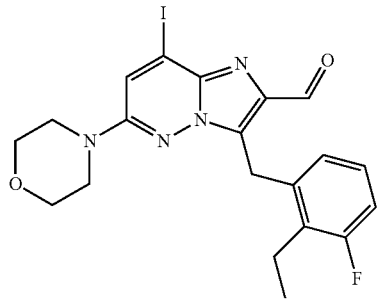 [SMILES: CCc1c(F)cccc1Cc1c(C=O)nc2c(I)cc(N3CCOCC3)nn12]

Intermediate 258 was prepared according to an analogous procedure as described for the synthesis of intermediate 226, using intermediate 257 as starting material (1.97 g, 88%, M.P.: 151° C. (K)). The reaction mixture was performed in 1,4-dioxane.

Example A57

Preparation of Intermediate 259

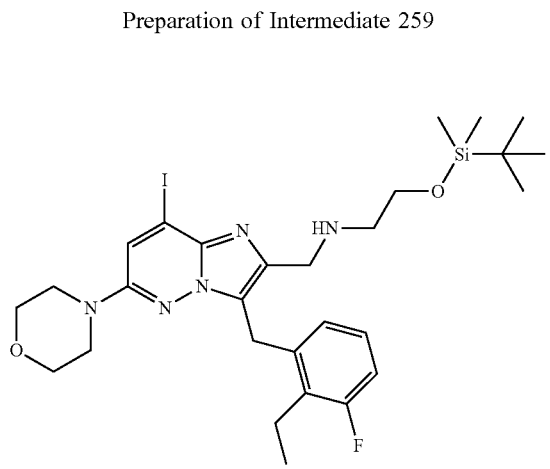

Intermediate 259 was prepared according to an analogous procedure as described for the synthesis of intermediate 250, using intermediate 258 and 2-11[[(1,1-dimethylethyl)dimethylsilyl]oxy]-ethanamine as starting material (572 mg, 88%).

Preparation of Intermediate 262

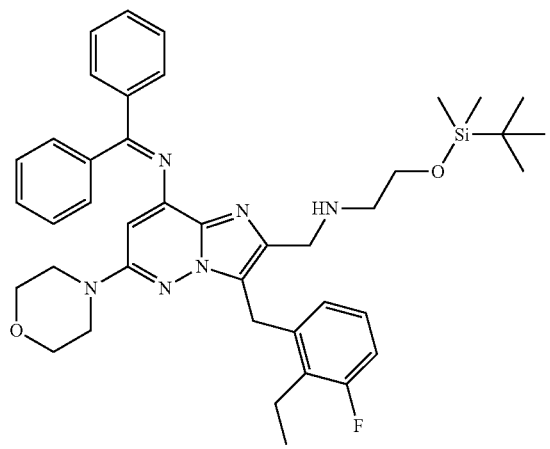 [SMILES: CCc1c(F)cccc1Cc1c(CNCCO[Si](C)(C)C(C)(C)C)nc2c(N=C(c3ccccc3)c3ccccc3)cc(N3CCOCC3)nn12]

Intermediate 262 was prepared according to an analogous procedure as described for the synthesis of intermediate 249, using intermediate 259 and benzophenone imine as starting materials (438 mg, 77%).

Example A58

Preparation of Intermediate 263

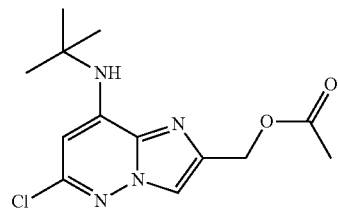 [SMILES: CC(=O)OCc1cn2nc(Cl)cc(NC(C)(C)C)c2n1]

In a schlenk tube, a mixture of 4-bromo-chloropyridazine-3-amine (5.00 g; 24.0 mmol), 1-acetoxy-3-chloroacetone (3.39 mL; 28.8 mmol) and molecular sieves 4A (10 g; 2 eq wt) in NMP (25 mL) was heated at 80° C. for 16 h then cooled to room temperature.

DIPEA (10.5 mL; 59.97 mmol) and tert-butylamine (15.12 mL; 143.92 mmol) were added and the mixture was stirred at 85° C. for 16 hours. The mixture was cooled to room temperature and concentrated under vacuum to remove residual DIPEA. The mixture was filtered on a glass frit to remove molecular sieves. The filtrate was cooled to 0° C. and water was added (175 mL). The mixture was stirred for 30 min then filtered on a glass frit to give 4.5 g of intermediate 263.

Preparation of Intermediate 264

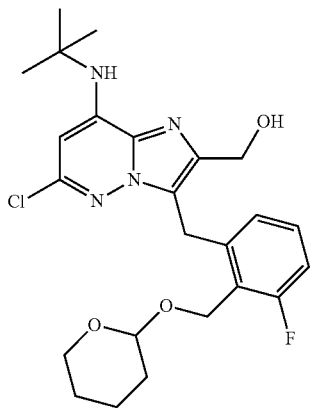 [SMILES: CC(C)(C)Nc1cc(Cl)nn2c(Cc3cccc(F)c3COC3CCCCO3)c(CO)nc12]

In a sealed tube, a mixture of intermediate 237, $K_2CO_3$ (14.01 g; 101.37 mmol) and intermediate 263 (13.37 g; 33.79 mmol) in 1,4-dioxane (400 mL) was purged with $N_2$. Triphenylphosphine ($PPh_3$) (0.886 g; 3.38 mmol) and Pd(OAc)$_2$ (0.379 g; 1.69 mmol) were added and the mixture was stirred (under $N_2$) at 120° C. for 24 h. The solvent was evaporated under vacuum. The crude was purified by chromatography over silica gel (irregular SiOH, gradient from 100% n-heptane to 100% Ethyl acetate). The fractions containing the product were collected and evaporated to dryness yielding 13.5 g (63%) of intermediate 264 as a dark oil.

Preparation of Intermediate 265

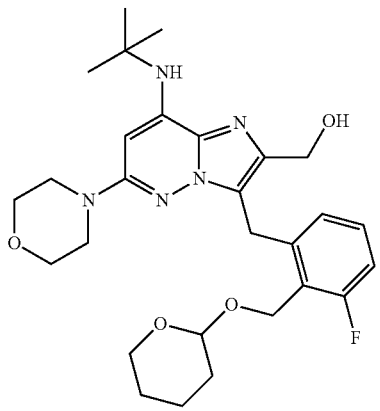 [SMILES: CC(C)(C)Nc1cc(N2CCOCC2)nn2c(Cc3cccc(F)c3COC3CCCCO3)c(CO)nc12]

A solution of intermediate 264 (4.25 g; 8.02 mmol), morpholine (7.01 mL; 80.194 mmol) and sodium phenoxide trihydrate (2.73 g; 16.039 mmol) in 1,4-dioxane (80 mL) were degassed with stream of $N_2$ for 10 min. Then, Pd(OAc)$_2$ (0.09 g; 0.4 mmol) and Xantphos (0.464 g; 0.802 mmol) were added and the resulting mixture was heated at 120° C. overnight. The solvent was evaporated under vacuum. The crude was purified by chromatography over silica gel (irregular SiOH, gradient from 100% DCM to 90% DCM 10% MeOH). The fractions containing the product were collected and evaporated to dryness yielding 3.8 g (81%) of intermediate 265 as a dark oil.

Preparation of Intermediate 266

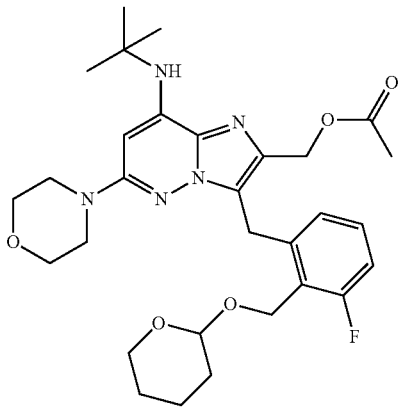 [SMILES: CC(=O)OCc1nc2c(NC(C)(C)C)cc(N3CCOCC3)nn2c1Cc1cccc(F)c1COC1CCCCO1]

Et$_3$N (3.92 mL; 28.145 mmol) was added to a mixture of intermediate 265 (6.6 g; 11.258 mmol), acetic anhydride (1.59 mL; 16.88 mmol) in dry DCM (120 mL) at room temperature. The mixture was stirred at room temperature overnight. The reaction mixture was concentrated and dry under reduced pressure. The crude was purified by chromatography over silica gel (irregular SiOH, gradient from 100% n-heptane to 50% n-heptane 50% Ethyl acetate). The fractions containing the product were collected and evaporated to dryness yielding 5.15 g (76%) of intermediate 266 as a brown oil.

Preparation of Intermediate 267

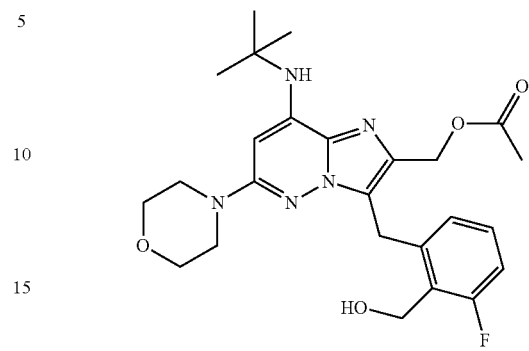

Magnesium bromide ethyl etherate (11.09 g; 42.94 mmol) was added portionwise to a solution of intermediate 266 (5.15 g; 8.59 mmol) dissolved in dry diethylether (85 mL). The reaction mixture was stirred at room temperature overnight. The solvent was evaporated under vacuum. The crude was purified by chromatography over silica gel (irregular SiOH, gradient from 50% n-heptane 50% Ethyl acetate to 100% Ethyl acetate). The fractions containing the product were collected and evaporated to dryness yielding 3.2 g (73%) of intermediate 267 as a yellow oil.

Preparation of Intermediate 268

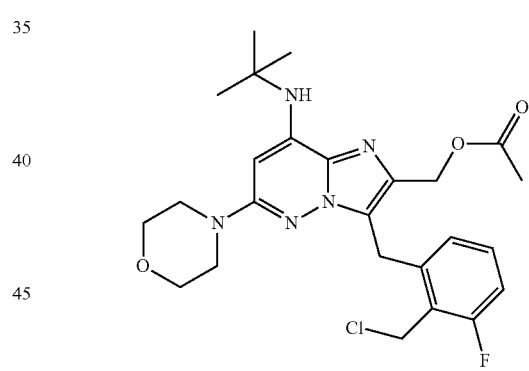

To a solution of intermediate 267 (3.2 g; 6.26 mmol) in DMF (25 mL) cooled to 0° C., was added slowly DIPEA (3.41 mL; 25.04 mmol) followed by methanesulfonylchloride (1.45 mL; 18.73 mmol). The mixture was stirred at room temperature for 3 h. The solution was poured into water and the product was extracted with Ethyl acetate. The organic layer was dried over MgSO, filtered and concentrated under vacuum. The crude was purified by chromatography over silica gel (irregular SiOH, gradient from 100% n-heptane to 70% n-heptane 30% Ethyl acetate). The fractions containing the product were collected and evaporated to dryness yielding, 2.25 g (68%) of intermediate 268 as a yellow oil.

Preparation of Intermediate 269

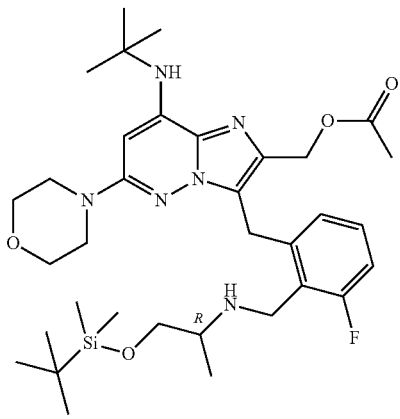

DIPEA (1.73 mL; 12.72 mmol) was added dropwise to a solution of intermediate 268 (2.25 g; 4.24 mmol) and (R)-1-((tert-butyldimethylsilyl)oxy)propan-2-amine (1.61 g; 8.48 mmol) in $CH_3CN$ (50 mL). The reaction mixture was refluxed overnight. The solvent was evaporated in vacuo. The crude was purified by chromatography over silica gel (irregular SiOH, gradient from 100% n-heptane to 50% n-heptane 50% Ethyl acetate). The fractions containing the product were collected and evaporated to dryness yielding 2.76 g (94%) of intermediate 269 as a clear solid.

Example A59

Preparation of Intermediate 270

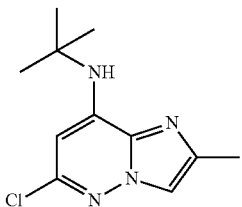 [SMILES: Cc1cn2nc(Cl)cc(NC(C)(C)C)c2n1]

In a sealed tube, DIPEA (14.68 mL; 85.18 mmol) was added to a mixture of intermediate 64 (10 g, 34.072 mmol) and tert-butylamine (21.48 mL, 204.4 mmol) in NMP (50 mL). The mixture was heated at 90° C. for 24 h. Tert-butylamine was evaporated and the mixture was poured into 150 mL of water. The precipitate was filtered off and dried under vacuum. The residue (6.6 g) was purified by chromatography over silica gel (irregular SiOH, mobile phase: 98% DCM, 2% MeOH). The pure fractions were collected and the solvent was evaporated until dryness to give 5.4 g (66%) of intermediate 270.

Preparation of Intermediate 271

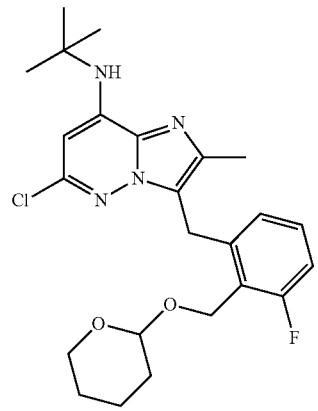 [SMILES: Cc1nc2c(NC(C)(C)C)cc(Cl)nn2c1Cc1cccc(F)c1COC1CCCCO1]

Intermediate 271 was prepared according to an analogous procedure as described for the synthesis of intermediate 264, using intermediate 270 and intermediate 237 as starting materials (11%).

Preparation of Intermediate 272

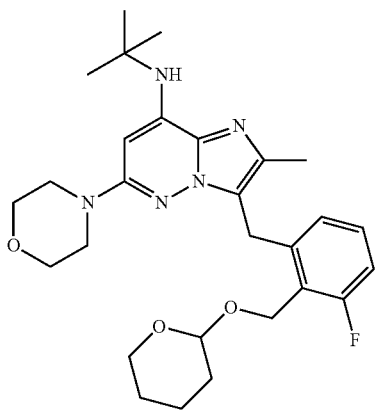 [SMILES: Cc1nc2c(NC(C)(C)C)cc(N3CCOCC3)nn2c1Cc1cccc(F)c1COC1CCCCO1]

Intermediate 272 was prepared according to an analogous procedure as described for the synthesis of intermediate 265, using intermediate 271 as starting material (28%).

Preparation of Intermediate 273

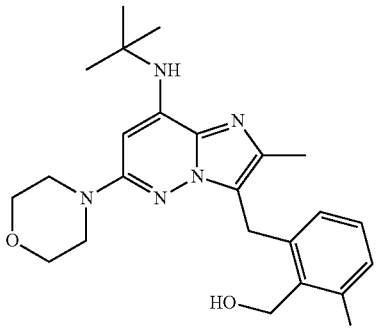

Intermediate 272 (0.634 g; 1.239 mmol) was dissolved in THF (56.3 mL) and an aqueous solution of HCl 1M (12.39 mL; 12.39 mmol) was added. The reaction mixture was stirred at room temperature overnight. Water was added and the product was extracted with DCM. The organic layer was dried over MgSO₄, filtered and concentrated. The crude was purified by chromatography over silica gel (irregular SiOH, gradient from 100% DCM to 90% DCM 10% MeOH). The pure fractions were collected and the solvent was evaporated until dryness to give 0.406 g (76%) of intermediate 273.

Preparation of Intermediate 274

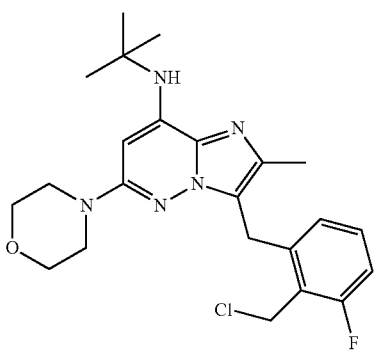 [SMILES: Cc1nc2c(NC(C)(C)C)cc(N3CCOCC3)nn2c1Cc1cccc(F)c1CO]

Intermediate 274 was prepared according to an analogous procedure as described for the synthesis of intermediate 268, using intermediate 273 as starting material (96%).

Preparation of Intermediate 275

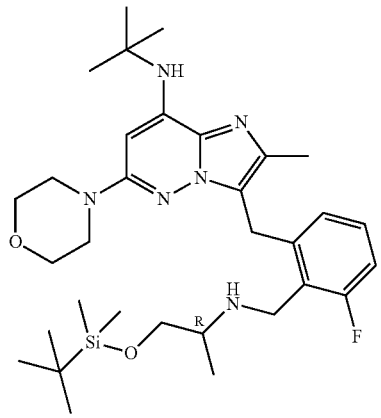

Intermediate 18 was prepared according to an analogous procedure as described for the synthesis of intermediate 269, using intermediate 274 as starting material (82%).

Example A60

Preparation of Intermediate 276

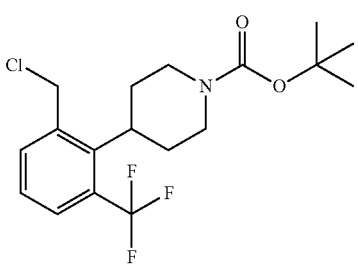 [SMILES: CC(C)(C)OC(=O)N1CCC(c2c(CCl)cccc2C(F)(F)F)CC1]

A solution of tert-butyl 4-[2-(hydroxymethyl)-6-(trifluoromethyl)phenyl]piperidine-1-carboxylate (2.5 g; 6.96 mmol) in DCM (25 mL) was cooled to 0° C. Et₃N (1.45 mL, 10.43 mmol) was slowly added followed by methanesulfonylchloride (0.81 mL, 10.434 mmol). The mixture was stirred at room temperature overnight. The solution was poured into water and the product was extracted with DCM. The organic layer was dried over MgSO₄, filtered and concentrated till dryness. The residue was purified by chromatography over silica gel (irregular SiOH, gradient from 80% Heptane, 20% AcOEt to 60% Heptane, 40% AcOEt). The pure fractions were collected and the solvent was evaporated until dryness to give 1.86 g (71%) of intermediate 276.

Example A61

Preparation of Intermediate 277

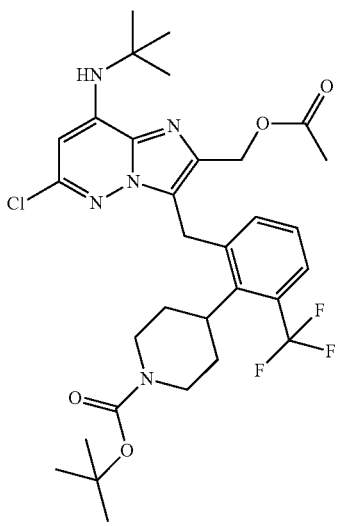 [SMILES: CC(=O)OCc1nc2c(NC(C)(C)C)cc(Cl)nn2c1Cc1cccc(C(F)(F)F)c1C1CCN(C(=O)OC(C)(C)C)CC1]

Intermediate 277 was prepared according to an analogous procedure as described for the synthesis of intermediate 264, using intermediate 263 and intermediate 276 as starting materials (42%).

Preparation of Intermediate 278a and Intermediate 278b

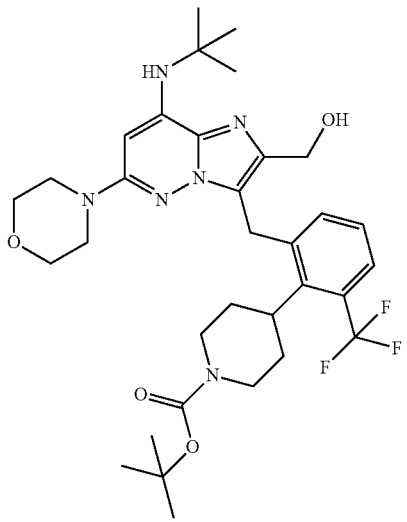

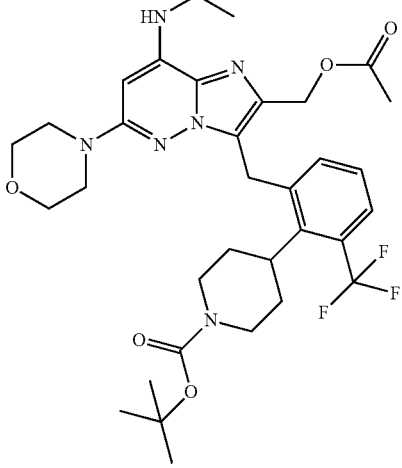

A mixture of intermediate 278a and 278b was prepared according to an analogous procedure as described for the synthesis of intermediate 265, using intermediate 277 as starting material (27%, 80% of intermediate 278a and 15% of intermediate 278b evaluated by LC/MS).

Preparation of Intermediate 279

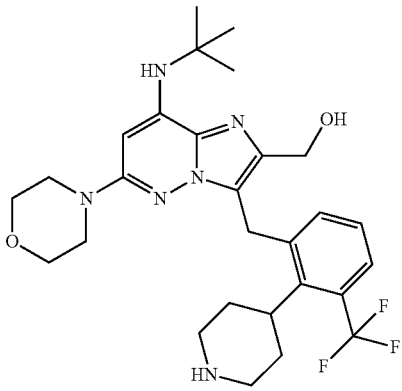 [SMILES: CC(C)(C)Nc1cc(N2CCOCC2)nn2c(Cc3cccc(C(F)(F)F)c3C3CCNCC3)c(CO)nc12]

A solution of a mixture of intermediates 278a and 278b (0.047 g; 0.073 mmol) and an aqueous solution of HCl 3N (1 mL) in THF (4 mL) was heated at 60° C. for 24 h. The mixture was poured into $H_2O$ and was basified with $K_2CO_3$ solid. The organic layer was separated and the aqueous layer was extracted with DCM (2×). The combined organic layers were dried over $MgSO_4$, filtered off and evaporated under vacuum to give 0.07 g of intermediate 279. This compound was used in the next step without any further purification.

239

Alternative for the Preparation of Intermediate 279

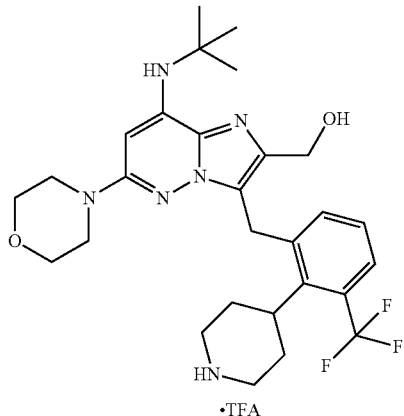 [SMILES: CC(C)(C)Nc1cc(N2CCOCC2)nn2c(Cc3cccc(C(F)(F)F)c3C3CCNCC3)c(CO)nc12]
·TFA

TFA (0.447 mL; 5.99 mmol) was added dropwise to a solution of intermediate 278 (0.194 g; 0.3 mmol) in DCM (10 mL) at 0° C. The mixture was allowed to warm to room temperature and was stirred for 16 h. The mixture was concentrated under vacuo to 0.198 g (99%) of intermediate 279. This compound was used in the next step without any further purification.

Preparation of Intermediate 280

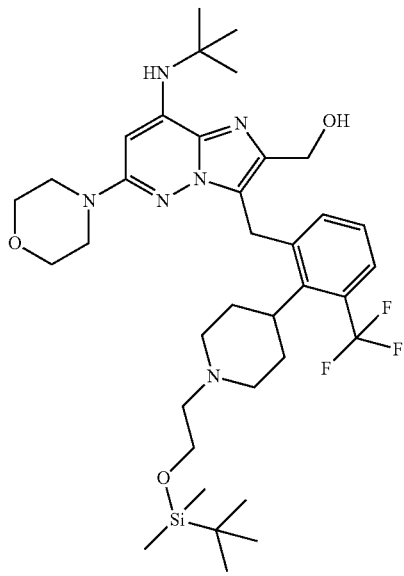 [SMILES: CC(C)(C)Nc1cc(N2CCOCC2)nn2c(Cc3cccc(C(F)(F)F)c3C3CCN(CCO[Si](C)(C)C(C)(C)C)CC3)c(CO)nc12]

(Tert-butyldimethylsilyloxy)acetaldehyde (0.074 mL; 0.39 mmol) and AcOH (0.05 mL) were successively added to a solution of intermediate 279 (0.198 g; 0.3 mmol) in anhydrous MeOH (10 mL). The reaction mixture was stirred at room temperature for 15 min then sodium cyanoborohydride (0.056 g; 0.899 mmol) was added portionwise. The reaction mixture was stirred at room temperature for 18 h. The mixture was poured into an aqueous solution of K$_2$CO$_3$ 10% and was extracted with DCM. The organic layer was dried (MgSO$_4$), filtered off and concentrated under vacuo. The residue was purified by chromatography over silica gel

240

(irregular SiOH, gradient from 98% DCM, 2% MeOH 0.1% NH$_4$OH to 90% DCM, 10% MeOH, 0.1% NH$_4$OH). The pure fractions were collected and the solvent was evaporated until dryness to give 0.24 g (100%) of intermediate 280. This compound was used in the next step without any further purification.

Example A62

Preparation of Intermediate 281

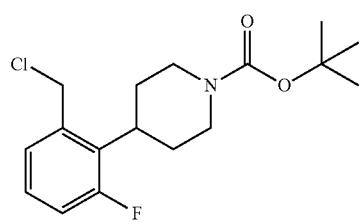 [SMILES: CC(C)(C)OC(=O)N1CCC(c2c(F)cccc2CCl)CC1]

Intermediate 281 was prepared according to an analogous procedure as described for the synthesis of intermediate 276, using intermediate 299 as starting material (61%).

Preparation of Intermediate 282

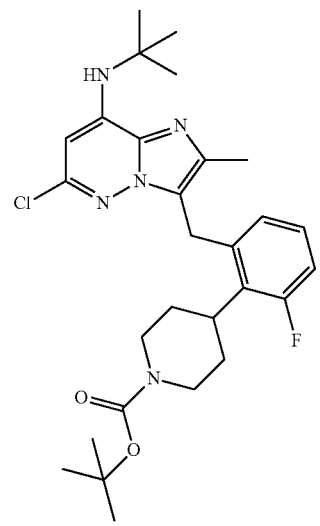 [SMILES: Cc1nc2c(NC(C)(C)C)cc(Cl)nn2c1Cc1cccc(F)c1C1CCN(C(=O)OC(C)(C)C)CC1]

Intermediate 282 was prepared according to an analogous procedure as described for the synthesis of intermediate 264, using intermediate 281 and intermediate 270 as starting materials (83%).

Preparation of Intermediate 283

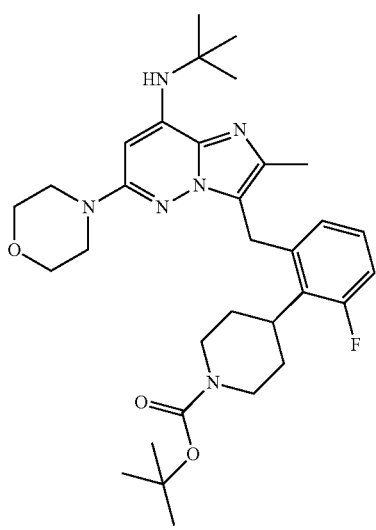 [SMILES: Cc1nc2c(NC(C)(C)C)cc(N3CCOCC3)nn2c1Cc1cccc(F)c1C1CCN(C(=O)OC(C)(C)C)CC1]

Intermediate 283 was prepared according to an analogous procedure as described for the synthesis of intermediate 265, using intermediate 282 as starting material (80%).

Preparation of Intermediate 284

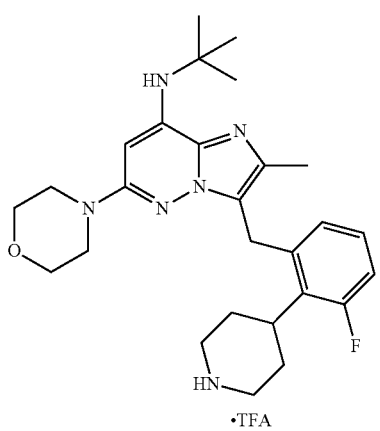 [SMILES: Cc1nc2c(NC(C)(C)C)cc(N3CCOCC3)nn2c1Cc1cccc(F)c1C1CCNCC1]

Intermediate 284 was prepared according to an analogous procedure as described for the synthesis of intermediate 279, using intermediate 283 as starting material (100%).

This compound was used in the next step without any further purification.

Preparation of Intermediate 285

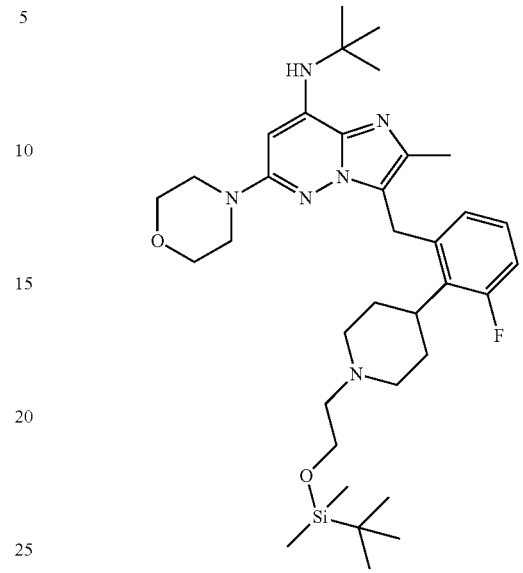

Intermediate 285 was prepared according to an analogous procedure as described for the synthesis of intermediate 280, using intermediate 284 as starting material (97%).

Example A63

Preparation of Intermediate 286

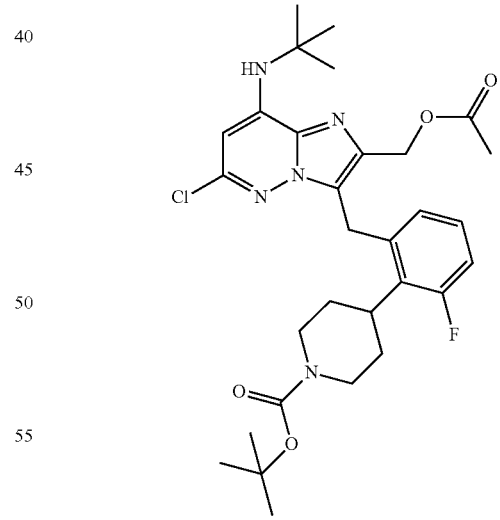

Intermediate 286 was prepared according to an analogous procedure as described for the synthesis of intermediate 264, using intermediate 263 and intermediate 281 as starting materials (38%).

243

Preparation of Intermediate 287

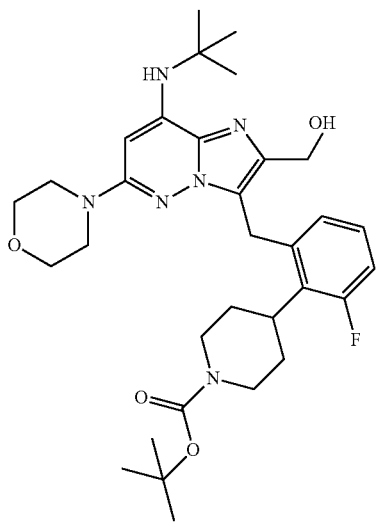 [SMILES: CC(C)(C)Nc1cc(N2CCOCC2)nn2c(Cc3cccc(F)c3C3CCN(C(=O)OC(C)(C)C)CC3)c(CO)nc12]

Intermediate 287 was prepared according to an analogous procedure as described for the synthesis of intermediate 265, using intermediate 286 as starting materials (53%).

Preparation of Intermediate 288

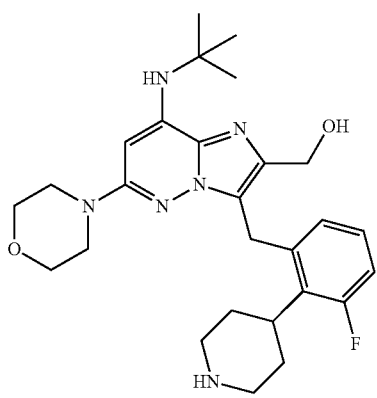 [SMILES: CC(C)(C)Nc1cc(N2CCOCC2)nn2c(Cc3cccc(F)c3C3CCNCC3)c(CO)nc12]

Intermediate 288 was prepared according to an analogous procedure as described for the synthesis of intermediate 279, using intermediate 287 as starting material (100%).
This compound was used in the next step without any further purification.

244

Preparation of Intermediate 289

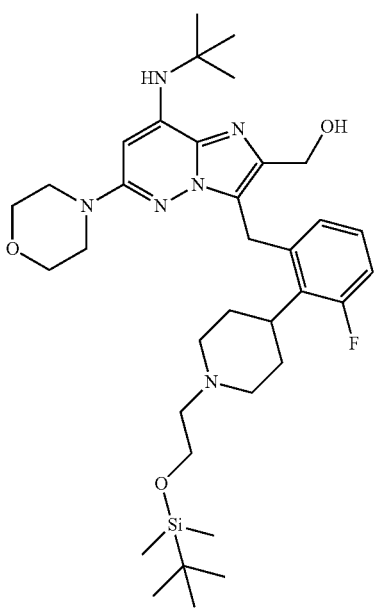 [SMILES: CC(C)(C)Nc1cc(N2CCOCC2)nn2c(Cc3cccc(F)c3C3CCN(CCO[Si](C)(C)C(C)(C)C)CC3)c(CO)nc12]

Intermediate 289 was prepared according to an analogous procedure as described for the synthesis of intermediate 280, using intermediate 288 as starting material (82%).

Example A64

Preparation of Intermediate 290

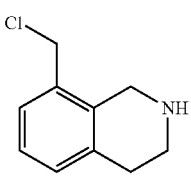 [SMILES: ClCc1cccc2c1CNCC2]

Intermediate 290 was prepared according to an analogous procedure as described for the synthesis of intermediate 237 using tert-butyl 8-(hydroxymethyl)-3,4-dihydro-1H-isoquinoline-2-carboxylate as starting material (84%).

Preparation of Intermediate 291

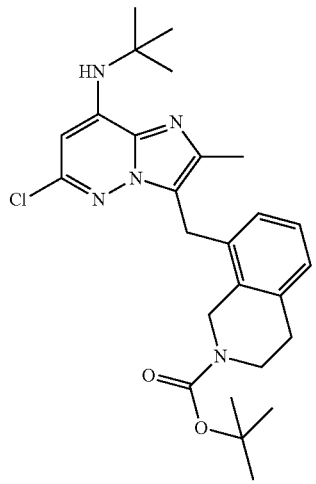 [SMILES: Cc1nc2c(NC(C)(C)C)cc(Cl)nn2c1Cc1cccc2c1CN(C(=O)OC(C)(C)C)CC2]

Intermediate 291 was prepared according to an analogous procedure as described for the synthesis of intermediate 264, using intermediate 270 and intermediate 290 as starting materials (64%).

Preparation of Intermediate 292

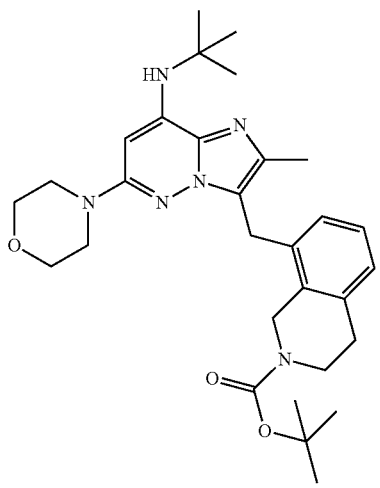 [SMILES: Cc1nc2c(NC(C)(C)C)cc(N3CCOCC3)nn2c1Cc1cccc2c1CN(C(=O)OC(C)(C)C)CC2]

Intermediate 292 was prepared according to an analogous procedure as described for the synthesis of intermediate 265, using intermediate 291 as starting material (78%).

Preparation of Intermediate 293

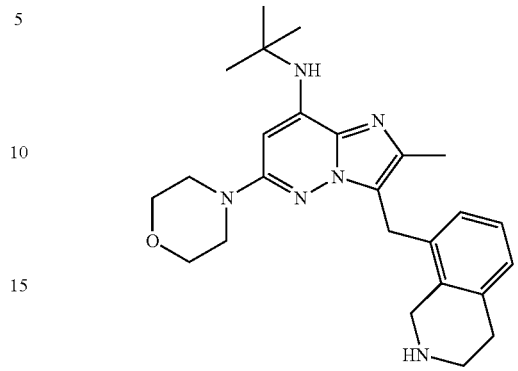

Intermediate 292 (1.83 g; 3.33 mmol) was dissolved in 1,4-dioxane (10 mL) and a solution of HCl in 1,4-dioxane 4M (4.16 mL; 16.64 mmol) was added. The mixture was stirred at room temperature for 4 h. A solution of HCl in 1,4-dioxane 4M (4.16 mL; 16.64 mmol) was added and the mixture was stirred at room temperature for 24 h. The mixture was evaporated under vacuo and the crude was neutralized with $Ca_2CO_3$ to pH=8. The residue was purified by chromatography over silica gel (irregular SiOH, gradient from 100% DCM to 80% DCM, 20% MeOH). The pure fractions were collected and the solvent was evaporated until dryness to give 1.06 g (73%) of intermediate 293.

Example A65

Preparation of Intermediate 294

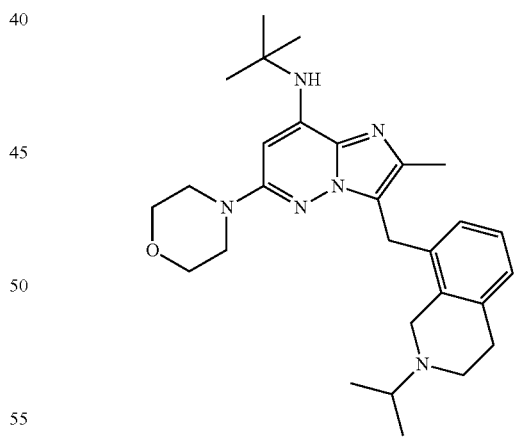

A solution of intermediate 293 (0.5 g; 1.116 mmol) and acetone (0.41 mL; 5.58 mmol) in DCE (15 mL) was stirred et room temperature for 30 min. Sodium triacetoxyborohydride (0.71 g; 3.35 mmol) was added and the solution was stirred at room temperature overnight. The mixture was diluted with EtOAc (10 mL) and washed with water (10 mL). The organic layer was dried over $MgSO_4$, filtered and evaporated until dryness. The residue was purified by chromatography over silica gel (irregular SiOH, gradient from 100% DCM to 80% DCM, 20% MeOH). The pure fractions

Example A66

Preparation of Intermediate 295

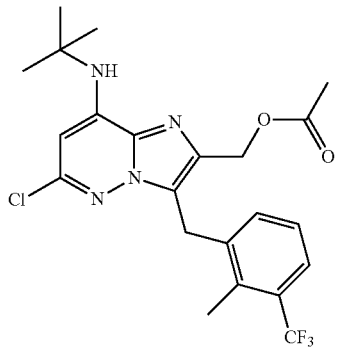 [SMILES: CC(=O)OCc1nc2c(NC(C)(C)C)cc(Cl)nn2c1Cc1cccc(C(F)(F)F)c1C]

Intermediate 263 (1350 g; 4.54 mol), 1-(chloromethyl)-2-methyl-3-(trifluoromethyl)benzene (14 g; 6.81 20.6 mol), potassium carbonate (941.2 g; 6.81 20.6 mol) and triphenylphosphine (178.6 g; 0.681 mol) in dioxane was degassed under nitrogen. Then, palladium acetate (76.4 g; 0.340 mol) was added and the reaction mixture was heated at 100° C. for 16 hours. The mixture was cooled down to room temperature, then filtered through a pad of Celite®. Methanol and water were added to the filtrate. The precipitate was filtered and dried to afford 1700 g of intermediate 295 (74% of purity by $^1$H NMR).

Preparation of Intermediate 296

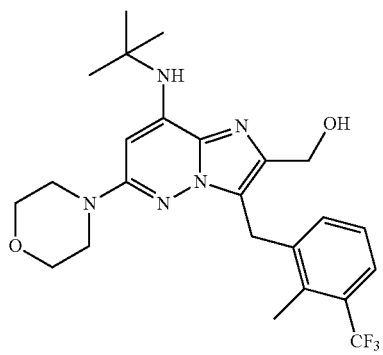 [SMILES: Cc1c(Cc2c(CO)nc3c(NC(C)(C)C)cc(N4CCOCC4)nn23)cccc1C(F)(F)F]

Intermediate 295 (1650 g; 3.52 mol), morpholine (919.7 mL; 10.55 mol), NaOH (281.6; 7.04 mol) and XPhos (47.7 g; 0.352 mol) in dioxane was degassed for 10 mn. Then, palladium acetate (35.5 g; 0.176 mol) was added and the reaction mixture was heated at 85° C. for 16 hours. The reaction mixture was cooled down to room temperature, filtered and the filtrate was concentrated. The resulting crude was slurried with MTBE. The precipitate was filtered and treated with N-Acetyl-cysteine, charcoal and silica thiol to remove residual palladium. 740 g of intermediate 296 (93.6% of purity evaluated by HPLC) was obtained.

Example A67

Preparation of Intermediate 297

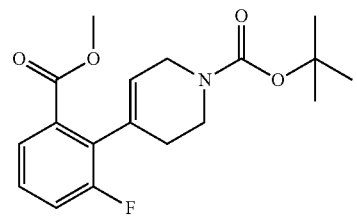 [SMILES: COC(=O)c1cccc(F)c1C1=CCN(C(=O)OC(C)(C)C)CC1]

The reaction was performed twice on 12.17 g of methyl-2-bromo-3-fluorobenzoate and the different reaction mixtures were mixed for the work-up and the purification.

Under $N_2$, to a mixture of methyl-2-bromo-3-fluorobenzoate (24.34 g, 104.45 mmol), tert-butyl-4-(4,4,5,5-tetramethyl-1,2,3,-dioxaborolan-2-yl)-5-6-dihydropyridine-1 (2H)-carboxylate (48.44 g, 156.67 mmol) and $K_3PO_4$ (66.51 g, 313.34 mmol) in a mixture of 1,4-dioxane (250 mL) and distilled water (75 mL) was added [1,1'-Bis(diphenylphosphino)ferrocene]dichloropalladium (II), complex with dichloromethane (4.27 g, 5.22 mmol). The reaction mixture was heated to 100° C. overnight, poured out into water and filtered through a Celite® layer. The organic layer was extracted with DCM, separated, dried, filtered and concentrated to dryness. The residue (55.6 g) was purified by column chromatography on silica gel (Irregular SiOH, 15-40 μm, 220 g, mobile phase: 100% DCM). The fractions containing the product were collected and the solvent was evaporated until dryness. The resulting residue (37.9 g) was crystallized from pentane and the precipitate was filtered off and dried under vacuum to give 17.6 g (50%) of intermediate 297.

Preparation of Intermediate 298

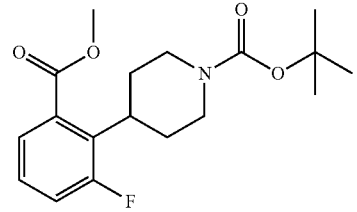 [SMILES: COC(=O)c1cccc(F)c1C1CCN(C(=O)OC(C)(C)C)CC1]

A mixture of intermediate 297 (16.50 g, 49.20 mmol) and Pearlman's catalyst (1.40 g, 9.84 mmol) in MeOH (170 mL) was hydrogenated in a Parr reactor (2 atmospheres) for 12 h at room temperature. After removal of $H_2$, the catalyst was filtered over a pad of Celite®, washed with DCM and the filtrate was concentrated to give 16.4 g (99%) of intermediate 298.

Preparation of Intermediate 299

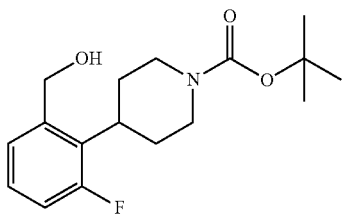 [SMILES: CC(C)(C)OC(=O)N1CCC(c2c(F)cccc2CO)CC1]

Lithium aluminium hydride (1.85 g, 48.61 mmol) was added portionwise to a mixture of intermediate 298 (16.40 g, 48.61 mmol) in THF (200 mL) at 5° C. under $N_2$. The mixture was stirred at 5° C. for 3 h. Then, EtOAc followed by water were added dropwise to the mixture at −5° C. The suspension was filtered through a pad of Celite®. The organic layer was separated, dried over $MgSO_4$, filtered and the solvent was evaporated to give 15.18 g (quantitative) of intermediate 299.

B. Preparation of the Final Compounds

Example B1

Preparation of Compound 33

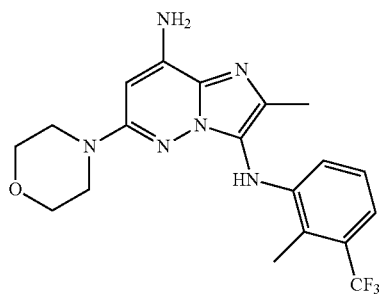

In a tube, under nitrogen, acetamidine hydrochloride (0.22 g; 2.32 mmol) was added to a mixture of intermediate 92 (1 g; 1.9 mmol), L-proline (0.044 g; 0.039 mmol), cesium carbonate (1.89 g; 5.8 mmol) and copper iodide (0.0037 g; 0.019 mmol) in DMF (7.5 mL). The tube was sealed and the reaction mixture was heated at 110° C. overnight. The mixture was concentrated and solubilized in EtOAc. The residue was washed with fifth with brine. The organic layer was separated, dried over $MgSO_4$, filtered and evaporated to dryness. The residue was purified by chromatography over silica gel (Irregular SiOH, 15-40 μm, 25 g, gradient from 99% DCM 1% $CH_3OH$ 0.1% $NH_4OH$. to 98% DCM 2% $CH_3OH$ 0.1% $NH_4OH$). The fractions containing the product were collected, evaporated to dryness and crystallized from $Et_2O$. The precipitate was filtered, dried to afford 0.205 g (26%) of compound 33. M.P: 223° C. (Kofler).

Preparation of Compound 1

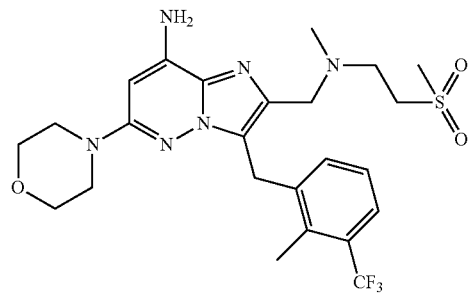

Compound 1 was prepared according to an analogous procedure as described for the synthesis of compound 33, using intermediate 48 as starting material (18%).

M.P: gum at 60-63° C. (Kofler).

Preparation of Compound 2

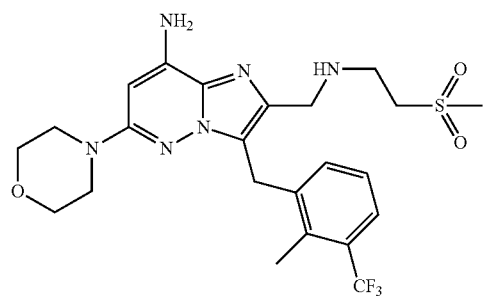 [SMILES: Cc1c(Cc2c(CNCCS(C)(=O)=O)nc3c(N)cc(N4CCOCC4)nn23)cccc1C(F)(F)F]

Compound 2 was prepared according to an analogous procedure as described for the synthesis of compound 33, using intermediate 50 as starting material (18%).

Preparation of Compound 3

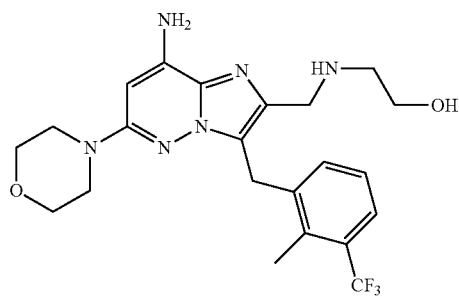

Compound 3 was prepared according to an analogous procedure as described for the synthesis of compound 33, using intermediate 51 as starting material (20%).

Preparation of Compound 6

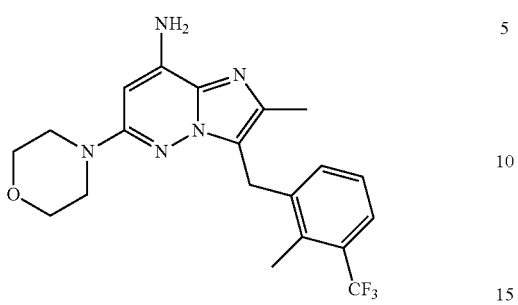

Compound 6 was prepared according to an analogous procedure as described for the synthesis of compound 33, using intermediate 15 as starting material (46%).
MP: 207° C. (Kofler)

Preparation of Compound 17

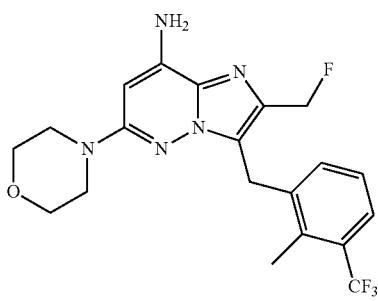

Compound 17 was prepared according to an analogous procedure as described for the synthesis of compound 33, using intermediate 34 as starting material (13%).

Preparation of Compound 88

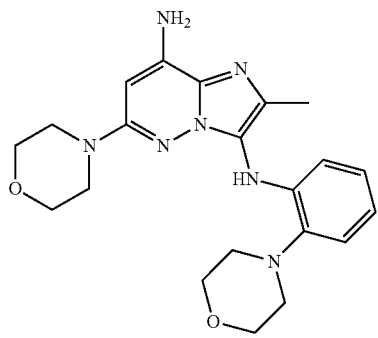 [SMILES: Cc1nc2c(N)cc(N3CCOCC3)nn2c1Nc1ccccc1N1CCOCC1]

Acetamidine hydrochloride (33 mg; 0.35 mmol) was added under $N_2$ to a flask charged with copper(I) iodide (5.5 mg; 0.03 mmol), L-proline (6.6 mg; 0.06 mmol), intermediate 217 (0.15 g; 0.29 mmol) and $Cs_2CO_3$ (0.28 g; 0.87 mmol) in DMF (1.1 mL). The reaction mixture was stirred at 110° C. overnight. The mixture was evaporated, then solubilized in EtOAc and washed fifth time with brine. The organic layer was dried over $MgSO_4$ and evaporated. The residue (160 mg, beige solid) was purified by chromatography over silica gel (Spherical bare silica 5 µm; 150×30.0 mm; gradient: from 98% DCM, 2% MeOH, 0.2% $NH_4OH$ to 92% DCM, 8% MeOH, 0.8% $NH_4OH$).

The pure fractions were collected and the solvent was evaporated to give 45 mg (38%, white solid) of compound 88.

Example B2

Preparation of Compound 14

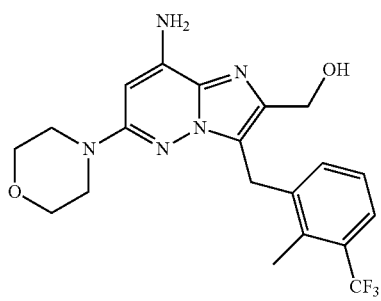

Tetrabutylammonium fluoride (2.99 mL, 2.99 mmol) was added dropwise to a solution of intermediate 52 (1.6 g, 2.99 mmol) in THF (26.67 mL) at room temperature. The mixture was stirred overnight and poured onto ice water. The precipitate was filtered, washed with water, dried and purified by chromatography over silica gel (Irregular SiOH, 40 µm, 200 g, gradient from 97% DCM 3% $CH_3OH$ 0.1% $NH_4OH$. to 95% DCM 5% $CH_3OH$ 0.1% $NH_4OH$). The fractions containing the product were collected and evaporated to dryness yielding 0.537 g (43%) of compound 14. M.P.: 241° C. (DSC).

Alternative Preparation of Compound 14

Intermediate 296 (740 g; 1.55 mol) was dissolved in THF and HCl (4N) in methanol was added. The reaction mixture was stirred for 72 hours at 60° C. The hydrochloride salt was filtered and the base was then released in a mixture of Me-THF/water. The organic layer was concentrated. The crude was precipitated in acetone. The precipitate was filtered and dried to afford 340 g of compound 14.

Preparation of Compound 14a

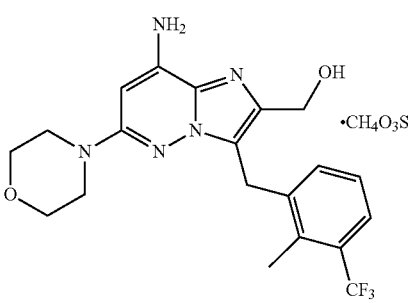

Methanesulfonic acid (62 µL; 0.95 mmol) was added to a solution of compound 14 (200 mg; 0.48 mmol) in MeOH (12 mL). The reaction mixture was heated at 50° C. for 15 min and concentrated to 6 mL. Diethylether was added and the mixture was stirred for 1 h at 5° C. The precipitate was filtered and dried to give 175 mg (71%) of compound 14a (mesylate salt form; 1 equivalent evaluated by $^1$H NMR). M.P.: 202° C. (DSC).

Preparation of Compound 14b

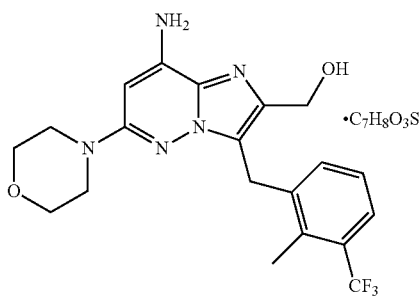

P-toluenesulfonic acid monohydrate (0.18 g; 0.95 mmol) was added to a solution of compound 14 (200 mg; 0.48 mmol) in MeOH (12 mL). The reaction mixture was heated at 50° C. for 15 min and concentrated at 6 mL. The solution was cooled, then diethylether was added and the mixture was stirred for 1 h at 5° C. The precipitate was filtered and dried to give 204 mg (72%) of compound 14b (tosylate salt form; 1 equivalent evaluated by $^1$H NMR). M.P.: 211° C. (DSC).

Preparation of Compound 14c

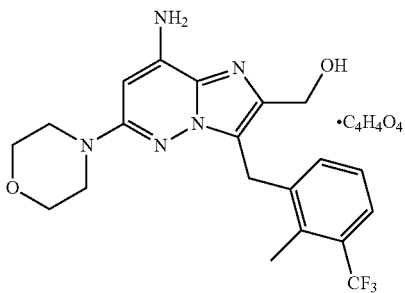

Maleic acid (0.11 g; 0.95 mmol) was added to a solution of compound 14 (200 mg; 0.48 mmol) in MeOH (12 mL). The reaction mixture was heated at 50° C. for 2 h and cooled down to room temperature. Then, the precipitate was filtered and dried to give 167 mg (66%) of compound 14c (maleate salt form; 0.96 equivalent evaluated by $^1$H NMR). M.P.: 214° C. (DSC).

Preparation of Compound 14d

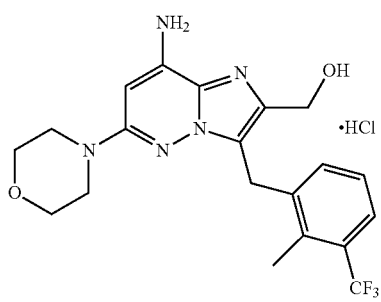 [SMILES: Cc1c(Cc2c(CO)nc3c(N)cc(N4CCOCC4)nn23)cccc1C(F)(F)F ; Cl]

HCl (4M in dioxane) (62 µL; 0.25 mmol) was added to compound 14 (100 mg; 0.24 mmol) in ACN (10 mL). The reaction mixture was heated at 50° C. for 16 h. The mixture was cooled down to room temperature and stirred at room temperature for a further 72 h. The precipitate was then filtered, washed with DIPE and dried under vacuum to give compound 14d (HCl salt form; 1 equivalent evaluated by titration). M.P.: 250° C. (DSC).

Preparation of Compound 14e

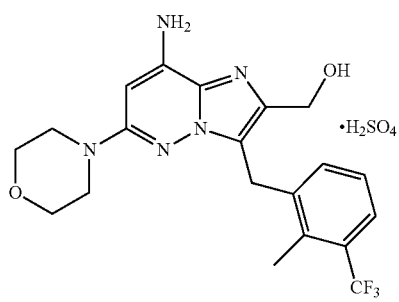

Sulfuric acid (7 µL; 0.13 mmol) was added to compound 14 (100 mg, 0.24 mmol) in iPrOH (1.2 mL). The reaction mixture was heated at 50° C. for 16 h. The mixture was cooled down to room temperature and stirred at room temperature for a further 72 h. The precipitate was then filtered, washed with DIPE and dried under vacuum to give compound 14e (1 equivalent of $H_2SO_4$ evaluated by elemental analysis prediction).

M.P.: 204° C. (DSC).

Preparation of Compound 4

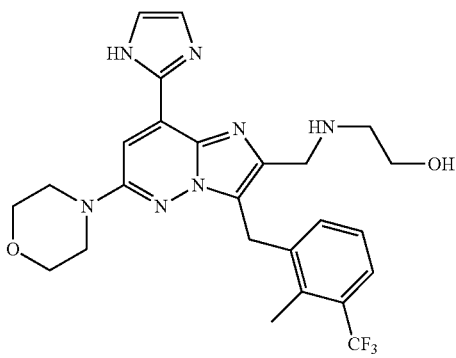 [SMILES: Cc1c(Cc2c(CNCCO)nc3c(-c4ncc[nH]4)cc(N4CCOCC4)nn23)cccc1C(F)(F)F]

Compound 4 was prepared according to an analogous procedure as described for the synthesis of compound 14, using intermediate 59 as starting material. The residue (0.043 g) was crystallized with ACN/Et$_2$O. The precipitate was filtered and dried to give compound 4 (0.024 g; 30%). M.P.: 128° C. (Kofler).

Preparation of Compound 15

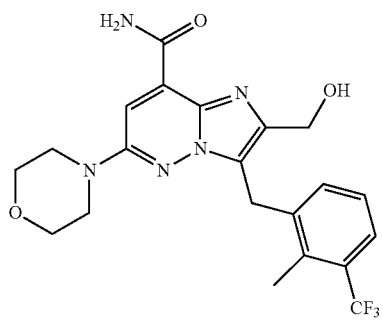 [SMILES: Cc1c(Cc2c(CO)nc3c(C(N)=O)cc(N4CCOCC4)nn23)cccc1C(F)(F)F]

Tetrabutylammonium fluoride (0.28 mL, 0.28 mmol) was added dropwise to a solution of intermediate 57 (0.156 g, 0.28 mmol) in THF (2.7 mL) at room temperature. The mixture was stirred for 48 hours. The mixture was concentrated and taken up with MeOH and Et$_2$O. The precipitate was filtered and dried to give 0.103 g (82%) of compound 15. M.P.: 240° C. (Kofler).

Preparation of Compound 21

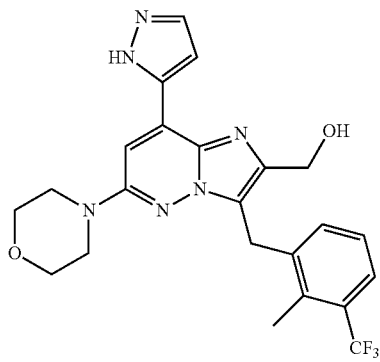 [SMILES: Cc1c(Cc2c(CO)nc3c(-c4ccn[nH]4)cc(N4CCOCC4)nn23)cccc1C(F)(F)F]

Compound 21 was prepared according to an analogous procedure as described for the synthesis of compound 14, using intermediate 40 as starting material (24%). M.P.: gum between 145-151° C. (Kofler).

Preparation of Compound 23

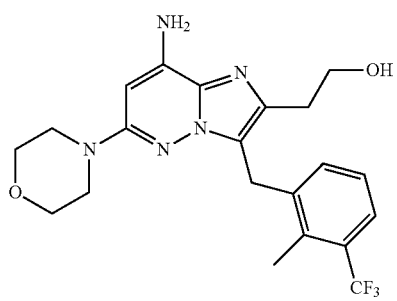 [SMILES: Cc1c(Cc2c(CCO)nc3c(N)cc(N4CCOCC4)nn23)cccc1C(F)(F)F]

Compound 23 was prepared according to an analogous procedure as described for the synthesis of compound 14, using intermediate 55 as starting material (47%).

M.P.: 198° C. (Kofler).

Preparation of Compound 26

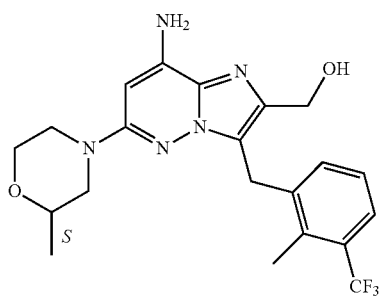

Compound 26 (S-enantiomer) was prepared according to an analogous procedure as described for the synthesis of compound 14, using intermediate 54 as starting material (20%).

Preparation of Compound 31

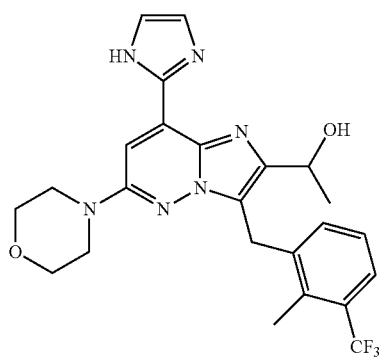 [SMILES: Cc1c(Cc2c(C(C)O)nc3c(-c4ncc[nH]4)cc(N4CCOCC4)nn23)cccc1C(F)(F)F]

Compound 31 was prepared according to an analogous procedure as described for the synthesis of compound 14, using intermediate 60 as starting material (25%).
M.P.:>260° C.

Preparation of Compound 32

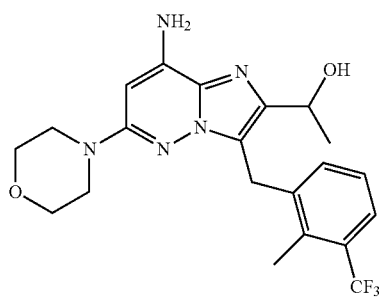 [SMILES: Cc1c(Cc2c(C(C)O)nc3c(N)cc(N4CCOCC4)nn23)cccc1C(F)(F)F]

Compound 32 was prepared according to an analogous procedure as described for the synthesis of compound 14, using intermediate 53 as starting material (52%).
M.P.: 184° C. (Kofler)

Preparation of Compound 37

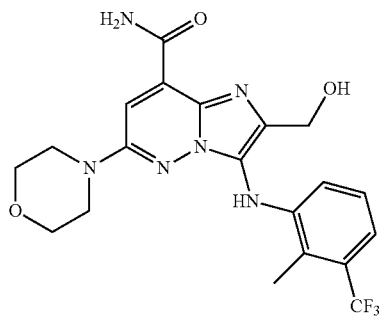 [SMILES: Cc1c(Nc2c(CO)nc3c(C(N)=O)cc(N4CCOCC4)nn23)cccc1C(F)(F)F]

Compound 37 was prepared according to an analogous procedure as described for the synthesis of compound 14, using intermediate 101 as starting material (72%).
M.P.: 232° C. (Kofler)

Example B3

Preparation of Compound 35

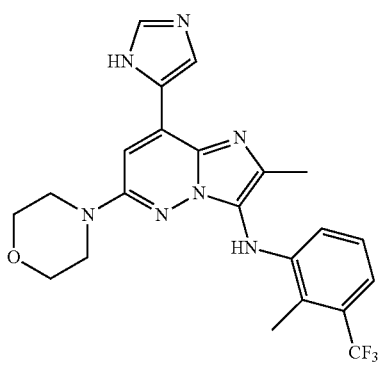 [SMILES: Cc1nc2c(-c3cnc[nH]3)cc(N3CCOCC3)nn2c1Nc1cccc(C(F)(F)F)c1C]

Intermediate 93 (0.22 g; 0.39 mmol) was dissolved in dioxane (7 mL) and an aqueous solution of HCl 6N (2.5 mL) was added. The reaction mixture was heated at 100° C. for 2 hours. The reaction mixture was cooled to room temperature, diluted with EtOAc and basified with a 10% aqueous solution of $K_2CO_3$. The organic layer was decanted, washed with brine, dried over $MgSO_4$, filtered and evaporated to dryness. The residue was crystallized from DCM/ACN. The precipitate was filtered, washed with ACN then $Et_2O$ and dried to afford 0.082 g (46%) of compound 35. M.P.:231° C. (Kofler)

Preparation of Compound 5

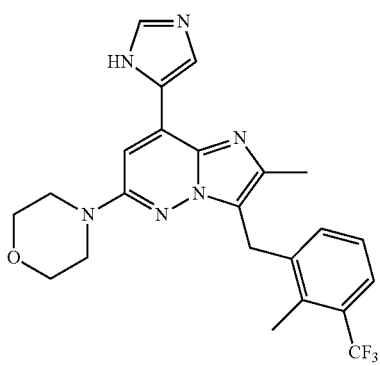 [SMILES: Cc1nc2c(-c3cnc[nH]3)cc(N3CCOCC3)nn2c1Cc1cccc(C(F)(F)F)c1C]

Compound 5 was prepared according to an analogous procedure as described for the synthesis of compound 35, using intermediate 42 as starting material (30%).
M.P.: 226° C. (Kofler)

Preparation of Compound 20

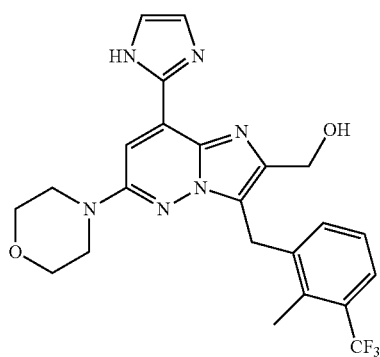 [SMILES: Cc1c(Cc2c(CO)nc3c(-c4ncc[nH]4)cc(N4CCOCC4)nn23)cccc1C(F)(F)F]

Compound 20 was prepared according to an analogous procedure as described for the synthesis of compound 35, using intermediate 61 as starting material (60%).

M.P.: 160° C. (Kofler)

Preparation of Compound 24

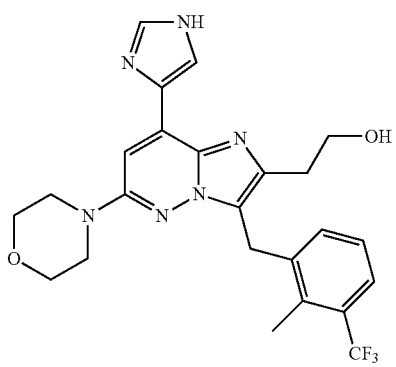 [SMILES: Cc1c(Cc2c(CCO)nc3c(-c4c[nH]cn4)cc(N4CCOCC4)nn23)cccc1C(F)(F)F]

Compound 24 was prepared according to an analogous procedure as described for the synthesis of compound 35, using intermediate 46 as starting material (47%).

M.P.: 212° C. (Kofler)

Preparation of Compound 25

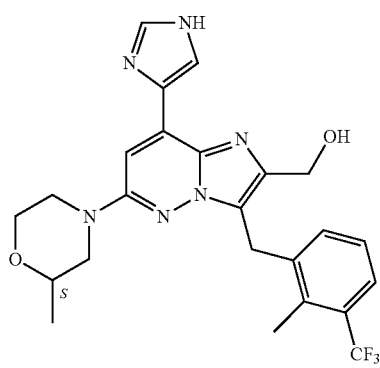 [SMILES: Cc1c(Cc2c(CO)nc3c(-c4c[nH]cn4)cc(N4CCOC(C)C4)nn23)cccc1C(F)(F)F]

Compound 25 (S-enantiomer) was prepared according to an analogous procedure as described for the synthesis of compound 35, using intermediate 44 as starting material (17%). M.P.: gum at 80° C. (Kofler)

Preparation of Compound 27

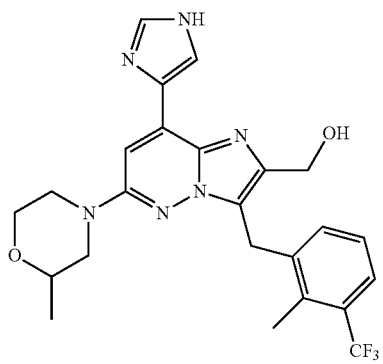

Compound 27 was prepared according to an analogous procedure as described for the synthesis of compound 35, using intermediate 45 as starting material (43%).

M.P.: 208° C. (Kofler)

Preparation of Compound 30

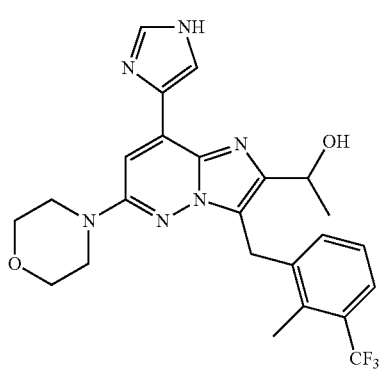 [SMILES: Cc1c(Cc2c(C(C)O)nc3c(-c4c[nH]cn4)cc(N4CCOCC4)nn23)cccc1C(F)(F)F]

Compound 30 was prepared according to an analogous procedure as described for the synthesis of compound 35, using intermediate 43 as starting material (24%).

M.P: 178° C. (Kofler)

Preparation of Compound 67

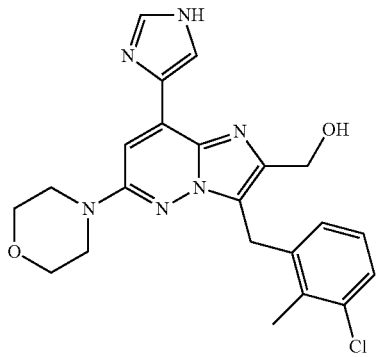 [SMILES: Cc1c(Cl)cccc1Cc1c(CO)nc2c(-c3c[nH]cn3)cc(N3CCOCC3)nn12]

Compound 67 was prepared according to an analogous procedure as described for the synthesis of compound 35, using intermediate 177 as starting material. The residue was recrystallized with a mixture of ACN/EtOH. The precipitate was filtered and dried to give 22 mg (21%) of compound 67. M.P.: 237° C. (Kofler).

Preparation of Compound 89

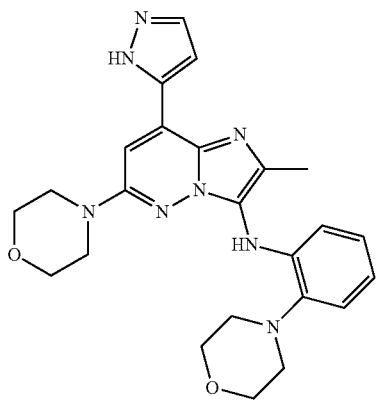 [SMILES: Cc1nc2c(-c3ccn[nH]3)cc(N3CCOCC3)nn2c1Nc1ccccc1N1CCOCC1]

Intermediate 219 (160 mg; 0.30 mmol) and HCl (37% in $H_2O$) (123 µL; 1.5 mmol) in MeOH (5 mL) were stirred at rt for 2 days. The mixture was poured into $H_2O$, basified with a saturated aqueous solution of $NaHCO_3$ and extracted with DCM. The organic layer was separated, dried over $MgSO_4$, filtered and evaporated under vacuum. The residue was purified by chromatography over silica gel (SiOH 30 m; 24 g; gradient: from 98% DCM, 2% MeOH, 0.1% $NH_4OH$ to 95% DCM, 5% MeOH, 0.1% $NH_4OH$).

The pure fractions were collected and the solvent was evaporated. The residue (80 mg, yellow solid) was taken up with diethylether, then triturated, filtered and washed to give 54 mg (40%, pale yellow solid) of compound 89.

Example B4

Preparation of Compound 7

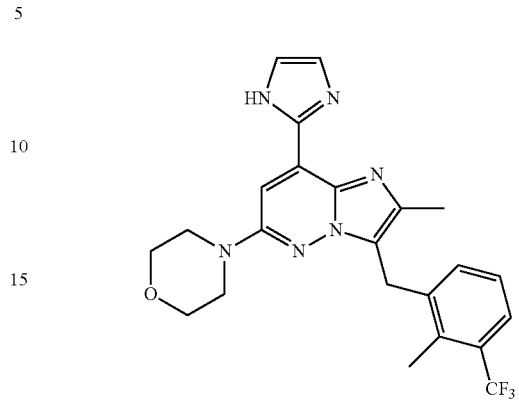

Intermediate 15 (0.3 g, 0.58 mmol), imadazole (0.99 g, 14.5 mmol), copper iodide (0.22 g, 1.2 mmol) in DMF (3 mL) were degassed under nitrogen for 15 minutes. Palladium acetate (0.39 g, 0.17 mmol) was added and the reaction mixture was stirred at 185° C. using one single mode microwave with a power output ranging from 0 to 400 W for 15 min. Water and EtOAc were added. The reaction mixture was filtered over Celite®, washed with EtOAc, the filtrate was extracted then the organic layer was separated, dried over $MgSO_4$, filtered and evaporated. The residue was purified by chromatography over silica gel (Irregular SiOH, 15-40 µm, 24 g, mobile phase 97% DCM 3% $CH_3OH$ 0.1% $NH_4OH$). The fractions containing the product were collected and evaporated to dryness. The residue (0.145 g; 55%) was crystallized from DIPE and the precipitate was filtered and dried yielding 0.064 g (24%) of compound 7.
M.P: 176° C. (Kofler)

Example B5

Preparation of Compound 8

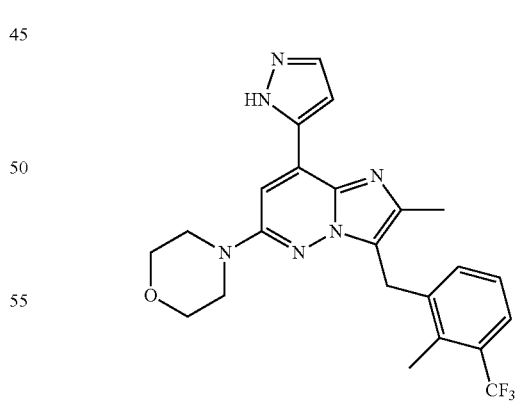

Intermediate 39 (0.062 g, 0.12 mmol) and p-toluenesulfonic acid (0.04 g, 0.023 mmol) in MeOH (5 mL) were heated at 50° C. for 2 hours. The mixture was poured into water, basified with an 10% aqueous solution of $K_2CO_3$ and extracted with DCM. The organic layer was separated, dried over $MgSO_4$, filtered and evaporated. The residue (0.048 g) was taken up in $Et_2O$, the precipitate was filtered off and dried to afford 0.029 g of impure solid. This solid was combined with the filtrate and the resulting residue was purified by chromatography over silica gel (Irregular SiOH, 15-40 μm, 12 g, mobile phase 97% DCM 3% CH₃OH 0.1% NH₄OH). The fractions containing the product were collected and evaporated to dryness to afford (0.025 g; 48%) of compound 8.

M.P.: 193° C. (Kofler)

Example B6

Preparation of Compound 9

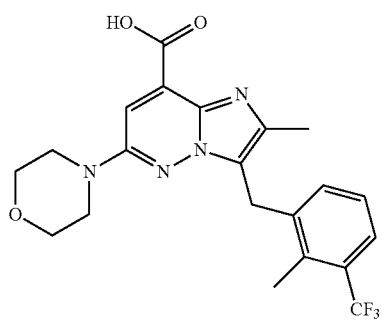

Lithium hydroxide monohydrate (0.41 g; 9.7 mmol) was added to a mixture of intermediate 72 (1.45 g; 3.2 mmol) in THF (18 mL) and water (6.1 mL). Then, the reaction mixture was stirred at room temperature for 15 hours, acidified with HCl 3N and THF was evaporated. The insoluble was filtered, washed with water then ACN and Et₂O and dried to give 0.91 g (65%) of compound 9. M.P.: 244° C. (DSC).

Alternative Route:

To a mixture of Intermediate 15 (0.74 g, 1.43 mmol), a aqueous solution of sodium carbonate 2M (0.84 mL, 14.3 mmol) in DMF (20 mL) previously purged with N₂ then was added Pd(PPh₃)₄ (0.165 g, 0.14 mmol). The reaction was then purged for 5 additional minutes and carbon monoxide was added (10 bars) the reaction was stirred for 3 hours at 120° C. and overnight at room temperature. The reaction was poured into water and extracted with EtOAc. The insoluble material was filtered and dissolved in DCM/MeOH. The filtrate was dried over MgSO4, filtered and evaporated to give 0.465 g (75%) of compound 9.

Preparation of Compound 12

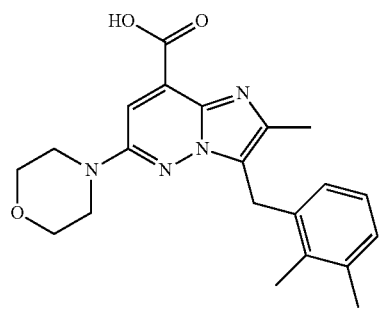 [SMILES: Cc1cccc(Cc2c(C)nc3c(C(=O)O)cc(N4CCOCC4)nn23)c1C]

Compound 12 was prepared according to an analogous procedure as described for the synthesis of compound 9, using intermediate 73 as starting material (84%).

M.P.: >260° C. (Kofler)

Preparation of Compound 13

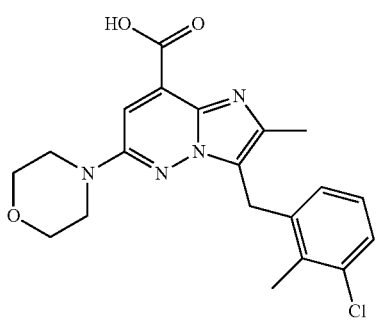 [SMILES: Cc1nc2c(C(=O)O)cc(N3CCOCC3)nn2c1Cc1cccc(Cl)c1C]

Compound 13 was prepared according to an analogous procedure as described for the synthesis of compound 9, using intermediate 74 as starting material (53%). M.P.: gum at 95° C. (Kofler)

Preparation of Compound 28

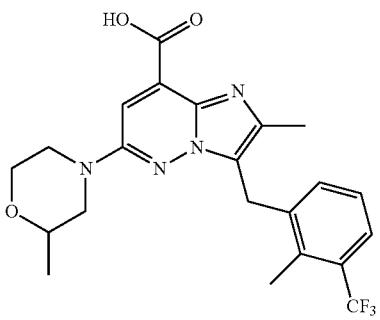

Compound 28 was prepared according to an analogous procedure as described for the synthesis of compound 9, using intermediate 75 as starting material (81%).

M.P.: 245° C. (Kofler)

Preparation of Compound 29

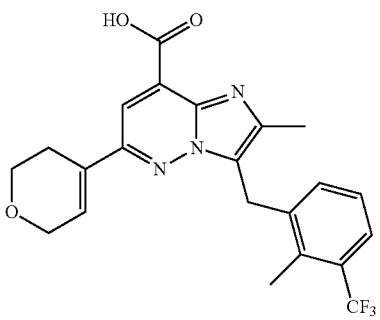

Compound 29 was prepared according to an analogous procedure as described for the synthesis of compound 9, using intermediate 76 as starting material (76%).

M.P.: 237° C. (Kofler)

Preparation of Compound 36

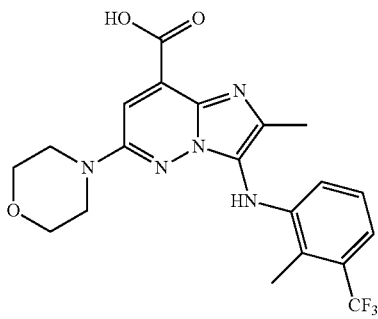

Compound 36 was prepared according to an analogous procedure as described for the synthesis of compound 9, using intermediate 94 as starting material (34%).
M.P.: 251° C. (Kofler)

Preparation of Compound 22

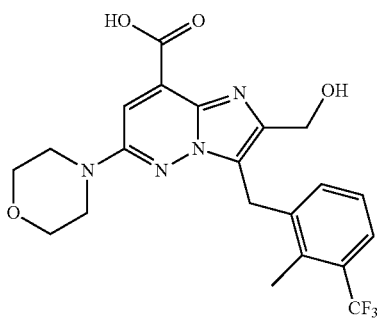

A mixture of intermediate 86 (0.042 g, 0.08 mmol), lithium hydroxide monohydrate (0.017 g, 0.4 mmol) in MeOH (3 mL) and water (0.5 mL) was stirred at room temperature for 3 days. The reaction mixture was evaporated and the residue was taken up with water, acidified with a solution of HCl 3N. The precipitate was filtered, washed with water then Et$_2$O and dried to afford 0.045 g (89%) of compound 22.
M.P.: 252° C. (DSC)

Preparation of Compound 86

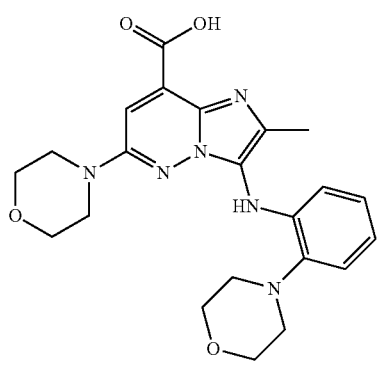 [SMILES: Cc1nc2c(C(=O)O)cc(N3CCOCC3)nn2c1Nc1ccccc1N1CCOCC1]

Compound 86 was prepared according to an analogous procedure as described for the synthesis of compound 9, using intermediate 218 and lithium hydroxide monohydrate as starting materials. The residue was taken up in water, extracted with DCM, dried and evaporated to give 15 mg (52%, yellow solid) of compound 86.

Example B7

Preparation of Compound 10

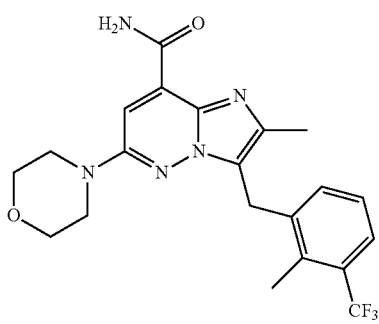

In a sealed tube, intermediate 72 (0.1 g, 0.22 mmol) in ammonia in MeOH 7N (3 mL) was stirred overnight at 65° C. The mixture was concentrated and taken up with MeOH. The precipitate was filtered and washed with Et$_2$O to afford 0.043 g (45%) of compound 10. M.P.: 226° C. (Kofler)

Preparation of Compound 11

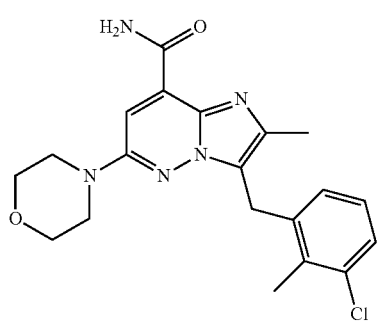

To a solution of intermediate 68 (0.35 g, 0.92 mmol) in THF (7 mL) and water (0.5 mL) was added hydrido(dimethylphosphinous acid-kP)[hydrogen bis(dimethylphosphinito-kP)]platinum(II) (0.79 g, 0.18 mmol). The resulting mixture was heated at 95° C. for 2 hours. The mixture was poured into water and extracted with DCM. The organic layer was dried over MgSO$_4$, filtered and evaporated to dryness. The residue (0.38 g) crystallized from DIPE. The precipitate was filtered and dried to give 0.33 g (90%) of compound 11.
M.P.: 217° C. (DSC)

Preparation of Compound 40

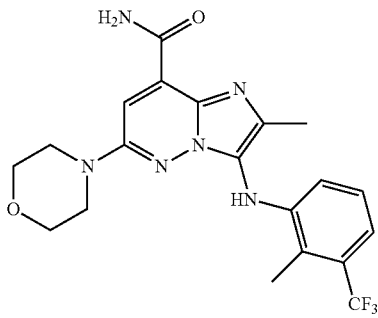 [SMILES: Cc1nc2c(C(N)=O)cc(N3CCOCC3)nn2c1Nc1cccc(C(F)(F)F)c1C]

In a sealed tube, intermediate 94 (0.35 g, 0.78 mmol) in ammonia in MeOH 7N (4.5 mL) was stirred overnight at 100° C. The mixture was allowed to warm room temperature then concentrated. A solid was obtained, washed with Et$_2$O, filtered and dried to give a yellow solid 0.172 g (51%) of compound 40.

Preparation of Compound 87

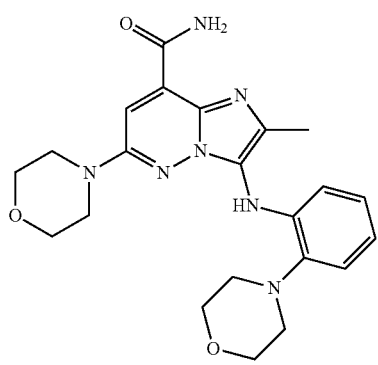

Compound 87 was prepared according to an analogous procedure as described for the synthesis of compound 40, using intermediate 218 and ammonia (7N in MeOH) as starting material. The solid was washed with diethylether and dried to give 200 mg (86%, yellow solid) of compound 87.

Example B8

Preparation of Compound 16

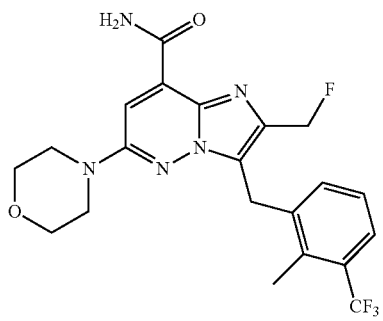 [SMILES: Cc1c(Cc2c(CF)nc3c(C(N)=O)cc(N4CCOCC4)nn23)cccc1C(F)(F)F]

Diethylaminosulfur trifluoride (0.0053 mL; 0.40 mmol) was added dropwise to a mixture of intermediate compound 15 (0.036 g, 0.080 mmol) in DCM (1 mL). The reaction mixture was stirred overnight at room temperature. A 10% aqueous solution of K$_2$CO$_3$ was added and stirred for 20 minutes. The organic layer was extracted, dried over MgSO$_4$, filtered and evaporated. The residue was purified by chromatography over silica gel (Irregular SiOH, 15-40 µm, 24 g, gradient from 100% DCM to 98% DCM 2% CH$_3$OH 0.1% NH$_4$OH). The fractions containing the product were collected and evaporated to dryness to afford 0.026 g (72%) of compound 16. M.P.: 200° C. (Kofler)

Example B9

Preparation of Compound 18

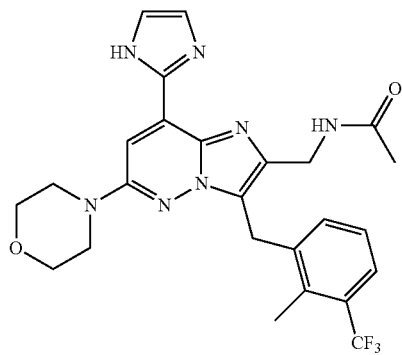 [SMILES: CC(=O)NCc1nc2c(-c3ncc[nH]3)cc(N3CCOCC3)nn2c1Cc1cccc(C(F)(F)F)c1C]

N-butillithium (1.07 mL (1.6 M in hexanes); 1.72 mmol) was added dropwise at −78° C. to a solution of N,N-Dimethyl imidazole-1-sulfonamide (301 mg; 1.72 mmol) in THF (5.3 mL) and the reaction mixture was stirred for 30 minutes. A solution of zinc chloride (3.4 mL (1 M in THF); 3.44 mmol) was added and the reaction mixture was allowed to warm to room temperature over 30 minutes. The solution was added to a previously degassed mixture of intermediate 37 (0.197 g; 0.34 mmol) and Pd(PPh$_3$)$_4$ (0.040 g; 0.03 mmol). The reaction mixture was heated at 100° C. overnight, cooled to room temperature, diluted with DCM and quenched with a 10% aqueous solution of K$_2$CO$_3$. The mixture was filtered through a pad of Celite® and washed with EtOAc. The filtrate was extracted with EtOAc. The organic layer was washed with brine, dried over MgSO$_4$, filtered and the solvent was evaporated. The residue (0.384 g) was purified by chromatography over silica gel (Irregular SiOH, 15-40 μm, 40 g, gradient from 96% DCM 4% CH$_3$OH 0.1% NH$_4$OH. to 83% DCM 17% CH$_3$OH 0.1% NH$_4$OH). The fractions containing the product were collected and evaporated to dryness. The residue (0.057 g; 32%) was crystallized from Et$_2$O. The precipitate was filtered and dried yielding 0.043 g (24%) of compound 18. M.P.: 247° C. (Kofler).

Preparation of Compound 34

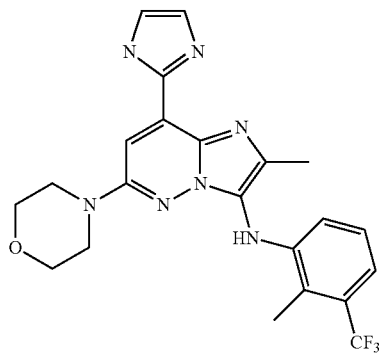 [SMILES: Cc1nc2c(-c3ncc[nH]3)cc(N3CCOCC3)nn2c1Nc1cccc(C(F)(F)F)c1C]

Compound 34 was prepared according to an analogous procedure as described for the synthesis of compound 18, using intermediate 92 as starting material (36%).

M.P.: 210° C. (Kofler)

Example B10

Preparation of Compound 19

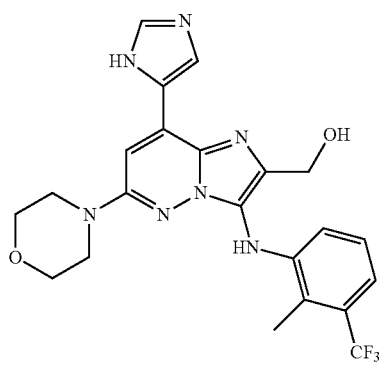

Intermediate 41 (0.4 g; 0.69 mmol) was dissolved in dioxane (12 mL) and an aqueous solution of HCl 6N (4.5 mL) was added. The reaction mixture was heated at 100° C. for 2 hours. The reaction mixture was cooled to room temperature, diluted with DCM/MeOH (80/20) and basified with a 10% aqueous solution of K$_2$CO$_3$. The organic layer was decanted, dried over MgSO$_4$, filtered and evaporated to dryness. The residue (0.3 g) was crystallized from ACN. The precipitate (0.227 g) was solubilized at reflux in EtOH for 20 minutes. The heating was stopped and the mixture was cooling down to room temperature overnight. The precipitate was filtered and dried to afford 0.168 g (52%) of pale yellow solid of compound 19. M.P.: 223° C. (DSC). The filtrate was evaporated. The residue (0.070 g) was purified by chromatography over silica gel (Irregular SiOH, 15-40 μm, 4 g, gradient from 95% DCM 5% CH$_3$OH 0.1% NH$_4$OH. to 90% DCM 10% CH$_3$OH 1% NH$_4$OH). The fractions containing the product were collected and evaporated to dryness to afford additional 0.013 g (4%) of compound 19.

Preparation of Compound 41 (see also A37, reaction for intermediate 111)

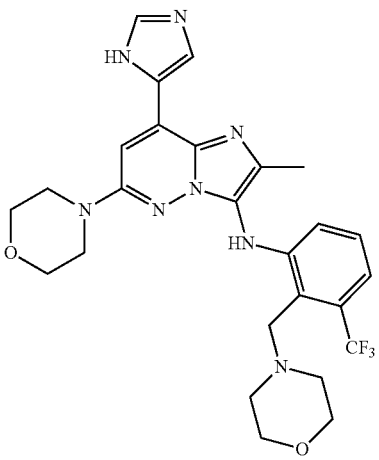 [SMILES: Cc1nc2c(-c3cnc[nH]3)cc(N3CCOCC3)nn2c1Nc1cccc(C(F)(F)F)c1CN1CCOCC1]

Compound 41 was prepared according to an analogous procedure as described for the synthesis of compound 19, using intermediate 111 as starting material (24%).

M.P.: 154° C. (Kofler)

Preparation of Compound 42

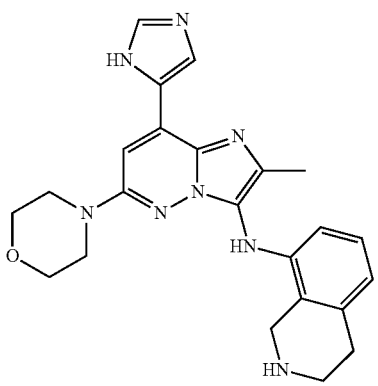 [SMILES: Cc1nc2c(-c3cnc[nH]3)cc(N3CCOCC3)nn2c1Nc1cccc2c1CNCC2]

Compound 42 was prepared according to an analogous procedure as described for the synthesis of compound 19, using intermediate 112 as starting material (13%). M.P.: 158° C. (Kofler)

Preparation of Compound 50 (See Also A37, Reaction for Intermediate 130)

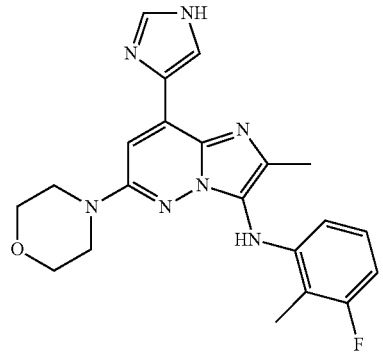 [SMILES: Cc1nc2c(-c3c[nH]cn3)cc(N3CCOCC3)nn2c1Nc1cccc(F)c1C]

A mixture of intermediate 130/compound 50 (212 mg; 0.41 mmol) was dissolved in HCl 6N (2.7 mL) and 1,4-dioxane (6.9 mL). The reaction mixture was heated at 70° C. for 2 h. The mixture was cooled to room temperature, diluted with DCM and basified with a 10% aqueous solution of $K_2CO_3$ at 0° C. The mixture was extracted with DCM (3×). The organic layer was dried over $MgSO_4$, filtered and the solvent was evaporated. The residue (207 mg) was purified by chromatography over silica gel (Spherical bare silica 5 µm 150×30.0 mm, gradient from 97% DCM, 3% MeOH (+10% $NH_4OH$) to 87% DCM, 13% MeOH (+10% $NH_4OH$)). The pure fractions were collected and the solvent was evaporated to give 26 mg (15%) of a yellow oil. This fraction was recrystallized with diethylether. The precipitate was filtered and dried to give 13 mg (8%, yellow solid) of compound 50. M.P.: >260° C. (Köfler).

Preparation of Compound 57 (See Also A37, Reaction for Intermediate 151)

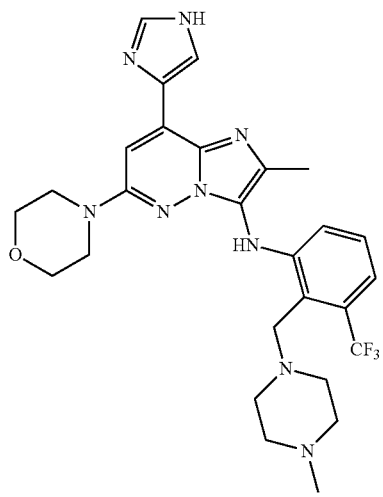 [SMILES: Cc1nc2c(-c3c[nH]cn3)cc(N3CCOCC3)nn2c1Nc1cccc(C(F)(F)F)c1CN1CCN(C)CC1]

Compound 57 was prepared according to an analogous procedure as described for the synthesis of compound 50, using intermediate 151 as starting material (7%).

Example B11

Preparation of Compound 38

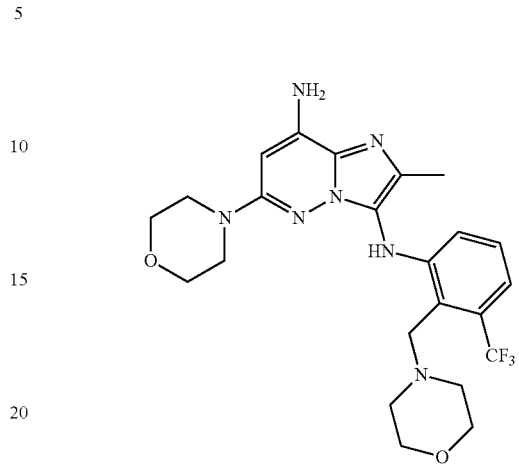

Under nitrogen, in a sealed tube, to a mixture of intermediate 81 ((0.13 g, 0.42 mmol), intermediate 83 ((0.13 g, 0.5 mmol) and sodium tert-butoxide (0.080 g, 0.83 mmol) in dioxane (1.4 mL), previously degassed with nitrogen then were added $Pd_2dba_3$ (0.038 g, 0.042 mmol) and 2-(di-t-butylphosphino)biphenyl (0.025 mg, 0.083 mmol). The reaction mixture was heated to 100° C. for overnight. The reaction mixture was solubilized in EtOAc. The organic layer was washed with brine, dried over $MgSO_4$, filtered and evaporated. The residue (0.250 g) was purified by chromatography over silica gel (Irregular SiOH, 15-40 µm, gradient from 98% DCM 2% $CH_3OH$ 0.1% $NH_4OH$ to 87% DCM 13% $CH_3OH$ 1.3% $NH_4OH$). The fractions containing the product were collected and evaporated to dryness to afford 0.006 g (3%) of compound 38.

Preparation of Compound 39

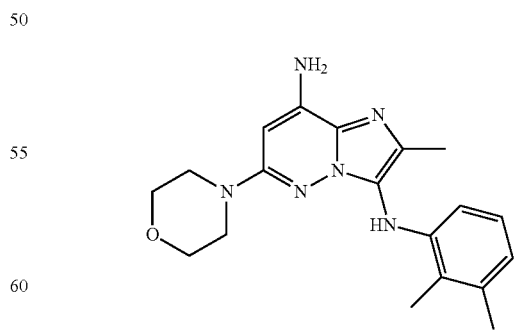

Compound 39 was prepared according to an analogous procedure as described for the synthesis of compound 38, using intermediate 81 as starting material (5%).

Preparation of Compound 43

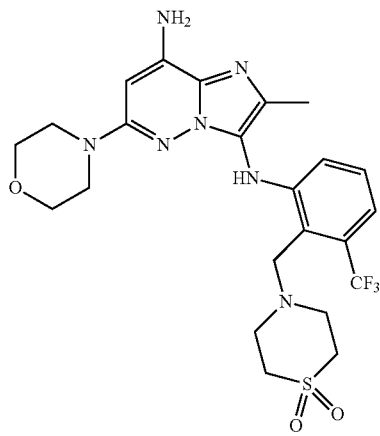 [SMILES: Cc1nc2c(N)cc(N3CCOCC3)nn2c1Nc1cccc(C(F)(F)F)c1CN1CCS(=O)(=O)CC1]

Compound 43 was obtained during the preparation of intermediate 116 (31%).
M.P.: gum at 167° C. (Kofler).

Preparation of Compound 44

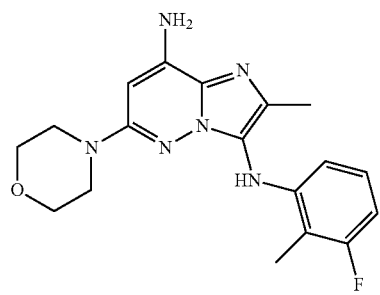 [SMILES: Cc1nc2c(N)cc(N3CCOCC3)nn2c1Nc1cccc(F)c1C]

Compound 44 was prepared according to an analogous procedure as described for the synthesis of compound 38, using intermediate 115 and 3-fluoro-2-methylbenzenamine as starting materials (38%). M.P.: gum at 232° C. (Kofler).

Example B12

Preparation of Compound 46

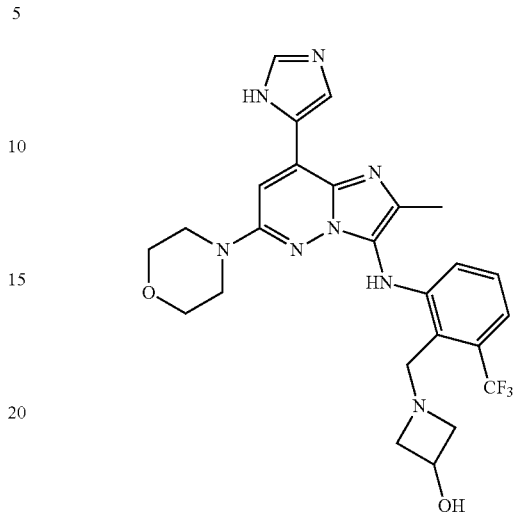

TBAF (1M in THF) (2.8 mL; 2.86 mmol) was added at 5° C. to a solution of intermediate 120/intermediate 121 (613 mg; 0.95 mmol) in THF (10 mL). The reaction mixture was stirred at room temperature for 2 hours, diluted with DCM and 10% aqueous solution of $K_2CO_3$ was added. The mixture was filtered through Chromabond® and the organic layer was evaporated to dryness. The residue was purified by chromatography over silica gel (irregular SiOH, 30 g; gradient from 10% MeOH, 90% DCM to 15% MeOH, 85% DCM). The fractions containing the product were collected and evaporated to dryness. The residue (93 mg) was purified by reverse phase chromatography (C18 5 μm 30*150 mm; gradient from 80% $NH_4HCOO$ 0.6 g/L, 20% MeOH to 0% $NH_4HCOO$ 0.6 g/L, 100/6 MeOH). The pure fractions were collected and evaporated to dryness. The residue (42 mg; 8%) was taken up with DiPE/pentane and the precipitate was filtered and dried yielding 34 mg (7%) of compound 46.
M.P.: gum at 140° C. (Kofler).

Example B13

Preparation of Compound 47

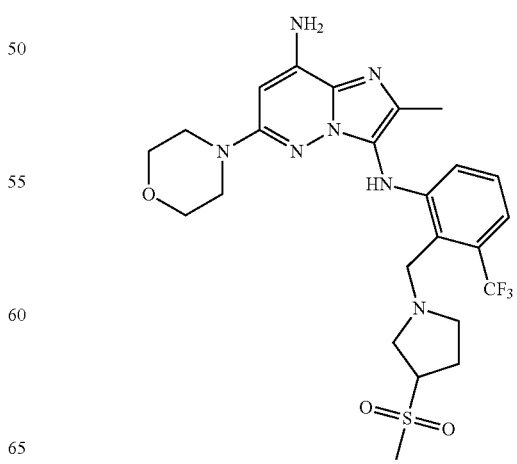

In a sealed tube, a mixture of intermediate 115 (0.15 g; 0.41 mmol), intermediate 123 (0.198 g; 0.61 mmol) and sodium tert-butoxide (0.079 g; 0.82 mmol) in toluene (3 mL) was degassed under N$_2$. Then, Pd$_2$(dba)$_3$ (0.037 mg, 0.04 mmol) and 2-(di-t-butylphosphino)biphenyl (0.024 mg; 0.08 mmol) were added and the reaction mixture was heated to 100° C. overnight. The mixture was poured out into water and filtered through a pad of Celite®. The organic layer was extracted with DCM, separated, dried over MgSO$_4$, filtered and concentrated to dryness. The residue (385 mg) was purified by chromatography over silica gel (SiOH 15 µm, 25 g; gradient from 100% DCM to 90% DCM, 10% MeOH, 0.5% NH$_4$OH). The pure fractions were collected and the solvent was evaporated. The residue (145 mg) was purified by chromatography over silica gel (irregular SiOH 40 g, mobile phase: 42% heptane, 8% MeOH (+10% NH$_4$OH), 50% EtOAc). The pure fractions were collected and the solvent was evaporated to give 57 mg of compound 47 (25%).

Preparation of Compound 53 (See Also A39, Reaction for Intermediate 138)

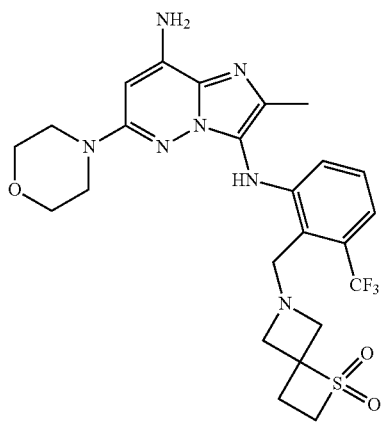 [SMILES: Cc1nc2c(N)cc(N3CCOCC3)nn2c1Nc1cccc(C(F)(F)F)c1CN1CC2(CCS2(=O)=O)C1]

In a sealed tube, a mixture of intermediate 115 (100 mg; 0.27 mmol), intermediate 137 (110 mg; 0.34 mmol) and sodium tert-butoxide (52 mg; 0.55 mmol) in toluene (2 mL) was degassed under N$_2$. Then, Pd$_2$(dba)$_3$ (25 mg; 0.03 mmol) and 2-(di-t-butylphosphino)biphenyl (16 mg; 0.05 mmol) were added. The reaction mixture was heated at 100° C. overnight. The mixture was cooled down to rt, then, poured onto water and filtered through a pad of Celite®. The organic layer was extracted with DCM, separated, dried over MgSO$_4$, filtered and concentrated to dryness. The residue (338 mg) was purified by chromatography over silica gel (SiOH 15 µm, 25 g, gradient from 100% DCM to 90% DCM, 10% MeOH, 0.5% NH$_4$OH). The pure fractions were collected and the solvent was evaporated to give 46 mg (31%). This fraction was dried-freeze to afford 36 mg (24%) of compound 53.

Alternative Route:

Compound 53 was prepared according to an analogous procedure as described for the synthesis of compound 45, using intermediate 138 as starting material (81%).

Preparation of Compound 58

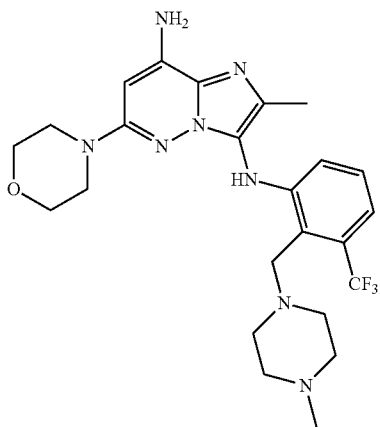 [SMILES: Cc1nc2c(N)cc(N3CCOCC3)nn2c1Nc1cccc(C(F)(F)F)c1CN1CCN(C)CC1]

Compound 58 was prepared according to an analogous procedure as described for the synthesis of compound 47, using intermediate 150 and intermediate 115 as starting material (5%).

Example B14

Alternative Preparation of Compound 38

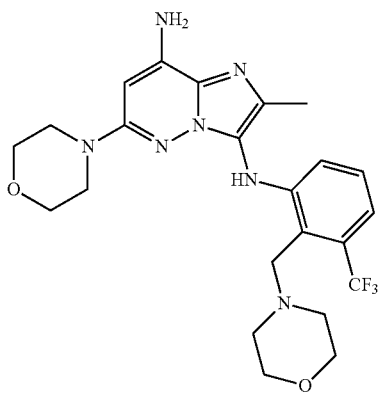 [SMILES: Cc1nc2c(N)cc(N3CCOCC3)nn2c1Nc1cccc(C(F)(F)F)c1CN1CCOCC1]

A mixture of intermediate 117 (100 mg; 0.18 mmol) and zinc chloride (150 mg; 1.10 mmol) in EtOH (3 mL) was stirred at 90° C. overnight. The reaction mixture was poured onto a 10% aqueous solution of K$_2$CO$_3$ and diluted with EtOAc. The organic layer was decanted, dried over MgSO$_4$ and evaporated under reduced pressure. The residue (90 mg) was purified by reverse phase (C18 5 µm 30*150 mm, gradient from 65% NH$_4$HCO$_3$ 0.5%, 35% ACN to 25% NH$_4$HCO$_3$ 0.5%, 75% ACN). The pure fractions were collected and the solvent was evaporated to give 73 mg (81%) of compound 38.

Preparation of Compound 48

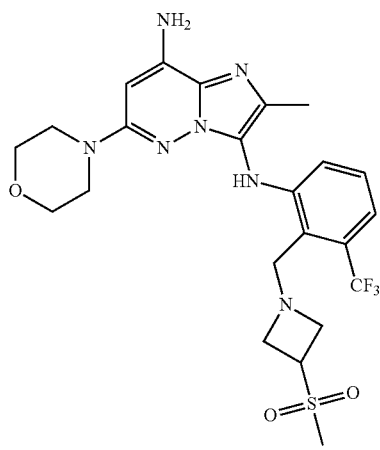 [SMILES: Cc1nc2c(N)cc(N3CCOCC3)nn2c1Nc1cccc(C(F)(F)F)c1CN1CC(S(C)(=O)=O)C1]

Compound 48 was prepared according to an analogous procedure as described for the synthesis of compound 38, using intermediate 126 as starting material (49%).

Preparation of Compound 49

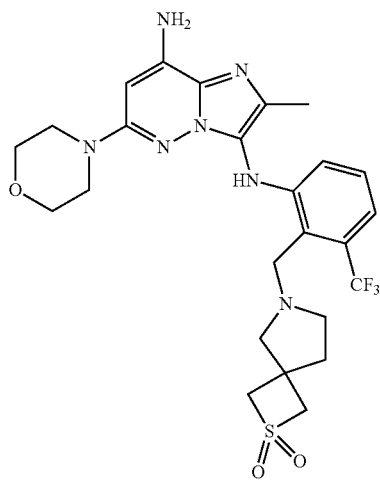 [SMILES: Cc1nc2c(N)cc(N3CCOCC3)nn2c1Nc1cccc(C(F)(F)F)c1CN1CCC2(C1)CS(=O)(=O)C2]

Compound 49 was prepared according to an analogous procedure as described for the synthesis of compound 38, using intermediate 129 as starting material (63%).

Preparation of Compound 54 (See Also A39, Reaction for Intermediate 141)

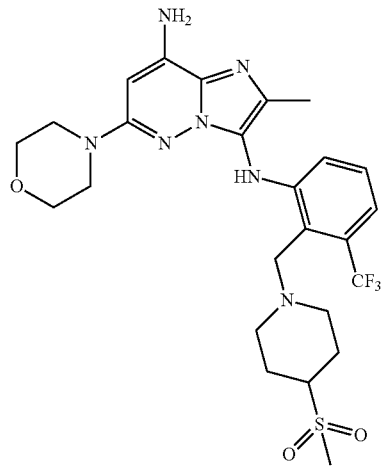 [SMILES: Cc1nc2c(N)cc(N3CCOCC3)nn2c1Nc1cccc(C(F)(F)F)c1CN1CCC(S(C)(=O)=O)CC1]

Compound 54 was prepared according to an analogous procedure as described for the synthesis of compound 38, using a mixture of intermediate 141 and compound 54 as starting material (58%).

Preparation of Compound 62 (See Also A39, Reaction for Intermediate 162)

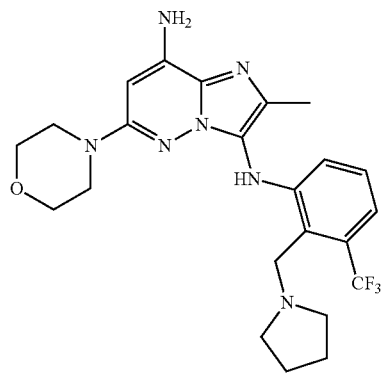 [SMILES: Cc1nc2c(N)cc(N3CCOCC3)nn2c1Nc1cccc(C(F)(F)F)c1CN1CCCC1]

Compound 62 was prepared according to an analogous procedure as described for the synthesis of compound 38, using a mixture of intermediate 162 and compound 62 as starting material (5%). M.P.: 201° C. (Kofler).

Preparation of Compound 63 (See Also A39, Reaction for Intermediate 163)

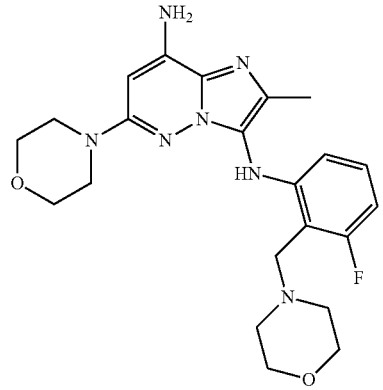 [SMILES: Cc1nc2c(N)cc(N3CCOCC3)nn2c1Nc1cccc(F)c1CN1CCOCC1]

Compound 63 was prepared according to an analogous procedure as described for the synthesis of compound 38, using a mixture of intermediate 163 and compound 63 as starting material (24%). M.P.: 120° C. (gum, Kofler).

Preparation of Compound 69

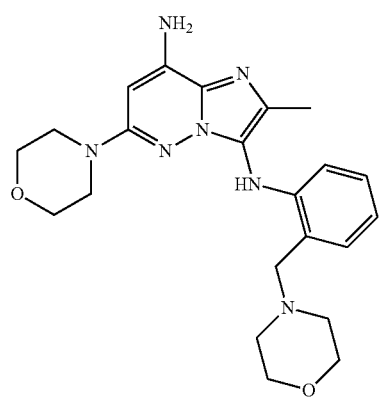 [SMILES: Cc1nc2c(N)cc(N3CCOCC3)nn2c1Nc1ccccc1CN1CCOCC1]

Compound 69 was prepared according to an analogous procedure as described for the synthesis of compound 38, using intermediate 179 as starting material (50%).

Example B15

Preparation of Compound 51

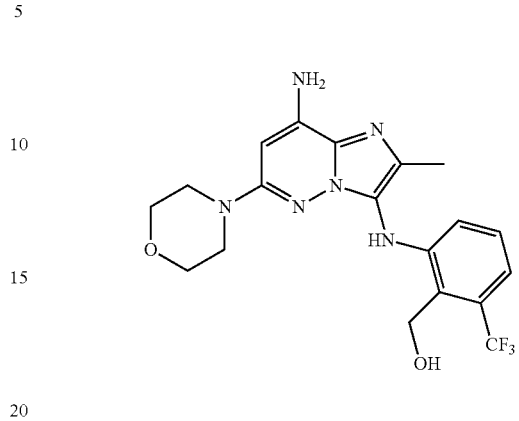

TBAF (1M in THF) (0.19 mL; 0.19 mmol) was added to a solution of intermediate 133 (89 mg; 0.17 mmol) in 1,4-dioxane (1 mL) at room temperature. The reaction mixture was stirred at room temperature for 16 hours, diluted with DCM and poured onto a 10% aqueous solution of $K_2CO_3$. The organic layer was decanted, dried over $MgSO_4$, filtered and evaporated. The residue (160 mg) was purified by chromatography over silica gel (Spherical bare silica 5 μm 150×30.0 mm, gradient from 98% DCM, 2% MeOH (+10% $NH_4OH$) to 87% DCM, 13% MeOH (+10% $NH_4OH$)). The pure fractions were collected and the solvent was evaporated to give 47 mg (67%) of compound 51.

Preparation of Compound 52

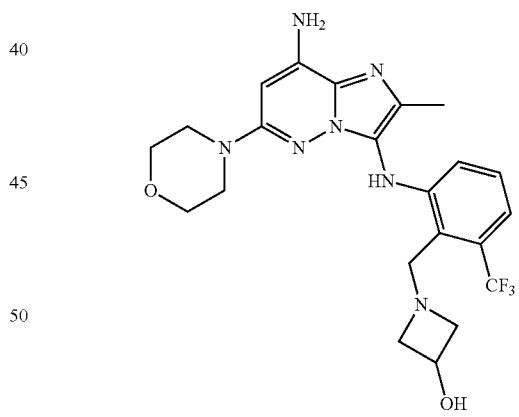

TBAF (1M in THF) (0.12 mL; 0.12 mmol) was added to a solution of intermediate 135 (131 mg, 0.22 mmol) in 1,4-dioxane (0.64 mL) at room temperature. The reaction mixture was stirred at room temperature for 16 hours, diluted with DCM and poured onto a 10% aqueous solution of $K_2CO_3$. The organic layer was decanted, dried over $MgSO_4$, filtered and concentrated. The residue (140 mg) was purified by reverse phase (C18 5 μm 30*150 mm, gradient from 65% aqueous $NH_4HCO_3$ 0.5%, 35% ACN to 25% aqueous $NH_4HCO_3$ 0.5%, 75% ACN). The pure fractions were collected and the solvent was evaporated to give 30 mg (28%) of compound 52.

Preparation of Compound 55

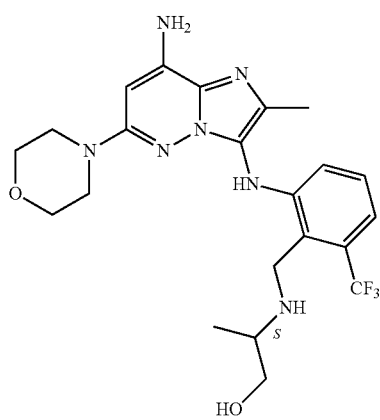

Compound 55 was prepared according to an analogous procedure as described for the synthesis of compound 52, using intermediate 144 as starting material (20%).

Preparation of Compound 56

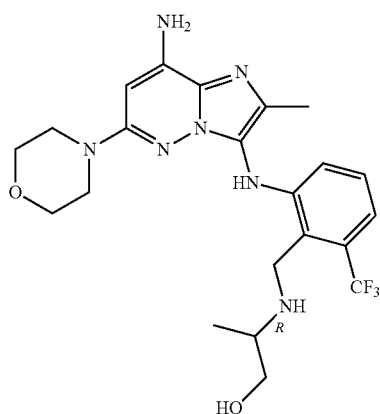

Compound 56 was prepared according to an analogous procedure as described for the synthesis of compound 52, using intermediate 148 as starting material (8%).

Preparation of Compound 71

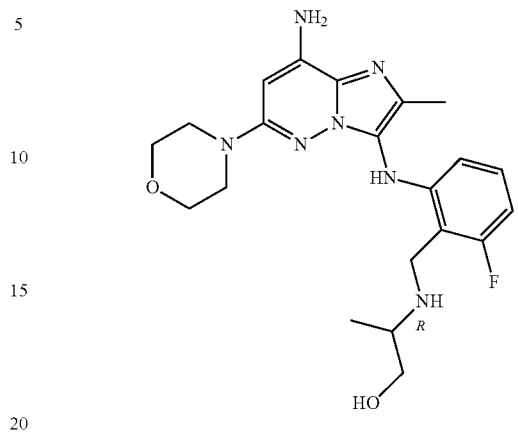

TBAF (1M in THF) (0.293 mL; 0.29 mmol) was added dropwise to a solution of intermediate 186 (0.145 g; 0.27 mmol) in THF (4 mL) at room temperature and the solution was stirred at this temperature overnight. The mixture was poured into water and extracted with DCM. The organic layer was dried over $MgSO_4$, filtered and the solvent was evaporated to dryness. The residue (0.165 g) was purified by chromatography over silica gel (Irregular SiOH 15-40 µm, 40 g: gradient from 100% DCM to 90% DCM, 10% MeOH, 0.1% $NH_4OH$). The pure fractions were collected and the solvent was evaporated until dryness. The residue was crystallized from DIPE. The precipitate was filtered off and dried under vacuum to yield 0.015 g (13%) of compound 71.

Example B16

Preparation of Compound 59

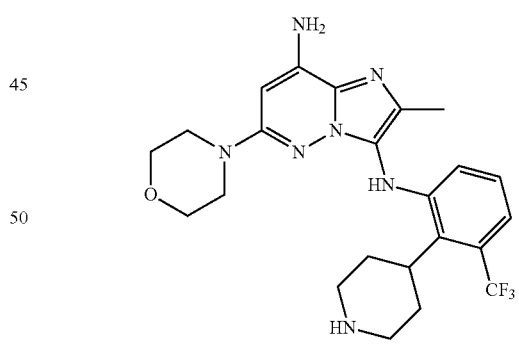

A mixture of intermediate 156 (0.22 g; 0.38 mmol) and HCl 3N (1.5 mL) and 1,4-dioxane (4 mL) was heated at 50° C. for 2 hours. The mixture was poured into $H_2O$ and basified with $K_2CO_3$. The product was extracted with DCM. Then, the organic layer was dried over $MgSO_4$, filtered and evaporated to dryness. The residue (0.18 g) was purified by chromatography over silica gel (Spherical bare silica 5 µm 150×30.0 mm, gradient from 95% DCM, 5% MeOH (+10% $NH_4OH$) to 82% DCM, 18% MeOH (+10% $NH_4OH$)). The pure fractions were collected and the solvent was evaporated until dryness. The residue (0.06 g) was crystallized from DIPE. The precipitate was filtered off and dried under vacuo to give 0.05 g (28%) of compound 59. M.P.: >250° C. (kofler).

Preparation of Compound 60

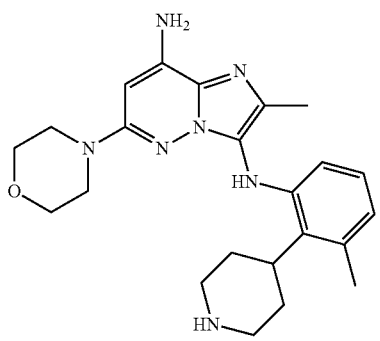 [SMILES: Cc1cccc(Nc2c(C)nc3c(N)cc(N4CCOCC4)nn23)c1C1CCNCC1]

Compound 60 was prepared according to an analogous procedure as described for the synthesis of compound 59, using intermediate 159 as starting material (24%). M.P.: 254° C. (Kofler).

Preparation of Compound 64

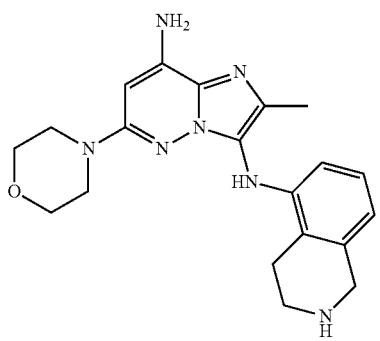 [SMILES: Cc1nc2c(N)cc(N3CCOCC3)nn2c1Nc1cccc2c1CCNC2]

A mixture of intermediate 164 (185 mg; 0.39 mmol) and HCl (4M in dioxane) (2.3 mL) and 1,4-dioxane (23 mL) was heated at 70° C. for 2 hours. Subsequently, the mixture was evaporated to dryness. The residue was triturated in diispropylether. The precipitate was filtered and dried under vacuum to give 140 mg (73%) of compound 64.

Example B17

Preparation of Compound 65 and Compound 66

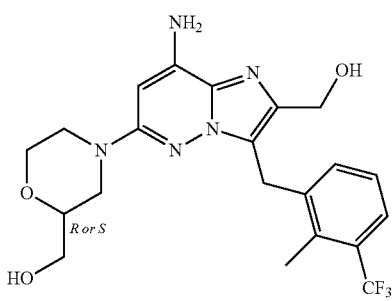

-continued

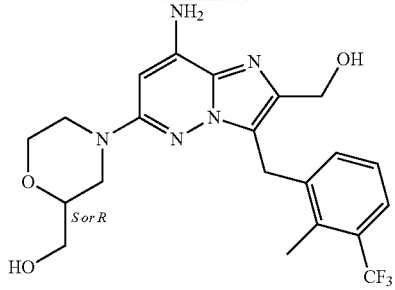

HCl (1M in water) (0.554 mL; 0.55 mmol) was added to a solution of intermediate 171 (80 mg; 0.11 mmol) in acetone (1.1 mL). The reaction mixture was stirred at rt for 18 h. The mixture was evaporated under vacuum. The residue (88 mg, orange oil) was solubilized in acetone (1.1 mL) and HCl (1M in water) (0.554 mL; 0.55 mmol) was added. The reaction mixture was stirred at rt for the weekend. The mixture was quenched with NaOH (1M in water) (1.11 mL; 1.11 mmol) and evaporated under vacuum. The residue (103 mg; orange solid) was triturated in DCM/MeOH (1:1) and filtered off. The filtrate was evaporated under vacuum. The residue (74 mg, beige solid) was purified by Reverse phase (C18 5 μm 30*150 mm, gradient from 85% (aq. NH$_4$HCO$_3$ 0.5%), 15% ACN to 45% (aq. NH$_4$HCO$_3$ 0.5%), 55% ACN). The pure fractions were collected and the solvent was evaporated. The residue (25 mg, beige solid) was solubilized in ACN/MeOH (1:1) (3 mL), extended with water (12 mL) and freeze-dried to afford 24 mg (white fluffy solid) of fraction 1. Fraction 1 was purified by chiral SFC (Lux cellulose 2 5 μm 250*21.2 mm, Mobile phase: 55% CO$_2$, 45% EtOH (0.3% iPrNH$_2$)). The pure fractions were collected and the solvent was evaporated to give 2 fractions which were solubilized in MeOH (2 mL), extended with water (16 mL) and freeze-dried to give 9 mg (16%, white fluffy solid) of compound 65 and 6 mg (11%, white fluffy solid) of compound 66.

Preparation of Compound 68

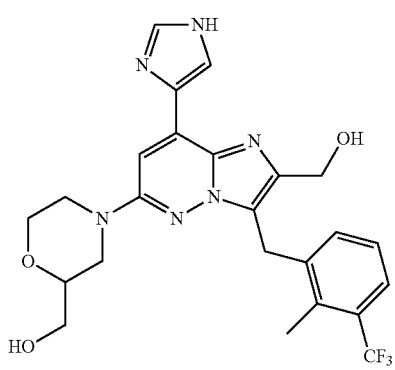 [SMILES: Cc1c(Cc2c(CO)nc3c(-c4c[nH]cn4)cc(N4CCOC(CO)C4)nn23)cccc1C(F)(F)F]

HCl (6M in water) (0.217 mL; 1.30 mmol) was added to a solution of intermediate 178 (210 mg; 0.26 mmol) in THF (2.6 mL). The reaction mixture was stirred at 50° C. overnight. EtOAc was added and the resulting emulsion was basified with NaHCO$_3$. The resulting emulsion was filtered on a glass-frit. The solid (90 mg, beige solid) was collected, then triturated in hot MeOH/EtOAc (1:1) and filtered off. The solid (40 mg, off-white solid) was purified by Reverse phase (C18 5 μm 30*150 mm, gradient from 25% (aq. NH₄HCO₃ 0.5% pH10), 75% ACN to 65% (aq. NH₄HCO₃ 0.5% pH10), 35% ACN). The pure fractions were collected and the solvent was evaporated. The residue was solubilized in MeOH (2 mL), extended with water (20 mL) and freeze-dried to give 18 mg (14%, white fluffy solid) of compound 68.

Example B18

Preparation of Compound 73

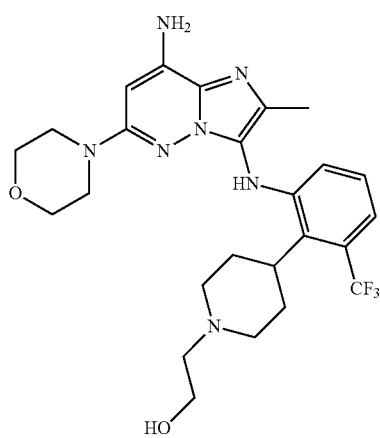 [SMILES: Cc1nc2c(N)cc(N3CCOCC3)nn2c1Nc1cccc(C(F)(F)F)c1C1CCN(CCO)CC1]

HCl (1M in water) (8.51 mL; 8.51 mmol) was added dropwise to a solution of a mixture of intermediates 194 and 195 (0.55 g; 0.87 mmol) in THF (33 mL) at room temperature. The solution was stirred at room temperature for 3 h. The mixture was poured onto water, basified with K₂CO₃ solid and extracted with DCM/MeOH (90/10). The organic layer was dried over MgSO₄, filtered and the solvent was evaporated. The residue (0.6 g) was purified immediately by chromatography over silica gel (irregular SiOH, 40 g; gradient: from 98% DCM, 2% MeOH to 900/DCM, 10% MeOH, 0.1% NH4OH). The pure fractions were collected and evaporated to dryness. The residue (0.368 g) was crystallized from DIPE (and 5% ACN). The precipitate was filtered off and dried under vacuum to give 0.278 g (62%) of compound 73. M.P.: 252° C. (DSC).

Preparation of Compound 74

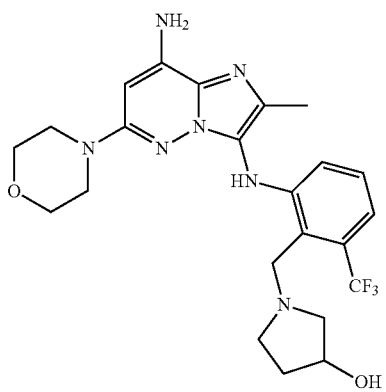 [SMILES: Cc1nc2c(N)cc(N3CCOCC3)nn2c1Nc1cccc(C(F)(F)F)c1CN1CCC(O)C1]

Compound 74 was prepared according to an analogous procedure as described for the synthesis of compound 73, using intermediate 199 as starting material (67%). The reaction mixture was stirred at rt overnight.

Example B19

Preparation of Compound 77 and Compound 78

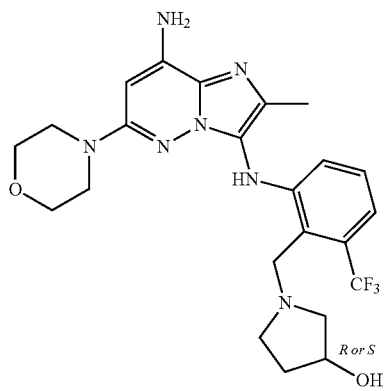

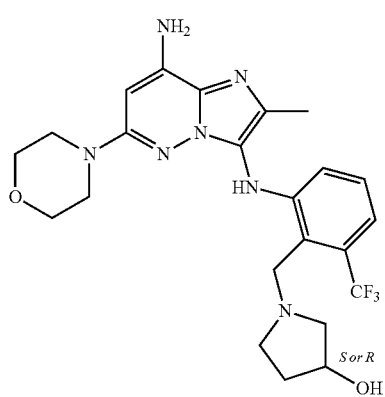

A part of compound 74 was purified by chiral SFC (CHIRALPAK AD-H, 5 μm 250×20 mm; mobile phase: 85% CO₂, 15% mixture of EtOH/iPrOH 50/50 v/v (+0.3% iPrNH₂). The pure fractions were collected and the solvent was evaporated to give 2 fractions (140 mg and 130 mg). Each fraction was taken-up with DIPE/ACN (drops). The precipitates were filtered and dried under vacuum at 50° C. for 3 hours to afford 99 mg (30%) of compound 77 (M.P.: 134° C. (gum, K)) and 106 mg (32%) of compound 78 (M.P.: 132° C., (gum. K)).

Example B20

Preparation of Compound 79

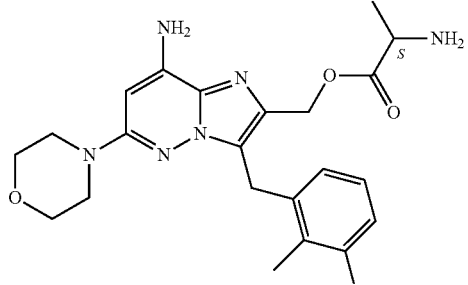

2.09 HCl 0.84 H₂O

At 0° C., HCl (4M in dioxane) (806 μL; 3.22 mmol) was added to a solution of intermediate 205 (191 mg; 0.32 mmol) in ACN (7 mL). The reaction mixture was stirred at 0° C. for 1 h and at rt overnight. The solution was evaporated to dryness. Et₂O was added and the precipitate was filtered and dried to give 97 mg (52%) of compound 79. M.P.: 185° C. (Kofler).

Preparation of Compound 80

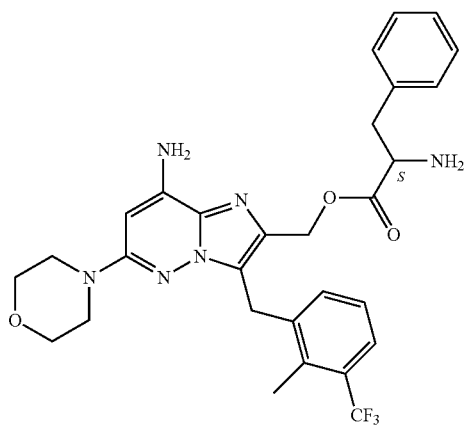

1.91 HCl 0.73 H₂O

At 0° C., HCl (4M in dioxane) (290 μL; 1.16 mmol) was added to a solution of intermediate 206 (155 mg; 0.23 mmol) in ACN (7 mL). The reaction mixture was stirred at 0° C. for 30 min and at rt for 3 hours. The solution was evaporated to dryness. Et₂O was added and the precipitate was filtered and dried to give 103 mg (68%) of compound 80. M.P.: 174° C. (Kofler).

Preparation of Compound 81

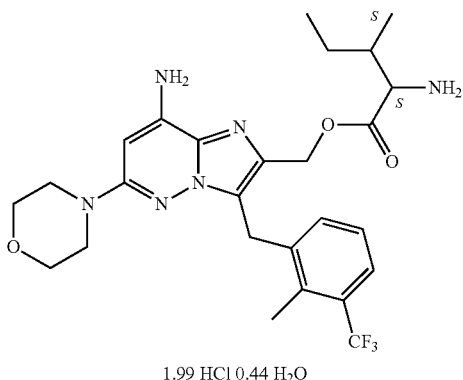

1.99 HCl 0.44 H₂O

Compound 81 was prepared according to an analogous procedure as described for the synthesis of compound 80, using intermediate 207 as starting material (72%; 111 mg). M.P.: 244° C. (Kofler).

Preparation of Compound 82

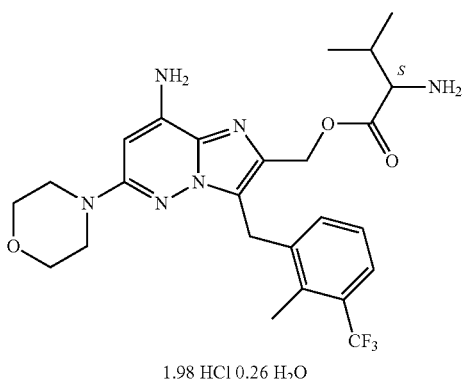

1.98 HCl 0.26 H₂O

Compound 82 was prepared according to an analogous procedure as described for the synthesis of compound 80, using intermediate 208 as starting material (83%; 129 mg). M.P.: 220° C. (Kofler).

Preparation of Compound 83

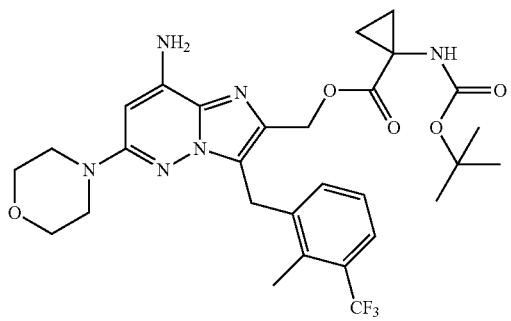

1.9 HCl 0.89 H₂O

Compound 83 was prepared according to an analogous procedure as described for the synthesis of compound 80, using intermediate 209 as starting material (59%; 58 mg). M.P.: 216° C. (Kofler).

Preparation of Compound 84

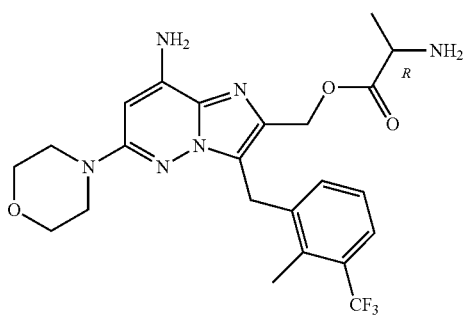

At rt, HCl (4M in dioxane) (1.2 mL; 4.64 mmol) was added to a solution of intermediate 210 (550 mg; 0.93 mmol) in ACN (24 mL). The reaction mixture was stirred at rt overnight. A precipitate was filtered and dried given 521 mg of fraction 1. EtOH (13 mL) was added and the solution was heated until dissolution for 20 min. Then, the solution was cooled and the precipitate was filtered and dried to give 291 mg (53%) of compound 84. M.P.: 177° C. (DSC).

Example B21

Preparation of Compound 85

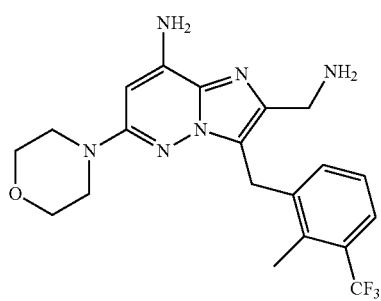

Hydrazine monohydrate (55 µL; 0.90 mmol) was added to a suspension of intermediate 212 (135 mg; 0.25 mmol) in EtOH (3.5 mL) at rt. The reaction mixture was heated at 80° C. overnight. The mixture was cooled down to rt. Then, DCM was added and the mixture was stirred at rt for 10 min. The insoluble was filtered and washed with DCM/MeOH (90/10) (3×). The filtrate was evaporated. The residue (93 mg, brown solid) was purified by chromatography over silica gel (Spherical bare silica 5 µm 150×30.0 mm; gradient: from 98% DCM, 2% MeOH, 0.2% NH$_4$OH to 87% DCM, 13% MeOH, 1.3% NH$_4$OH). The pure fractions were collected and the solvent was evaporated to give 23 mg (22%) of compound 85. M.P.: 191° C. (Kofler).

Alternative pathway: Hydrazine monohydrate (0.93 mL; 9.75 mmol) was added to a suspension of intermediate 215 (697 mg; 0.98 mmol) in EtOH (10 mL) at room temperature. The reaction mixture was heated at 80° C. overnight, cooled down to rt and diluted with DCM. The organic layer was washed with water, dried over MgSO$_4$, filtered and evaporated to dryness. The residue was taken up with ACN and the precipitate was filtered, washed with diethylether and dried to give 210 mg (51%) of compound 85.

Example B22

Preparation of Compound 91

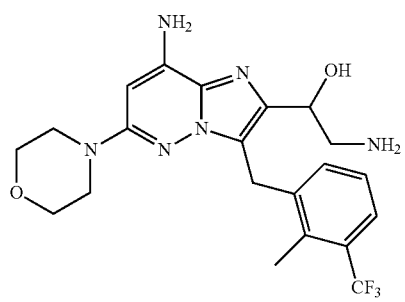

Sodium borohydride (0.217 g; 5.74 mmol) was added portionwise to a solution of intermediate 228 (0.23 g; 0.48 mmol) and nickel(II) chloride anhydrous (62 mg; 0.48 mmol) in MeOH (10 mL) at 0° C. The solution was stirred at 0° C. for 1 h. The reaction mixture was poured out into ice water and the aqueous layer was extracted with DCM (3×). The organic layers were combined, dried over MgSO$_4$ and evaporated to dryness. The residue was purified by chromatography over silica gel (SiOH 20-45 m; 27 g; gradient: from 95% DCM, 5% MeOH, 0.1% NH$_4$OH to 80% DCM, 20% MeOH, 0.1% NH$_4$OH). The pure fractions were collected and the solvent was evaporated until dryness. The residue (0.15 g) was crystallized from DIPE and ACN (90/10). The precipitate was filtered off and dried under vacuum to give 0.114 g (53%) of compound 91.

Example B23

Preparation of Compound 93

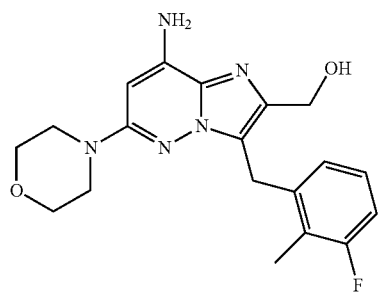 [SMILES: Cc1c(F)cccc1Cc1c(CO)nc2c(N)cc(N3CCOCC3)nn12]

HCl (1M in H$_2$O) (2.9 mL) was added to a solution of intermediate 233 (180 mg; 0.28 mmol) in THF (10 mL) and the reaction mixture was stirred overnight at rt. The reaction mixture was poured onto ice water, basified with an aqueous solution of NaHCO$_3$ and extracted with EtOAc. An insoluble material was filtered and dried to give a fraction A of 56 mg (54%) of compound 93. The organic layer was decanted and separated. The aqueous layer was extracted twice with EtOAc. The combined organic layers were washed with brine, dried over MgSO$_4$, filtered and evaporated to dryness. The residue was purified by chromatography over silica gel (irregular SiOH; 4 g; gradient: from 100% DCM to 1% NH$_4$OH, 10% MeOH, 90% DCM). The pure fractions were collected and evaporated to dryness. The residue was combined with the fraction A and the mixture was suspended in diethylether. The precipitate was filtered and dried to give 74 mg of (72%) of compound 93. M.P.: 241° C. (DSC).

Preparation of Compound 94

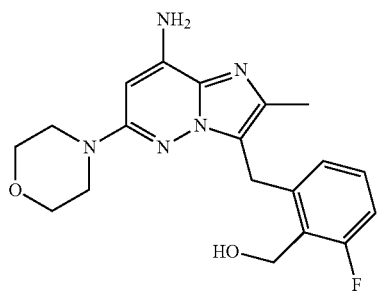 [SMILES: Cc1nc2c(N)cc(N3CCOCC3)nn2c1Cc1cccc(F)c1CO]

In a round bottom flask, intermediate 238 (80 mg; 0.13 mmol) was diluted in THF (3 mL). Then, HCl (1M in H$_2$O) (1.3 mL; 1.3 mmol) was added dropwise. The reaction mixture was stirred at rt for 3 h, then was heated at 60° C. for 3 h. The reaction mixture was poured into ice-water, neutralized with K$_2$CO$_3$ and the aqueous layer was extracted twice with DCM. The organic layers were combined, dried over MgSO$_4$ and evaporated. The residue (0.1 g) was purified by chromatography over silica gel (Irregular SiOH; 15-40 µm; 24 g; gradient: from 100% DCM to 90% DCM, 10% MeOH, 0.1% NH$_4$OH). The pure fractions were collected and the solvent was evaporated until dryness to give 8 mg (17%) of compound 94. M.P.: 201° C. (DSC).

Preparation of Compound 97

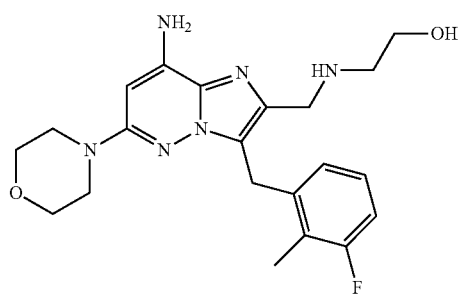 [SMILES: Cc1c(F)cccc1Cc1c(CNCCO)nc2c(N)cc(N3CCOCC3)nn12]

Compound 97 was prepared according to an analogous procedure as described for the synthesis of compound 93, using intermediate 251 as starting material (37 mg, 35%). M.P.: 178° C. (K). The reaction mixture was performed in Me-THF.

Preparation of Compound 99

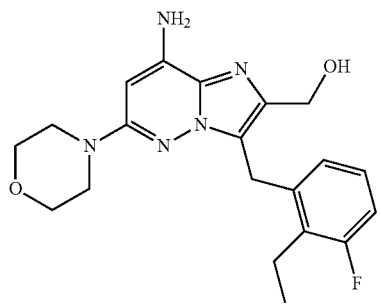

1.11 HCl 0.03 H$_2$O

Compound 99 was prepared according to an analogous procedure as described for the synthesis of compound 93, using intermediate 256as starting material (62 mg, 46%). M.P.: 236° C. (K). The reaction mixture was performed in Me-THF.

Preparation of Compound 101

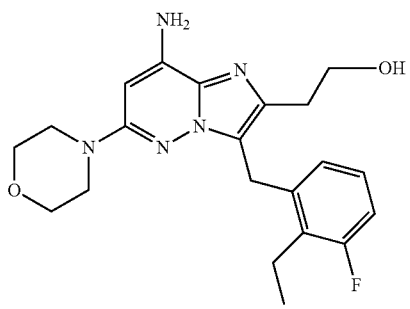 [SMILES: CCc1c(F)cccc1Cc1c(CCO)nc2c(N)cc(N3CCOCC3)nn12]

Compound 101 was prepared according to an analogous procedure as described for the synthesis of compound 93, using intermediate 262as starting material (51 mg, 36%). M.P.: 148° C. (K). The reaction mixture was performed in Me-THF.

Preparation of Compound 102

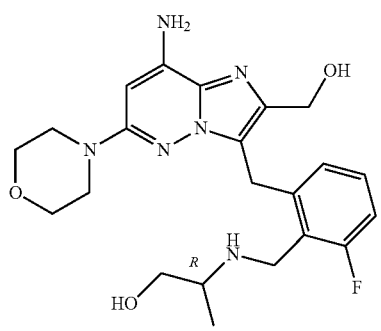

A mixture of intermediate 26 (0.873 g; 1.196 mmol) in HCl 37% (5 mL) in MeOH (15 mL) was stirred for 16 h at 60° C. The solvent was evaporated under vacuum. The crude was taken up in methanol and NaHCO₃ was added carefully until basic pH. The salts were filtered and the filtrate was evaporated under vacuum. The crude was purified by chromatography over silica gel (irregular SiOH, gradient from 100% DCM to 75% DCM 25% MeOH). The fractions containing the product were collected and evaporated to dryness. The oil was treated with diethyl ether until a white solid was formed. The precipitate was filtered off and dried under vacuum to yield 0.3 g (56%) of compound 102 as a white residue. M.P.: 175.6° C. (DSC).

Preparation of Compound 103

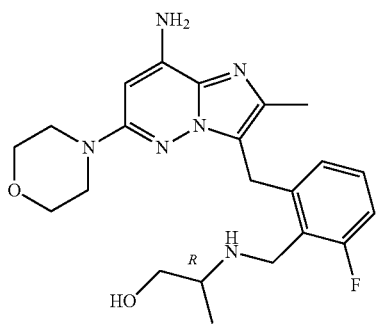

Intermediate 275 (1.92 g; 3.2 mmol) was dissolved in a solution of HCl in MeOH 6M (50 mL) and was heated at 65° C. overnight. The crude was dried under vacuo and the crude was neutralized with Ca₂CO₃ to pH=8. The crude was purified by chromatography over silica gel (irregular SiOH, gradient from 100% DCM to 80% DCM 20% MeOH). The pure fractions were collected and the solvent was evaporated until dryness. The residue (0.59 g) was taken up with ACN and was sonicated for 5 mn. The precipitate was filtered off, washed with DIPE and dried under vacuo to afford 0.285 g (21%) of compound 103. M.P.: 176.13° C. (DSC)

Preparation of Compound 104

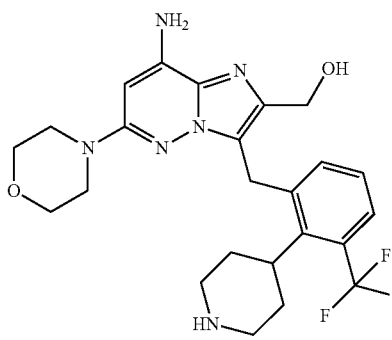

A mixture of intermediate 279 (0.07 g, 0.128 mmol) in HCl 12N (2 mL) was refluxed for 1h30. The mixture was poured into ice water, basified with K₂CO₃ solid and was extracted with DCM. The organic layer was dried over MgSO₄, filtered off and evaporated until dryness. The residue (0.06 g) was purified by chromatography over silica gel (irregular SiOH, gradient from 98% DCM, 2% MeOH to 80% DCM, 20% MeOH, 0.1% NH₄OH). The pure fractions were collected and the solvent was evaporated until dryness.

The residue was purified via reverse phase (Stationary phase: X-Bridge-C18 5 μm 30*150 mm, mobile phase: gradient from 85% NH₄HCO₃ 0.2%, 15% ACN to 45% NH₄HCO₃ 0.2%, 55% ACN). The pure fractions were collected and the solvent was evaporated until dryness to give 4 mg (6%) of compound 104.

Preparation of Compound 105

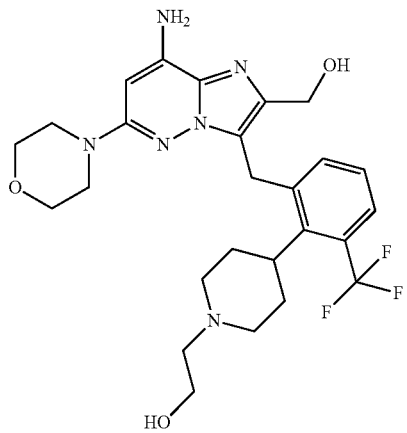 [SMILES: Nc1cc(N2CCOCC2)nn2c(Cc3cccc(C(F)(F)F)c3C3CCN(CCO)CC3)c(CO)nc12]

A solution of HCl 4N in dioxane (2 mL) was added dropwise to a solution of intermediate 280 (0.24 g, 0.34 mmol) in MeOH (2 mL) at room temperature. The solution was heated at 55° C. for 2 h. HCl 12N (0.5 mL) was added and the solution was heated at 60° C. overnight. The solution was evaporated until dryness. The residue (0.36 g) was purified via Reverse phase (Stationary phase: X-Bridge-C18 5 μm 30*150 mm, mobile phase: gradient from 75% NH₄HCO₃ 0.2%, 25% ACN to 35% NH₄HCO₃ 0.2%, 65% ACN). The pure fractions were collected and the solvent was evaporated until dryness. The residue (0.096 g, y=53%) was crystallized from DIPE. The precipitate was filtered off and dried in vacuo. The solid (0.078 g) was purified via achiral SFC (Stationary phase: AMINO 6 μm 150×21.2 mm, Mobile phase: 80% CO₂, 20% MeOH (0.3% iPrNH₂)). The pure fractions were collected and the solvent was evaporated until dryness to give 0.065 g (36%) of compound 105. M.P.: 249° C. (DSC)

Preparation of Compound 106

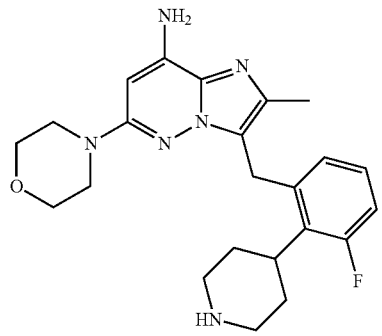 [SMILES: Cc1nc2c(N)cc(N3CCOCC3)nn2c1Cc1cccc(F)c1C1CCNCC1]

A solution of HCl 4N in dioxane (14.78 mL; 59.147 mmol) was added dropwise to a solution of intermediate 283

(2.24 g; 3.86 mmol) in MeOH (3 mL) at room temperature. The solution was heated at 55° C. for 2 h. Solvents were evaporated under reduced pressure. The residue (0.325 g) was purified via reverse phase (Stationary phase: X-Bridge-C18 5 μm 30*150 mm, mobile phase: gradient from 85% NH₄HCO₃ 0.2%, 15% ACN to 45% NH₄HCO₃ 0.2%, 55% ACN). The pure fractions were collected and the solvent was evaporated until dryness to give 1.32 g (80%) of compound 106. M.P.: 189° C. (DSC)

Preparation of Compound 107

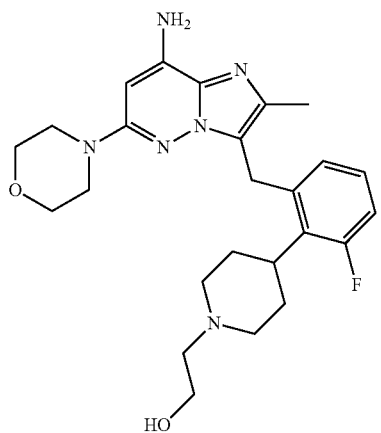 [SMILES: Cc1nc2c(N)cc(N3CCOCC3)nn2c1Cc1cccc(F)c1C1CCN(CCO)CC1]

A solution of HCl 4N in 1,4-dioxane (3 mL; 12 mmol) was added dropwise to a solution of intermediate 285 (0.5 g; 0.783 mmol) in MeOH (3 mL) at room temperature. The solution was heated at 55° C. for 2 h. Solvents were evaporated under reduced pressure. The residue (0.325 g) was purified via reverse phase (Stationary phase: X-Bridge-C18 5 μm 30*150 mm, mobile phase: gradient from 85% NH₄HCO₃ 0.2%, 15% ACN to 45% NH₄HCO₃ 0.2%, 55% ACN). The pure fractions were collected and the solvent was evaporated until dryness to give 0.139 g (38%) of compound 107. M.P.: 139° C. (DSC)

Preparation of Compound 108

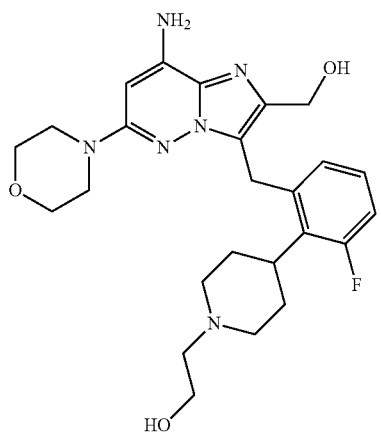 [SMILES: Nc1cc(N2CCOCC2)nn2c(Cc3cccc(F)c3C3CCN(CCO)CC3)c(CO)nc12]

A solution of HCl 4N in 1,4-dioxane (3 mL) was added dropwise to a solution of intermediate 289 (0.797 g, 1.217 mmol) in MeOH (3 mL) at room temperature. The solution was heated at 55° C. for 2 h. HCl 12N (1 mL) was added and the solution was heated at 60° C. overnight. The solution was evaporated until. The residue was purified via Reverse phase (Stationary phase: X-Bridge-C18 5 μm 30*150 mm, Mobile phase: Gradient from 90% NH₄HCO₃ 0.2%, 10% ACN to 60% NH₄HCO₃ 0.2%, 40% ACN). The pure fractions were collected and the solvent was evaporated until dryness to give 0.064 g of a first residue and 0.14 g of a second residue.

The first residue (0.064 g) was crystallized from DIPE. The precipitate was filtered off and dried in vacuo to yield 0.038 g (6%) of a first batch of compound 108.

The second residue (0.14 g) was crystallized from DIPE. The precipitate was filtered off and dried in vacuo to yield 0.134 g (23%) of a second batch of compound 108. global yield=29%

Preparation of Compound 109

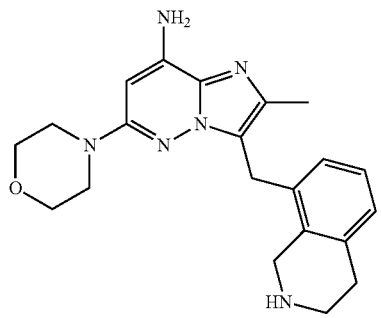 [SMILES: Cc1nc2c(N)cc(N3CCOCC3)nn2c1Cc1cccc2c1CNCC2]

Intermediate 292 (0.667 g; 1.21 mmol) was dissolved in a solution of HCl in MeOH 6M (16.67 mL) and the mixture was stirred at 65° C. overnight. The crude was evaporated under vacuo and the residue was taken up in an aqueous solution of NaOH 2N. The product was extracted with DCM; dried over MgSO₄ and concentrated under vacuum. The residue was purified by chromatography over silica gel (irregular SiOH, gradient from 100% DCM to 80% DCM, 20% MeOH). The pure fractions were collected and the solvent was evaporated until dryness to give 0.246 g (53%) of compound 109. M.P.: 205° C. (MP50 Metter Toledo)

Preparation of Compound 110

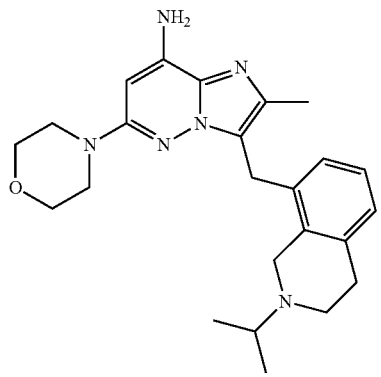 [SMILES: Cc1nc2c(N)cc(N3CCOCC3)nn2c1Cc1cccc2c1CN(C(C)C)CC2]

A reaction mixture of intermediate 294 (0.49 g; 0.977 mmol) in a solution of HCl in MeOH 6M (15 mL) was stirred for 16 h at 60° C. The mixture was evaporated until dryness. The crude was taken up with MeOH and NaHCO$_3$ was added carefully until basic pH. The salts were filtered off and the filtrate was evaporated in vacuo. The residue was purified by chromatography over silica gel (irregular SiOH, gradient from 100% DCM to 75% DCM, 25% MeOH). The pure fractions were collected and the solvent was evaporated until dryness. The oil was treated with Diethyl Ether until a white solid appeared. The precipitate was filtered off and dried in vacuum to yield 0.255 g (60%) of compound 110 as a white solid. M.P.: 262° C. (Mettler Toledo MP50).

Conversion

Conversion C1

Preparation of Compound 61

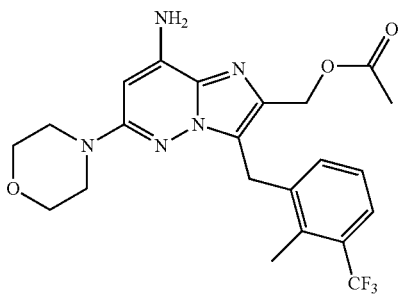 [SMILES: CC(=O)OCc1nc2c(N)cc(N3CCOCC3)nn2c1Cc1cccc(C(F)(F)F)c1C]

Acetyl chloride (25 µL; 0.36 mmol) was added dropwise to a solution of compound 14 (125 mg; 0.3 mmol) and triethylamine (62 µL; 0.44 mmol) in DCM (5 mL) at 5° C. The reaction mixture was stirred at rt overnight. Acetyl chloride (25 µL; 0.36 mmol) and triethylamine (62 µL; 0.44 mmol) were added a second time. Then, the solution was stirred at rt for 1 hour. The solvent was evaporated and the residue (140 mg) was crystallized from Et$_2$O to give, after filtration, 34 mg (25%) of compound 61. M.P.: 110° C. (Kofler).

Conversion C2

Alternative for the Preparation of Compound 110

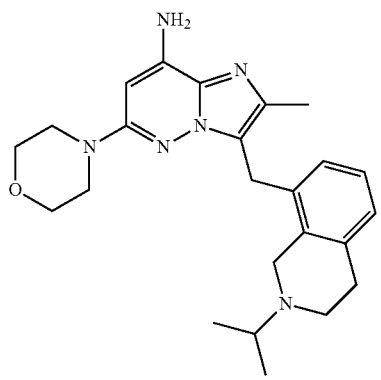 [SMILES: Cc1nc2c(N)cc(N3CCOCC3)nn2c1Cc1cccc2c1CN(C(C)C)CC2]

A solution of compound 109 (0.2 g; 0.513 mmol) and acetone (0.188 mL; 2.56 mmol) in MeOH (15 mL) was stirred at room temperature for 30 min. Sodium triacetoxyborohydride (0.326 g; 1.54 mmol) was added and the solution was stirred at room temperature overnight. The solvents were evaporated to dryness and the residue was purified by chromatography over silica gel (irregular SiOH, gradient from 100% DCM to 50% DCM, 50% MeOH). The pure fractions were collected and the solvent was evaporated until dryness. The residue was purified by reverse phase (Stationary phase: Phenomenex Gemini C18 100A column 5 µm 30*100 mm, Mobile phase: Gradient from 50% 25 mM NH$_4$HCO$_3$, 50% MeCN: MeOH (1:1) to 25% 25 mM NH$_4$HCO$_3$, 75% MeCN: MeOH (1:1)). The pure fractions were collected and the solvent was evaporated until dryness to give 0.12 g (54%) of compound 110. M.P.: 251° C. (DSC)

Analytical Part

LCMS (Liquid chromatography/Mass spectrometry)

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times (R$_t$) and ions. If not specified differently in the table of data, the reported molecular ion corresponds to the [M+H]$^+$ (protonated molecule) and/or [M-H]$^-$ (deprotonated molecule). In case the compound was not directly ionizable the type of adduct is specified (i.e. [M+NH$_4$]$^+$, [M+HCOO]$^-$, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector.

TABLE

LCMS Method codes (Flow expressed in mL/min; column temperature (T) in ° C.; Run time in minutes).

| Method code | Instrument | Column | Mobile phase | gradient | Flow Column T | Run time |
|---|---|---|---|---|---|---|
| Method 1 | Waters: Acquity UPLC ®-DAD and Quattro Micro ™ | Waters: BEH C18 (1.7 µm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 40 | 6.2 |
| Method 2 | Waters: Acquity UPLC ® H-Class - DAD and SQD 2 | Waters: BEH C18 (1.7 µm, 2.1 × 100 mm) | A: 95% $CH_3COONH_4$ 7 mM/5% $CH_3CN$, B: $CH_3CN$ | From 84.2% A to 10.5% A in 2.18 min, held for 1.94 min, back to 84.2% A in 0.73 min, held for 0.73 min. | 0.343 40 | 6.1 |
| Method 3 | Agilent: 1100-DAD and MSD | YMC: Pack ODS-AQ (3 µm, 4.6 × 50 mm) | A: HCOOH 0.1% in water, B: $CH_3CN$ | 95% A to 5% A in 4.8 min, held for 1 min, back to 95% A in 0.2 min. | 2.6 35 | 6 |

DSC/Kofler

For a number of compounds, melting points (MP) were determined with a DSC 1 (Mettler-Toledo). Melting points were measured with a temperature gradient of 10° C./minute. Maximum temperature was 350° C. Values are peak values.

For a number of compounds, melting points were obtained with a Kofler hot bench, consisting of a heated plate with linear temperature gradient, a sliding pointer and a temperature scale in degrees Celsius.

For a number of compounds, melting points were obtained with or a MP50 (Mettler Toledo) with which melting points were measured with a temperature gradient of 10° C./minute. Starting temperature was 50° C. and maximum temperature was 300° C.

NMR

The NMR experiments were carried out using a Bruker Avance 500 III using internal deuterium lock and equipped with reverse triple-resonance ($^1$H, $^{13}$C, $^{15}$N TXI) probe head. Chemical shifts (δ) are reported in parts per million (ppm). DMSO-$d_6$ (deuterated DMSO, dimethyl-d6 sulfoxide) was used as solvent.

OR:

Optical Rotation is measured with a polarimeter 341 Perkin Elmer. The polarized light is passed through a sample with a path length of 1 decimeter and a sample concentration of 0.2 to 0.4 gram per 100 milliliters.

2 to 4 mg of the product in vial are weight, then dissolved with 1 to 1.2 ml of spectroscopy solvent (Dimethylformamide for example). The cell is filled with the solution and put into the polarimeter at a temperature of 20° C. The OR is read with 0.004° of precision.

Calculation of the concentration: weight in gram×100/volume in ml $[\alpha]_d^{20}$: (read rotation×100)/(1.000 dm×concentration).

d is sodium D line (589 nanometer).

TABLE

| Co. No. | Compound Structure | M.P. (° C.) | Kofler (K) or DSC | $R_t$ | $[M + H]^+$ | LCMS Method |
|---|---|---|---|---|---|---|
| 1 | 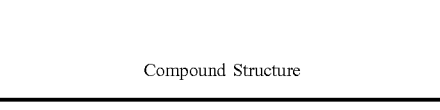 | 60-63 gum | K | 2.83 | 541 | Method 1 |

TABLE-continued

| Co. No. | Compound Structure | M.P. (° C.) | Kofler (K) or DSC | R$_t$ | [M + H]$^+$ | LCMS Method |
|---|---|---|---|---|---|---|
| 2 | 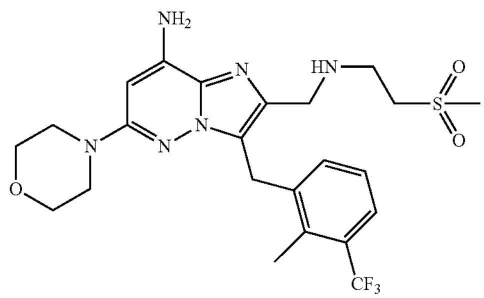 [SMILES: Cc1c(Cc2c(CNCCS(C)(=O)=O)nc3c(N)cc(N4CCOCC4)nn23)cccc1C(F)(F)F] | n.d. | — | 2.66 | 527 | Method 1 |
| 3 | 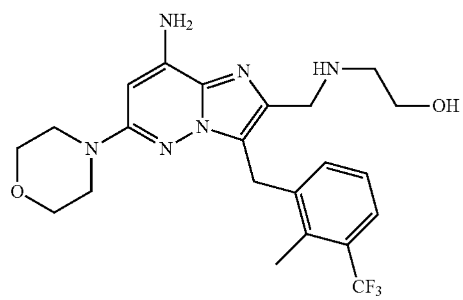 [SMILES: Cc1c(Cc2c(CNCCO)nc3c(N)cc(N4CCOCC4)nn23)cccc1C(F)(F)F] | n.d. | — | 2.44 | 465 | Method 1 |
| 4 | 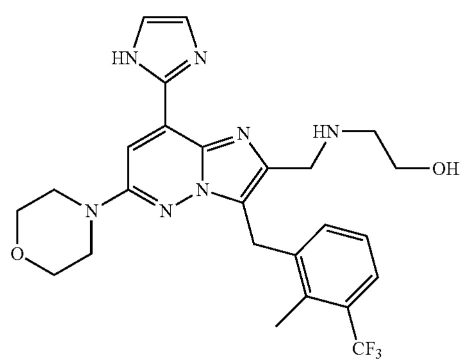 [SMILES: Cc1c(Cc2c(CNCCO)nc3c(-c4ncc[nH]4)cc(N4CCOCC4)nn23)cccc1C(F)(F)F] | 128 | K | 2.53 | 516 | Method 1 |
| 5 | 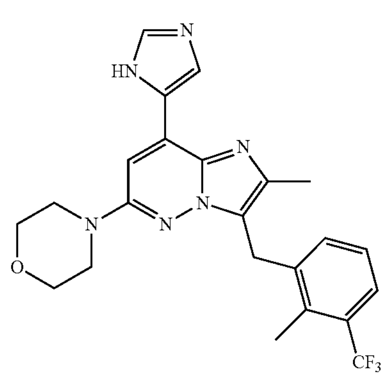 [SMILES: Cc1nc2c(-c3cnc[nH]3)cc(N3CCOCC3)nn2c1Cc1cccc(C(F)(F)F)c1C] | 226 | K | 3.08 | 457 | Method 1 |

TABLE-continued

| Co. No. | Compound Structure | M.P. (°C.) | Kofler (K) or DSC | $R_t$ | $[M + H]^+$ | LCMS Method |
|---|---|---|---|---|---|---|
| 6 | 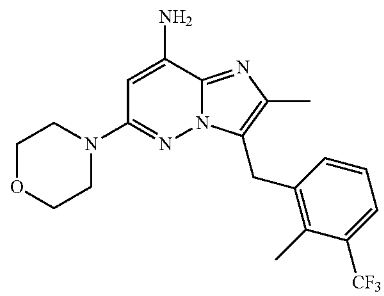 | 207 | K | 3.1 | 406 | Method 1 |
| 7 | 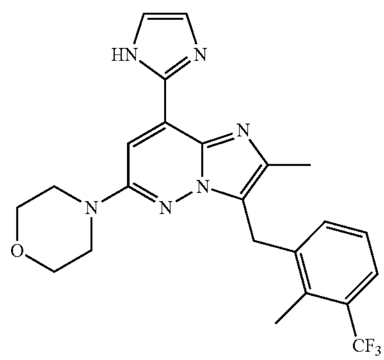 [SMILES: Cc1nc2c(-c3ncc[nH]3)cc(N3CCOCC3)nn2c1Cc1cccc(C(F)(F)F)c1C] | 176 | K | 3.50 | 457 | Method 1 |
| 8 | 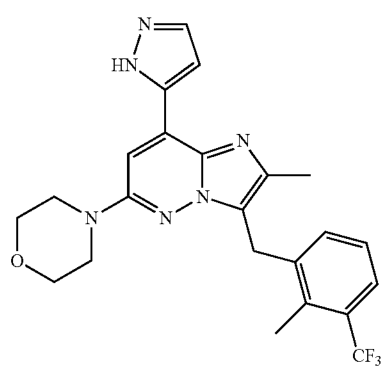 [SMILES: Cc1nc2c(-c3ccn[nH]3)cc(N3CCOCC3)nn2c1Cc1cccc(C(F)(F)F)c1C] | 193 | K | 3.37 | 457 | Method 1 |
| 9 | 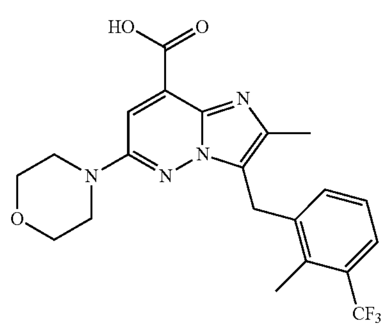 | 244 | DSC | 2.38 | 435 | Method 1 |

TABLE-continued

| Co. No. | Compound Structure | M.P. (° C.) | Kofler (K) or DSC | R$_t$ | [M + H]$^+$ | LCMS Method |
|---|---|---|---|---|---|---|
| 10 | H$_2$N-CO-imidazo[1,2-b]pyridazine(morpholine, 2-Me, 3-CH$_2$-(2-Me-3-CF$_3$-phenyl)) | 226 | K | 3.28 | 434 | Method 1 |
| 11 | H$_2$N-CO-imidazo[1,2-b]pyridazine(morpholine, 2-Me, 3-CH$_2$-(2-Me-3-Cl-phenyl)) | 217 | DSC | 3.30 | 400 | Method 1 |
| 12 | HO-CO-imidazo[1,2-b]pyridazine(morpholine, 2-Me, 3-CH$_2$-(2,3-diMe-phenyl)) | >260 | K | 2.27 | 381 | Method 1 |
| 13 | HO-CO-imidazo[1,2-b]pyridazine(morpholine, 2-Me, 3-CH$_2$-(2-Me-3-Cl-phenyl)) | 95 gum | K | 2.32 | 401 | Method 1 |
| 14 | NH$_2$-imidazo[1,2-b]pyridazine(morpholine, 2-CH$_2$OH, 3-CH$_2$-(2-Me-3-CF$_3$-phenyl)) | 241 | DSC | 2.70 | 422 | Method 1 |

TABLE-continued

| Co. No. | Compound Structure | M.P. (° C.) | Kofler (K) or DSC | $R_t$ | [M + H]+ | LCMS Method |
|---|---|---|---|---|---|---|
| 14a | NH2, morpholine, imidazopyridazine, CH2OH, CH2-(2-methyl-3-CF3-phenyl) · CH4O3S | 202 | DSC | 2.70 | 422 | Method 1 |
| 14b | NH2, morpholine, imidazopyridazine, CH2OH, CH2-(2-methyl-3-CF3-phenyl) · C7H8O3S | 211 | DSC | 2.70 | 422 | Method 1 |
| 14c | NH2, morpholine, imidazopyridazine, CH2OH, CH2-(2-methyl-3-CF3-phenyl) · C4H4O4 | 214 | DSC | 2.70 | 422 | Method 1 |
| 14d | NH2, morpholine, imidazopyridazine, CH2OH, CH2-(2-methyl-3-CF3-phenyl) · HCl | 250 | DSC | 2.70 | 422 | Method 1 |
| 14e | NH2, morpholine, imidazopyridazine, CH2OH, CH2-(2-methyl-3-CF3-phenyl) · H2SO4 | 204 | DSC | 2.70 | 422 | Method 1 |

TABLE-continued
| Co. No. | Compound Structure | M.P. (° C.) | Kofler (K) or DSC | $R_f$ | $[M + H]^+$ | LCMS Method |
|---|---|---|---|---|---|---|
| 15 | 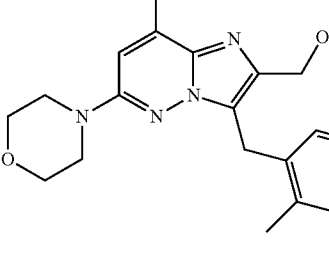 | 240 | K | 3.17 | 450 | Method 1 |
| 16 | 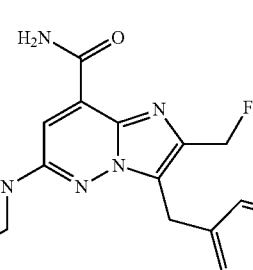 | 200 | K | 3.17 | 452 | Method 1 |
| 17 | 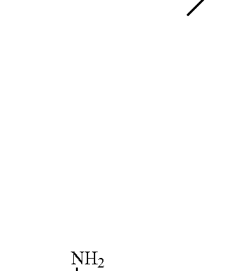 | n.d. | — | 3.09 | 424 | Method 1 |
| 18 | 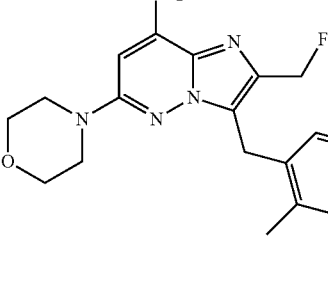 | 247 | DSC | 2.74 | 514 | Method 1 |

TABLE-continued
| Co. No. | Compound Structure | M.P. (° C.) | Kofler (K) or DSC | $R_t$ | $[M + H]^+$ | LCMS Method |
|---|---|---|---|---|---|---|
| 19 | 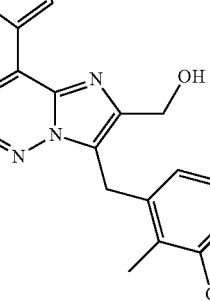 | 223 | DSC | 2.65 | 473 | Method 1 |
| 20 | 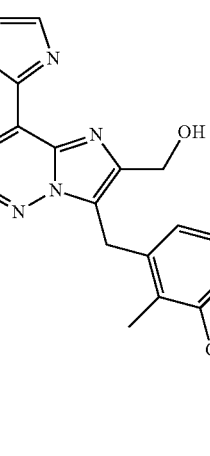 | n.d. | — | 2.87 | 473 | Method 1 |
| 21 | 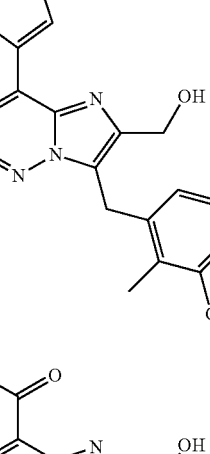 | 145-151 gum | K | 2.84 | 473 | Method 1 |
| 22 | 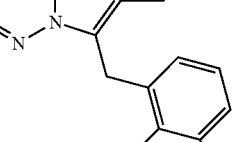 | 252 | DSC | 2.14 | 451 | Method 1 |

TABLE-continued

| Co. No. | Compound Structure | M.P. (° C.) | Kofler (K) or DSC | $R_t$ | [M + H]$^+$ | LCMS Method |
|---|---|---|---|---|---|---|
| 23 | 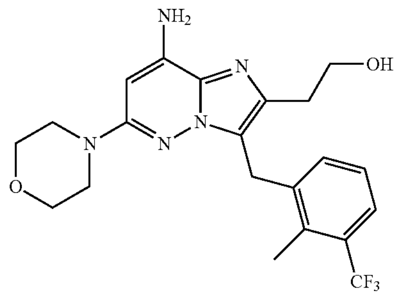 [SMILES: Cc1c(Cc2c(CCO)nc3c(N)cc(N4CCOCC4)nn23)cccc1C(F)(F)F] | 198 | K | 2.75 | 436 | Method 1 |
| 24 | 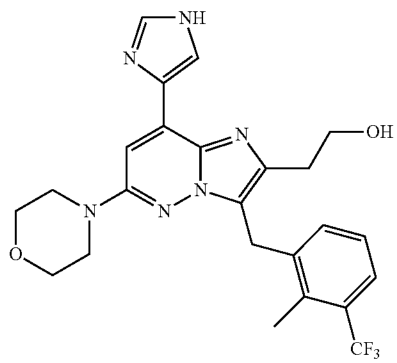 [SMILES: Cc1c(Cc2c(CCO)nc3c(-c4c[nH]cn4)cc(N4CCOCC4)nn23)cccc1C(F)(F)F] | 212 | K | 2.72 | 487 | Method 1 |
| 25 | S-enantiomer | 80 gum | K | 2.79 | 487 | Method 1 |
| 26 | S-enantiomer | n.d. | — | 2.81 | 436 | Method 1 |

TABLE-continued
| Co. No. | Compound Structure | M.P. (° C.) | Kofler (K) or DSC | $R_t$ | $[M + H]^+$ | LCMS Method |
|---|---|---|---|---|---|---|
| 27 | 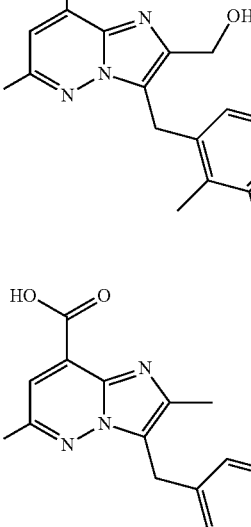 | 208 | K | 2.78 | 487 | Method 1 |
| 28 | 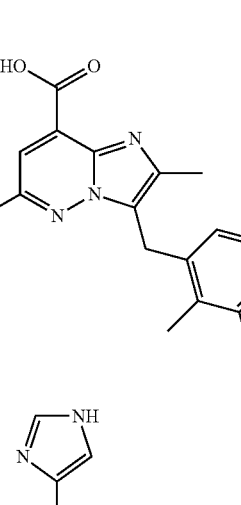 | 245 | K | 2.47 | 449 | Method 1 |
| 29 | 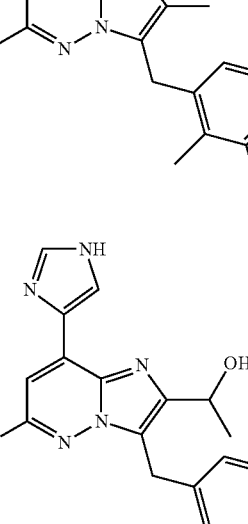 | 237 | K | 2.32 | 432 | Method 1 |
| 30 | 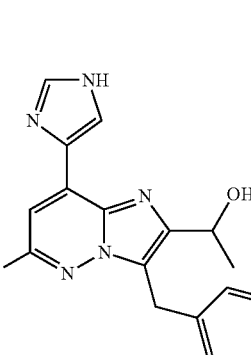 | 178 | K | 2.81 | 487 | Method 1 |

TABLE-continued

| Co. No. | Compound Structure | M.P. (°C.) | Kofler (K) or DSC | $R_t$ | [M + H]+ | LCMS Method |
|---|---|---|---|---|---|---|
| 31 | 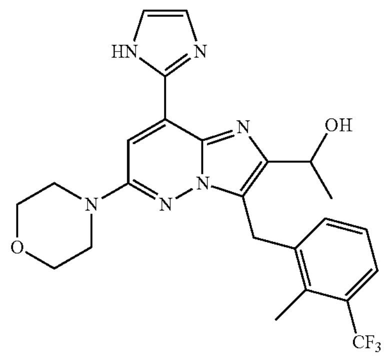 [SMILES: Cc1c(Cc2c(C(C)O)nc3c(-c4ncc[nH]4)cc(N4CCOCC4)nn23)cccc1C(F)(F)F] | >260 | K | 3.01 | 487 | Method 1 |
| 32 | 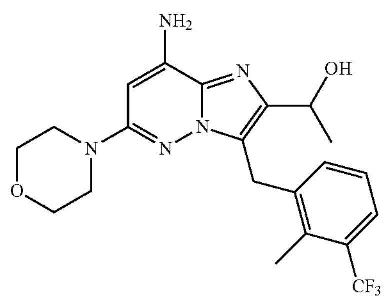 [SMILES: Cc1c(Cc2c(C(C)O)nc3c(N)cc(N4CCOCC4)nn23)cccc1C(F)(F)F] | 184 | K | 2.8 | 436 | Method 1 |
| 33 | 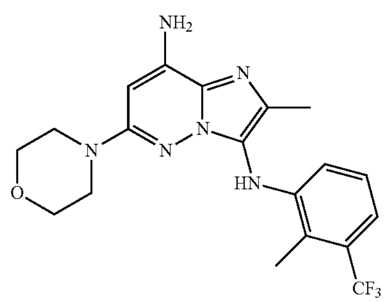 | 223 | K | 2.92 | 407 | Method 1 |
| 34 | 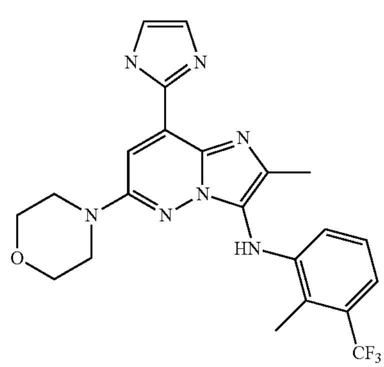 [SMILES: Cc1nc2c(-c3ncc[nH]3)cc(N3CCOCC3)nn2c1Nc1cccc(C(F)(F)F)c1C] | 210 | K | 3.79 | 458 | Method 2 |

TABLE-continued

| Co. No. | Compound Structure | M.P. (°C.) | Kofler (K) or DSC | $R_t$ | $[M + H]^+$ | LCMS Method |
|---|---|---|---|---|---|---|
| 35 | 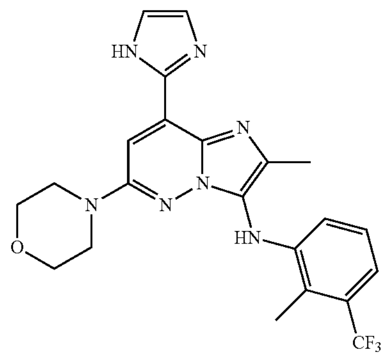 [SMILES: Cc1nc2c(-c3ncc[nH]3)cc(N3CCOCC3)nn2c1Nc1cccc(C(F)(F)F)c1C] | 231 | K | 3.38 | 458 | Method 2 |
| 36 | 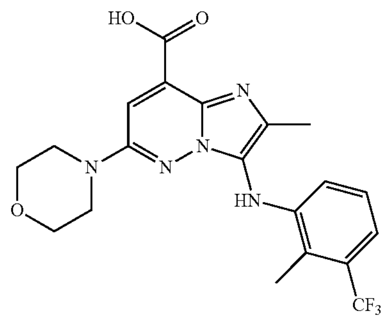 [SMILES: Cc1nc2c(C(=O)O)cc(N3CCOCC3)nn2c1Nc1cccc(C(F)(F)F)c1C] | 251 | K | 2.32 | 436 | Method 1 |
| 37 | 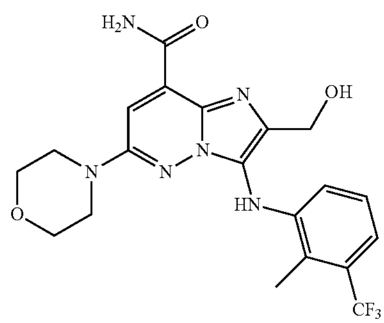 [SMILES: Cc1c(Nc2c(CO)nc3c(C(N)=O)cc(N4CCOCC4)nn23)cccc1C(F)(F)F] | 232 | K | 2.61 | 451 | Method 1 |
| 38 | 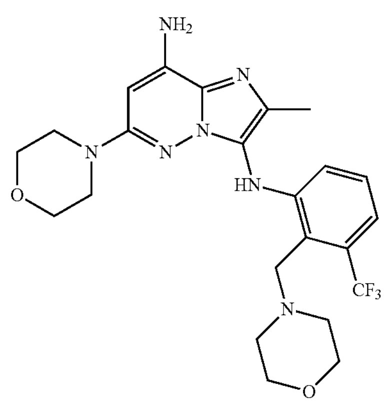 [SMILES: Cc1nc2c(N)cc(N3CCOCC3)nn2c1Nc1cccc(C(F)(F)F)c1CN1CCOCC1] | n.d. | — | 3.05 | 492 | Method 1 |

TABLE-continued

| Co. No. | Compound Structure | M.P. (°C.) | Kofler (K) or DSC | R$_f$ | [M + H]$^+$ | LCMS Method |
|---|---|---|---|---|---|---|
| 39 | 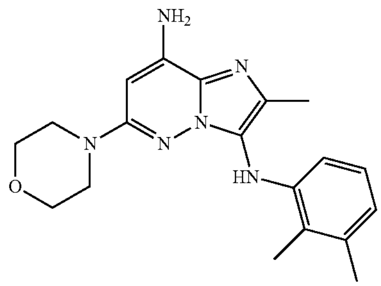 [SMILES: Cc1cccc(Nc2c(C)nc3c(N)cc(N4CCOCC4)nn23)c1C] | n.d. | — | 2.73 | 353 | Method 1 |
| 40 | 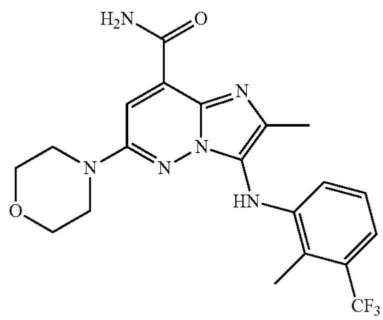 [SMILES: Cc1nc2c(C(N)=O)cc(N3CCOCC3)nn2c1Nc1cccc(C(F)(F)F)c1C] | n.d. | — | 3.10 | 435 | Method 1 |
| 41 | 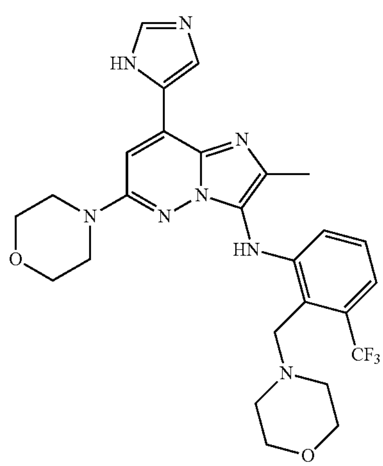 [SMILES: Cc1nc2c(-c3cnc[nH]3)cc(N3CCOCC3)nn2c1Nc1cccc(C(F)(F)F)c1CN1CCOCC1] | 154 | K | 3.02 | 543 | Method 1 |
| 42 | 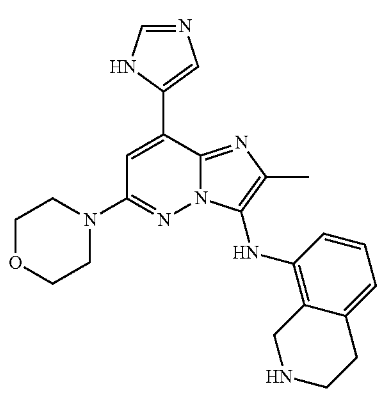 [SMILES: Cc1nc2c(-c3cnc[nH]3)cc(N3CCOCC3)nn2c1Nc1cccc2c1CNCC2] | 158 | K | 1.78 | 431 | Method 1 |

TABLE-continued

| Co. No. | Compound Structure | M.P. (° C.) | Kofler (K) or DSC | $R_t$ | $[M + H]^+$ | LCMS Method |
|---|---|---|---|---|---|---|
| 43 | 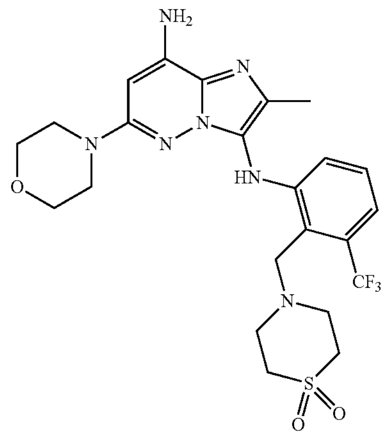 [SMILES: Cc1nc2c(N)cc(N3CCOCC3)nn2c1Nc1cccc(C(F)(F)F)c1CN1CCS(=O)(=O)CC1] | 167 gum | K | 2.74 | 540 | Method 1 |
| 44 | 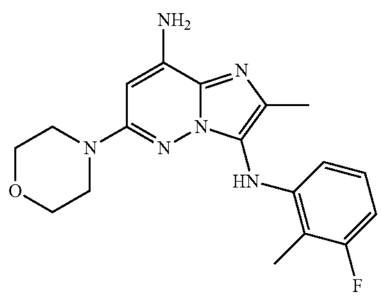 [SMILES: Cc1nc2c(N)cc(N3CCOCC3)nn2c1Nc1cccc(F)c1C] | 232 | K | 2.66 | 357 | Method 1 |
| 46 | 0.2 HCOOH | Gum 140 | K | 2.66 | 529 | Method 1 |

TABLE-continued

| Co. No. | Compound Structure | M.P. (° C.) | Kofler (K) or DSC | $R_t$ | $[M + H]^+$ | LCMS Method |
|---|---|---|---|---|---|---|
| 47 | 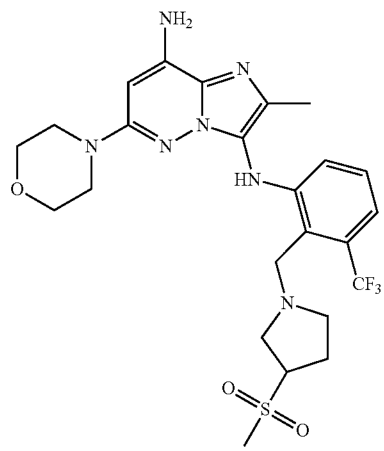 [SMILES: Cc1nc2c(N)cc(N3CCOCC3)nn2c1Nc1cccc(C(F)(F)F)c1CN1CCC(S(C)(=O)=O)C1] | n.d. | — | 2.76 | 554 | Method 1 |
| 48 | 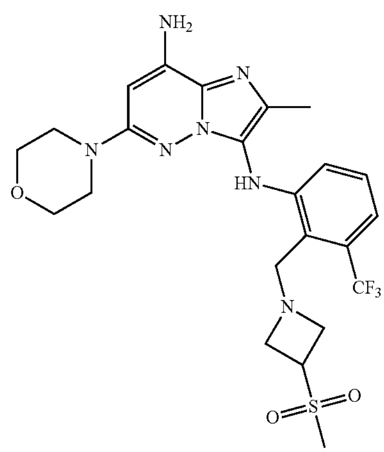 [SMILES: Cc1nc2c(N)cc(N3CCOCC3)nn2c1Nc1cccc(C(F)(F)F)c1CN1CC(S(C)(=O)=O)C1] | n.d. | — | 2.69 | 540 | Method 1 |
| 49 | 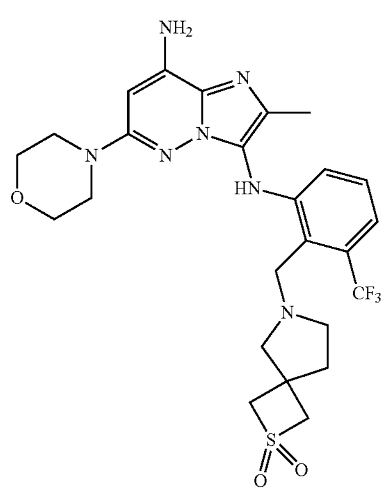 [SMILES: Cc1nc2c(N)cc(N3CCOCC3)nn2c1Nc1cccc(C(F)(F)F)c1CN1CCC2(C1)CS(=O)(=O)C2] | n.d. | — | 2.94 | 566 | Method 1 |

TABLE-continued

| Co. No. | Compound Structure | M.P. (° C.) | Kofler (K) or DSC | $R_t$ | $[M + H]^+$ | LCMS Method |
|---|---|---|---|---|---|---|
| 50 | 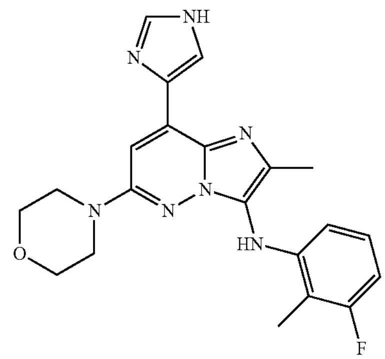 [SMILES: Cc1nc2c(-c3c[nH]cn3)cc(N3CCOCC3)nn2c1Nc1cccc(F)c1C] | >260 | K | 2.67 | 408 | Method 1 |
| 51 | 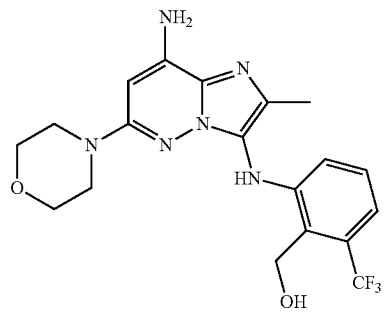 [SMILES: Cc1nc2c(N)cc(N3CCOCC3)nn2c1Nc1cccc(C(F)(F)F)c1CO] | n.d. | — | 2.56 | 423 | Method 1 |
| 52 | 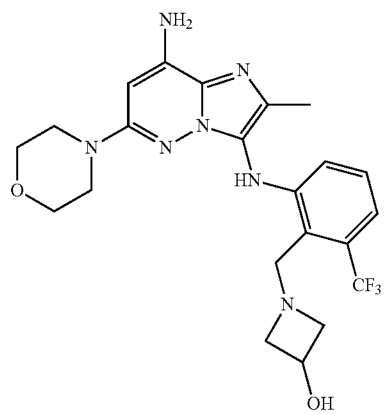 [SMILES: Cc1nc2c(N)cc(N3CCOCC3)nn2c1Nc1cccc(C(F)(F)F)c1CN1CC(O)C1] | n.d. | — | 2.69 | 478 | Method 1 |
| 53 | 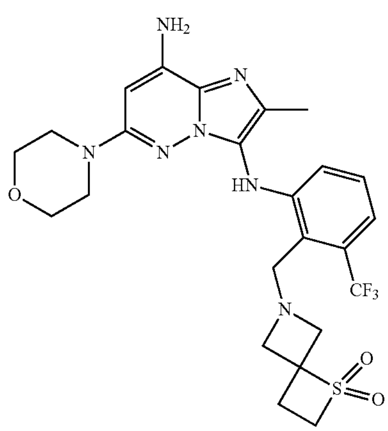 [SMILES: Cc1nc2c(N)cc(N3CCOCC3)nn2c1Nc1cccc(C(F)(F)F)c1CN1CC2(CCS2(=O)=O)C1] | n.d. | — | 2.81 | 552 | Method 1 |

TABLE-continued
| Co. No. | Compound Structure | M.P. (° C.) | Kofler (K) or DSC | $R_t$ | $[M + H]^+$ | LCMS Method |
|---|---|---|---|---|---|---|
| 54 | 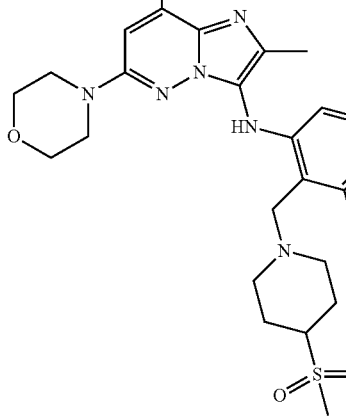 | n.d. | — | 2.85 | 568 | Method 1 |
| 55 | 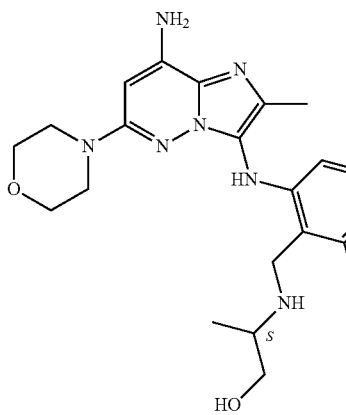 | n.d. | — | 2.74 | 480 | Method 1 |
| 56 | 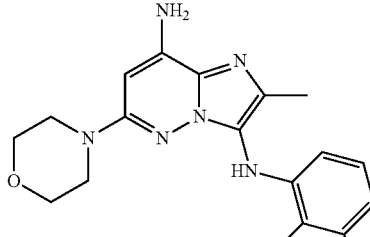 | n.d. | — | 2.74 | 480 | Method 1 |

TABLE-continued
| Co. No. | Compound Structure | M.P. (° C.) | Kofler (K) or DSC | $R_f$ | $[M + H]^+$ | LCMS Method |
|---|---|---|---|---|---|---|
| 57 | 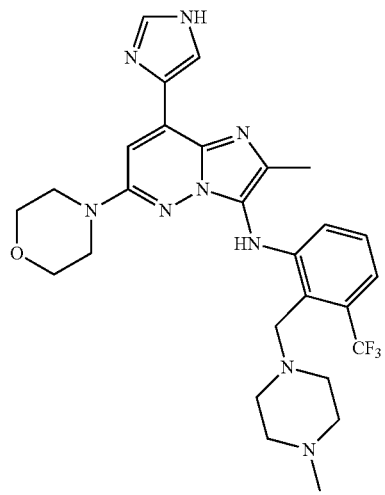 [SMILES: Cc1nc2c(-c3c[nH]cn3)cc(N3CCOCC3)nn2c1Nc1cccc(C(F)(F)F)c1CN1CCN(C)CC1] | 140 (gum) | K | 2.63 | 556 | Method 1 |
| 58 | 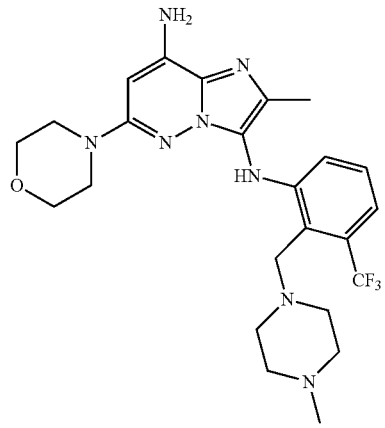 [SMILES: Cc1nc2c(N)cc(N3CCOCC3)nn2c1Nc1cccc(C(F)(F)F)c1CN1CCN(C)CC1] | 213 | K | 2.63 | 505 | Method 1 |
| 59 | 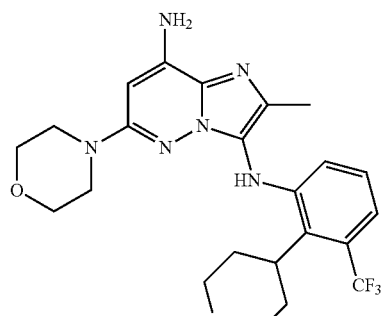 | >250 | K | 2.27 | 476 | Method 1 |

| Co. No. | Compound Structure | M.P. (° C.) | Kofler (K) or DSC | $R_t$ | $[M + H]^+$ | LCMS Method |
|---|---|---|---|---|---|---|
| 60 | 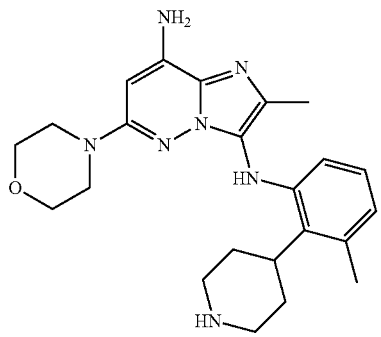 [SMILES: Cc1cccc(Nc2c(C)nc3c(N)cc(N4CCOCC4)nn23)c1C1CCNCC1] | 254 | K | 2.03 | 422 | Method 1 |
| 61 | 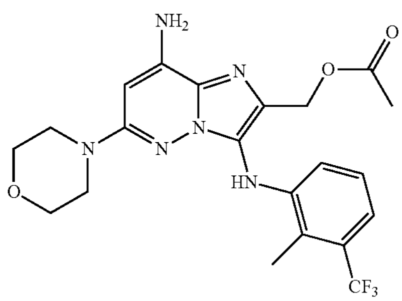 [SMILES: CC(=O)OCc1nc2c(N)cc(N3CCOCC3)nn2c1Nc1cccc(C(F)(F)F)c1C] | 110 | K | 3.02 | 464 | Method 1 |
| 62 | 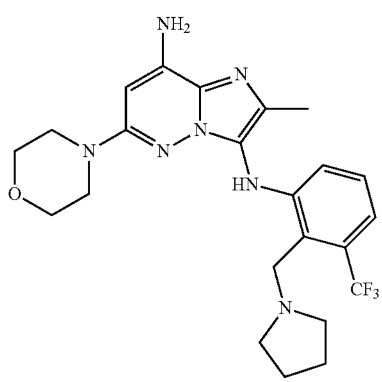 [SMILES: Cc1nc2c(N)cc(N3CCOCC3)nn2c1Nc1cccc(C(F)(F)F)c1CN1CCCC1] | 201 | K | 3.59 | 476 | Method 1 |
| 63 | 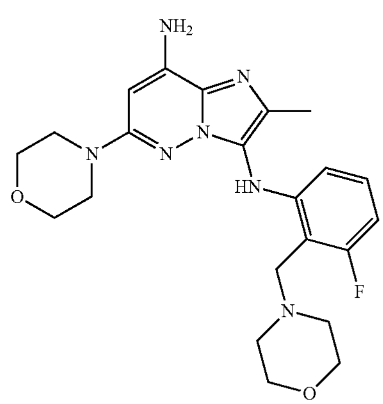 [SMILES: Cc1nc2c(N)cc(N3CCOCC3)nn2c1Nc1cccc(F)c1CN1CCOCC1] | 120 (gum) | K | 2.79 | 442 | Method 1 |

TABLE-continued

| Co. No. | Compound Structure | M.P. (°C.) | Kofler (K) or DSC | $R_t$ | $[M + H]^+$ | LCMS Method |
|---|---|---|---|---|---|---|
| 64 | (structure; 2.02 HCl 2.44 H₂O) | n.d. | — | 1.56 | 380 | Method 1 |
| 65 | (structure; R or S) | n.d. | — | 2.37 | 452 | Method 1 |
| 66 | (structure; S or R) | n.d. | — | 2.37 | 452 | Method 1 |
| 67 | (structure) | 237 | K | 2.58 | 439 | Method 1 |

TABLE-continued

| Co. No. | Compound Structure | M.P. (° C.) | Kofler (K) or DSC | $R_t$ | $[M + H]^+$ | LCMS Method |
|---|---|---|---|---|---|---|
| 68 | 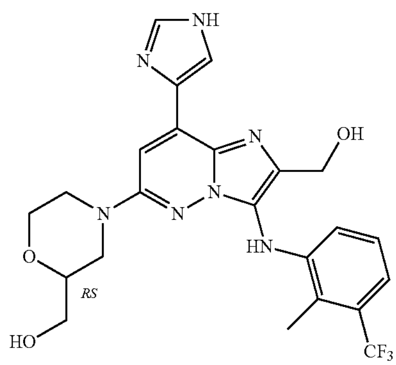 [SMILES: Cc1c(Nc2c(CO)nc3c(-c4c[nH]cn4)cc(N4CCOC(CO)C4)nn23)cccc1C(F)(F)F] | n.d. | — | 2.38 | 203 | Method 1 |
| 69 | 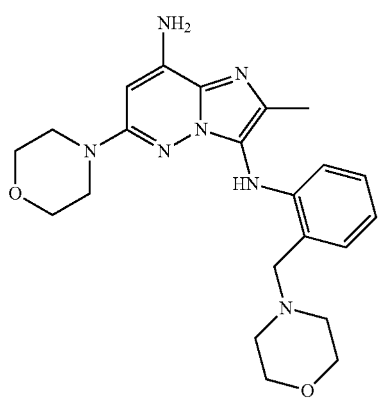 [SMILES: Cc1nc2c(N)cc(N3CCOCC3)nn2c1Nc1ccccc1CN1CCOCC1] | 119 (gum) | K | 2.71 | 424 | Method 1 |
| 71 | 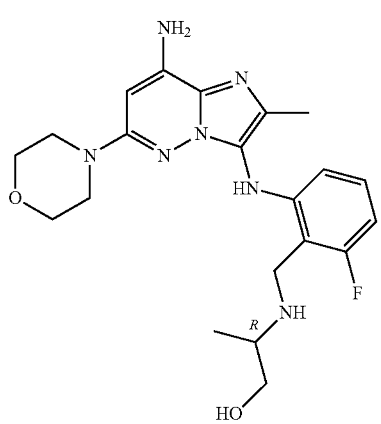 | n.d. | — | 2.19 | 430 | Method 1 |

TABLE-continued

| Co. No. | Compound Structure | M.P. (° C.) | Kofler (K) or DSC | $R_t$ | $[M + H]^+$ | LCMS Method |
|---|---|---|---|---|---|---|
| 73 | 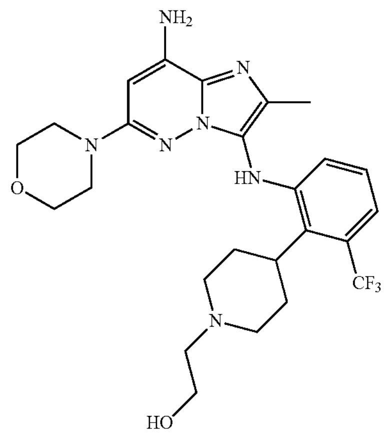 [SMILES: Cc1nc2c(N)cc(N3CCOCC3)nn2c1Nc1cccc(C(F)(F)F)c1C1CCN(CCO)CC1] | 252 | DSC | 2.58 | 520 | Method 1 |
| 74 | 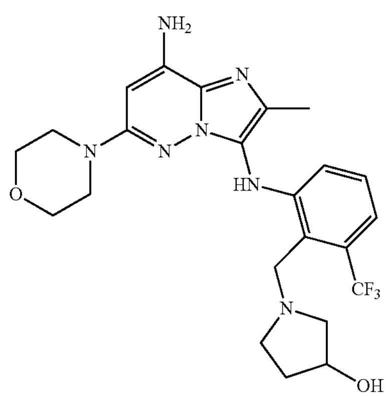 [SMILES: Cc1nc2c(N)cc(N3CCOCC3)nn2c1Nc1cccc(C(F)(F)F)c1CN1CCC(O)C1] | 180 | DSC | 2.83 | 492 | Method 1 |
| 77 | 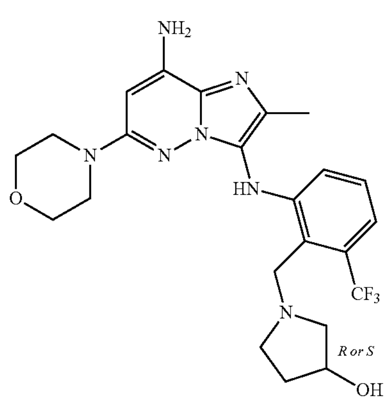 [SMILES: Cc1nc2c(N)cc(N3CCOCC3)nn2c1Nc1cccc(C(F)(F)F)c1CN1CCC(O)C1] | 134 (gum) | K | 2.82 | 492 | Method 1 |

TABLE-continued
| Co. No. | Compound Structure | M.P. (° C.) | Kofler (K) or DSC | R$_t$ | [M + H]$^+$ | LCMS Method |
|---|---|---|---|---|---|---|
| 78 | 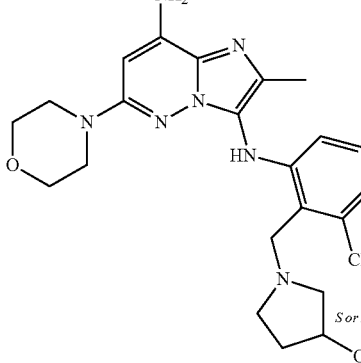 | 132 (gum) | K | 2.83 | 492 | Method 1 |
| 79 | 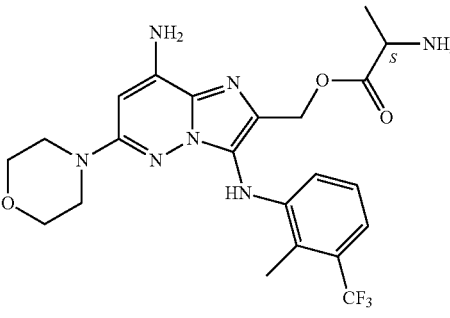<br>2.09 HCl 0.84 H$_2$O | 185 | K | 2.68 | 493 | Method 1 |
| 80 | 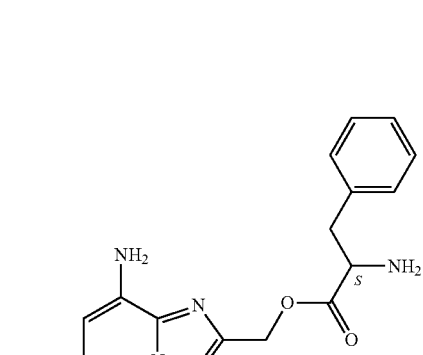<br>1.91 HCl 0.73 H$_2$O | 174 | K | 3.08 | 569 | Method 1 |

TABLE-continued

| Co. No. | Compound Structure | M.P. (°C.) | Kofler (K) or DSC | $R_t$ | $[M + H]^+$ | LCMS Method |
|---|---|---|---|---|---|---|
| 81 | (structure) 1.99 HCl 0.44 H₂O | 244 | K | 3.10 | 535 | Method 1 |
| 82 | (structure) 1.98 HCl 0.26 H₂O | 220 | K | 2.97 | 521 | Method 1 |
| 83 | (structure) 1.9 HCl 0.89 H₂O | 216 | K | 2.81 | 505 | Method 1 |
| 84 | (structure) 1.96 HCl 1.39 H₂O | 177 | DSC | 2.68 | 493 | Method 1 |

| Co. No. | Compound Structure | M.P. (° C.) | Kofler (K) or DSC | R$_t$ | [M + H]$^+$ | LCMS Method |
|---|---|---|---|---|---|---|
| 85 | 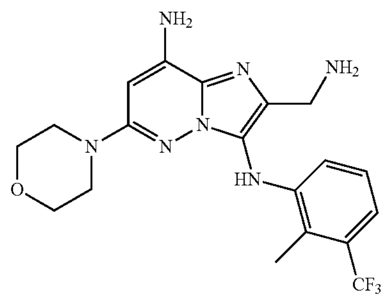 [SMILES: Cc1c(Nc2c(CN)nc3c(N)cc(N4CCOCC4)nn23)cccc1C(F)(F)F] | 191 | K | 2.42 | 404 (—NH$_3$) | Method 1 |
| 86 | 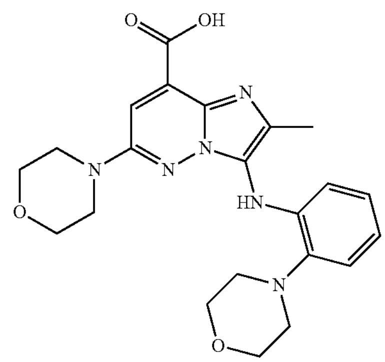 [SMILES: Cc1nc2c(C(=O)O)cc(N3CCOCC3)nn2c1Nc1ccccc1N1CCOCC1] | n.d. | — | 2.02 | 439 | Method 1 |
| 87 | 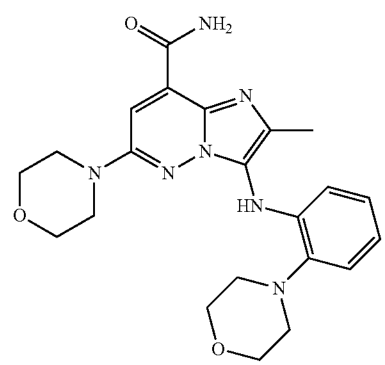 [SMILES: Cc1nc2c(C(N)=O)cc(N3CCOCC3)nn2c1Nc1ccccc1N1CCOCC1] | n.d. | — | 2.76 | 438 | Method 1 |
| 88 | 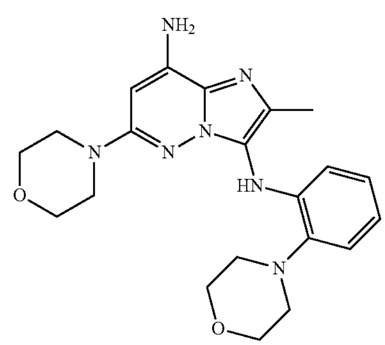 [SMILES: Cc1nc2c(N)cc(N3CCOCC3)nn2c1Nc1ccccc1N1CCOCC1] | n.d. | — | 2.57 | 410 | Method 1 |

TABLE-continued

| Co. No. | Compound Structure | M.P. (° C.) | Kofler (K) or DSC | R$_t$ | [M + H]$^+$ | LCMS Method |
|---|---|---|---|---|---|---|
| 89 | 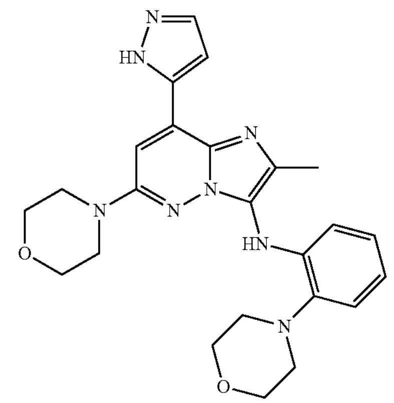 [SMILES: Cc1nc2c(-c3ccn[nH]3)cc(N3CCOCC3)nn2c1Nc1ccccc1N1CCOCC1] | n.d. | — | 2.80 | 461 | Method 1 |
| 91 | 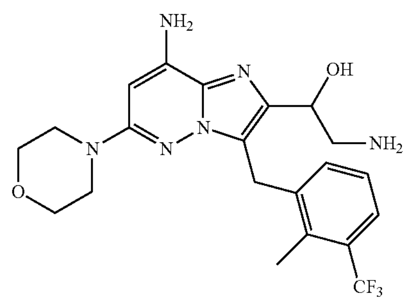 | n.d. | — | 2.38 | 451 | Method 1 |
| 93 | 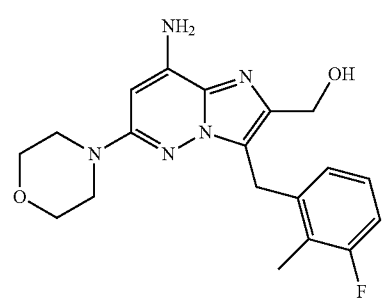 [SMILES: Cc1c(F)cccc1Cc1c(CO)nc2c(N)cc(N3CCOCC3)nn12] | 241 | DSC | 2.45 | 372 | Method 1 |
| 94 | 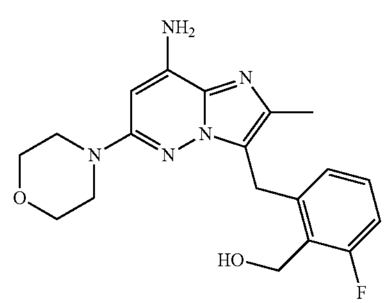 [SMILES: Cc1nc2c(N)cc(N3CCOCC3)nn2c1Cc1cccc(F)c1CO] | 201 | DSC | 2.20 | 372 | Method 1 |

| Co. No. | Compound Structure | M.P. (° C.) | Kofler (K) or DSC | $R_t$ | $[M + H]^+$ | LCMS Method |
|---|---|---|---|---|---|---|
| 97 | 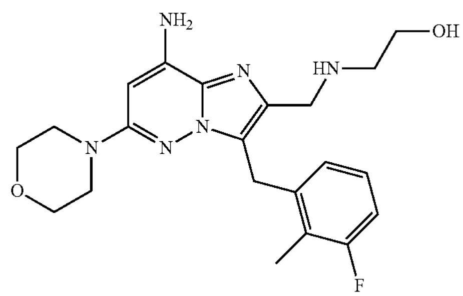 [SMILES: Cc1c(F)cccc1Cc1c(CNCCO)nc2c(N)cc(N3CCOCC3)nn12] | 178 | K | 2.24 | 415 | Method 1 |
| 99 | 1.11 HCl 0.03 H$_2$O | 236 | K | 2.58 | 386 | Method 1 |
| 101 | 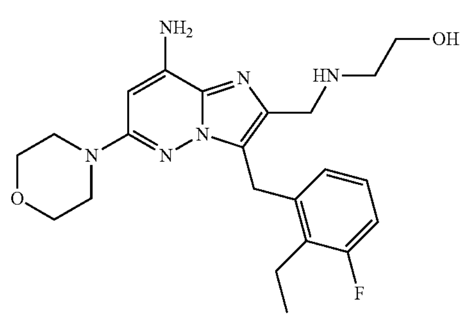 [SMILES: CCc1c(F)cccc1Cc1c(CNCCO)nc2c(N)cc(N3CCOCC3)nn12] | 148 | K | 2.31 | 429 | Method 1 |
| 102 | 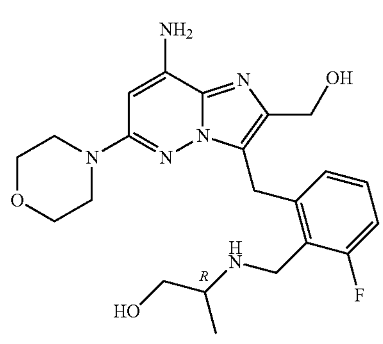 | 175.6 | DSC | 1.84 | 445 | Method 1 |

| Co. No. | Compound Structure | M.P. (° C.) | Kofler (K) or DSC | R_t | [M + H]+ | LCMS Method |
|---|---|---|---|---|---|---|
| 103 | 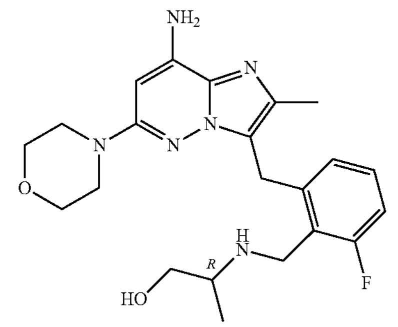 | 176.1 | DSC | 2.02 | 429 | Method 1 |
| 104 | 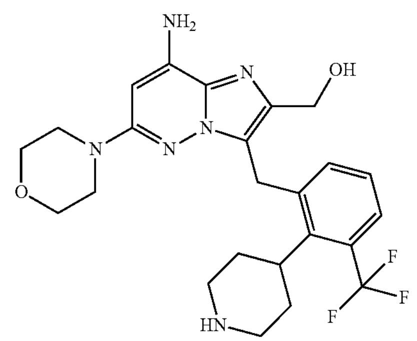 [SMILES: Nc1cc(N2CCOCC2)nn2c(Cc3cccc(C(F)(F)F)c3C3CCNCC3)c(CO)nc12] | n.d. | — | 0.95 | 491 | Method 1 |
| 105 | 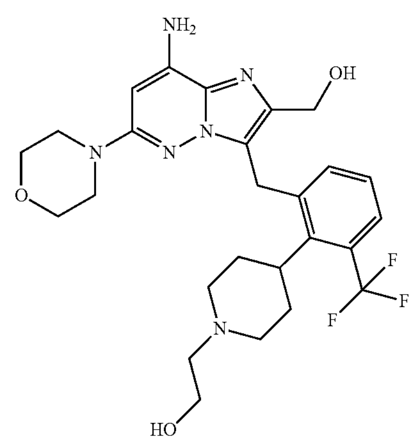 [SMILES: Nc1cc(N2CCOCC2)nn2c(Cc3cccc(C(F)(F)F)c3C3CCN(CCO)CC3)c(CO)nc12] | 249 | DSC | 2.19 | 535 | Method 1 |
| 106 | 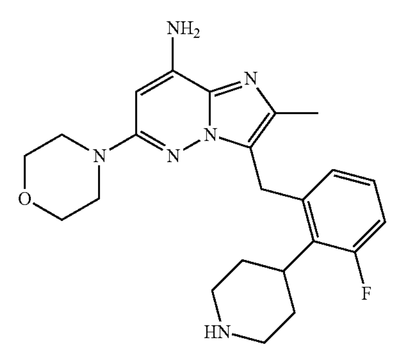 [SMILES: Cc1nc2c(N)cc(N3CCOCC3)nn2c1Cc1cccc(F)c1C1CCNCC1] | 189 | DSC | 2.12 | 425 | Method 1 |

TABLE-continued

| Co. No. | Compound Structure | M.P. (° C.) | Kofler (K) or DSC | $R_t$ | $[M + H]^+$ | LCMS Method |
|---|---|---|---|---|---|---|
| 107 | 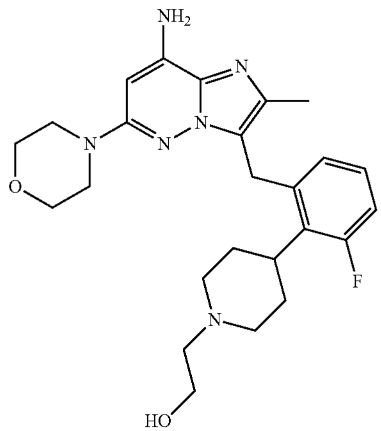 [SMILES: Cc1nc2c(N)cc(N3CCOCC3)nn2c1Cc1cccc(F)c1C1CCN(CCO)CC1] | 139 | DSC | 2.13 | 469 | Method 1 |
| 108 | 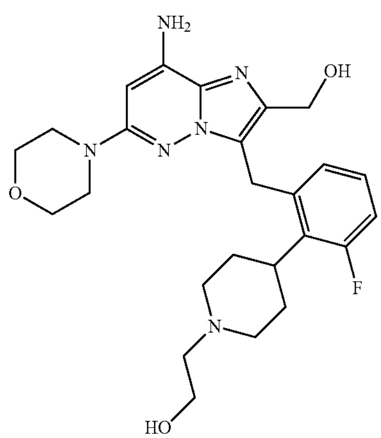 [SMILES: Nc1cc(N2CCOCC2)nn2c(Cc3cccc(F)c3C3CCN(CCO)CC3)c(CO)nc12] | n.d. | — | 1.87 | 485 | Method 1 |
| 109 | 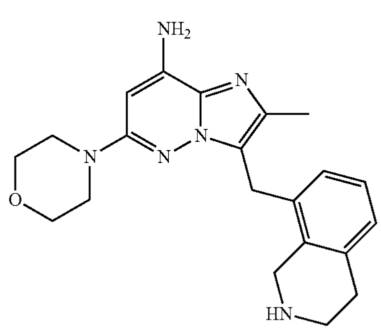 [SMILES: Cc1nc2c(N)cc(N3CCOCC3)nn2c1Cc1cccc2c1CNCC2] | 205 | DSC | 1.44 | 379 | Method 3 |

TABLE-continued

| Co. No. | Compound Structure | M.P. (° C.) | Kofler (K) or DSC | $R_t$ | $[M + H]^+$ | LCMS Method |
|---|---|---|---|---|---|---|
| 110 | 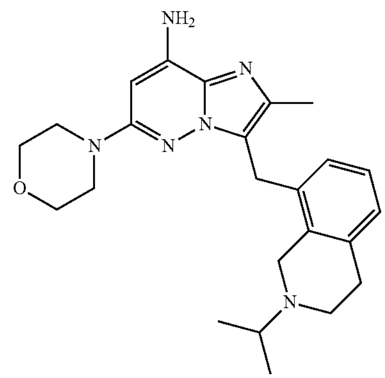 [SMILES: Cc1nc2c(N)cc(N3CCOCC3)nn2c1Cc1cccc2c1CN(C(C)C)CC2] | 262<br>251 | DSC<br>DSC | 1.51 | 421 | Method 3 |

Co. No. means compound number; Retention time ($R_t$) in min; M.P. means melting point (° C.); n.d. means not determined.

Compound 14

$^1$H NMR (DMSO-$d_6$): 7.49 (d, J=7.6 Hz, 1H), 7.30 (d, J=7.6 Hz, 1H), 7.24 (t, J=7.6 Hz, 1H), 6.53 (s, 2H), 5.85 (s, 1H), 4.96 (t, J=5.4 Hz, 1H), 4.54 (d, J=5.4 Hz, 2H), 4.27 (s, 2H), 3.57-3.66 (m, 4H), 3.11-3.19 (m, 4H), 2.5 (s, 3H-partially obscured by solvent peak).

Compound 19

$^1$H NMR (DMSO-$d_6$): 12.54 (br. s., 1H), 8.44 (br. s., 1H), 7.87 (br. s., 1H), 7.52 (d, J=7.8 Hz 1H), 7.44 (s, 1H), 7.31 (d, J=7.8 Hz, 1H), 7.24 (d, J=7.28 Hz, 1H), 5.09 (t, J=5.4 Hz, 1H), 4.63 (d, J=5.4 Hz, 2H), 4.37 (s, 2H), 3.71-3.65 (m, 4H), 3.35-3.31 (m, 4H—partially obscured by solvent peak), 2.52 (s, 3H—partially obscured by solvent peak).

Compound 33

$^1$H NMR (DMSO-$d_6$): 7.26 (s, 1H), 7.05 (t, J=7.8 Hz, 1H), 7.01 (d, J=7.8 Hz, 1H), 6.54 (s, 2H), 6.30 (d, J=7.8 Hz, 1H), 5.87 (s, 1H), 3.56-3.65 (m, 4H), 3.09-3.17 (m, 4H), 2.38 (s, 3H), 2.17 (s, 3H).

Compound 15

$^1$H NMR (DMSO-$d_6$): 9.29 (br. s., 1H), 8.32 (br. s., 1H), 7.47-7.57 (m, 2H), 7.20-7.32 (m, 2H), 5.22 (t, J=5.2 Hz, 1H), 4.62 (d, J=5.2 Hz, 2H), 4.38 (s, 2H), 3.70-3.63 (m, 4H), 3.38-3.32 (m, 4H), 2.45 (s, 3H—partially obscured by solvent peak).

Compound 18

$^1$H NMR (DMSO-$d_6$): 12.64 (br. s., 1H), 8.29 (br. s., 1H), 7.48-7.57 (m, 3H), 7.14-7.29 (m, 3H), 4.44 (d, J=5.2 Hz, 2H), 4.35 (s, 2H), 3.67-3.63 (m., 4H), 3.45-3.3 (m, 4H), 2.45 (s, 3H—partially obscured by solvent peak), 1.74 (s, 3H).

Compound 35

$^1$H NMR (DMSO-$d_6$): 12.57 (br. s., 1H), 8.42 (br. s., 1H), 7.89 (s, 1H), 7.49 (s, 1H), 7.40 (s, 1H), 7.11-6.97 (m, 2H), 6.34 (d, J=7.6 Hz, 1H), 3.41-3.22 (m, 4H), 3.35-3.25 (m, 4H), 2.42 (s, 3H), 2.28 (s, 3H).

OR data: Solvent: DMF; temperature: 20° C.; wavelength: 589 nm

| Compound number | OR (°) | Concentration (g/100 mL) |
|---|---|---|
| 77 | +2.2 | 0.273 |
| 78 | −2.78 | 0.324 |
| 79 | +11.22 | 0.365 |
| 80 | +6.89 | 0.348 |
| 82 | +5.69 | 0.193 |
| 84 | −3.63 | 0.358 |
| 102 | −8.2 | 0.317 |
| 103 | −14.55 | 0.323 |

Pharmacology

Enzyme Binding Assays (KINOMEscan®) Kinase enzyme binding affinities of compounds disclosed herein were determined using the KINOMEscan technology performed by DiscoveRx Corporation, San Diego, Calif., USA (www.kinomescan.com). Table A reports the obtained Kd values (nM), with the Kd being the inhibitor binding constant:

| Compound | Kd PIK3Cα_h (nM) | Kd PIK3Cβ_h (nM) | Kd PIK3Cδ_h (nM) | Kd PIK3Cγ_h (nM) | Kd MTOR_h (nM) |
|---|---|---|---|---|---|
| 1 | 16596 | 2.4 | 513 | >30200 | 23442 |
| 2 | 8128 | 1.4 | 178 | >30200 | 23442 |
| 3 | 9550 | 1.1 | 105 | 15488 | 7943 |
| 4 | 933 | 3.3 | 74 | 1148 | >3311 |

-continued

| Compound | Kd PIK3Cα_h (nM) | Kd PIK3Cβ_h (nM) | Kd PIK3Cδ_h (nM) | Kd PIK3Cγ_h (nM) | Kd MTOR_h (nM) |
|---|---|---|---|---|---|
| 5 | 617 | 6 | 316 | 10233 | 2399 |
| 6 | >30200 | 5 | 955 | >30200 | >30200 |
| 7 | >3311 | 15 | 525 | >30200 | >10000 |
| 8 | 30200 | 31 | 891 | 14454 | 525 |
| 9 | 1349 | 1.4 | 174 | 5248 | 12882 |
| 10 | >30200 | 20 | 12589 | >30200 | >30200 |
| 11 | 2692 | 21 | 955 | 6918 | 22387 |
| 12 | 1072 | <1.5 | 69 | 6166 | 9333 |
| 13 | 525 | 0.5 | 56 | 3548 | 9550 |
| 14 | >9184 | 1.3 | 207 | >8885 | >5689 |
| 14a | >30200 | 1.2 | 225 | >10000 | 6761 |
| 14b | >10000 | 1.5 | 253 | >8130 | >30200 |
| 14c | >10000 | 1.2 | 194 | >30200 | 5248 |
| 14d | n.d. | n.d. | n.d. | n.d. | n.d. |
| 14e | n.d. | n.d. | n.d. | n.d. | n.d. |
| 15 | 1096 | 7 | 479 | 1995 | >30200 |
| 16 | >10000 | 10 | >3311 | >3311 | >30200 |
| 17 | 16982 | 3.3 | 427 | 15849 | 14125 |
| 18 | >30200 | 2.0 | 59 | >30200 | >30200 |
| 19 | 886 | 1.9 | 80 | 1760 | 1286 |
| 20 | 1698 | 2.2 | 85 | 4786 | >10000 |
| 21 | 1585 | 9 | 240 | 617 | 178 |
| 22 | 1585 | 1.2 | 48 | >15136 | 10715 |
| 23 | 20853 | 3.0 | 276 | 23024 | 20582 |
| 24 | 1110 | 3.0 | 147 | 3361 | 2487 |
| 25 | >30200 | 200 | >30200 | >30200 | 1175 |
| 26 | >30200 | 331 | 13804 | 11749 | 8511 |
| 27 | 617 | 2.4 | 58 | 479 | 447 |
| 28 | 2089 | 2.5 | 83 | 5495 | 21380 |
| 29 | 3388 | 7 | 200 | 12303 | >30200 |
| 30 | 1175 | 2.6 | 129 | 4571 | 2188 |
| 31 | 2291 | 2.5 | 71 | 16982 | >10000 |
| 32 | 14791 | 1.8 | 355 | 12023 | 22387 |
| 33 | 5130 | 6 | 171 | 11357 | 20292 |
| 34 | 2239 | 3.0 | 81 | 6918 | >10000 |
| 35 | 912 | 2.6 | 49 | 2291 | 4677 |
| 36 | 669 | 0.9 | 58 | 4051 | 21691 |
| 37 | 575 | 2.2 | 214 | 759 | 3236 |
| 38 | 4054 | 4 | 15 | 12931 | 9368 |
| 39 | 2570 | 1.1 | 31 | 8511 | 4898 |
| 40 | 2041 | 4 | 372 | 3900 | 20100 |
| 41 | 275 | 7 | 12 | 955 | 1698 |
| 42 | 347 | 0.6 | 5 | 2291 | 1445 |
| 43 | 3311 | 2 | 47 | 7762 | >30200 |
| 44 | 9333 | 1.5 | 105 | 14791 | 5370 |
| 46 | 661 | 3.0 | 11 | 741 | 1230 |
| 47 | 10471 | 2.5 | 47 | 20893 | >30200 |
| 48 | 2754 | 1.7 | 34 | 6166 | >30200 |
| 49 | 13490 | 9 | 331 | >30200 | >30200 |
| 50 | 537 | 1.3 | 33 | 1259 | 776 |
| 51 | 10000 | 2.1 | 166 | 10000 | 11482 |
| 52 | 5754 | 1.9 | 40 | 4786 | 10715 |
| 53 | 10003 | 5 | 73 | 19628 | >30200 |
| 54 | 16218 | 12 | 490 | >30200 | >30200 |
| 55 | 1122 | 0.9 | 9 | 12589 | >30200 |
| 56 | 1709 | 1.2 | 16 | 8683 | >30200 |
| 57 | 339 | 0.7 | 9 | 891 | 6310 |
| 58 | 4266 | 0.4 | 20 | 12303 | 21380 |
| 59 | 6457 | 0.1 | 11 | 3388 | >30200 |
| 60 | 7244 | 0.2 | 16 | 9772 | >30200 |
| 61 | >30200 | 12 | 1660 | >30200 | >30200 |
| 62 | 22387 | 10 | 35 | 30200 | >30200 |
| 63 | 4169 | 2.2 | 42 | 19953 | 3162 |
| 64 | 20893 | 8 | 34 | >30200 | 16982 |
| 65 | 6607 | 1.3 | 138 | 692 | 355 |
| 66 | >30200 | 138 | 10965 | 13490 | 1380 |
| 67 | 195 | 0.5 | 17 | 324 | 186 |
| 68 | 2754 | 1.9 | 62 | 234 | 56 |
| 69 | 5370 | 15 | 56 | 24547 | 1514 |
| 71 | 16987 | 6 | 75 | >30200 | >30200 |
| 73 | 3236 | 0.3 | 28 | 23988 | >30200 |
| 74 | 4898 | 2.2 | 31 | 12589 | 20893 |
| 77 | 3162 | 1.4 | 47 | 9772 | 16982 |
| 78 | 3236 | 1.3 | 35 | 8318 | 12589 |
| 79 | 8710 | 0.8 | 120 | 17378 | 8913 |

-continued

| Compound | Kd PIK3Cα_h (nM) | Kd PIK3Cβ_h (nM) | Kd PIK3Cδ_h (nM) | Kd PIK3Cγ_h (nM) | Kd MTOR_h (nM) |
|---|---|---|---|---|---|
| 80 | >30200 | 44 | 6026 | >30200 | >30200 |
| 81 | 26915 | 5 | 724 | >30200 | >30200 |
| 82 | 32359 | 1.3 | 263 | >30200 | 25119 |
| 83 | 22168 | 2.1 | 309 | >30200 | >28250 |
| 84 | 12023 | 0.5 | 48 | 12589 | 7943 |
| 85 | >23016 | 0.7 | 75 | 7476 | 2681 |
| 86 | 1778 | 10 | 117 | 13183 | 19498 |
| 87 | 1202 | 43 | 219 | 3631 | 5888 |
| 88 | 11220 | 12 | 69 | 8318 | 8710 |
| 89 | 631 | 22 | 44 | 851 | 85 |
| 91 | 8913 | 1.1 | 148 | 8128 | 776 |
| 93 | >30200 | 2.7 | 166 | 3890 | 1905 |
| 94 | 16596 | 18 | 1413 | 10471 | 5754 |
| 97 | 11220 | 1.6 | 200 | 3715 | 912 |
| 99 | 10471 | 8.3 | 832 | 3311 | 1622 |
| 101 | 5888 | 6.2 | 427 | 724 | 1585 |
| 102 | >30200 | 141 | 1514 | >30200 | >30200 |
| 103 | >30200 | 74 | 1000 | 31623 | 24547 |
| 104 | 9333 | 0.7 | 138 | 15136 | >30200 |
| 105 | 26303 | 1.2 | 537 | >30200 | >30200 |
| 106 | 2754 | 0.5 | 372 | 5012 | >30200 |
| 107 | 11749 | 12 | 355 | 8710 | 11482 |
| 108 | 21380 | 14 | 376 | 13647 | 18665 |
| 109 | 12756 | 9 | 98 | 2903 | 22250 |
| 110 | >30200 | 513 | 2375 | >30200 | >30200 |

Cellular Assays:

Cellular activity of PI3Kβ inhibitors was determined by quantifying the phosphorylation of Akt in PC-3 cells. Akt phosphorylated at Ser473 and Thr308 were measured using an enzyme-linked immunosorbent assay (ELISA; Meso Scale Discovery (MSD), Gaithersburg, Md.) and specific primary antibodies from MSD.

On day 1, PC3 cells (ATCC # CRL-14351) were seeded into PerkinElmer MW96 plates at 25.000 cells per well, in 75 µl complete culture medium (DMEM (Dulbecco's Modified Eagle's Medium) high glucose, AQmedia™, D0819, Sigma-Aldrich) containing 10% heat inactivated FCS (Fetal Bovine Serum) and incubated at 37° C., 5% $CO_2$ during 24 hours. On day 2, compound or DMSO (dimethyl sulfoxide) (0.3%) was added and cells were further incubated for 60 min at 37° C., 5% $CO_2$ in a total volume of 100 µl of medium.

The phosphoprotein assay was executed according to vendor instructions in the Phospho-Akt (Ser473) Assay Whole Cell Lysate Kit (MSD # K15100D-3) and the Phospho-Akt (Thr308) Assay Whole Cell Lysate Kit (MSD # K151DYD-3) using the lysis, blocking and wash buffer provided.

Briefly, at the end of the cell treatment period, media were removed by aspiration and adherent cells were lysed in 50 µl ice-cold lysis buffer. MSD plates are supplied pre-coated with capture antibodies for Phospho-Akt (Ser473 and Thr308). After blocking, lysates from tissue culture plates were added and plates were washed. Then, a solution containing the detection antibody (anti-total Akt conjugated with an electrochemiluminescent compound-MSD Sulfo-tag label) was added. The signals were detected using an MSD SECTOR Imager 6000 and are proportional to the phospho-Akt titres.

Data were processed. The percentage of inhibition was plotted against the log concentration of test compounds, and the sigmoidal log concentration-effect curve of best fit was calculated by nonlinear regression analysis. From these concentration-response curves, the $IC_{50}$ values were calculated. Five concentrations were used for curve fitting.

Table B reports the obtained $IC_{50}$ values (nM):

| Compound | $IC_{50}$ pAkt_S473 (nM) | $IC_{50}$ pAkt_Thr308 (nM) |
|---|---|---|
| 14e | 52 | 41 |
| 1 | ~34 | 74 |
| 2 | 138 | 186 |
| 3 | 120 | ~71 |
| 4 | ~135 | ~120 |
| 5 | ~59 | ~48 |
| 6 | 123 | ~85 |
| 7 | 269 | 135 |
| 8 | 263 | 204 |
| 9 | 513 | 316 |
| 10 | 501 | >513 |
| 11 | ~158 | 355 |
| 12 | ~316 | ~151 |
| 13 | >513 | ~263 |
| 14c | 50 | ~49 |
| 14b | 60 | 38 |
| 14a | ~46 | 38 |
| 14d | 67 | 29 |
| 14 | ~63 | ~38 |
| 15 | ~91 | ~43 |
| 16 | 123 | 155 |
| 17 | 81 | ~50 |
| 18 | 33 | 11 |
| 19 | 28 | 26 |
| 20 | 33 | ~25 |
| 21 | 148 | 50 |
| 22 | >513 | >513 |
| 23 | 64 | 49 |
| 24 | 43 | 37 |
| 25 | 447 | >513 |
| 26 | >513 | ~309 |
| 27 | 42 | 14 |
| 28 | ~407 | 380 |
| 29 | >513 | ~513 |
| 30 | 59 | ~42 |
| 31 | 46 | 22 |
| 32 | 87 | 35 |

-continued

| Compound | IC$_{50}$ pAkt_S473 (nM) | IC$_{50}$ pAkt_Thr308 (nM) |
|---|---|---|
| 33 | 12 | 17 |
| 34 | ~56 | ~32 |
| 35 | 12 | 8 |
| 36 | ~331 | 195 |
| 37 | 11 | 20 |
| 38 | 18 | 10 |
| 39 | 34 | ~43 |
| 40 | 105 | 60 |
| 41 | ~37 | 22 |
| 42 | >513 | >513 |
| 43 | ~339 | 170 |
| 44 | 34 | ~11 |
| 46 | 174 | 17 |
| 47 | 59 | 44 |
| 48 | 98 | 55 |
| 49 | 45 | ~21 |
| 50 | 60 | 38 |
| 51 | 145 | ~81 |
| 52 | 44 | 33 |
| 53 | ~176 | ~87 |
| 54 | 200 | 98 |
| 55 | 10 | 7 |
| 56 | ~7 | ~5 |
| 57 | 34 | 26 |
| 58 | 21 | 17 |
| 59 | 85 | ~60 |
| 60 | 219 | ~148 |
| 61 | 105 | 151 |
| 62 | 110 | ~74 |
| 63 | 138 | 96 |
| 64 | 166 | 112 |
| 65 | 79 | 43 |
| 66 | >513 | ~513 |
| 67 | 23 | 74 |
| 68 | ~23 | 69 |
| 69 | 186 | 151 |
| 71 | 246 | 107 |
| 73 | 89 | ~72 |
| 74 | 30 | 26 |
| 77 | 58 | 25 |
| 78 | 51 | 26 |
| 79 | 27 | 45 |
| 80 | 209 | ~195 |
| 81 | >513 | 282 |
| 82 | 380 | ~123 |
| 83 | 159 | 81 |
| 84 | 141 | 98 |
| 85 | 115 | 86 |
| 86 | >513 | >513 |
| 87 | 257 | ~224 |
| 88 | | 120 |
| 89 | 115 | 83 |
| 91 | >513 | >513 |
| 93 | 174 | 120 |
| 94 | >513 | 417 |
| 97 | 79 | 40 |
| 99 | 257 | 200 |
| 101 | >513 | >513 |
| 102 | >513 | >513 |
| 103 | >423 | >382 |
| 104 | 78 | 29 |
| 105 | | 85 |
| 106 | 174 | 129 |
| 107 | 158 | 115 |
| 108 | >513 | >513 |
| 109 | 136 | 82 |
| 110 | 324 | 222 |

Composition Examples

"Active ingredient" (a.i.) as used throughout these examples relates to a compound of Formula (I), including any tautomer or stereoisomeric form thereof, or a N-oxide, a pharmaceutically acceptable addition salt or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:
1. A compound of Formula (I)

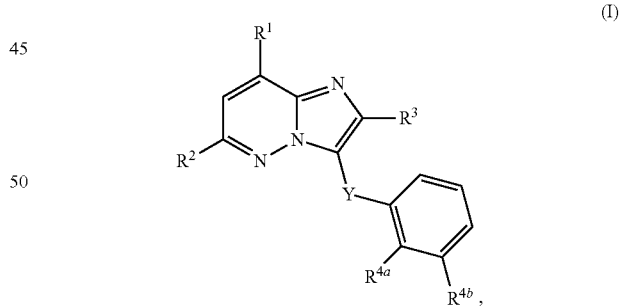

a tautomer or a stereoisomeric form thereof, wherein
R$^1$ represents —C(=O)OH, —C(=O)NH$_2$, —NH$_2$,

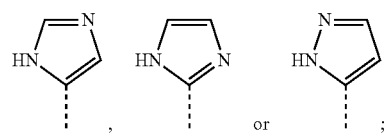

$R^2$ represents

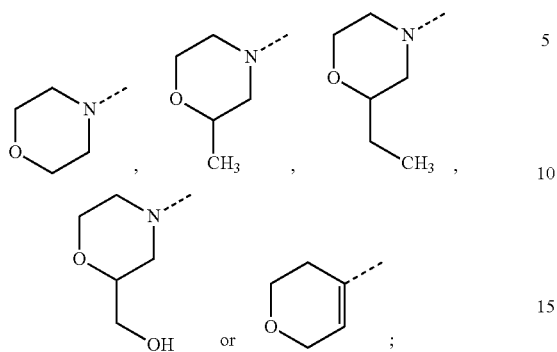

$R^3$ represents $C_{1-4}$alkyl; —CH(OH)—CH$_2$—R$^q$; or $C_{1-4}$alkyl substituted with one substituent selected from the group consisting of halo, —OH, —NH$_2$, —O—(C=O)—C$_{1-4}$alkyl,
NH—(C=O)—C$_{1-4}$alkyl, —NH—(SO$_2$)—C$_{1-4}$alkyl —N(CH$_3$)—C$_{1-4}$alkyl-SO$_2$—CH$_3$, —NH—C$_{1-4}$alkyl-SO$_2$—CH$_3$, —N(CH$_3$)—C$_{1-4}$alkyl-OH, —(C=O)—NH—C$_{1-4}$alkyl-OH, —O—(C=O)—CH(NH$_2$)—C$_{1-4}$alkyl, —O—(C=O)—CH(NH$_2$)—C$_{1-4}$alkyl-Ar,

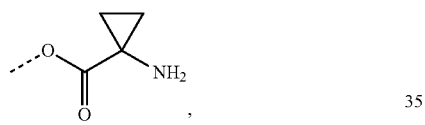

and —NH—C$_{1-4}$alkyl-OH;

$R^q$ represents halo, —OH, —NH$_2$, —O—(C=O)—C$_{1-4}$ alkyl, —NH—(C=O)—C$_{1-4}$alkyl, —NH—(SO$_2$)—C$_{1-4}$alkyl, —N(CH$_3$)—C$_{1-4}$alkyl-SO$_2$—CH$_3$, —NH—C$_{1-4}$alkyl-SO$_2$—CH$_3$, —N(CH$_3$)—C$_{1-4}$alkyl-OH, —O—(C=O)—CH(NH$_2$)—C$_{1-4}$alkyl,
O—(C=O)—CH(NH$_2$)—C$_{1-4}$alkyl-Ar,

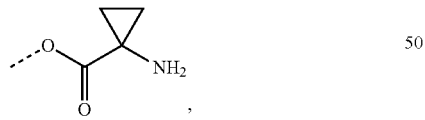

or —NH—C$_{1-4}$alkyl-OH;

Y represents —CH$_2$— or —NH—;

$R^{4a}$ represents hydrogen, C$_{1-4}$alkyl, Het$^a$, or C$_{1-4}$alkyl substituted with one or more substituents each independently selected from the group consisting of —OH, —NR$^5$R$^6$ and Het$^a$;

$R^{4b}$ represents hydrogen, halo, C$_{1-4}$alkyl, or C$_{1-4}$alkyl substituted with one or more halo substituents;

or $R^{4a}$ and $R^{4b}$ are taken together to form together with the phenyl ring to which they are attached a structure of Formula (a-1), (a-2), (a-3), (a-4) or (a-5):

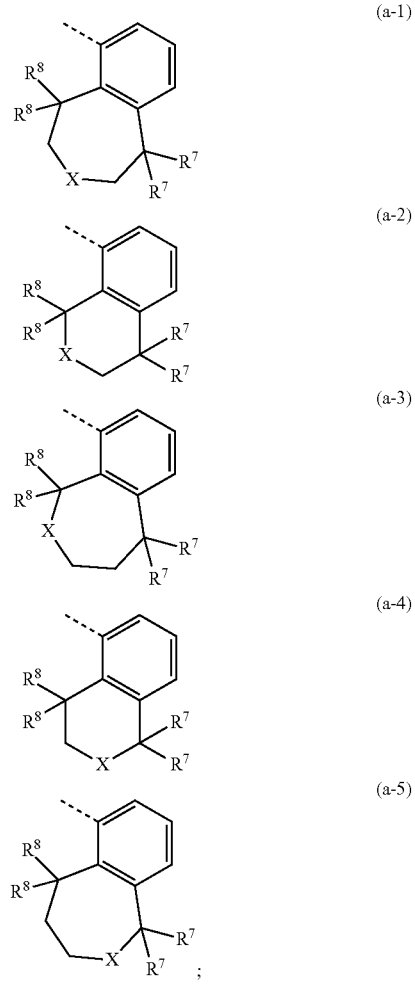

X represents —NH—, —O— or —N(C$_{1-3}$alkyl)-;

both R$^7$ substituents are the same and are selected from the group consisting of hydrogen, fluoro and methyl; or both R$^7$ substituents are taken together to form together with the common carbon atom to which they are attached a cyclopropyl, cyclobutyl or oxetanyl;

both R$^8$ substituents are the same and are selected from the group consisting of hydrogen and methyl; or both R$^8$ substituents are taken together to form together with the common carbon atom to which they are attached a cyclopropyl, cyclobutyl or oxetanyl;

$R^5$ represents hydrogen, C$_{1-6}$alkyl, or C$_{1-6}$alkyl substituted with one —OH;

$R^6$ represents hydrogen, C$_{1-6}$alkyl, or C$_{1-6}$alkyl substituted with one —OH;

Ar represents phenyl optionally substituted with hydroxy;

each Het$^a$ independently represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of C$_{1-4}$alkyl, —S(=O)$_2$—C$_{1-6}$alkyl, hydroxy, —C$_{1-4}$alkyl-S(=O)$_2$—C$_{1-6}$alkyl, and C$_{1-4}$alkyl substituted with one hydroxy; or two substituents on the same carbon atom of said 4-, 5- or 6-membered saturated heterocyclyl are taken together to form together with the common carbon atom to which they are attached Ring B;

Ring B represents cyclobutyl, cyclopentyl, cyclohexyl or a 4-, 5- or 6-membered saturated heterocyclyl containing at least one heteroatom each independently selected from O, S, S(=O)$_p$ and N; said cyclobutyl, cyclopentyl, cyclohexyl or 4-, 5- or 6-membered saturated heterocyclyl is optionally substituted with one or two C$_{1-4}$alkyl substituents, with one C$_{1-4}$alkyl and one hydroxy substituent, or with one hydroxy substituent;

p represents 1 or 2;

or a N-oxide, a pharmaceutically acceptable addition salt or a solvate thereof.

2. The compound according to claim 1, wherein
R$^{4a}$ represents C$_{1-4}$alkyl, Het$^a$, or C$_{1-4}$alkyl substituted with one or more substituents each independently selected from the group consisting of —OH, —NR$^5$R$^6$ and Het$^a$;

R$^{4b}$ represents hydrogen, halo, C$_{1-4}$alkyl, or C$_{1-4}$alkyl substituted with one or more halo substituents;

or R$^{4a}$ and R$^{4b}$ are taken together to form together with the phenyl ring to which they are attached a structure of Formula (a-1), (a-2), (a-3), (a-4) or (a-5);

X represents —NH— or —O—;

both R$^7$ substituents are the same and are selected from the group consisting of hydrogen, fluoro and methyl;

both R$^8$ substituents are the same and are selected from the group consisting of hydrogen and methyl;

R$^5$ represents hydrogen, C$_{1-6}$alkyl, or C$_{1-6}$alkyl substituted with one —OH;

R$^6$ represents hydrogen, C$_{1-6}$alkyl, or C$_{1-6}$alkyl substituted with one —OH;

each Het$^a$ independently represents a 4-, 5- or 6-membered saturated heterocyclyl containing at least one heteroatom each independently selected from O, S, S(=O)$_p$ and N; said 4-, 5- or 6-membered saturated heterocyclyl is optionally substituted with one or two substituents each independently selected from the group consisting of C$_{1-4}$alkyl, —S(=O)$_2$—C$_{1-6}$alkyl, hydroxy, —C$_{1-4}$alkyl-S(=O)$_2$—C$_{1-6}$alkyl, and C$_{1-4}$alkyl substituted with one hydroxy; or two substituents on the same carbon atom of said 4-, 5- or 6-membered saturated heterocyclyl are taken together to form together with the common carbon atom to which they are attached Ring B;

Ring B represents cyclobutyl, cyclopentyl, cyclohexyl or a 4-, 5- or 6-membered saturated heterocyclyl containing one S(=O)$_2$.

3. The compound according to claim 1, wherein
R$^2$ represents

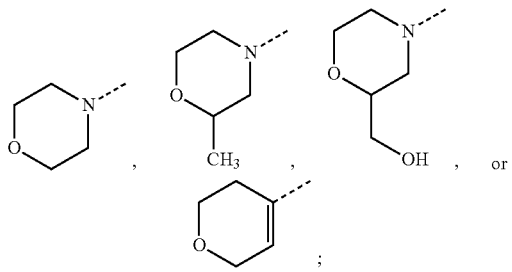

;

R$^3$ represents C$_{1-4}$alkyl; —CH(OH)—CH$_2$—R$^q$; or C$_{1-4}$alkyl substituted with one substituent selected from the group consisting of halo, —OH, —NH$_2$, —O—(C=O)—C$_{1-4}$alkyl,
NH—(C=O)—C$_{1-4}$alkyl, —N(CH$_3$)—C$_{1-4}$alkyl-SO$_2$—CH$_3$, —NH—C$_{1-4}$alkyl-SO$_2$—CH$_3$, —O—(C=O)—CH(NH$_2$)—C$_{1-4}$alkyl, —O—(C=O)—CH(NH$_2$)—C$_{1-4}$alkyl-Ar,

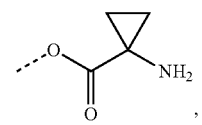

and —NH—C$_{1-4}$alkyl-OH;

R$^q$ represents —NH$_2$;

R$^{4a}$ represents C$_{1-4}$alkyl, Het$^a$, or C$_{1-4}$alkyl substituted with one or more substituents each independently selected from the group consisting of —OH, —NR$^5$R$^6$ and Het$^a$;

R$^{4b}$ represents hydrogen, halo, C$_{1-4}$alkyl, or C$_{1-4}$alkyl substituted with one or more halo substituents;

or R$^{4a}$ and R$^{4b}$ are taken together to form together with the phenyl ring to which they are attached a structure of Formula (a-2) or (a-4);

X represents —NH—;

both R$^7$ substituents are hydrogen;

both R$^8$ substituents are hydrogen;

R$^5$ represents hydrogen;

R$^6$ represents C$_{1-6}$alkyl substituted with one —OH;

Ar represents phenyl;

each Het$^a$ independently represents a 4-, 5- or 6-membered saturated heterocyclyl containing at least one heteroatom each independently selected from O, S(=O)$_p$ and N; said 4-, 5- or 6-membered saturated heterocylcyl is optionally substituted with one or two substituents each independently selected from the group consisting of C$_{1-4}$alkyl, —S(=O)$_2$—C$_{1-6}$alkyl, hydroxy, and C$_{1-4}$alkyl substituted with one hydroxy; or two substituents on the same carbon atom of said 4-, 5- or 6-membered saturated heterocyclyl are taken together to form together with the common carbon atom to which they are attached Ring B;

Ring B represents a 4-membered saturated heterocyclyl containing one S(=O)$_p$;

p represents 2.

4. The compound according to claim 1, wherein
R$^2$ represents

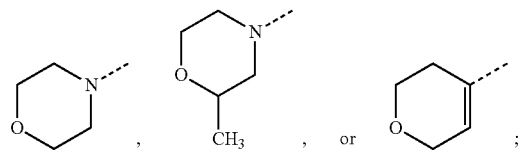

R$^3$ represents C$_{1-4}$alkyl; or C$_{1-4}$alkyl substituted with one substituent selected from the group consisting of halo, —OH, —NH—(C=O)—C$_{1-4}$alkyl, —N(CH$_3$)—C$_{1-4}$alkyl-SO$_2$—CH$_3$, —NH—C$_{1-4}$alkyl-SO$_2$—CH$_3$, and —NH—C$_{1-4}$alkyl-OH;

R$^{4a}$ represents C$_{1-4}$alkyl, or C$_{1-4}$alkyl substituted with one or more Het$^a$ substituents;

$R^{4b}$ represents halo, $C_{1-4}$alkyl, or $C_{1-4}$alkyl substituted with one or more halo substituents;
or $R^{4a}$ and $R^{4b}$ are taken together to form together with the phenyl ring to which they are attached a structure of Formula (a-2);
X represents —NH—;
both $R^7$ substituents are hydrogen;
both $R^8$ substituents are hydrogen;
each $Het^a$ independently represents a 6-membered saturated heterocyclyl containing at least one heteroatom each independently selected from O, $S(=O)_p$ and N;
p represents 2.

5. The compound according to claim 1, wherein
$R^1$ represents —NH$_2$;
$R^2$ represents

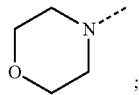

and Y represents —CH$_2$—.

6. The compound according to claim 1, wherein Y represents —CH$_2$—.

7. The compound according to claim 1, wherein $R^1$ represents —C(=O)OH, —C(=O)NH$_2$, or —NH$_2$.

8. The compound according to claim 1, wherein
$R^{4a}$ represents $C_{1-4}$alkyl;
$R^{4b}$ represents $C_{1-4}$alkyl substituted with one or more halo substituents.

9. The compound according to claim 1, wherein
$R^3$ represents $C_{1-4}$alkyl; or $C_{1-4}$alkyl substituted with one substituent selected from the group consisting of halo, —OH, —NH$_2$, —O—(C=O)—C$_{1-4}$alkyl, —NH—(C=O)—C$_{1-4}$alkyl, —NH—(SO$_2$)—C$_{1-4}$alkyl, —N(CH$_3$)—C$_{1-4}$alkyl-SO$_2$—CH$_3$, —NH—C$_{1-4}$alkyl-SO$_2$—CH$_3$, —N(CH$_3$)—C$_{1-4}$alkyl-OH, —(C=O)—NH—C$_{1-4}$alkyl-OH, —O—(C=O)—CH(NH$_2$)—C$_{1-4}$alkyl, —O—(C=O))—CH(NH$_2$)—C$_{1-4}$alkyl-Ar,

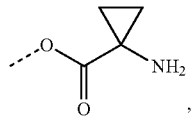

and —NH—C$_{1-4}$alkyl-OH.

10. The compound according to claim 1, wherein Y represents —NH—.

11. A pharmaceutical composition comprising a pharmaceutically acceptable carrier and, as active ingredient, a therapeutically effective amount of a compound according to claim 1.

12. A method of treating a disease or condition selected from the group consisting of cancer, autoimmune disorders, cardiovascular diseases, inflammatory diseases, neurodegenerative diseases, allergy, pancreatitis, asthma, multiorgan failure, kidney diseases, platelet aggregation, sperm motility, transplantation rejection, graft rejection, and lung injuries in a human comprising administering a therapeutically effective amount of a compound of claim 1.

13. The method according to claim 12 wherein the disease or condition is cancer.

14. The method according to claim 13 wherein the disease or condition is prostate cancer.

* * * * *